United States Patent
Naito et al.

(10) Patent No.: US 9,872,924 B2
(45) Date of Patent: *Jan. 23, 2018

(54) ANTIBODY-DRUG CONJUGATE PRODUCED BY BINDING THROUGH LINKER HAVING HYDROPHILIC STRUCTURE

(71) Applicant: Daiichi Sankyo Company, Limited, Tokyo (JP)

(72) Inventors: Hiroyuki Naito, Tokyo (JP); Takashi Nakada, Tokyo (JP); Masao Yoshida, Tokyo (JP); Shinji Ashida, Tokyo (JP); Takeshi Masuda, Tokyo (JP); Hideki Miyazaki, Tokyo (JP); Yuji Kasuya, Tokyo (JP); Yuki Abe, Tokyo (JP); Yusuke Ogitani, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/436,458

(22) PCT Filed: Oct. 17, 2013

(86) PCT No.: PCT/JP2013/006178
§ 371 (c)(1),
(2) Date: Apr. 23, 2015

(87) PCT Pub. No.: WO2014/061277
PCT Pub. Date: Apr. 24, 2014

(65) Prior Publication Data
US 2015/0352224 A1 Dec. 10, 2015

(30) Foreign Application Priority Data
Oct. 19, 2012 (JP) .................... 2012-231579

(51) Int. Cl.
A61K 49/00 (2006.01)
A61K 47/48 (2006.01)
C07K 16/30 (2006.01)
C07K 16/28 (2006.01)
C07K 16/00 (2006.01)
A61K 47/68 (2017.01)

(52) U.S. Cl.
CPC .... A61K 47/48715 (2013.01); A61K 47/6803 (2017.08); A61K 47/6851 (2017.08); A61K 47/6889 (2017.08); C07K 16/00 (2013.01); C07K 16/28 (2013.01); C07K 16/2803 (2013.01); C07K 16/2827 (2013.01); C07K 16/2875 (2013.01); C07K 16/2878 (2013.01); C07K 16/2896 (2013.01); C07K 16/30 (2013.01)

(58) Field of Classification Search
None
See application file for complete search history.

(56) References Cited

U.S. PATENT DOCUMENTS

| | | | |
|---|---|---|---|
| 5,834,476 A | 11/1998 | Terasawa et al. | |
| 5,837,673 A | 11/1998 | Tsujihara et al. | |
| 5,892,043 A | 4/1999 | Tsujihara et al. | |
| 6,214,345 B1 | 4/2001 | Firestone et al. | |
| 6,291,671 B1 | 9/2001 | Inoue et al. | |
| 6,835,807 B1* | 12/2004 | Susaki ............ | A61K 47/48169 530/322 |
| 7,833,979 B2 | 11/2010 | Sullivan et al. | |
| 7,837,980 B2 | 11/2010 | Alley et al. | |
| 8,226,945 B2 | 7/2012 | Ebens, Jr. et al. | |
| 8,394,607 B2 | 3/2013 | Ebens, Jr. et al. | |
| 8,425,912 B2 | 4/2013 | Govindan | |
| 8,524,865 B2 | 9/2013 | Ebens, Jr. et al. | |
| 8,741,291 B2 | 6/2014 | Bhat et al. | |
| 8,907,071 B2 | 12/2014 | Sullivan et al. | |
| 8,968,741 B2 | 3/2015 | Ebens et al. | |
| 2003/0148931 A1 | 8/2003 | Takahashi et al. | |
| 2003/0166513 A1 | 9/2003 | Imura et al. | |

(Continued)

FOREIGN PATENT DOCUMENTS

CN 101490087 A 7/2009
EP 0 495 432 A1 7/1992

(Continued)

OTHER PUBLICATIONS

Loo et al. ("Loo", Clin. Cancer Res. Jul. 15, 2012, 18, 3834-3845.*
International Search Report corresponding to Application No. PCT/JP2014/006421, dated Mar. 17, 2015.
International Search Report corresponding to Application No. PCT/JP2015/000355, dated Apr. 21, 2015.
International Search Report corresponding to Application No. PCT/JP2015/001624, dated May 12, 2015.
International Search Report corresponding to Application No. PCT/JP2015/001922, dated May 26, 2015.
F. Dosio et al., "Antibody-targeted leucinostatin A", Journal of Controlled Release, No. 32, (1994), pp. 37-44.
L. Ducry et al., "Antibody-Drug Conjugates: Linking Cytotoxic Payloads to Monoclonal Antibodies", Bioconjugate Chem., No. 21, (2009), pp. 5-13.
S. Alley et al., "Antibody-drug conjugates: targeted drug delivery for cancer", Current Opinion in Chemical Biology, No. 14, (2010), pp. 529-537.
N. Damlie, "Tumour-targeted chemotherapy with immunoconjugates of calicheamicin", Expert Opinion, Vacinese & Antibodies, No. 4(9), (2004), pp. 1445-1452.

(Continued)

Primary Examiner — Mark Halvorson
Assistant Examiner — Kauser Akhoon
(74) Attorney, Agent, or Firm — Foley & Lardner LLP

(57) ABSTRACT

As an antitumor drug which is excellent in terms of antitumor effect and safety, there is provided an antibody-drug conjugate in which an antitumor compound represented by the following formula (I) is conjugated to an antibody via a linker having a structure represented by the following formula: $-L^1-L^2-L^P-NH-(CH_2)n^1-L^a-L^b-L^c-$ or $-L^1-L^2-L^P-$ wherein the antibody is connected to the terminal of $L^1$, the antitumor compound is connected to the terminal of $L^c$ or $L^P$, and any one or two or more of linkers of $L^1$, $L^2$, and $L^P$ has a hydrophilic structure.

47 Claims, 20 Drawing Sheets

(56) References Cited

U.S. PATENT DOCUMENTS

| | | |
|---|---|---|
| 2004/0185053 A1 | 9/2004 | Govindan |
| 2005/0123536 A1 | 6/2005 | Law et al. |
| 2005/0228007 A1 | 10/2005 | Jagtap et al. |
| 2006/0193865 A1 | 8/2006 | Govindan |
| 2008/0050310 A1 | 2/2008 | Ebens, Jr. et al. |
| 2008/0161245 A1 | 7/2008 | Kratz et al. |
| 2008/0305044 A1 | 12/2008 | McDonagh et al. |
| 2009/0274713 A1 | 11/2009 | Chari et al. |
| 2010/0068181 A1 | 3/2010 | Paliwal et al. |
| 2010/0120816 A1 | 5/2010 | Fontana et al. |
| 2011/0070248 A1 | 3/2011 | Ichikawa et al. |
| 2011/0293513 A1 | 12/2011 | Govindan et al. |
| 2012/0121615 A1 | 5/2012 | Flygare et al. |
| 2012/0201809 A1 | 8/2012 | Bhat et al. |
| 2013/0123178 A1 | 5/2013 | Dimarchi et al. |
| 2014/0004078 A1 | 1/2014 | Govindan |
| 2016/0287722 A1 | 10/2016 | Govindan |

FOREIGN PATENT DOCUMENTS

| | | | |
|---|---|---|---|
| EP | 0 737 686 A1 | 10/1996 | |
| EP | 0 916 348 A1 | 5/1999 | |
| EP | 1 155 702 A1 | 11/2001 | |
| EP | 2 907 824 A1 | 8/2015 | |
| JP | 05-059061 A | 3/1993 | |
| JP | H06-87746 A | 3/1994 | |
| JP | 08-337584 A | 12/1996 | |
| JP | 10-095802 A | 4/1998 | |
| JP | 11-092405 A | 4/1999 | |
| JP | 2002-060351 A | 2/2002 | |
| JP | 2005-511627 A | 4/2005 | |
| JP | 2006-511526 A | 4/2006 | |
| JP | 2007-527872 A | 10/2007 | |
| JP | 2008-521828 A | 6/2008 | |
| JP | 2009-538629 A | 11/2009 | |
| JP | 2010-513524 A | 4/2010 | |
| JP | 2012-100671 A | 5/2012 | |
| JP | 2013-534535 A | 9/2012 | |
| JP | 2013-534906 A | 9/2013 | |
| RU | 2 450 008 C2 | 5/2012 | |
| TW | I232930 | 5/2005 | |
| TW | 200817434 A | 4/2008 | |
| WO | WO 1997/46260 A1 | 12/1997 | |
| WO | WO 2000/25825 A1 | 5/2000 | |
| WO | WO 2002/00734 A1 | 1/2002 | |
| WO | WO-03/015826 A1 | 2/2003 | |
| WO | WO 03/043583 A2 | 5/2003 | |
| WO | WO 2013/188740 A1 | 12/2003 | |
| WO | WO 2005112919 A2 * | 12/2005 | ........... A61K 31/403 |
| WO | WO 2006/065533 A2 | 6/2006 | |
| WO | WO 2006/092230 A2 | 9/2006 | |
| WO | WO 2007/140371 A2 | 12/2007 | |
| WO | WO 2011/021397 A1 | 2/2011 | |
| WO | WO 2013/163229 A1 | 10/2013 | |
| WO | WO 2014/057687 A1 | 4/2014 | |
| WO | WO 2014/061277 A1 | 4/2014 | |
| WO | WO 2014/107024 A1 | 7/2014 | |

OTHER PUBLICATIONS

P. Senter et al., "The discovery and development of brentuximab vedotin for use in relapsed Hodgkin lymphoma and systemic anaplastic large cell lymphoma", Nature Biotechnology, vol. 30, No. 7 (Jul. 2012), pp. 631-637.

E. Kumazawa et al., "Antitumour activity of DX-8951f: a new camptothecin derivative", Expert Opinion Invest. Drugs, No. 7(4), (1998), pp. 625-632.

I. Mitsui, "A New Water-soluble Camptotheicn Derivative, DX-8951f, Exhibits Potent Antitumor Activity against Human Tumors in vitro and invivo", Japan J. Cancer Res., No. 86, (Aug. 1995), pp. 776-782.

S. Takiguchi et al., "Antitumor Effect of DX-8951, a Novel Camptothecin Analog, on Human Pancreatic Tumor Cells and Their CPT-11-resistant Variants Cultured in vitro and Xenografted into Nude Mice", Japan J. Cancer Res., No. 88 (Aug. 1997), pp. 760-769.

N. Joto et al., "DX-8951F, A water-soluble camptothecin analog, exhibits potent antitumor activity against a human lung cancer call line and its SN-38-resistant variant", Japan J. Cancer, No. 72, (1997), pp. 680-686.

E. Kumazawa et al., "Potent and broad antitumor effects of DX-8951f, a water-soluble camptotecin derivative, against various human tumors xenografted in nude mice", Cancer Chemother Pharmacol, No. 42, (1998), pp. 210-220.

R. De Jager et al., "DX-8951f: summary of phase I clinical trials", Annals New York Academy of Sciences, pp. 260-273.

K. Inoue et al., "CM-Dextran-Polyalcohol-Camptothecin Conjugate", Polymer Drugs in the Clinical Stage, (2003), pp. 145-153.

E. Kumazawa et al., "DE-310, a novel macromolecular carrier system for the camptothecin analog DX-8951f: Potent antitumor activities in various murine tumor models", Cancer Sci, vol. 95, No. 2 (Feb. 2004), pp. 168-175.

O. Soepenberg et al., "Phase I and Pharmacokinetic Study of DE-310 in Patients with Advanced Solid Tumors", Clinical Cancer Research, vol. 11, (Jan. 15, 2005), pp. 703-711.

M. Wente et al., "DE-310, a Macromolecular prodrug of the topoisomerase-I-inhibitor exatecan (DX-8951), in patients with operable solid tumors", Investigational New Drugs, No. 23 (2005), pp. 339-347.

International Search Report for PCT/JP2013/006069, dated Dec. 17, 2013, 3 pages.

International Search Report for PCT/JP2013/006178, dated Dec. 17, 2013, 3 pages.

Beck Alain, The Discovery Medicine, The Next Generation of Antibody-drug Conjugates Comes of Age, Oct. 16, 2010, vol. 10, No. 53, pp. 329-339.

Nakada et al., Bioorganic & Medicinal Chemistry Letters, Novel antibody drug conjugates containing exatecan derivative-based cytotoxic payloads, vol. 26, No. 6, pp. 1542-1545.

Office Action issued in Singapore Application No. 11201502887W dated Apr. 22, 2016.

The Extended European Search Report issued in Application No. 13845596.9 dated May 6, 2016.

The Extended European Search Report issued in Application No. 13847461.4 dated May 13, 2016.

Barginear et al., The Open Breast Cancer Journal, Trastuzumab-DM1: A Review of the Novel Immuno-Conjugate for HER2-Overexpressing Breast Cancer, Dec. 31, 2009, vol. 1, pp. 25-30.

Office Action issued in U.S. Appl. No. 15/187,179 dated Oct. 21, 2016.

Notice of Allowance issued in Japanese Application No. 2016-166850 dated Oct. 18, 2016.

Office Action issued in Chinese Application No. 201380053256.2 dated Nov. 1, 2016.

Office Action issued in Japanese Application No. 2016-540705 dated Dec. 6, 2016.

Ochi et al., Cancer Chemotherapy and Pharmacology, Apr. 1, 2005, vol. 55, No. 4, pp. 323-332.

Shiose et al., "Bioconjugate Chem", Jan. 21, 2009, vol. 20, No. 1, pp. 60-70.

Soepenberg et al., "Journal of Chromatography B", 2004, vol. 799, pp. 15-22.

Masubuchi N et al., "Pharmazie", 2004, vol. 59, pp. 374-377.

Gomez-Monterrey I et al., "J Med Chem", 2011, vol. 54, No. 12, pp. 4077-4091 with abstract.

Extended European Search Report issued on May 10, 2017 in European Patent Application No. 14874745.4.

Opposition dated May 3, 2017 in Colombian Patent Application No. NC2016/0000187.

Interview Summary dated Mar. 28, 2017 in Canadian Patent Application No. 2,885,800.

Notice of Allowance dated Jul. 4, 2017 in Japanese Patent Application No. 2016-117096.

Office Action dated May 11, 2017 in Taiwanese Patent Application No. 102136742.

Office Action dated Aug. 29, 2017 in Russian Patent Application No. 2015113767 with its English translation.

(56) References Cited

OTHER PUBLICATIONS

Extended European Search Report dated Aug. 9, 2017 in European Patent Application No. 15743738.5.
Extended European Search Report dated Aug. 11, 2017 in European Patent Application No. 15776810.2.
Burke et al., "Design, Synthesis, and Biological Evaluation of Antibody-Drug Conjugates Comprised of Potent Camptothecin Analogues, Bioconjugate Chemistry", vol. 20, No. 6, pp. 1242-1250, Jun. 17, 2009, XP55079987.
McDonagh et al., "Engineered antibody-drug conjugates with defined sites and stoichiometries of drug attachment", Protein Engineering, Design and Selection, vol. 19, No. 7, pp. 299-307, Apr. 27, 2006.

* cited by examiner

FIG.1

Amino acid sequence of B7-H3 variant 1 (SEQ ID NO: 1)

MLRRRGSPGMGVHVGAALGALWFCLTGALEVQVPEDPVVALVGTD
ATLCCSFSPEPGFSLAQLNLIWQLTDTKQLVHSFAEGQDQGSAYA
NRTALFPDLLAQGNASLRLQRVRVADEGSFTCFVSIRDFGSAAVS
LQVAAPYSKPSMTLEPNKDLRPGDTVTITCSSYQGYPEAEVFWQD
GQGVPLTGNVTTSQMANEQGLFDVHSILRVVLGANGTYSCLVRNP
VLQQDAHSSVTITPQRSPTGAVEVQVPEDPVVALVGTDATLRCSF
SPEPGFSLAQLNLIWQLTDTKQLVHSFTEGRDQGSAYANRTALFP
DLLAQGNASLRLQRVRVADEGSFTCFVSIRDFGSAAVSLQVAAPY
SKPSMTLEPNKDLRPGDTVTITCSSYRGYPEAEVFWQDGQGVPLT
GNVTTSQMANEQGLFDVHSVLRVVLGANGTYSCLVRNPVLQQDAH
GSVTITGQPMTFPPEALWVTVGLSVCLIALLVALAFVCWRKIKQS
CEEENAGAEDQDGEGEGSKTALQPLKHSDSKEDDGQEIA

FIG.2

Amino acid sequence of B7-H3 variant 2 (SEQ ID NO: 2)

MLRRRGSPGMGVHVGAALGALWFCLTGALEVQVPEDPVVALVGTD
ATLCCSFSPEPGFSLAQLNLIWQLTDTKQLVHSFAEGQDQGSAYA
NRTALFPDLLAQGNASLRLQRVRVADEGSFTCFVSIRDFGSAAVS
LQVAAPYSKPSMTLEPNKDLRPGDTVTITCSSYRGYPEAEVFWQD
GQGVPLTGNVTTSQMANEQGLFDVHSVLRVVLGANGTYSCLVRNP
VLQQDAHGSVTITGQPMTFPPEALWVTVGLSVCLIALLVALAFVC
WRKIKQSCEEENAGAEDQDGEGEGSKTALQPLKHSDSKEDDGQEI
A

FIG.3

Amino acid sequence of M30-H1-type heavy chain (SEQ ID NO: 9)

MKHLWFFLLLVAAPRWVLSQVQLVQSGAEVKKPGSSVKVSCKASG
YTFTNYVMHWVRQAPGQGLEWMGYINPYNDDVKYNEKFKGRVTIT
ADESTSTAYMELSSLRSEDTAVYYCARWGYYGSPLYYFDYWGQGT
LVTVSSASTKGPSVFPLAPSSKSTSGGTAALGCLVKDYFPEPVTV
SWNSGALTSGVHTFPAVLQSSGLYSLSSVVTVPSSSLGTQTYICN
VNHKPSNTKVDKRVEPKSCDKTHTCPPCPAPELLGGPSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPAPIEKTI
SKAKGQPREPQVYTLPPSREEMTKNQVSLTCLVKGFYPSDIAVEW
ESNGQPENNYKTTPPVLDSDGSFFLYSKLTVDKSRWQQGNVFSCS
VMHEALHNHYTQKSLSLSPGK

FIG.4

Amino acid sequence of M30-H2-type heavy chain (SEQ ID NO: 10)

MKHLWFFLLLVAAPRWVLSQVQLVQSGAEVKKPGSSVKVSCKASG
YTFTNYVMHWVRQAPGQGLEWIGYINPYNDDVKYNEKFKGRVTIT
ADESTSTAYMELSSLRSEDTAVYYCARWGYYGSPLYYFDYWGQGT
LVTVSSASTKGPSVFPLAPSSKSTSGGTAALGCLVKDYFPEPVTV
SWNSGALTSGVHTFPAVLQSSGLYSLSSVVTVPSSSLGTQTYICN
VNHKPSNTKVDKRVEPKSCDKTHTCPPCPAPELLGGPSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPAPIEKTI
SKAKGQPREPQVYTLPPSREEMTKNQVSLTCLVKGFYPSDIAVEW
ESNGQPENNYKTTPPVLDSDGSFFLYSKLTVDKSRWQQGNVFSCS
VMHEALHNHYTQKSLSLSPGK

FIG.5

Amino acid sequence of M30-H3-type heavy chain (SEQ ID NO: 11)

MKHLWFFLLLVAAPRWVLSEVQLVQSGAEVKKPGSSVKVSCKASG
YTFTNYVMHWVKQAPGQGLEWIGYINPYNDDVKYNEKFKGKATIT
ADESTSTAYMELSSLRSEDTAVYYCARWGYYGSPLYYFDYWGQGT
LVTVSSASTKGPSVFPLAPSSKSTSGGTAALGCLVKDYFPEPVTV
SWNSGALTSGVHTFPAVLQSSGLYSLSSVVTVPSSSLGTQTYICN
VNHKPSNTKVDKRVEPKSCDKTHTCPPCPAPELLGGPSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPAPIEKTI
SKAKGQPREPQVYTLPPSREEMTKNQVSLTCLVKGFYPSDIAVEW
ESNGQPENNYKTTPPVLDSDGSFFLYSKLTVDKSRWQQGNVFSCS
VMHEALHNHYTQKSLSLSPGK

FIG.6

Amino acid sequence of M30-H4-type heavy chain (SEQ ID NO: 12)

MKHLWFFLLLVAAPRWVLSEVQLVQSGAEVKKPGSSVKVSCKASG
YTFTNYVMHWVKQAPGQGLEWIGYINPYNDDVKYNEKFKGKATQT
SDKSTSTAYMELSSLRSEDTAVYYCARWGYYGSPLYYFDYWGQGT
LVTVSSASTKGPSVFPLAPSSKSTSGGTAALGCLVKDYFPEPVTV
SWNSGALTSGVHTFPAVLQSSGLYSLSSVVTVPSSSLGTQTYICN
VNHKPSNTKVDKRVEPKSCDKTHTCPPCPAPELLGGPSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPAPIEKTI
SKAKGQPREPQVYTLPPSREEMTKNQVSLTCLVKGFYPSDIAVEW
ESNGQPENNYKTTPPVLDSDGSFFLYSKLTVDKSRWQQGNVFSCS
VMHEALHNHYTQKSLSLSPGK

FIG.7

Amino acid sequence of M30-L1-type light chain (SEQ ID NO: 13)

MVLQTQVFISLLLWISGAYGEIVLTQSPATLSLSPGERATLSCRA
SSRLIYMHWYQQKPGQAPRLLIYATSNLASGIPARFSGSGSGTDF
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

FIG.8

Amino acid sequence of M30-L2-type light chain (SEQ ID NO: 14)

MVLQTQVFISLLLWISGAYGEIVLTQSPATLSLSPGERATLSCRA
SSRLIYMHWYQQKPGQAPRLWIYATSNLASGIPARFSGSGSGTDY
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

FIG.9

Amino acid sequence of M30-L3-type light chain (SEQ ID NO: 15)

MVLQTQVFISLLLWISGAYGQIVLSQSPATLSLSPGERATLTCRA
SSRLIYMHWYQQKPGSAPKLWIYATSNLASGIPARFSGSGSGTSY
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

FIG.10

Amino acid sequence of M30-L4-type light chain (SEQ ID NO: 16)

MVLQTQVFISLLLWISGAYGEIVLTQSPATLSLSPGERATLSCRA
SSRLIYMHWYQQKPGQAPRPLIYATSNLASGIPARFSGSGSGTDF
TLTISSLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

FIG.11

Amino acid sequence of M30-L5-type light chain (SEQ ID NO: 17)

MVLQTQVFISLLLWISGAYGQIVLSQSPATLSLSPGERATLTCRA
SSRLIYMHWYQQKPGSAPKPWIYATSNLASGIPARFSGSGSGTSY
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

FIG. 12

Amino acid sequence of M30-L6-type light chain (SEQ ID NO: 18)

MVLQTQVFISLLLWISGAYGEIVLTQSPATLSLSPGERATLSCRA
SSRLIYMHWYQQKPGQAPRPLIYATSNLASGIPARFSGSGSGTDF
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

FIG. 13

Amino acid sequence of M30-L7-type light chain (SEQ ID NO: 19)

MVLQTQVFISLLLWISGAYGEIVLTQSPATLSLSPGERATLSCRA
SSRLIYMHWYQQKPGQAPRPLIYATSNLASGIPARFSGSGSGTDY
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

FIG.14

Amino acid sequence of M30 antibody heavy chain (SEQ ID NO: 20)

MEWSWIFLFLLSGTAGVHSEVQLQQSGPELVKPGASVKMSCKASG
YTFTNYVMHWVKQKPGQGLEWIGYINPYNDDVKYNEKFKGKATQT
SDKSSSTAYMELSSLTSEDSAVYYCARWGYYGSPLYYFDYWGQGT
TLTVSSAKTTAPSVYPLAPVCGDTTGSSVTLGCLVKGYFPEPVTL
TWNSGSLSSGVHTFPAVLQSDLYTLSSSVTVTSSTWPSQSITCNV
AHPASSTKVDKKIEPRGPTIKPCPPCKCPAPNLLGGPSVFIFPPK
IKDVLMISLSPIVTCVVVDVSEDDPDVQISWFVNNVEVHTAQTQT
HREDYNSTLRVVSALPIQHQDWMSGKEFKCKVNNKDLPAPIERTI
SKPKGSVRAPQVYVLPPPEEEMTKKQVTLTCMVTDFMPEDIYVEW
TNNGKTELNYKNTEPVLDSDGSYFMYSKLRVEKKNWVERNSYSCS
VVHEGLHNHHTTKSFSRTPGK

FIG.15

Amino acid sequence of M30 antibody light chain (SEQ ID NO: 21)

```
MDFLVQIFSFLLISASVIMSRGQIVLSQSPTILSASPGEKVTMTC
RASSRLIYMHWYQQKPGSSPKPWIYATSNLASGVPARFSGSGSGT
SYSLTISRVEAEDAATYYCQQWNSNPPTFGTGTKLELKRADAAPT
VSIFPPSSEQLTSGGASVVCFLNNFYPKDINVKWKIDGSERQNGV
LNSWTDQDSKDSTYSMSSTLTLTKDEYERHNSYTCEATHKTSTSP
IVKSFNRNEC
```

FIG.16

Nucleotide sequence of B7-H3 variant 1 (SEQ ID NO: 26)

```
atgctgcgtcggcggggcagccctggcatgggtgtgcatgtgggt
gcagccctgggagcactgtggttctgcctcacaggagccctggag
gtccaggtccctgaagacccagtggtggcactggtgggcaccgat
gccaccctgtgctgctccttctccctgagcctggcttcagcctg
gcacagctcaacctcatctggcagctgacagataccaaacagctg
gtgcacagcttgctgaggccaggaccagggcagcgcctatgcc
aaccgcacggccctcttccggacctgctggcacagggcaacgca
tccctgaggctgcagcgcgtgcgtgtggcggacgagggcagcttc
acctgcttcgtgagcatccgggattcggcagcgctgccgtcagc
ctgcaggtggccgctccctactcgaagcccagcatgaccctggag
cccaacaaggacctgcggccaggggacacggtgaccatcacgtgc
tccagctaccagggctaccctgaggctgaggtgttctggcaggat
gggcagggtgtgcccctgactggcaacgtgaccacgtcgcagatg
gccaacgagcagggcttgtttgatgtgcacagcatcctgcgggtg
gtgctgggtgcaaatggcacctacagctgcctggtgcgcaacccc
gtgctgcagcaggatgcgcacagctctgtcaccatcacacccag
agaagccccacaggagccgtggaggtccaggtccctgaggacccg
gtggtgcccagtgggcaccgatgccaccctgcgctgctccttc
tccctgagcctggcttcagcctggcacagctcaacctcatctgg
cagctgacagacaccaaacagctggtgcacagtttcaccgaaggc
cgggaccagggcagcgcctatgccaaccgcacggccctcttccgg
gacctgctggcacaaggcaatgcatccctgaggctgcagcgcgtg
cgtgtggcggacgagggcagcttcacctgcttcgtgagcatccgg
gatttcggcagcgctgccgtcagcctgcaggtggccgctccctac
tcgaagcccagcatgaccctggagcccaacaaggacctgcggcca
ggggacacggtgaccatcacgtgctccagctaccggggctaccct
gaggctgaggtgttctggcaggatgggcagggtgtgcccctgact
ggcaacgtgaccacgtcgcagatggccaacgagcagggcttgttt
gatgtgcacagcgtcctgcgggtggtgctgggtgcgaatggcacc
tacagctgcctggtgcgcaaccccgtgctgcagcaggatgcgcac
ggctctgtcaccatcacagggcagcctatgacattccccagag
gccctgtgggtgaccgtggggctgtctgtctgtctcattgcactg
ctggtggccctggctttcgtgtgctggagaaagatcaaacagagc
tgtgaggaggagaatgcaggagctgaggaccaggatggggagga
gaaggctccaagacagccctgcagcctctgaaacactctgacaga
aaagaagatgatggacaagaaatagcctgagcggccgccactgtg
ctggatatctgcagaattccaccacactggactagtggatccgag
ctcggtaccaagcttaagtttaaaccgctgatcagcctgactgt
gccttctagttgccagccatctgttgtttgcccctcccccgtgcc
ttccttgaccctggaaggtgccactcccactgtcctttcctaata
aaatgaggaaattgc
```

ANTIBODY-DRUG CONJUGATE PRODUCED BY BINDING THROUGH LINKER HAVING HYDROPHILIC STRUCTURE

SEQUENCE LISTING

The instant application contains a Sequence Listing which has been submitted electronically in ASCII format and is hereby incorporated by reference in its entirety. Said ASCII copy, created on Oct. 18, 2016, is named 111119-0103_SL.txt and is 71,402 bytes in size.

TECHNICAL FIELD

The present invention relates to an antibody-drug conjugate having an antitumor compound conjugated to an antibody capable of targeting tumor cells via a linker structure moiety having a hydrophilic structure, the conjugate being useful as an antitumor drug.

BACKGROUND ART

An antibody-drug conjugate (ADC) having a drug with cytotoxicity conjugated to an antibody, whose antigen is expressed on a surface of cancer cells and which also binds to an antigen capable of cellular internalization, and therefore can deliver the drug selectively to cancer cells and is thus expected to cause accumulation of the drug within cancer cells and to kill the cancer cells (see, Non Patent Literatures 1 to 3). As an ADC, Mylotarg (Gemtuzumab ozogamicin) in which calicheamicin is conjugated to an anti-CD33 antibody is approved as a therapeutic agent for acute myeloid leukemia. Further, Adcetris (Brentuximab vedotin), in which auristatin E is conjugated to an anti-CD30 antibody, has recently been approved as a therapeutic agent for Hodgkin's lymphoma and anaplastic large cell lymphoma (see, Non Patent Literature 4). The drugs contained in ADCs which have been approved until now target DNA or tubulin.

With regard to an antitumor, low-molecular-weight compounds, camptothecin derivatives, compounds that inhibit topoisomerase I to exhibit an antitumor effect, are known. Among them, an antitumor compound represented by the formula below

[Formula 1]

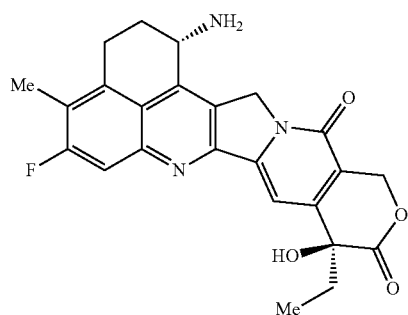

(exatecan, chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione) is a water soluble derivative of camptothecin (Patent Literature 1 and 2). Unlike irinotecan currently used in clinical settings, an activation by an enzyme is unnecessary. Further, the inhibitory activity on topoisomerase I is higher than SN-38 which is a main pharmaceutically active substance of irinotecan and topotecan also used in clinical settings, and higher in vitro cytocidal activity is yielded for against various cancer cells. In particular, it exhibits the effect against cancer cells which have resistance to SN-38 or the like due to expression of P-glycoprotein. Further, in a human tumor subcutaneously transplanted mouse model, it exhibited a potent antitumor effect, and thus has undergone the clinical studies, but has not been put on the market yet (see, Non Patent Literatures 5 to 10). However, it remains unclear whether or not exatecan functions effectively as an ADC.

DE-310 is a complex in which exatecan is conjugated to a biodegradable carboxymethyldextran polyalcohol polymer via a GGFG (SEQ ID NO: 33) peptide spacer (Patent Literature 3). By converting exatecan into a form of a polymer prodrug, so that a high blood retention property can be maintained and also a high targetable property to a tumor area is passively increased by utilizing the increased permeability of newly formed blood vessels within tumor and retention property in tumor tissues. With DE-310, through a cleavage of the peptide spacer by enzyme, exatecan and exatecan with glycine connected to an amino group are continuously released as a main active substance. As a result, the pharmacokinetics are improved and DE-310 was found to have higher effectiveness than exatecan administered alone even though the dosage of exatecan is lower than the case of administration of exatecan alone according to various tumor evaluation models in non-clinical studies. A clinical study was conducted for DE-310, and effective cases were confirmed in humans, in which a report suggesting that the main active substance accumulates in a tumor than in normal tissues was present, however, there is also a report indicating that the accumulation of DE-310 and the main active substance in a tumor is not much different from the accumulation in normal tissues in humans, and thus no passive targeting is observed in humans (see, Non Patent Literatures 11 to 14). As a result, DE-310 was not also commercialized, and it remains unclear whether or not exatecan effectively functions as a drug oriented for such targeting.

As a compound relating to DE-310, a complex in which —NH(CH$_2$)$_4$C(=O)— is inserted between -GGFG (SEQ ID NO: 33)-spacer and exatecan to form -GGFG (SEQ ID NO: 33)-NH(CH$_2$)$_4$C(=O)— spacer structure is also known (Patent Literature 4). However, the antitumor effect of the complex is not known at all.

CITATION LIST

Patent Literature

[Patent Literature 1] Japanese Patent Laid-Open No. 5-59061
[Patent Literature 2] Japanese Patent Laid-Open No. 8-337584
[Patent Literature 3] International Publication No. WO 1997/46260
[Patent Literature 4] International Publication No. WO 2000/25825

Non Patent Literature

[Non Patent Literature 1] Ducry, L., et al. Bioconjugate Chem. (2010) 21, 5-13; Antibody-Drug Conjugates: Linking cytotoxic payloads to monoclonal antibodies.

[Non Patent Literature 2] Alley, S. C., et al. Current Opinion in Chemical Biology (2010) 14, 529-537; Antibody-drug conjugates: targeted drug delivery for cancer.

[Non Patent Literature 3] Damle N. K. Expert Opin. Biol. Ther. (2004) 4, 1445-1452; Tumour-targeted chemotherapy with immunoconjugates of calicheamicin.

[Non Patent Literature 4] Senter P. D., et al. Nature Biotechnology (2012) 30, 631-637; The discovery and development of brentuximab vedotin for use in relapsed Hodgkin lymphoma and systemic anaplastic large cell lymphoma.

[Non Patent Literature 5] Kumazawa, E., Tohgo, A., Exp. Opin. Invest. Drugs (1998) 7, 625-632; Antitumour activity of DX-8951f: a new camptothecin derivative.

[Non Patent Literature 6] Mitsui, I., Kumazawa, E., Hirota, Y., et al. Jpn J. Cancer Res. (1995) 86, 776-782; A new water-soluble camptothecin derivative, DX-8951f, exhibits potent antitumor activity against human tumors in vitro and in vivo.

[Non Patent Literature 7] Takiguchi, S., Tohgo, A., et al. Jpn J. Cancer Res. (1997) 88, 760-769; Antitumor effect of DX-8951, a novel camptothecin analog, on human pancreatic tumor cells and their CPT-11-resistant variants cultured in vitro and xenografted into nude mice.

[Non Patent Literature 8] Joto, N. et al. Int J Cancer (1997) 72, 680-686; DX-8951f, a water-soluble camptothecin analog, exhibits potent antitumor activity against a human lung cancer cell line and its SN-38-resistant variant.

[Non Patent Literature 9] Kumazawa, E. et al. Cancer Chemother. Pharmacol. (1998) 42, 210-220; Potent and broad antitumor effects of DX-8951f, a water-soluble camptothecin derivative, against various human tumors xenografted in nude mice.

[Non Patent Literature 10] De Jager, R., et al. Ann N Y Acad Sci (2000) 922, 260-273; DX-8951f: summary of phase I clinical trials.

[Non Patent Literature 11] Inoue, K. et al. Polymer Drugs in the Clinical Stage, Edited by Maeda et al. (2003), 145-153; CM-dextran-polyalcohol-camptothecin conjugate, DE-310 with a novel carrier system and its preclinical data.

[Non Patent Literature 12] Kumazawa, E. et al. Cancer Sci (2004) 95, 168-175; DE-310, a novel macromolecular carrier system for the camptothecin analog DX-8951f: Potent antitumor activities in various murine tumor models.

[Non Patent Literature 13] Soepenberg, O. et al. Clinical Cancer Research, (2005) 11, 703-711; Phase I and pharmacokinetic study of DE-310 in Patients with Advanced Solid Tumors.

[Non Patent Literature 14] Wente M. N. et al. Investigational New Drugs (2005) 23, 339-347; DE-310, a macromolecular prodrug of the topoisomerase-I-inhibitor exatecan (DX-8951), in patients with operable solid tumors.

SUMMARY OF INVENTION

Technical Problem

With regard to the treatment of tumor by an antibody, an insufficient antitumor effect may be observed even when the antibody recognizes an antigen and binds to tumor cells, and there is a case in which a more effective antitumor antibody is needed. Further, many antitumor low-molecular-weight compounds have a problem in safety like side effect and toxicity even the compounds have an excellent antitumor effect, it remains as a subject to achieve a superior therapeutic effect by further enhancing the safety. Thus, an object of the present invention is to yield to provide an antitumor drug having an excellent therapeutic effect, which is excellent in terms of antitumor effect and safety.

Means to Solve the Problem

The inventors thought that, when an antitumor compound exatecan is converted into an antibody-drug conjugate, via a linker, by conjugation to the antibody, which is capable of targeting tumor cells, that is having a property of recognizing tumor cells, a property of binding to tumor cells, a property of internalizing within tumor cells, a cytocidal activity against tumor cells, or the like, the antitumor compound can be more surely delivered to tumor cells to specifically exhibit the antitumor effect of the compound in tumor cells, and thus the antitumor effect can be surely exhibited and also an enhanced cytocidal effect of the antibody is expected, and a dose of the antitumor compound can be reduced compared to a case of administering the compound alone, and thus an influence of the antitumor compound on normal cells can be alleviated so that higher safety can be achieved.

In this connection, the inventors created a linker with a specific structure.

The present inventors have particularly constructed a linker having:
a linker structure in which a hydrophilic amino acid other than glycin is connected at the N terminal of a peptide moiety of the linker;
a linker structure in which glycine or glycylglycine is connected at the C terminal of a peptide moiety of the linker; or
a linker structure in which a linker element having a hydrophilic structure is inserted between a peptide moiety in the linker and an antibody;
and successfully obtained an antibody-drug conjugate having exatecan conjugated to an antibody via such a linker. The present inventors have further found that this antibody-drug conjugate is excellent in the release of the drug component having an antitumor effect, and as a result, the antibody-drug conjugate of the present invention exerts an excellent antitumor effect, leading to the completion of the present invention.

Specifically, the present invention relates to the followings.

[1] An antibody-drug conjugate wherein an antitumor compound represented by the following formula:

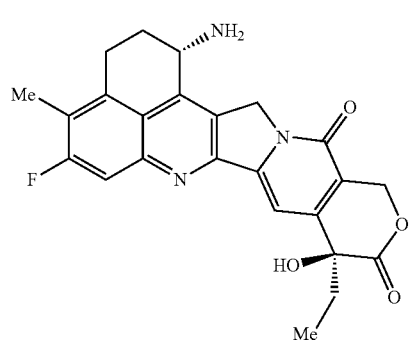

[Formula 2]

is conjugated to an antibody via a linker having a structure represented by the following formula:
-$L^1$-$L^2$-$L^P$-NH—(CH$_2$)n$^1$-$L^a$-$L^b$-$L^c$- or -$L^1$-$L^2$-$L^P$-.

Here, the antibody is connected to the terminal of $L^1$, the antitumor compound is connected to the terminal of $L^c$ or $L^P$,
wherein
n$^1$ represents an integer of 0 to 6,
$L^1$ represents -(Succinimid-3-yl-N)—(CH$_2$)n$^2$-C(=O)—, -(Succinimid-3-yl-N)—CH[—(CH$_2$)n$^3$-COOH]—C(=O)—, —CH$_2$—C(=O)—NH—(CH$_2$)n$^4$-C(=O)—, —C(=O)-cyc.Hex(1,4)-CH$_2$—(N-ly-3-diminiccuS)-, or —C(=O)—(CH$_2$)n$^5$-C(=O)—,
wherein n$^2$ represents an integer of 2 to 8, n$^3$ represents an integer of 1 to 8, n$^4$ represents an integer of 1 to 8, n$^5$ represents an integer of 1 to 8,
$L^2$ represents —NH—(CH$_2$—CH$_2$—O)n$^6$-CH$_2$—CH$_2$—C(=O)—, —N[—(CH$_2$CH$_2$—O)n$^7$-CH$_2$CH$_2$—OH]—CH$_2$—C(=O)—, —S—(CH$_2$)n$^8$-C(=O)—, or a single bond,
wherein n$^6$ represents an integer of 0 to 6, n$^7$ represents an integer of 1 to 4, n$^8$ represents an integer of 1 to 6,
$L^P$ represents a peptide residue consisting of 3 to 8 amino acids,
$L^a$ represents —C(=O)—NH—, —NR$^1$—(CH$_2$)n$^9$-, —O—, or a single bond,
wherein n$^9$ represents an integer of 1 to 6, R$^1$ represents a hydrogen atom, an alkyl group having 1 to 6 carbon atoms, —(CH$_2$)n$^a$-COOH, or —(CH$_2$)n$^b$-OH, n$^a$ represents an integer of 1 to 4, n$^b$ represents an integer of 1 to 6,
$L^b$ represents —CR$^2$(—R$^3$)—, —O—, —NR$^4$—, or a single bond,
wherein R$^2$ and R$^3$ each independently represent a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ represents a hydrogen atom or an alkyl group having 1 to 6 carbon atoms, n$^c$ represents an integer of 0 to 6, n$^d$ represents an integer of 1 to 4, n$^e$ represents an integer of 1 to 4, provided that when n$^c$ is 0, R$^2$ and R$^3$ are not the same as each other,
$L^c$ represents —CH$_2$— or —C(=O)—,
-(Succinimid-3-yl-N)— has a structure represented by the following formula:

[Formula 3]

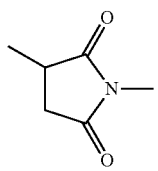

which is connected to the antibody at position 3 thereof and is connected to a methylene group in the linker structure containing this structure on the nitrogen atom at position 1,
—(N-ly-3-diminiccuS)- has a structure represented by the following formula:

[Formula 4]

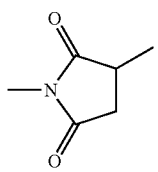

which is connected to $L^2$ at position 3 thereof and is connected to a methylene group in the linker structure containing this structure on the nitrogen atom at position 1, cyc.Hex(1,4) represents a 1,4-cyclohexylene group, and when $L^2$ is —S—(CH$_2$)n$^8$-C(=O)—, $L^1$ is —C(=O)-cyc.Hex(1,4)-CH$_2$—(N-ly-3-diminiccuS)-.
provided that any one or two or more of linkers of $L^1$, $L^2$, and $L^P$ have a structure containing a hydrophilic structure, and
said hydrophilic structure means,
as for linker $L^P$, the case in which,
$L^P$ is a peptide residue having a hydrophilic amino acid other than glycin at the N terminal, or
$L^P$ is a peptide residue in which the C terminal is an oligopeptide consisting of 2 or 3 or more glycines and is connected to the antitumor compound, and even in case that a hydrophilic amino acid is present at N terminal, no other hydrophilic amino acid than glycine is present thereat, or
as for linker $L^1$, the case in which $L^1$ is -(Succinimid-3-yl-N)—CH[—(CH$_2$)n$^3$-COOH]—C(=O)—, or
as for linker $L^2$, the case in which $L^2$ is —N[—(CH$_2$CH$_2$—O)n$^7$-CH$_2$CH$_2$—OH]—CH$_2$—C(=O)—.

The present invention also relates to each of the followings.

[2] The antibody-drug conjugate according to [1], wherein $L^1$ is -(Succinimid-3-yl-N)—(CH$_2$)n$^2$-C(=O)—, -(Succinimid-3-yl-N)—CH[—(CH$_2$)n$^3$-COOH]—C(=O)—, or —CH$_2$—C(=O)—NH—(CH$_2$)n$^4$-C(=O)—,
wherein n$^2$ represents an integer of 2 to 8, n$^3$ represents an integer of 1 to 8, n$^4$ represents an integer of 1 to 8,
$L^2$ is —NH—(CH$_2$—CH$_2$—O)n$^6$-CH$_2$—CH$_2$—C(=O)—, —N[—(CH$_2$CH$_2$—O)n$^7$-CH$_2$CH$_2$—OH]—CH$_2$—C(=O)—, or a single bond,
wherein n$^6$ represents an integer of 0 to 6, n$^7$ represents an integer of 1 to 4,
$L^P$ is a peptide residue consisting of 3 to 8 amino acids,
each of $L^a$ and $L^b$ is a single bond, and
$L^c$ is —C(=O).

[3] The antibody-drug conjugate according to [1] or [2], wherein any one of linkers of $L^1$, $L^2$, and $L^P$ is the linker containing the hydrophilic structure.

[4] The antibody-drug conjugate according to [3], wherein the linker containing the hydrophilic structure is $L^P$.

[5] The antibody-drug conjugate according to [4], wherein $L^P$ is a peptide residue having a hydrophilic amino acid other than glycin at the N terminal.

[6] The antibody-drug conjugate according to [5], wherein the hydrophilic amino acid other than glycin is aspartic acid, glutamic acid, lysine, serine, threonine, glutamine, asparagine, histidine, tyrosine, or arginine.

[7] The antibody-drug conjugate according to [5], wherein the N-terminal hydrophilic amino acid other than glycin in $L^P$ is glutamic acid, aspartic acid, or lysine.

[8] The antibody-drug conjugate according to [6] or [7], wherein a peptide residue following the N-terminal hydrophilic amino acid in $L^P$ is amino acid residue consisting of amino acids selected from phenylalanine, glycine, valine, lysine, citrulline, serine, glutamic acid, and aspartic acid.

[9] The antibody-drug conjugate according to [8], wherein a peptide residue following the N-terminal hydrophilic amino acid in $L^P$ is a peptide residue consisting of 3 or 4 amino acids.

[10] The antibody-drug conjugate according to [9], wherein the peptide residue following the N-terminal hydrophilic amino acid in $L^P$ is GGF or GGFG (SEQ ID NO: 33).

[11] The antibody-drug conjugate according to any one of [5] to [10], wherein $L^P$ is DGGF (SEQ ID NO: 34), KGGF (SEQ ID NO: 35), EGGF (SEQ ID NO: 36), DGGFG (SEQ ID NO: 37), KGGFG (SEQ ID NO: 38), or EGGFG (SEQ ID NO: 39).

[12] The antibody-drug conjugate according to any one of [5] to [10], wherein $L^P$ is DGGFG (SEQ ID NO: 37), KGGFG (SEQ ID NO: 38), or EGGFG (SEQ ID NO: 39).

[13] The antibody-drug conjugate according to any one of [1] to [12], wherein the linker is a linker having a structure represented by -$L^1$-$L^2$-$L^P$-NH—(CH$_2$)n$^1$-$L^a$-$L^b$-$L^c$-.

[14] The antibody-drug conjugate according to [13], wherein $L^c$ is —C(=O)—.

[15] The antibody-drug conjugate according to [14], wherein $L^1$ is -(Succinimid-3-yl-N)—(CH$_2$)n$^2$-C(=O)—, n$^2$ is an integer of 2 to 5, and $L^2$ is a single bond.

[16] The antibody-drug conjugate according to [15], wherein n$^2$ is 5.

[17] The antibody-drug conjugate according to [15] or [16], wherein n$^1$ is 1 to 3.

[18] The antibody-drug conjugate according to any one of [5] to [17], wherein the structure of the —NH—(CH$_2$)n$^1$-$L^a$-$L^b$-$L^c$- moiety in the linker is
—NH—CH$_2$—C(=O)—,
—NH—(CH$_2$)$_2$—C(=O)—,
—NH—(CH$_2$)$_3$—C(=O)—,
—NH—CH$_2$—O—CH$_2$—C(=O)—, or
—NH—(CH$_2$)$_2$—O—CH$_2$—C(=O)—.

[19] The antibody-drug conjugate according to any one of [5] to [17], wherein the structure of the —NH—(CH$_2$)n$^1$-$L^a$-$L^b$-$L^c$- moiety in the linker is
—NH—CH$_2$—C(=O)—,
—NH—(CH$_2$)$_2$—C(=O)—, or
—NH—(CH$_2$)$_3$—C(=O)—.

[20] The antibody-drug conjugate according to any one of [1] to [12], wherein the linker is a linker having a structure represented by -$L^1$-$L^2$-$L^P$-.

[21] The antibody-drug conjugate according to [20], wherein $L^1$ is -(Succinimid-3-yl-N)—(CH$_2$)n$^2$-C(=O)—, n$^2$ is an integer of 2 to 5, and $L^2$ is a single bond.

[22] The antibody-drug conjugate according to [21], wherein n$^2$ is 5.

[23] The antibody-drug conjugate according to [4], wherein $L^P$ is a peptide residue in which the C terminal is an oligopeptide consisting of 2 or 3 or more glycines and is connected to the antitumor compound, and the N terminal is not a hydrophilic amino acid other than glycin, even in case that a hydrophilic amino acid is present at N terminal.

[24] The antibody-drug conjugate according to [23], wherein the peptide residue is a linker consists of 4 to 8 amino acids.

[25] The antibody-drug conjugate according to [23], wherein the C-terminal glycine oligopeptide is an oligopeptide consisting of 2 or 3 glycines.

[26] The antibody-drug conjugate according to any one of [23] to [25], wherein the peptide residue of the linker is GGFGG (SEQ ID NO: 40) or GGFGGG (SEQ ID NO: 41).

[27] The antibody-drug conjugate according to any one of [23] to [26], wherein $L^1$ is -(Succinimid-3-yl-N)—(CH$_2$)n$^2$-C(=O)—, and n$^2$ is an integer of 2 to 5.

[28] The antibody-drug conjugate according to [27], wherein n$^2$ is 5.

[29] The antibody-drug conjugate according to [3], wherein $L^1$ is -(Succinimid-3-yl-N)—CH[—(CH$_2$)n$^3$-COOH]—C(=O)—.

[30] The antibody-drug conjugate according to [29], wherein n$^3$ is 2 or 3.

[31] The antibody-drug conjugate according to [3], wherein $L^2$ is —N[—(CH$_2$CH$_2$—O)n$^7$-CH$_2$CH$_2$—OH]—CH$_2$—C(=O)—.

[32] The antibody-drug conjugate according to [31], wherein n$^7$ is 2 to 4.

[33] The antibody-drug conjugate according to any one of [29] to [32], wherein the linker is a linker having a structure represented by -$L^1$-$L^2$-$L^P$-NH—(CH$_2$)n$^1$-$L^a$-$L^b$-$L^c$-.

[34] The antibody-drug conjugate according to [33], wherein $L^c$ is —C(=O)—.

[35] The antibody-drug conjugate according to any one of [29] to [34], wherein n$^1$ is 1 to 3.

[36] The antibody-drug conjugate according to any one of [29] to [35], wherein $L^P$ is GGFG (SEQ ID NO: 33).

[37] The antibody-drug conjugate according to any one of [29] to [36], wherein the structure of the —NH—(CH$_2$)n$^1$-$L^a$-$L^b$-$L^c$- moiety in the linker is
—NH—CH$_2$—C(=O)—,
—NH—(CH$_2$)$_2$—C(=O)—,
—NH—(CH$_2$)$_3$—C(=O)—,
—NH—CH$_2$—O—CH$_2$—C(=O)—, or
—NH—(CH$_2$)$_2$—O—CH$_2$—C(=O)—.

[38] The antibody-drug conjugate according to any one of [29] to [36], wherein the structure of the —NH—(CH$_2$)n$^1$-$L^a$-$L^b$-$L^c$- moiety in the linker is
—NH—CH$_2$—C(=O)—,
—NH—(CH$_2$)$_2$—C(=O)—, or
—NH—(CH$_2$)$_3$—C(=O)—.

[39] The antibody-drug conjugate according to any one of [1] to [38], wherein the bond between the antibody and $L^1$ is
a thioether bond which is formed at a disulfide bond moiety present in a hinge part of the antibody,
a disulfide bond which is formed at a disulfide bond moiety present in a hinge part of the antibody, or
an amide bond which is formed at an amino group present on a side chain of an amino acid constituting the antibody or at the terminal amino group.

[40] The antibody-drug conjugate according to any one of [1] to [38], wherein the bond between the antibody and $L^1$ is
a thioether bond which is formed at a disulfide bond moiety present in a hinge part of the antibody, or
an amide bond which is formed at an amino group present on a side chain of an amino acid constituting the antibody or at the terminal amino group.

[41] The antibody-drug conjugate according to [1], [2], [39], or [40], wherein the drug-linker structure moiety in the antibody-drug conjugate is one structure selected from the following group:
-(Succinimid-3-yl-N)—CH$_2$CH$_2$CH$_2$CH$_2$CH$_2$—C(=O)-DGGF (SEQ ID NO: 34)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-DGGF (SEQ ID NO: 34)-NH—CH$_2$—O—CH$_2$—C(=)—(NH-DX),
-(Succinimid-3-yl-N)—CH$_2$CH$_2$CH$_2$CH$_2$CH$_2$—C(=O)-DGGF (SEQ ID NO: 34)-NH—CH$_2$CH$_2$—O—CH$_2$—C(=O)—(NH-DX),
-(Succinimid-3-yl-N)—CH$_2$CH$_2$CH$_2$CH$_2$CH$_2$—C(=O)-DGGFG (SEQ ID NO: 37)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-DGGFG (SEQ ID NO: 37)-NH—CH$_2$—O—CH$_2$—C(=O)—(NH-DX), -(Succinimid-3-yl-N)—CH₂CH₂CH₂CH₂CH₂—C(=O)-DGGFG (SEQ ID NO: 37)-NH—CH₂CH₂—O—CH₂—C(=O)—(NH-DX), -(Succinimid-3-yl-N)—CH₂CH₂CH₂CH₂CH₂—C(=O)-KGGF (SEQ ID NO: 35)-NH—CH₂CH₂CH₂—C(=O)—(NH-DX), -(Succinimid-3-yl-N)—CH₂CH₂CH₂CH₂CH₂—C(=O)-KGGF (SEQ ID NO: 35)-NH—CH₂—O—CH₂—C(=O)—(NH-DX), -(Succinimid-3-yl-N)—CH₂CH₂CH₂CH₂CH₂—C(=O)-KGGF (SEQ ID NO: 35)-NH—CH₂CH₂—O—CH₂—C(=O)—(NH-DX), -(Succinimid-3-yl-N)—CH₂CH₂CH₂CH₂CH₂—C(=O)-KGGFG (SEQ ID NO: 38)-NH—CH₂CH₂CH₂—C(=O)—(NH-DX), -(Succinimid-3-yl-N)—CH₂CH₂CH₂CH₂CH₂—C(=O)-KGGFG (SEQ ID NO: 38)-NH—CH₂—O—CH₂—C(=O)—(NH-DX), -(Succinimid-3-yl-N)—CH₂CH₂CH₂CH₂CH₂—C(=O)-KGGFG (SEQ ID NO: 38)-NH—CH₂CH₂—O—CH₂—C(=O)—(NH-DX),

—CH₂—C(=O)—NH—CH₂CH₂—C(=O)-DGGF (SEQ ID NO: 34)-NH—CH₂CH₂CH₂—C(=O)—(NH-DX),

—CH₂—C(=O)—NH—CH₂CH₂—C(=O)-DGGF (SEQ ID NO: 34)-NH—CH₂—O—CH₂—C(=O)—(NH-DX),

—CH₂—C(=O)—NH—CH₂CH₂—C(=O)-DGGF (SEQ ID NO: 34)-NH—CH₂CH₂—O—CH₂—C(=O)—(NH-DX),

—CH₂—C(=O)—NH—CH₂CH₂—C(=O)-DGGFG (SEQ ID NO: 37)-NH—CH₂CH₂CH₂—C(=O)—(NH-DX),

—CH₂—C(=O)—NH—CH₂CH₂—C(=O)-DGGFG (SEQ ID NO: 37)-NH—CH₂—O—CH₂—C(=O)—(NH-DX),

—CH₂—C(=O)—NH—CH₂CH₂—C(=O)-DGGFG (SEQ ID NO: 37)-NH—CH₂CH₂—O—CH₂—C(=O)—(NH-DX),

—CH₂—C(=O)—NH—CH₂CH₂—C(=O)-KGGF (SEQ ID NO: 35)-NH—CH₂CH₂CH₂—C(=O)—(NH-DX),

—CH₂—C(=O)—NH—CH₂CH₂—C(=O)-KGGF (SEQ ID NO: 35)-NH—CH₂—O—CH₂—C(=O)—(NH-DX),

—CH₂—C(=O)—NH—CH₂CH₂—C(=O)-KGGF (SEQ ID NO: 35)-NH—CH₂CH₂—O—CH₂—C(=O)—(NH-DX),

—CH₂—C(=O)—NH—CH₂CH₂—C(=O)-KGGFG (SEQ ID NO: 38)-NH—CH₂CH₂CH₂—C(=O)—(NH-DX),

—CH₂—C(=O)—NH—CH₂CH₂—C(=O)-KGGFG (SEQ ID NO: 38)-NH—CH₂—O—CH₂—C(=O)—(NH-DX),

—CH₂—C(=O)—NH—CH₂CH₂—C(=O)-KGGFG (SEQ ID NO: 38)-NH—CH₂CH₂—O—CH₂—C(=O)—(NH-DX),

—C(=O)-cyc.Hex(1,4)-CH₂—(N-ly-3-diminiccuS)-S—CH₂CH₂—C(=O)-DGGF (SEQ ID NO: 34)-NH—CH₂CH₂CH₂—C(=O)—(NH-DX), —C(=O)-cyc.Hex(1,4)-CH₂—(N-ly-3-diminiccuS)-S—CH₂CH₂—C(=O)-DGGF (SEQ ID NO: 34)-NH—CH₂—O—CH₂—C(=O)—(NH-DX), —C(=O)-cyc.Hex(1,4)-CH₂—(N-ly-3-diminiccuS)-S—CH₂CH₂—C(=O)-DGGF (SEQ ID NO: 34)-NH—CH₂CH₂—O—CH₂—C(=O)—(NH-DX), —C(=O)-cyc.Hex(1,4)-CH₂—(N-ly-3-diminiccuS)-S—CH₂CH₂—C(=O)-DGGFG (SEQ ID NO: 37)-NH—CH₂CH₂CH₂—C(=O)—(NH-DX), —C(=O)-cyc.Hex(1,4)-CH₂—(N-ly-3-diminiccuS)-S—CH₂CH₂—C(=O)-DGGFG (SEQ ID NO: 37)-NH—CH₂—O—CH₂—C(=O)—(NH-DX), —C(=O)-cyc.Hex(1,4)-CH₂—(N-ly-3-diminiccuS)-S—CH₂CH₂—C(=O)-DGGFG (SEQ ID NO: 37)-NH—CH₂CH₂—O—CH₂—C(=O)—(NH-DX), —C(=O)-cyc.Hex(1,4)-CH₂—(N-ly-3-diminiccuS)-S—CH₂CH₂—C(=O)-KGGF (SEQ ID NO: 35)-NH—CH₂CH₂CH₂—C(=O)—(NH-DX), —C(=O)-cyc.Hex(1,4)-CH₂—(N-ly-3-diminiccuS)-S—CH₂CH₂—C(=O)-KGGF (SEQ ID NO: 35)-NH—CH₂—O—CH₂—C(=O)—(NH-DX), —C(=O)-cyc.Hex(1,4)-CH₂—(N-ly-3-diminiccuS)-S—CH₂CH₂—C(=O)-KGGF (SEQ ID NO: 35)-NH—CH₂CH₂—O—CH₂—C(=O)—(NH-DX), —C(=O)-cyc.Hex(1,4)-CH₂—(N-ly-3-diminiccuS)-S—CH₂CH₂—C(=O)-KGGFG (SEQ ID NO: 38)-NH—CH₂CH₂CH₂—C(=O)—(NH-DX), —C(=O)-cyc.Hex(1,4)-CH₂—(N-ly-3-diminiccuS)-S—CH₂CH₂—C(=O)-KGGFG (SEQ ID NO: 38)-NH—CH₂—O—CH₂—C(=O)—(NH-DX), —C(=O)-cyc.Hex(1,4)-CH₂—(N-ly-3-diminiccuS)-S—CH₂CH₂—C(=O)-KGGFG (SEQ ID NO: 38)-NH—CH₂CH₂—O—CH₂—C(=O)—(NH-DX).

[42] The antibody-drug conjugate according to [1], [2], [39], or [40], wherein the drug-linker structure moiety in the antibody-drug conjugate is one structure selected from the following group:

-(Succinimid-3-yl-N)—CH₂CH₂CH₂CH₂CH₂—C(=O)-DGGF (SEQ ID NO: 34)-NH—CH₂CH₂CH₂—C(=O)—(NH-DX), -(Succinimid-3-yl-N)—CH₂CH₂CH₂CH₂CH₂—C(=O)-DGGFG (SEQ ID NO: 37)-NH—CH₂CH₂CH₂—C(=O)—(NH-DX), -(Succinimid-3-yl-N)—CH₂CH₂CH₂CH₂CH₂—C(=O)-KGGF (SEQ ID NO: 35)-NH—CH₂CH₂CH₂—C(=O)—(NH-DX), -(Succinimid-3-yl-N)—CH₂CH₂CH₂CH₂CH₂—C(=O)-KGGFG (SEQ ID NO: 38)-NH—CH₂CH₂CH₂—C(=O)—(NH-DX).

[43] The antibody-drug conjugate according to [1], [2], [39], or [40], wherein the drug-linker structure moiety in the antibody-drug conjugate is one structure selected from the following group:

—CH₂—C(=O)—NH—CH₂CH₂—C(=O)-DGGF (SEQ ID NO: 34)-NH—CH₂CH₂CH₂—C(=O)—(NH-DX),

—CH₂—C(=O)—NH—CH₂CH₂—C(=O)-DGGFG (SEQ ID NO: 37)-NH—CH₂CH₂CH₂—C(=O)—(NH-DX),

—CH₂—C(=O)—NH—CH₂CH₂—C(=O)-KGGF (SEQ ID NO: 35)-NH—CH₂CH₂CH₂—C(=O)—(NH-DX),

—CH₂—C(=O)—NH—CH₂CH₂—C(=O)-KGGFG (SEQ ID NO: 38)-NH—CH₂CH₂CH₂—C(=O)—(NH-DX).

[44] The antibody-drug conjugate according to [1], [2], [39], or [40], wherein the drug-linker structure moiety in the antibody-drug conjugate is one structure selected from the following group:

—C(=O)-cyc.Hex(1,4)-CH₂—(N-ly-3-diminiccuS)-S—CH₂CH₂—C(=O)-DGGF (SEQ ID NO: 34)-NH—CH₂CH₂CH₂—C(=O)—(NH-DX), —C(=O)-cyc.Hex(1,4)-CH₂—(N-ly-3-diminiccuS)-S—CH₂CH₂—C(=O)-DGGFG (SEQ ID NO: 37)-NH—CH₂CH₂CH₂—C(=O)—(NH-DX), —C(=O)-cyc.Hex(1,4)-CH₂—(N-ly-3-diminiccuS)-S—CH₂CH₂—C(=O)-KGGF (SEQ ID NO: 35)-NH—CH₂CH₂CH₂—C(=O)—(NH-DX), —C(=O)-cyc.Hex(1,4)-CH$_2$—(N-ly-3-diminiccuS)-S—CH$_2$CH$_2$—C(=O)-KGGFG (SEQ ID NO: 38)-NH—CH$_2$CH$_2$CH$_2$—C(=O)—(NH-DX).

[45] The antibody-drug conjugate according to [1], [2], [39], or [40], wherein the drug-linker structure moiety in the antibody-drug conjugate is one structure selected from the following group:
-(Succinimid-3-yl-N)—CH$_2$CH$_2$CH$_2$CH$_2$CH$_2$—C(=O)-DGGF (SEQ ID NO: 34)-(NH-DX),
-(Succinimid-3-yl-N)—CH$_2$CH$_2$CH$_2$CH$_2$CH$_2$—C(=O)-KGGF (SEQ ID NO: 35)-(NH-DX),
-(Succinimid-3-yl-N)—CH$_2$CH$_2$CH$_2$CH$_2$CH$_2$—C(=O)-DGGFG (SEQ ID NO: 37)-(NH-DX),
-(Succinimid-3-yl-N)—CH$_2$CH$_2$CH$_2$CH$_2$CH$_2$—C(=O)-KGGFG (SEQ ID NO: 38)-(NH-DX).

[46] The antibody-drug conjugate according to [1], [2], [39], or [40], wherein the drug-linker structure moiety in the antibody-drug conjugate is any of the following structures:
-(Succinimid-3-yl-N)—CH$_2$CH$_2$CH$_2$CH$_2$CH$_2$—C(=O)-DGGFG (SEQ ID NO: 37)-(NH-DX),
-(Succinimid-3-yl-N)—CH$_2$CH$_2$CH$_2$CH$_2$CH$_2$—C(=O)-KGGFG (SEQ ID NO: 38)-(NH-DX).

[47] The antibody-drug conjugate according to [1], [2], [39], or [40], wherein the drug-linker structure moiety in the antibody-drug conjugate is the following structure:
-(Succinimid-3-yl-N)—CH$_2$CH$_2$CH$_2$CH$_2$CH$_2$—C(=O)-DGGFG (SEQ ID NO: 37)-(NH-DX).

[48] The antibody-drug conjugate according to [1], [2], [39], or [40], wherein the drug-linker structure moiety in the antibody-drug conjugate is one structure selected from the following group:
—CH$_2$—C(=O)—NH—CH$_2$CH$_2$—C(=O)-DGGF (SEQ ID NO: 34)-(NH-DX),
—CH$_2$—C(=O)—NH—CH$_2$CH$_2$—C(=O)-KGGF (SEQ ID NO: 35)-(NH-DX),
—CH$_2$—C(=O)—NH—CH$_2$CH$_2$—C(=O)-DGGFG (SEQ ID NO: 37)-(NH-DX),
—CH$_2$—C(=O)—NH—CH$_2$CH$_2$—C(=O)-KGGFG (SEQ ID NO: 38)-(NH-DX).

[49] The antibody-drug conjugate according to [1], [2], [39], or [40], wherein the drug-linker structure moiety in the antibody-drug conjugate is any of the following structures:
—CH$_2$—C(=O)—NH—CH$_2$CH$_2$—C(=O)-DGGFG (SEQ ID NO: 37)-(NH-DX),
—CH$_2$—C(=O)—NH—CH$_2$CH$_2$—C(=O)-KGGFG (SEQ ID NO: 38)-(NH-DX).

[50] The antibody-drug conjugate according to [1], [2], [39], or [40], wherein the drug-linker structure moiety in the antibody-drug conjugate is the following structure:
—CH$_2$—C(=O)—NH—CH$_2$CH$_2$—C(=O)-DGGFG (SEQ ID NO: 37)-(NH-DX)

[51] The antibody-drug conjugate according to [1], [2], [39], or [40], wherein the drug-linker structure moiety in the antibody-drug conjugate is one structure selected from the following group:
—C(=O)-cyc.Hex(1,4)-CH$_2$—(N-ly-3-diminiccuS)-S—CH$_2$CH$_2$—C(=O)-DGGF (SEQ ID NO: 34)-(NH-DX),
—C(=O)-cyc.Hex(1,4)-CH$_2$—(N-ly-3-diminiccuS)-S—CH$_2$CH$_2$—C(=O)-KGGF (SEQ ID NO: 35)-(NH-DX),
—C(=O)-cyc.Hex(1,4)-CH$_2$—(N-ly-3-diminiccuS)-S—CH$_2$CH$_2$—C(=O)-DGGFG (SEQ ID NO: 37)-(NH-DX),
—C(=O)-cyc.Hex(1,4)-CH$_2$—(N-ly-3-diminiccuS)-S—CH$_2$CH$_2$—C(=O)-KGGFG (SEQ ID NO: 38)-(NH-DX).

[52] The antibody-drug conjugate according to [1], [2], [39], or [40], wherein the drug-linker structure moiety in the antibody-drug conjugate is any of the following structures:
—C(=O)-cyc.Hex(1,4)-CH$_2$—(N-ly-3-diminiccuS)-S—CH$_2$CH$_2$—C(=O)-DGGFG (SEQ ID NO: 37)-(NH-DX),
—C(=O)-cyc.Hex(1,4)-CH$_2$—(N-ly-3-diminiccuS)-S—CH$_2$CH$_2$—C(=O)-KGGFG (SEQ ID NO: 38)-(NH-DX).

[53] The antibody-drug conjugate according to [1], [2], [39], or [40], wherein the drug-linker structure moiety in the antibody-drug conjugate is the following structure:
—C(=O)-cyc.Hex(1,4)-CH$_2$—(N-ly-3-diminiccuS)-S—CH$_2$CH$_2$—C(=O)-DGGFG (SEQ ID NO: 37)-(NH-DX).

[54] The antibody-drug conjugate according to [1], [2], [39], or [40], wherein the drug-linker structure moiety in the antibody-drug conjugate is one structure selected from the following group:
—C(=O)—CH$_2$CH$_2$CH$_2$CH$_2$CH$_2$—C(=O)-DGGF (SEQ ID NO: 34)-(NH-DX),
—C(=O)—CH$_2$CH$_2$CH$_2$CH$_2$CH$_2$—C(=O)-KGGF (SEQ ID NO: 35)-(NH-DX),
—C(=O)—CH$_2$CH$_2$CH$_2$CH$_2$CH$_2$—C(=O)-DGGFG (SEQ ID NO: 37)-(NH-DX),
—C(=O)—CH$_2$CH$_2$CH$_2$CH$_2$CH$_2$—C(=O)-KGGFG (SEQ ID NO: 38)-(NH-DX).

[55] The antibody-drug conjugate according to [1], [2], [39], or [40], wherein the drug-linker structure moiety in the antibody-drug conjugate is one structure selected from the following group:
-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$CH$_2$—C(=O)—(NH-DX),
-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$CH$_2$CH$_2$—C(=O)—(NH-DX),
-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$—O—CH$_2$—C(=O)—(NH-DX),
-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$CH$_2$—O—CH$_2$—C(=O)—(NH-DX).

[56] The antibody-drug conjugate according to [1], [2], [39], or [40], wherein the drug-linker structure moiety in the antibody-drug conjugate is any of the following structures:
-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$CH$_2$—C(=O)—(NH-DX),
-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$CH$_2$CH$_2$—C(=O)—(NH-DX).

[57] The antibody-drug conjugate according to [1], [2], [39], or [40], wherein the drug-linker structure moiety in the antibody-drug conjugate is the following structure:
-(Succinimid-3-yl-N)—CH(CH$_2$CH$_2$—COOH)—C(=O)—NH—CH$_2$CH$_2$—C(=O)-GGFG (SEQ ID NO: 33)-(NH-DX).

[58] The antibody-drug conjugate according to [1], [2], [39], or [40], wherein the drug-linker structure moiety in the antibody-drug conjugate is one structure selected from the following group:
-(Succinimid-3-yl-N)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—C(=O)—(NH-DX),
-(Succinimid-3-yl-N)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)—N(—CH$_2$CH$_2$—O—CH$_2$CH$_2$—O—CH$_2$CH$_2$—O—

CH₂CH₂—OH)—CH₂—C(=O)-GGFG (SEQ ID NO: 33)-
NH—CH₂—O—CH₂—C(=O)—(NH-DX),
-(Succinimid-3-yl-N)—CH₂CH₂CH₂CH₂CH₂—C(=O)—
N(—CH₂CH₂—O—CH₂CH₂—O—CH₂CH₂—O—
CH₂CH₂—OH)—CH₂—C(=O)-GGFG (SEQ ID NO: 33)-
NH—CH₂CH₂—O—CH₂—C(=O)—(NH-DX).

[59] The antibody-drug conjugate according to [1], [2], [39], or [40], wherein the drug-linker structure moiety in the antibody-drug conjugate is the following structure:
-(Succinimid-3-yl-N)—CH₂CH₂CH₂CH₂CH₂—C(=O)—
N(—CH₂CH₂—O—CH₂CH₂—O—CH₂CH₂—O—
CH₂CH₂—OH)—CH₂—C(=O)-GGFG (SEQ ID NO: 33)-
(NH-DX).

[60] The antibody-drug conjugate according to [1], [2], [39], or [40], wherein the drug-linker structure moiety in the antibody-drug conjugate is one structure selected from the following group:
—CH₂—C(=O)—NH—CH₂CH₂—C(=O)—N(—
CH₂CH₂OCH₂CH₂CH₂—O—CH₂CH₂—O—CH₂CH₂—
O—CH₂CH₂—OH)—CH₂—C(=O)-GGFG (SEQ ID NO: 33)-NH—CH₂CH₂—C(=O)—(NH-DX),
—CH₂—C(=O)—NH—CH₂CH₂—C(=O)—N(—
CH₂CH₂OCH₂CH₂CH₂—O—CH₂CH₂—O—CH₂CH₂—
O—CH₂CH₂—OH)—CH₂—C(=O)-GGFG (SEQ ID NO: 33)-NH—CH₂CH₂CH₂—C(=O)—(NH-DX),
—CH₂—C(=O)—NH—CH₂CH₂—C(=O)—N(—
CH₂CH₂—O—CH₂CH₂CH₂—O—CH₂CH₂—O—
CH₂CH₂—O—CH₂CH₂—OH)—CH₂—C(=O)-GGFG (SEQ ID NO: 33)-NH—CH₂—O—CH₂—C(=O)—(NH-DX),
—CH₂—C(=O)—NH—CH₂CH₂—C(=O)—N(—
CH₂CH₂—O—CH₂CH₂CH₂—O—CH₂CH₂—O—
CH₂CH₂—O—CH₂CH₂—OH)—CH₂—C(=O)-GGFG (SEQ ID NO: 33)-NH—CH₂CH₂—O—CH₂—C(=O)—(NH-DX).

[61] The antibody-drug conjugate according to [1], [2], [39], or [40], wherein the drug-linker structure moiety in the antibody-drug conjugate is the following structure:
—CH₂—C(=O)—NH—CH₂CH₂—C(=O)—N(—
CH₂CH₂—O—CH₂CH₂—O—CH₂CH₂—O—CH₂CH₂—
OH)—CH₂—C(=O)-GGFG (SEQ ID NO: 33)-(NH-DX),

[62] The antibody-drug conjugate according to [1], [2], [39], or [40], wherein the drug-linker structure moiety in the antibody-drug conjugate is one structure selected from the following group:
—C(=O)—CH₂CH₂CH₂CH₂CH₂—C(=O)—N(—
CH₂CH₂—O—CH₂CH₂—O—CH₂CH₂—O—CH₂CH₂—
OH)—CH₂—C(=O)-GGFG (SEQ ID NO: 33)-NH—
CH₂CH₂—C(=O)—(NH-DX),
—C(=O)—CH₂CH₂CH₂CH₂CH₂—C(=O)—N(—
CH₂CH₂—O—CH₂CH₂—O—CH₂CH₂—O—CH₂CH₂—
OH)—CH₂—C(=O)-GGFG (SEQ ID NO: 33)-NH—
CH₂CH₂CH₂—C(=O)—(NH-DX),
—C(=O)—CH₂CH₂CH₂CH₂CH₂—C(=O)—N(—
CH₂CH₂—O—CH₂CH₂—O—CH₂CH₂—O—CH₂CH₂—
OH)—CH₂—C(=O)-GGFG (SEQ ID NO: 33)-NH—
CH₂—O—CH₂—C(=O)—(NH-DX),
—C(=O)—CH₂CH₂CH₂CH₂CH₂—C(=O)—N(—
CH₂CH₂—O—CH₂CH₂—O—CH₂CH₂—O—CH₂CH₂—
OH)—CH₂—C(=O)—C(=O)-GGFG (SEQ ID NO: 33)-
NH—CH₂CH₂—O—CH₂—C(=O)—(NH-DX).

[63] The antibody-drug conjugate according to [1], [2], [39], or [40], wherein the drug-linker structure moiety in the antibody-drug conjugate is the following structure:
—C(=O)—CH₂CH₂CH₂CH₂CH₂—C(=O)—N(—
CH₂CH₂—O—CH₂CH₂—O—CH₂CH₂—O—CH₂CH₂—
OH)—CH₂—C(=O)-GGFG (SEQ ID NO: 33)-(NH-DX).

[64] The antibody-drug conjugate according to [1], [2], [39], or [40], wherein the drug-linker structure moiety in the antibody-drug conjugate is any of the following structures:
-(Succinimid-3-yl-N)—CH₂CH₂CH₂CH₂CH₂—C(=O)-
GGFGG (SEQ ID NO: 40)-(NH-DX),
-(Succinimid-3-yl-N)—CH₂CH₂CH₂CH₂CH₂—C(=O)-
GGFGGG (SEQ ID NO: 41)-(NH-DX).

[65] The antibody-drug conjugate according to [1], [2], [39], or [40], wherein the drug-linker structure moiety in the antibody-drug conjugate is any of the following structures:
—CH₂—C(=O)—NH—CH₂CH₂—C(=O)-GGFGG (SEQ ID NO: 40)-(NH-DX), —CH₂—C(=O)—NH—
CH₂CH₂—C(=O)-GGFGGG (SEQ ID NO: 41)-(NH-DX).

[66] The antibody-drug conjugate according to [1], [2], [39], or [40], wherein the drug-linker structure moiety in the antibody-drug conjugate is any of the following structures:
—C(=O)-cyc.Hex(1,4)-CH₂—(N-ly-3-diminiccuS)-S—
CH₂CH₂—C(=O)-GGFGG (SEQ ID NO: 40)-(NH-DX),
—C(=O)-cyc.Hex(1,4)-CH₂—(N-ly-3-diminiccuS)-S—
CH₂CH₂—C(=O)-GGFGGG (SEQ ID NO: 41)-(NH-DX).

[67] The antibody-drug conjugate according to [1], [2], [39], or [40], wherein the drug-linker structure moiety in the antibody-drug conjugate is any of the following structures:
—C(=O)—CH₂CH₂CH₂CH₂CH₂—C(=O)-GGFGG (SEQ ID NO: 40)-(NH-DX),
—C(=O)—CH₂CH₂CH₂CH₂CH₂—C(=O)-GGF-GGG (SEQ ID NO: 41)-(NH-DX).

Here, according to any one of [41] to [67], -(Succinimid-3-yl-N)— has a structure represented by the following formula:

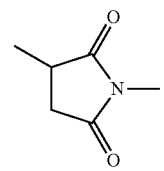

[Formula 5]

which is connected to the antibody at position 3 thereof and is connected to a methylene group in the linker structure containing this structure on the nitrogen atom at position 1, cyc.Hex(1,4) represents a 1,4-cyclohexylene group, —(N-ly-3-diminiccuS)- has a structure represented by the following formula:

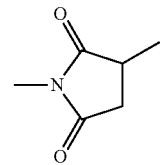

[Formula 6]

which is connected to L² at position 3 thereof and is connected to a methylene group in the linker structure containing this structure on the nitrogen atom at position 1, and —(NH-DX) is a group represented by the following formula:

[Formula 7]

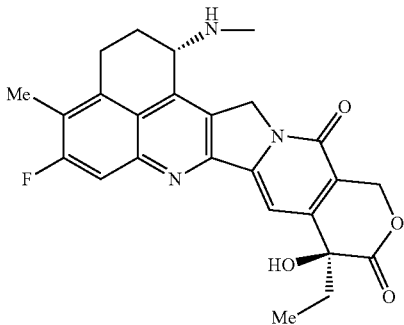

wherein the nitrogen atom of the amino group at position 1 is the connecting position.
[68] The antibody-drug conjugate according to any one of [1] to [67], wherein an average number of conjugated antitumor compounds per antibody is in a range of from 1 to 10.
[69] The antibody-drug conjugate according to any one of [1] to [67], wherein an average number of conjugated antitumor compounds per antibody is in a range of from 1 to 8.
[70] The antibody-drug conjugate according to any one of [1] to [67], wherein an average number of conjugated antitumor compounds per antibody is in a range of from 3 to 8.
[71] The antibody-drug conjugate according to any one of [1] to [70], wherein the antibody is an antibody having one or more of a property of recognizing a target cell, a property of binding to a target cell, a property of internalizing in a target cell, and a property of damaging a target cell.
[72] The antibody-drug conjugate according to [71], wherein the target cell is a tumor cell.
[73] The antibody-drug conjugate according to any one of [1] to [72], wherein the antibody is an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-Cripto antibody, an anti-EphA2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, or an anti-mesothelin antibody.
[74] The antibody-drug conjugate according to any one of [1] to [72], wherein the antibody is an anti-B7-H3 antibody, an anti-CD30 antibody, an anti-CD33 antibody, or an anti-CD70 antibody.
[75] The antibody-drug conjugate according to any one of [1] to [72], wherein the antibody is an anti-B7-H3 antibody.
[76] A drug containing the antibody-drug conjugate according to any one of [1] to [75], a salt thereof or a hydrate thereof.
[77] An antitumor drug and/or anticancer drug containing the antibody-drug conjugate according to any one of [1] to [75], a salt thereof or a hydrate thereof.
[78] The antitumor drug and/or anticancer drug according to [77], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.
[79] A pharmaceutical composition containing the antibody-drug conjugate according to any one of [1] to [75], a salt thereof or a hydrate thereof as an active component, and a pharmaceutically acceptable formulation component.
[80] The pharmaceutical composition according to [79], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.
[81] A method for treating tumor and/or cancer comprising administering the antibody-drug conjugate according to any one of [1] to [75], a salt thereof or a hydrate thereof.
[82] The pharmaceutical composition according to [81], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.
[83] An antibody-drug conjugate wherein an antitumor compound represented by the following formula:

[Formula 8]

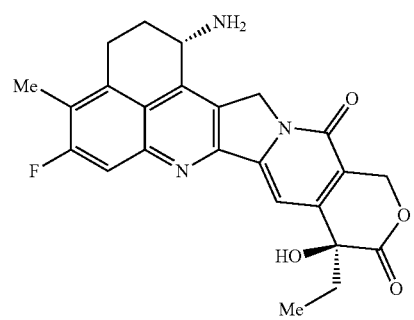

is conjugated to an antibody via a linker having a structure represented by the following formula:
-$L^1$-$L^2$-$L^P$-NH—$(CH_2)n^1$-$L^a$-$L^b$-$L^c$- or -$L^1$-$L^2$-$L^P$-.

Here, the antibody is connected to the terminal of $L^1$, the antitumor compound is connected to the terminal of $L^c$ or $L^P$,
wherein
$n^1$ represents an integer of 0 to 6,
$L^1$ represents -(Succinimid-3-yl-N)—$(CH_2)n^2$-C(=O)—, -(Succinimid-3-yl-N)—CH[—$(CH_2)n^3$-COOH]—C(=O)—, or —$CH_2$—C(=O)—NH—$(CH_2)n^4$-C(=O)—,
wherein $n^2$ represents an integer of 2 to 8, $n^3$ represents an integer of 1 to 8, $n^4$ represents an integer of 1 to 8,
$L^2$ represents —NH—$(CH_2$—$CH_2$—O)$n^6$-$CH_2$—$CH_2$—C(=O)—, —N[—$(CH_2CH_2$—O)$n^7$-$CH_2CH_2$—OH]—$CH_2$—C(=O)—, or a single bond,
wherein $n^6$ represents an integer of 0 to 6, $n^7$ represents an integer of 1 to 4,
$L^P$ represents a peptide residue consisting of 3 to 8 amino acids,
$L^a$ represents —O— or a single bond,
$L^b$ represents $CR^2(-R^3)$— or a single bond,
wherein $R^2$ and $R^3$ each independently represent a hydrogen atom,
$L^c$ represents —C(=O)—,
-(Succinimid-3-yl-N)— has a structure represented by the following formula:

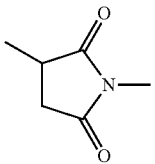

which is connected to the antibody at position 3 thereof and is connected to a methylene group in the linker structure containing this structure on the nitrogen atom at position 1, provided that any one or two or more of linkers of $L^1$, $L^2$, and $L^P$ have a structure containing a hydrophilic structure, said hydrophilic structure means,
as for linker $L^P$, the case in which,
$L^P$ is a peptide residue having a hydrophilic amino acid other than glycine at the N terminal, or
$L^P$ is a peptide residue in which the C terminal is an oligopeptide consisting of 2 or 3 or more glycines and is connected to the antitumor compound, and even in case that a hydrophilic amino acid is present at N terminal, no other hydrophilic amino acid than glycine is present thereat, or
as for linker $L^1$, in case that $L^1$ is -(Succinimid-3-yl-N)—CH[—(CH$_2$)n$^3$-COOH]—C(=O)—, or as for linker $L^2$, in case that $L^2$ is —N[—(CH$_2$CH$_2$—O)n$^7$-CH$_2$CH$_2$—OH]—CH$_2$—C(=O)—.

[84] An antibody-drug conjugate wherein an antitumor compound represented by the following formula:

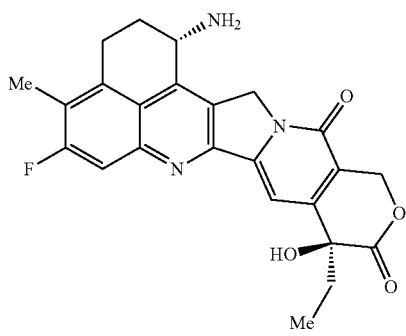

is conjugated to an antibody via a linker having a structure represented by the following formula:
-$L^1$-$L^2$-$L^P$-NH—(CH$_2$)n$^1$-$L^a$-$L^b$-$L^c$- or -$L^1$-$L^2$-$L^P$-.

Here, the antibody is connected to the terminal of $L^1$, the antitumor compound is connected to the terminal of $L^c$ or $L^P$ with the nitrogen atom of the amino group at position 1 as the connecting position,
wherein
$n^1$ represents an integer of 0 to 6,
$L^1$ represents -(Succinimid-3-yl-N)—(CH$_2$)n$^2$-C(=O)— or -(Succinimid-3-yl-N)—CH[—(CH$_2$)n$^3$-COOH]—C(=O)— and is connected to the antibody via a thioether bond at a disulfide bond moiety in a hinge part of the antibody,
wherein $n^2$ represents an integer of 2 to 8, $n^3$ represents an integer of 1 to 8,
$L^2$ represents —N[—(CH$_2$CH$_2$—O)n$^7$-CH$_2$CH$_2$—OH]—CH$_2$—C(=O)— or a single bond,
wherein $n^7$ represents an integer of 1 to 4,
$L^P$ represents a peptide residue consisting of 3 to 8 amino acids, $L^a$ represents a single bond,
$L^b$ represents a single bond,
$L^c$ represents —C(=O)—,
-(Succinimid-3-yl-N)— has a structure represented by the following formula:

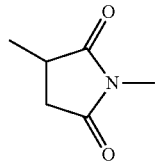

which is connected to the antibody at position 3 thereof and is connected to a methylene group in the linker structure containing this structure on the nitrogen atom at position 1, provided that any one or two or more of linkers of $L^1$, $L^2$, and $L^P$ have a structure containing a hydrophilic structure, and
said hydrophilic structure means,
as for linker $L^P$, the case in which,
$L^P$ is a peptide residue having a hydrophilic amino acid other than glycine at the N terminal, or
$L^P$ is a peptide residue in which the C terminal is an oligopeptide consisting of 2 or 3 or more glycines and is connected to the antitumor compound, and even in case that a hydrophilic amino acid is present at N terminal, no other hydrophilic amino acid than glycine is present thereat, or
as for linker $L^1$, the case in which $L^1$ is -(Succinimid-3-yl-N)—CH[—(CH$_2$)n$^3$-COOH]—C(=O)—, or
as for linker $L^2$, the case in which $L^2$ is —N[—(CH$_2$CH$_2$—O)n$^7$-CH$_2$CH$_2$—OH]—CH$_2$—C(=O)—.

[85] A drug-linker intermediate compound represented by the following formula:
Q-$L^{1a}$-(CH$_2$)n$^Q$-C(=O)-$L^{2a}$-$L^P$-NH—(CH$_2$)n$^1$-$L^a$-$L^b$-$L^c$-(NH-DX), or
Q-$L^{1a}$-(CH$_2$)n$^Q$-C(=O)-$L^{2a}$-$L^P$-(NH-DX).

In the formula, Q represents (maleimid-N-yl)-, HS—, X—CH$_2$—C(=O)—NH—, or (Pyrrolidine-2,5-dione-N-yl)-O—C(=O)—, X represents a bromine atom or an iodine atom,
$L^{1a}$ represents —CH[—(CH$_2$)n$^3$-COOH]— or a single bond,
$n^Q$ represents an integer of 0 to 8,
$L^{2a}$ represents —NH—(CH$_2$—CH$_2$—O)n$^6$-CH$_2$—CH$_2$—C(=O)—, —N[—(CH$_2$CH$_2$—O)n$^7$-CH$_2$CH$_2$—OH]—CH$_2$—C(=O)—, or a single bond,
wherein $n^6$ represents an integer of 0 to 6, $n^7$ represents an integer of 1 to 4,
$L^P$ represents a peptide residue consisting of 3 to 8 amino acids,
$n^1$ represents an integer of 0 to 6,
$L^a$ represents —C(=O)—NH—, —NR$^1$—(CH$_2$)n$^9$-, —O—, or a single bond,
wherein $n^9$ represents an integer of 1 to 6, $R^1$ represents a hydrogen atom, an alkyl group having 1 to 6 carbon atoms, —(CH$_2$)n$^a$-COOH, or —(CH$_2$)n$^b$-OH, $n^a$ represents an integer of 1 to 4, $n^b$ represents an integer of 1 to 6, $L^b$ represents —CR$^2$(—R$^3$)—, —O—, —NR$^4$—, or a single bond,
wherein R$^2$ and R$^3$ each independently represent a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ represents a hydrogen atom or an alkyl group having 1 to 6 carbon atoms, $n^c$ represents an integer of 0 to 6, $n^d$ represents an integer of 1 to 4, $n^e$ represents an integer of 1 to 4, provided that when $n^e$ is 0, $R^2$ and $R^3$ are not the same as each other, $L^c$ represents —CH$_2$— or —C(=O)—, In the above, (maleimid-N-yl)- is a group represented by the following formula:

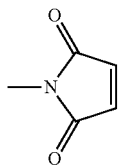

[Formula 12]

wherein the nitrogen atom is the connecting position, (Pyrrolidine-2,5-dione-N-yl) is a group represented by the following formula:

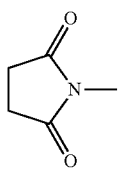

[Formula 13]

wherein the nitrogen atom is the connecting position, and —(NH-DX) is a group represented by the following formula:

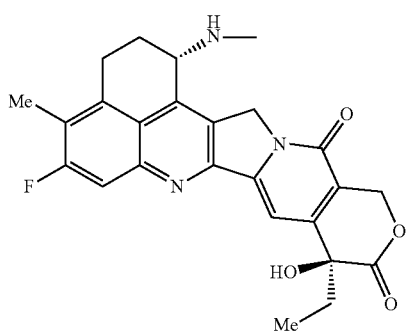

[Formula 14]

wherein the nitrogen atom of the amino group at position 1 is the connecting position, provided that any one or two or more of linkers of $L^{1a}$-(CH$_2$)n$^Q$-C(=O)—, $L^{2a}$ and $L^P$ have a structure containing hydrophilic structure, and said hydrophilic structure means, as for linker $L^P$, the case in which, $L^P$ is a peptide residue having a hydrophilic amino acid other than glycin at the N terminal, or $L^P$ is a peptide residue in which the C terminal is an oligopeptide consisting of 2 or 3 or more glycines and is connected to the antitumor compound, and even in case that a hydrophilic amino acid is present at N terminal, no other hydrophilic amino acid than glycine is present thereat, or as for linker $L^{1a}$-(CH$_2$)n$^Q$-C(=O)—, the case in which $L^{1a}$-(CH$_2$)n$^Q$-C(=O)— is —CH[—(CH$_2$)n$^3$-COOH]—C(=O)—, or as for linker $L^{2a}$, the case in which $L^{2a}$ is —N[—(CH$_2$CH$_2$—O)n$^7$-CH$_2$CH$_2$—OH]—CH$_2$—C(=O)—.

[86] A drug-linker intermediate compound represented by the following formula:

Q-$L^{1a}$-(CH$_2$)n$^Q$-C(=O)-$L^{2a}$-$L^P$-NH—(CH$_2$)n$^1$-$L^a$-$L^b$-$L^c$-(NH-DX), or

Q-$L^{1a}$-(CH$_2$)n$^Q$-C(=O)-$L^{2a}$-$L^P$-(NH-DX), wherein Q represents (maleimid-N-yl)-, HS—, X—CH$_2$—C(=O)—NH—, or (Pyrrolidine-2,5-dione-N-yl)-O—C(=O)—, X represents a bromine atom or an iodine atom, $L^{1a}$ represents —CH[—(CH$_2$)n$^3$-COOH]— or a single bond, n$^Q$ represents an integer of 0 to 8, $L^{2a}$ represents —NH—(CH$_2$—CH$_2$—O)n$^6$-CH$_2$—CH$_2$—C(=O)—, —N[—(CH$_2$CH$_2$—O)n$^7$-CH$_2$CH$_2$—OH]—CH$_2$—C(=O)—, or a single bond, wherein n$^6$ represents an integer of 0 to 6, n$^7$ represents an integer of 1 to 4, $L^P$ represents a peptide residue consisting of 3 to 8 amino acids, n$^1$ represents an integer of 0 to 6, $L^a$ and $L^b$ each independently represent a single bond, $L^c$ represents —C(=O)—, (maleimid-N-yl)- is a group represented by the following formula:

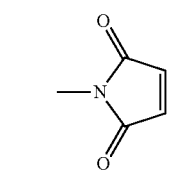

[Formula 15]

wherein the nitrogen atom is the connecting position, (Pyrrolidine-2,5-dione-N-yl) is a group represented by the following formula:

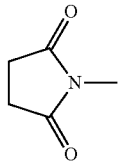

[Formula 16]

wherein the nitrogen atom is the connecting position, and —(NH-DX) is a group represented by the following formula:

[Formula 17]

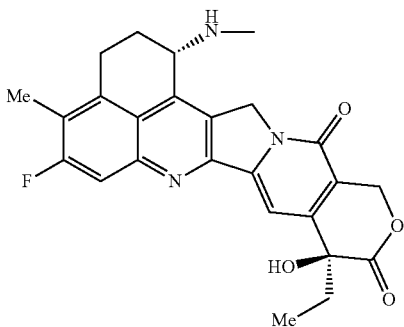

wherein the nitrogen atom of the amino group at position 1 is the connecting position.

[87] The compound according to [86], which is selected from the following group:
(maleimid-N-yl)-CH₂CH₂CH₂CH₂CH₂—C(=O)-DGGF (SEQ ID NO: 34)-NH—CH₂CH₂—C(=O)—(NH-DX),
(maleimid-N-yl)-CH₂CH₂CH₂CH₂CH₂—C(=O)-DGGF (SEQ ID NO: 34)-NH—CH₂CH₂CH₂—C(=O)—(NH-DX),
(maleimid-N-yl)-CH₂CH₂CH₂CH₂CH₂—C(=O)-DGGF (SEQ ID NO: 34)-NH—CH₂—O—CH₂—C(=O)—(NH-DX),
(maleimid-N-yl)-CH₂CH₂CH₂CH₂CH₂—C(=O)-DGGF (SEQ ID NO: 34)-NH—CH₂CH₂—O—CH₂—C(=O)—(NH-DX),
(maleimid-N-yl)-CH₂CH₂CH₂CH₂CH₂—C(=O)-KGGF (SEQ ID NO: 35)-NH—CH₂CH₂—C(=O)—(NH-DX),
(maleimid-N-yl)-CH₂CH₂CH₂CH₂CH₂—C(=O)-KGGF (SEQ ID NO: 35)-NH—CH₂CH₂CH₂—C(=O)—(NH-DX),
(maleimid-N-yl)-CH₂CH₂CH₂CH₂CH₂—C(=O)-KGGF (SEQ ID NO: 35)-NH—CH₂—O—CH₂—C(=O)—(NH-DX),
(maleimid-N-yl)-CH₂CH₂CH₂CH₂CH₂—C(=O)-KGGF (SEQ ID NO: 35)-NH—CH₂CH₂—O—CH₂—C(=O)—(NH-DX),
(maleimid-N-yl)-CH₂CH₂CH₂CH₂CH₂—C(=O)-DGGFG (SEQ ID NO: 37)-NH—CH₂CH₂—C(=O)—(NH-DX),
(maleimid-N-yl)-CH₂CH₂CH₂CH₂CH₂—C(=O)-DGGFG (SEQ ID NO: 37)-NH—CH₂CH₂CH₂—C(=O)—(NH-DX),
(maleimid-N-yl)-CH₂CH₂CH₂CH₂CH₂—C(=O)-DGGFG (SEQ ID NO: 37)-NH—CH₂—O—CH₂—C(=O)—(NH-DX),
(maleimid-N-yl)-CH₂CH₂CH₂CH₂CH₂—C(=O)-DGGFG (SEQ ID NO: 37)-NH—CH₂CH₂—O—CH₂—C(=O)—(NH-DX),
(maleimid-N-yl)-CH₂CH₂CH₂CH₂CH₂—C(=O)-KGGFG (SEQ ID NO: 38)-NH—CH₂CH₂—C(=O)—(NH-DX),
(maleimid-N-yl)-CH₂CH₂CH₂CH₂CH₂—C(=O)-KGGFG (SEQ ID NO: 38)-NH—CH₂CH₂CH₂—C(=O)—(NH-DX),
(maleimid-N-yl)-CH₂CH₂CH₂CH₂CH₂—C(=O)-KGGFG (SEQ ID NO: 38)-NH—CH₂—O—CH₂—C(=O)—(NH-DX),
(maleimid-N-yl)-CH₂CH₂CH₂CH₂CH₂—C(=O)-KGGFG (SEQ ID NO: 38)-NH—CH₂CH₂—O—CH₂—C(=O)—(NH-DX).

[88] The compound according to [86], which is selected from the following group:
(maleimid-N-yl)-CH₂CH₂CH₂CH₂CH₂—C(=O)-DGGF (SEQ ID NO: 34)-NH—CH₂CH₂—C(=O)—(NH-DX),
(maleimid-N-yl)-CH₂CH₂CH₂CH₂CH₂—C(=O)-DGGF (SEQ ID NO: 34)-NH—CH₂CH₂CH₂—C(=O)—(NH-DX),
(maleimid-N-yl)-CH₂CH₂CH₂CH₂CH₂—C(=O)-KGGF (SEQ ID NO: 35)-NH—CH₂CH₂—C(=O)—(NH-DX),
(maleimid-N-yl)-CH₂CH₂CH₂CH₂CH₂—C(=O)-KGGF (SEQ ID NO: 35)-NH—CH₂CH₂CH₂—C(=O)—(NH-DX),
(maleimid-N-yl)-CH₂CH₂CH₂CH₂CH₂—C(=O)-DGGFG (SEQ ID NO: 37)-NH—CH₂CH₂—C(=O)—(NH-DX),
(maleimid-N-yl)-CH₂CH₂CH₂CH₂CH₂—C(=O)-DGGFG (SEQ ID NO: 37)-NH—CH₂CH₂CH₂—C(=O)—(NH-DX),
(maleimid-N-yl)-CH₂CH₂CH₂CH₂CH₂—C(=O)-KGGFG (SEQ ID NO: 38)-NH—CH₂CH₂—C(=O)—(NH-DX),
(maleimid-N-yl)-CH₂CH₂CH₂CH₂CH₂—C(=O)-KGGFG (SEQ ID NO: 38)-NH—CH₂CH₂CH₂—C(=O)—(NH-DX).

[89] The compound according to [86], which is selected from the following group:
X—CH₂—C(=O)—NH—CH₂CH₂—C(=O)-DGGF (SEQ ID NO: 34)-NH—CH₂CH₂—C(=O)—(NH-DX),
X—CH₂—C(=O)—NH—CH₂CH₂—C(=O)-DGGF (SEQ ID NO: 34)-NH—CH₂CH₂CH₂—C(=O)—(NH-DX),
X—CH₂—C(=O)—NH—CH₂CH₂—C(=O)-DGGF (SEQ ID NO: 34)-NH—CH₂—O—CH₂—C(=O)—(NH-DX),
X—CH₂—C(=O)—NH—CH₂CH₂—C(=O)-DGGF (SEQ ID NO: 34)-NH—CH₂CH₂—O—CH₂—C(=O)—(NH-DX),
X—CH₂—C(=O)—NH—CH₂CH₂—C(=O)-KGGF (SEQ ID NO: 35)-NH—CH₂CH₂—C(=O)—(NH-DX),
X—CH₂—C(=O)—NH—CH₂CH₂—C(=O)-KGGF (SEQ ID NO: 35)-NH—CH₂CH₂CH₂—C(=O)—(NH-DX),
X—CH₂—C(=O)—NH—CH₂CH₂—C(=O)-KGGF (SEQ ID NO: 35)-NH—CH₂—O—CH₂—C(=O)—(NH-DX),
X—CH₂—C(=O)—NH—CH₂CH₂—C(=O)-KGGF (SEQ ID NO: 35)-NH—CH₂CH₂—O—CH₂—C(=O)—(NH-DX),
X—CH₂—C(=O)—NH—CH₂CH₂—C(=O)-DGGFG (SEQ ID NO: 37)-NH—CH₂CH₂—C(=O)—(NH-DX),
X—CH₂—C(=O)—NH—CH₂CH₂—C(=O)-DGGFG (SEQ ID NO: 37)-NH—CH₂CH₂CH₂—C(=O)—(NH-DX),
X—CH₂—C(=O)—NH—CH₂CH₂—C(=O)-DGGFG (SEQ ID NO: 37)-NH—CH₂—O—CH₂—C(=O)—(NH-DX),
X—CH₂—C(=O)—NH—CH₂CH₂—C(=O)-DGGFG (SEQ ID NO: 37)-NH—CH₂CH₂—O—CH₂—C(=O)—(NH-DX),
X—CH₂—C(=O)—NH—CH₂CH₂—C(=O)-KGGFG (SEQ ID NO: 38)-NH—CH₂CH₂—C(=O)—(NH-DX),
X—CH₂—C(=O)—NH—CH₂CH₂—C(=O)-KGGFG (SEQ ID NO: 38)-NH—CH₂CH₂CH₂—C(=O)—(NH-DX),
X—CH₂—C(=O)—NH—CH₂CH₂—C(=O)-KGGFG (SEQ ID NO: 38)-NH—CH₂—O—CH₂—C(=O)—(NH-DX),
X—CH₂—C(=O)—NH—CH₂CH₂—C(=O)-KGGFG (SEQ ID NO: 38)-NH—CH₂CH₂—O—CH₂—C(=O)—(NH-DX).

[90] The compound according to [86], which is selected from the following group:
X—CH$_2$—C(=O)—NH—CH$_2$CH$_2$—C(=O)-DGGF (SEQ ID NO: 34)-NH—CH$_2$CH$_2$—C(=O)—(NH-DX),
X—CH$_2$—C(=O)—NH—CH$_2$CH$_2$—C(=O)-DGGF (SEQ ID NO: 34)-NH—CH$_2$CH$_2$CH$_2$—C(=O)—(NH-DX),
X—CH$_2$—C(=O)—NH—CH$_2$CH$_2$—C(=O)-KGGF (SEQ ID NO: 35)-NH—CH$_2$CH$_2$—C(=O)—(NH-DX),
X—CH$_2$—C(=O)—NH—CH$_2$CH$_2$—C(=O)-KGGF (SEQ ID NO: 35)-NH—CH$_2$CH$_2$CH$_2$—C(=O)—(NH-DX),
X—CH$_2$—C(=O)—NH—CH$_2$CH$_2$—C(=O)-DGGFG (SEQ ID NO: 37)-NH—CH$_2$CH$_2$—C(=O)—(NH-DX),
X—CH$_2$—C(=O)—NH—CH$_2$CH$_2$—C(=O)-DGGFG (SEQ ID NO: 37)-NH—CH$_2$CH$_2$CH$_2$—C(=O)—(NH-DX),
X—CH$_2$—C(=O)—NH—CH$_2$CH$_2$—C(=O)-KGGFG (SEQ ID NO: 38)-NH—CH$_2$CH$_2$—C(=O)—(NH-DX),
X—CH$_2$—C(=O)—NH—CH$_2$CH$_2$—C(=O)-KGGFG (SEQ ID NO: 38)-NH—CH$_2$CH$_2$CH$_2$—C(=O)—(NH-DX).

[91] The compound according to [86], which is selected from the following group:
(Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-NH—CH$_2$CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-NH—CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-NH—CH$_2$CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$—O—CH$_2$—C(=O)—(NH-DX).

[92] The compound according to [86], which is selected from the following group:
(Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-NH—CH$_2$CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$CH$_2$—C(=O)—(NH-DX).

[93] The compound according to [86], which is selected from the following group:
HS—CH$_2$CH$_2$—C(=O)-DGGF (SEQ ID NO: 34)-NH—CH$_2$CH$_2$—C(=O)—(NH-DX),
HS—CH$_2$CH$_2$—C(=O)-DGGF (SEQ ID NO: 34)-NH—CH$_2$CH$_2$CH$_2$—C(=O)—(NH-DX),
HS—CH$_2$CH$_2$—C(=O)-DGGF (SEQ ID NO: 34)-NH—CH$_2$—O—CH$_2$—C(=O)—(NH-DX),
HS—CH$_2$CH$_2$—C(=O)-DGGF (SEQ ID NO: 34)-NH—CH$_2$CH$_2$—O—CH$_2$—C(=O)—(NH-DX),
HS—CH$_2$CH$_2$—C(=O)-KGGF (SEQ ID NO: 35)-NH—CH$_2$CH$_2$—C(=O)—(NH-DX),
HS—CH$_2$CH$_2$—C(=O)-KGGF (SEQ ID NO: 35)-NH—CH$_2$CH$_2$CH$_2$—C(=O)—(NH-DX),
HS—CH$_2$CH$_2$—C(=O)-KGGF (SEQ ID NO: 35)-NH—CH$_2$—O—CH$_2$—C(=O)—(NH-DX),
HS—CH$_2$CH$_2$—C(=O)-KGGF (SEQ ID NO: 35)-NH—CH$_2$CH$_2$—O—CH$_2$—C(=O)—(NH-DX),
HS—CH$_2$CH$_2$—C(=O)-DGGFG (SEQ ID NO: 37)-NH—CH$_2$CH$_2$—C(=O)—(NH-DX),
HS—CH$_2$CH$_2$—C(=O)-DGGFG (SEQ ID NO: 37)-NH—CH$_2$CH$_2$CH$_2$—C(=O)—(NH-DX),
HS—CH$_2$CH$_2$—C(=O)-DGGFG (SEQ ID NO: 37)-NH—CH$_2$—O—CH$_2$—C(=O)—(NH-DX),
HS—CH$_2$CH$_2$—C(=O)-DGGFG (SEQ ID NO: 37)-NH—CH$_2$CH$_2$—O—CH$_2$—C(=O)—(NH-DX),
HS—CH$_2$CH$_2$—C(=O)-KGGFG (SEQ ID NO: 38)-NH—CH$_2$CH$_2$—C(=O)—(NH-DX),
HS—CH$_2$CH$_2$—C(=O)-KGGFG (SEQ ID NO: 38)-NH—CH$_2$CH$_2$CH$_2$—C(=O)—(NH-DX),
HS—CH$_2$CH$_2$—C(=O)-KGGFG (SEQ ID NO: 38)-NH—CH$_2$—O—CH$_2$—C(=O)—(NH-DX),
HS—CH$_2$CH$_2$—C(=O)-KGGFG (SEQ ID NO: 38)-NH—CH$_2$CH$_2$—O—CH$_2$—C(=O)—(NH-DX).

[94] The compound according to [86], which is selected from the following group:
HS—CH$_2$CH$_2$—C(=O)-DGGF (SEQ ID NO: 34)-NH—CH$_2$CH$_2$—C(=O)—(NH-DX),
HS—CH$_2$CH$_2$—C(=O)-DGGF (SEQ ID NO: 34)-NH—CH$_2$CH$_2$CH$_2$—C(=O)—(NH-DX),
HS—CH$_2$CH$_2$—C(=O)-KGGF (SEQ ID NO: 35)-NH—CH$_2$CH$_2$—C(=O)—(NH-DX),
HS—CH$_2$CH$_2$—C(=O)-KGGF (SEQ ID NO: 35)-NH—CH$_2$CH$_2$CH$_2$—C(=O)—(NH-DX),
HS—CH$_2$CH$_2$—C(=O)-DGGFG (SEQ ID NO: 37)-NH—CH$_2$CH$_2$—C(=O)—(NH-DX),
HS—CH$_2$CH$_2$—C(=O)-DGGFG (SEQ ID NO: 37)-NH—CH$_2$CH$_2$CH$_2$—C(=O)—(NH-DX),
HS—CH$_2$CH$_2$—C(=O)-KGGFG (SEQ ID NO: 38)-NH—CH$_2$CH$_2$—C(=O)—(NH-DX),
HS—CH$_2$CH$_2$—C(=O)-KGGFG (SEQ ID NO: 38)-NH—CH$_2$CH$_2$CH$_2$—C(=O)—(NH-DX).

[95] The compound according to [86], which is selected from the following group:
(maleimid-N-yl)-CH$_2$CH$_2$CH$_2$CH$_2$CH$_2$—C(=O)-DGGF (SEQ ID NO: 34)-(NH-DX),
(maleimid-N-yl)-CH$_2$CH$_2$CH$_2$CH$_2$CH$_2$—C(=O)-KGGF (SEQ ID NO: 35)-(NH-DX),
(maleimid-N-yl)-CH$_2$CH$_2$CH$_2$CH$_2$CH$_2$—C(=O)-DGGFG (SEQ ID NO: 37)-(NH-DX),
(maleimid-N-yl)-CH$_2$CH$_2$CH$_2$CH$_2$CH$_2$—C(=O)-KGGFG (SEQ ID NO: 38)-(NH-DX).

[96] The compound according to [86], which is any of the followings:
(maleimid-N-yl)-CH$_2$CH$_2$CH$_2$CH$_2$CH$_2$—C(=O)-GGFGG (SEQ ID NO: 40)-(NH-DX),
(maleimid-N-yl)-CH$_2$CH$_2$CH$_2$CH$_2$CH$_2$—C(=O)-GGFGGG (SEQ ID NO: 41)-(NH-DX).

[97] The compound according to [86], which is selected from the following group:
X—CH$_2$—C(=O)—NH—CH$_2$CH$_2$—C(=O)-DGGF (SEQ ID NO: 34)-(NH-DX),
X—CH$_2$—C(=O)—NH—CH$_2$CH$_2$—C(=O)-KGGF (SEQ ID NO: 35)-(NH-DX),
X—CH$_2$—C(=O)—NH—CH$_2$CH$_2$—C(=O)-DGGFG (SEQ ID NO: 37)-(NH-DX),
X—CH$_2$—C(=O)—NH—CH$_2$CH$_2$—C(=O)-KGGFG (SEQ ID NO: 38)-(NH-DX).

[98] The compound according to [86], which is any of the followings:
X—CH$_2$—C(=O)—NH—CH$_2$CH$_2$—C(=O)-GGFGG (SEQ ID NO: 40)-(NH-DX),
X—CH$_2$—C(=O)—NH—CH$_2$CH$_2$—C(=O)-GGFGGG (SEQ ID NO: 41)-(NH-DX).

[99] The compound according to [86], which is selected from the following group:
(Pyrrolidine-2,5-dione-N-yl)-O—C(=O)—CH$_2$CH$_2$CH$_2$CH$_2$CH$_2$—C(=O)-DGGF (SEQ ID NO: 34)-(NH-DX),
(Pyrrolidine-2,5-dione-N-yl)-O—C(=O)—CH$_2$CH$_2$CH$_2$CH$_2$CH$_2$—C(=O)-KGGF (SEQ ID NO: 35)-(NH-DX),
(Pyrrolidine-2,5-dione-N-yl)-O—C(=O)—CH$_2$CH$_2$CH$_2$CH$_2$CH$_2$—C(=O)-DGGFG (SEQ ID NO: 37)-(NH-DX),
(Pyrrolidine-2,5-dione-N-yl)-O—C(=O)—CH$_2$CH$_2$CH$_2$CH$_2$CH$_2$—C(=O)-KGGFG (SEQ ID NO: 38)-(NH-DX).

[100] The compound according to [86], which is any of the followings:
(Pyrrolidine-2,5-dione-N-yl)-O—C(=O)—CH$_2$CH$_2$CH$_2$CH$_2$CH$_2$—C(=O)-GGFGG (SEQ ID NO: 40)-(NH-DX),
(Pyrrolidine-2,5-dione-N-yl)-O—C(=O)—CH$_2$CH$_2$CH$_2$CH$_2$CH$_2$—C(=O)-GGFGGG (SEQ ID NO: 41)-(NH-DX).

[101] The compound according to [86], which is selected from the following group:
HS—CH$_2$CH$_2$—C(=O)-DGGF (SEQ ID NO: 34)-(NH-DX),
HS—CH$_2$CH$_2$—C(=O)-KGGF (SEQ ID NO: 35)-(NH-DX),
HS—CH$_2$CH$_2$—C(=O)-DGGFG (SEQ ID NO: 37)-(NH-DX),
HS—CH$_2$CH$_2$—C(=O)-KGGFG (SEQ ID NO: 38)-(NH-DX).

[102] The compound according to [86], which is selected from the following group:
(maleimid-N-yl)-CH(CH$_2$CH$_2$—COOH)—C(=O)—NH—CH$_2$CH$_2$—C(=O)-GGFG (SEQ ID NO: 33)-NH—CH$_2$CH$_2$—C(=O)—(NH-DX),
(maleimid-N-yl)-CH(CH$_2$CH$_2$—COOH)—C(=O)—NH—CH$_2$CH$_2$—C(=O)-GGFG (SEQ ID NO: 33)-NH—CH$_2$CH$_2$CH$_2$—C(=O)—(NH-DX),
(maleimid-N-yl)-CH(CH$_2$CH$_2$—COOH)—C(=O)—NH—CH$_2$CH$_2$—C(=O)-GGFG (SEQ ID NO: 33)-NH—CH$_2$—O—CH$_2$—C(=O)—(NH-DX),
(maleimid-N-yl)-CH(CH$_2$CH$_2$—COOH)—C(=O)—NH—CH$_2$CH$_2$—C(=O)-GGFG (SEQ ID NO: 33)-NH—CH$_2$CH$_2$—O—CH$_2$—C(=O)—(NH-DX).

[103] The compound according to [86], which has a structure of the following formula:
(maleimid-N-yl)-CH(CH$_2$CH$_2$—COOH)—C(=O)—NH—CH$_2$CH$_2$—C(=O)-GGFG (SEQ ID NO: 33)-(NH-DX).

[104] The compound according to [86], which is selected from the following group:
(Pyrrolidine-2,5-dione-N-yl)-O—C(=O)—CH(CH$_2$CH$_2$—COOH)—CH$_2$—C(=O)—NH—CH$_2$CH$_2$—C(=O)-GGFG (SEQ ID NO: 33)-NH—CH$_2$CH$_2$—C(=O)—(NH-DX),
(Pyrrolidine-2,5-dione-N-yl)-O—C(=O)—CH(CH$_2$CH$_2$—COOH)—CH$_2$—C(=O)—NH—CH$_2$CH$_2$—C(=O)-GGFG (SEQ ID NO: 33)-NH—CH$_2$CH$_2$CH$_2$—C(=O)—(NH-DX),
(Pyrrolidine-2,5-dione-N-yl)-O—C(=O)—CH(CH$_2$CH$_2$—COOH)—CH$_2$—C(=O)—NH—CH$_2$CH$_2$—C(=O)-GGFG (SEQ ID NO: 33)-NH—CH$_2$—O—CH$_2$—C(=O)—(NH-DX),
(Pyrrolidine-2,5-dione-N-yl)-O—C(=O)—CH(CH$_2$CH$_2$—COOH)—CH$_2$—C(=O)—NH—CH$_2$CH$_2$—C(=O)-GGFG (SEQ ID NO: 33)-NH—CH$_2$CH$_2$—O—CH$_2$—C(=O)—(NH-DX).

[105] The compound according to [86], which is selected from the following group:
(maleimid-N-yl)-CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—C(=O)—(NH-DX),
(maleimid-N-yl)-CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$CH$_2$—C(=O)—(NH-DX),
(maleimid-N-yl)-CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$—O—CH$_2$—C(=O)—(NH-DX), (maleimid-N-yl)-CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—O—CH₂—C(=O)—(NH-DX).

[106] The compound according to [86], which is selected from the following group:

X—CH₂—C(=O)—NH—CH₂CH—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—C(=O)—(NH-DX),

X—CH₂—C(=O)—NH—CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂CH₂—C(=O)—(NH-DX),

X—CH₂—C(=O)—NH—CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂—O—CH₂—C(=O)—(NH-DX),

X—CH₂—C(=O)—NH—CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—O—CH₂—C(=O)—(NH-DX).

[107] The compound according to [86], which is selected from the following group:

(Pyrrolidine-2,5-dione-N-yl)-O—C(=O)—CH₂CH₂CH₂CH₂CH₂CH₂—C(=O)—N(—CH₂CH₂—O—CH₂CH₂—O—CH₂CH₂—O—CH₂—C(=O)-GGFG (SEQ ID NO: 33)-NH—CH₂CH₂—C(=O)—(NH-DX), (Pyrrolidine-2,5-dione-N-yl)-O—C(=O)—CH₂CH₂CH₂CH₂CH₂CH₂—C(=O)—N(—CH₂CH₂—O—CH₂CH₂—O—CH₂CH₂—O—CH₂—C(=O)-GGFG (SEQ ID NO: 33)-NH—CH₂CH₂CH₂—C(=O)—(NH-DX), (Pyrrolidine-2,5-dione-N-yl)-O—C(=O)—CH₂CH₂CH₂CH₂CH₂CH₂—C(=O)—N(—CH₂CH₂—O—CH₂CH₂—O—CH₂CH₂—O—CH₂—C(=O)-GGFG (SEQ ID NO: 33)-NH—CH₂—O—CH₂—C(=O)—(NH-DX), (Pyrrolidine-2,5-dione-N-yl)-O—C(=O)—CH₂CH₂CH₂CH₂CH₂CH₂—C(=O)—N(—CH₂CH₂—O—CH₂CH₂—O—CH₂CH₂—O—CH₂—C(=O)-GGFG (SEQ ID NO: 33)-NH—CH₂CH₂—O—CH₂—C(=O)—(NH-DX).

In the linker according to any one of [87] to [107], (maleimid-N-yl)- is a group represented by the following formula:

[Formula 18]

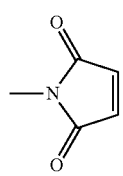

wherein the nitrogen atom is the connecting position, X represents a halogen atom, (Pyrrolidine-2,5-dione-N-yl)- is a group represented by the following formula:

[Formula 19]

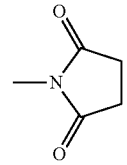

wherein the nitrogen atom is the connecting position, and —(NH-DX) is a group represented by the following formula:

[Formula 20]

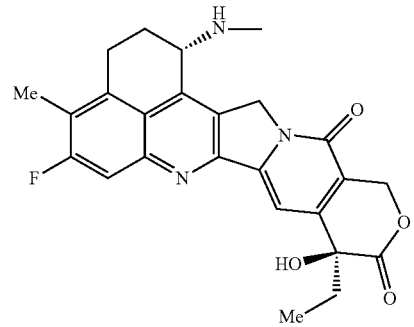

wherein the nitrogen atom of the amino group at position 1 is the connecting position.

[108] A linker having a structure represented by the following formula:
-L¹-L²-L^P-NH—(CH₂)n¹-L^a-L^b-L^c- or -L¹-L²-L^P-
for obtaining an antibody-drug conjugate in which a antitumor compound is conjugated to an antibody via the linker.

In the above, the antibody is connected to the terminal of L¹, the antitumor compound is connected to the terminal of L^c or L^P, wherein
n¹ represents an integer of 0 to 6,
L¹ represents -(Succinimid-3-yl-N)—(CH₂)n²-C(=O)—, -(Succinimid-3-yl-N)—CH[—(CH₂)n³-COOH]—C(=O)—, —CH₂—C(=O)—NH—(CH₂)n⁴-C(=O)—, —C(=O)-cyc.Hex(1,4)-CH₂—(N-ly-3-diminiccuS)-, or —C(=O)—(CH₂)n⁵-C(=O)—,
wherein n² represents an integer of 2 to 8, n³ represents an integer of 1 to 8, n⁴ represents an integer of 1 to 8, n⁵ represents an integer of 1 to 8,
L² represents —NH—(CH₂—CH₂—O)n⁶-CH₂—CH₂—C(=O)—, —N[—(CH₂CH₂—O)n⁷-CH₂CH₂—OH]—CH₂—C(=O)—, —S—(CH₂)n⁸-C(=O)—, or a single bond,
wherein n⁶ represents an integer of 0 to 6, n⁷ represents an integer of 1 to 4, n⁸ represents an integer of 1 to 6,
L^P represents a peptide residue consisting of 3 to 8 amino acids,
L^a represents —C(=O)—NH—, —NR¹—(CH₂)n⁹-, —O—, or a single bond,
wherein n⁹ represents an integer of 1 to 6, R¹ represents a hydrogen atom, an alkyl group having 1 to 6 carbon atoms, —(CH₂)n^a-COOH, or —(CH₂)n^b-OH, n^a represents an integer of 1 to 4, n^b represents an integer of 1 to 6, L^b represents —CR²(—R³)—, —O—, —NR⁴—, or a single bond,
wherein R² and R³ each independently represent a hydrogen atom, an alkyl group having 1 to 6 carbon atoms, —(CH₂)n^c-NH₂, —(CH₂)n^d-COOH, or —(CH₂)n^e-OH, R⁴ represents a hydrogen atom or an alkyl group having 1 to 6 carbon atoms, $n^c$ represents an integer of 0 to 6, $n^d$ represents an integer of 1 to 4, $n^e$ represents an integer of 1 to 4, provided that when $n^c$ is 0, $R^2$ and $R^3$ are not the same as each other, $L^c$ represents —CH$_2$— or —C(=O)—, -(Succinimid-3-yl-N)— has a structure represented by the following formula:

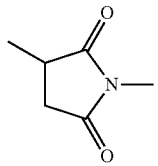

[Formula 21]

which is connected to the antibody at position 3 thereof and is connected to a methylene group in the linker structure containing this structure on the nitrogen atom at position 1, —(N-ly-3-diminiccuS)- has a structure represented by the following formula:

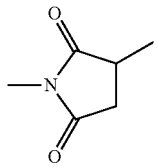

[Formula 22]

which is connected to $L^2$ at position 3 thereof and is connected to a methylene group in the linker structure containing this structure on the nitrogen atom at position 1, cyc.Hex(1,4) represents a 1,4-cyclohexylene group, and when $L^2$ is —S—(CH$_2$)$n^8$-C(=O)—, $L^1$ is —C(=O)-cyc.Hex(1,4)-CH$_2$—(N-ly-3-diminiccuS)-.

provided that any one or two or more of linkers of $L^1$, $L^2$, and $L^P$ have a structure containing a hydrophilic structure, said hydrophilic structure means, as for linker $L^P$, the case in which, $L^P$ is a peptide residue having a hydrophilic amino acid other than glycin at the N terminal, or $L^P$ is a peptide residue in which the C terminal is an oligopeptide consisting of 2 or 3 or more glycines and is connected to the antitumor compound, and even in case that a hydrophilic amino acid is present at N terminal, no other hydrophilic amino acid than glycine is present thereat, as for linker $L^1$, the case in which $L^1$ is -(Succinimid-3-yl-N)—CH[—(CH$_2$)$n^3$-COOH]—C(=O)—, or as for linker $L^2$, the case in which $L^2$ is —N[—(CH$_2$CH$_2$—O)$n^7$-CH$_2$CH$_2$—OH]—CH$_2$—C(=O)—.

[109] The linker according to [108], which is selected from the following group, provided that the left terminal is a connecting position to the antibody and the right terminal is a connecting position to the antitumor compound:

-(Succinimid-3-yl-N)—CH$_2$CH$_2$CH$_2$CH$_2$CH$_2$—C(=O)-DGGF (SEQ ID NO: 34)-NH—CH$_2$CH$_2$CH$_2$—C(=O)—, -(Succinimid-3-yl-N)—CH$_2$CH$_2$CH$_2$CH$_2$CH$_2$—C(=O)-DGGF (SEQ ID NO: 34)-NH—CH$_2$—O—CH$_2$—C(=O)—, -(Succinimid-3-yl-N)—CH$_2$CH$_2$CH$_2$CH$_2$CH$_2$—C(=O)-DGGF (SEQ ID NO: 34)-NH—CH$_2$CH$_2$—O—CH$_2$—C(=O)—, -(Succinimid-3-yl-N)—CH$_2$CH$_2$CH$_2$CH$_2$CH$_2$—C(=O)-DGGFG (SEQ ID NO: 37)-NH—CH$_2$CH$_2$CH$_2$—C(=O)—, -(Succinimid-3-yl-N)—CH$_2$CH$_2$CH$_2$CH$_2$CH$_2$—C(=O)-DGGFG (SEQ ID NO: 37)-NH—CH$_2$—O—CH$_2$—C(=O)—, -(Succinimid-3-yl-N)—CH$_2$CH$_2$CH$_2$CH$_2$CH$_2$—C(=O)-DGGFG (SEQ ID NO: 37)-NH—CH$_2$CH$_2$—O—CH$_2$—C(=O)—, -(Succinimid-3-yl-N)—CH$_2$CH$_2$CH$_2$CH$_2$CH$_2$—C(=O)-KGGF (SEQ ID NO: 35)-NH—CH$_2$CH$_2$CH$_2$—C(=O)—, -(Succinimid-3-yl-N)—CH$_2$CH$_2$CH$_2$CH$_2$CH$_2$—C(=O)-KGGF (SEQ ID NO: 35)-NH—CH$_2$—O—CH$_2$—C(=O)—, -(Succinimid-3-yl-N)—CH$_2$CH$_2$CH$_2$CH$_2$CH$_2$—C(=O)-KGGF (SEQ ID NO: 35)-NH—CH$_2$CH$_2$—O—CH$_2$—C(=O)—, -(Succinimid-3-yl-N)—CH$_2$CH$_2$CH$_2$CH$_2$CH$_2$—C(=O)-KGGFG (SEQ ID NO: 38)-NH—CH$_2$CH$_2$CH$_2$—C(=O)—, -(Succinimid-3-yl-N)—CH$_2$CH$_2$CH$_2$CH$_2$CH$_2$—C(=O)-KGGFG (SEQ ID NO: 38)-NH—CH$_2$—O—CH$_2$—C(=O)—, -(Succinimid-3-yl-N)—CH$_2$CH$_2$CH$_2$CH$_2$CH$_2$—C(=O)-KGGFG (SEQ ID NO: 38)-NH—CH$_2$CH$_2$—O—CH$_2$—C(=O)—, —CH$_2$—C(=O)—NH—CH$_2$CH$_2$—C(=O)-DGGF (SEQ ID NO: 34)-NH—CH$_2$CH$_2$CH$_2$—C(=O)—, —CH$_2$—C(=O)—NH—CH$_2$CH$_2$—C(=O)-DGGF (SEQ ID NO: 34)-NH—CH$_2$—O—CH$_2$—C(=O)—, —CH$_2$—C(=O)—NH—CH$_2$CH$_2$—C(=O)-DGGF (SEQ ID NO: 34)-NH—CH$_2$CH$_2$—O—CH$_2$—C(=O)—, —CH$_2$—C(=O)—NH—CH$_2$CH$_2$—C(=O)-DGGFG (SEQ ID NO: 37)-NH—CH$_2$CH$_2$CH$_2$—C(=O)—, —CH$_2$—C(=O)—NH—CH$_2$CH$_2$—C(=O)-DGGFG (SEQ ID NO: 37)-NH—CH$_2$—O—CH$_2$—C(=O)—, —CH$_2$—C(=O)—NH—CH$_2$CH$_2$—C(=O)-DGGFG (SEQ ID NO: 37)-NH—CH$_2$CH$_2$—O—CH$_2$—C(=O)—, —CH$_2$—C(=O)—NH—CH$_2$CH$_2$—C(=O)-KGGF (SEQ ID NO: 35)-NH—CH$_2$CH$_2$CH$_2$—C(=O)—, —CH$_2$—C(=O)—NH—CH$_2$CH$_2$—C(=O)-KGGF (SEQ ID NO: 35)-NH—CH$_2$—O—CH$_2$—C(=O)—, —CH$_2$—C(=O)—NH—CH$_2$CH$_2$—C(=O)-KGGF (SEQ ID NO: 35)-NH—CH$_2$CH$_2$—O—CH$_2$—C(=O)—, —CH$_2$—C(=O)—NH—CH$_2$CH$_2$—C(=O)-KGGFG (SEQ ID NO: 38)-NH—CH$_2$CH$_2$CH$_2$—C(=O)—, —CH$_2$—C(=O)—NH—CH$_2$CH$_2$—C(=O)-KGGFG (SEQ ID NO: 38)-NH—CH$_2$—O—CH$_2$—C(=O)—, —CH$_2$—C(=O)—NH—CH$_2$CH$_2$—C(=O)-KGGFG (SEQ ID NO: 38)-NH—CH$_2$CH$_2$—O—CH$_2$—C(=O)—, —C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$CH$_2$CH$_2$—C(=O)—, —C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$—O—CH$_2$—C(=O)—, —C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$CH$_2$—O—CH$_2$—C(=O)—, —C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$CH$_2$CH$_2$—C(=O)—, —C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$—O—CH$_2$—C(=O)—, —C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$CH$_2$—O—CH$_2$—C(=O)—, —C(=O)-cyc.Hex(1,4)-

CH₂—(N-ly-3-diminiccuS)-S—CH₂CH₂—C(=O)-KGGF (SEQ ID NO: 35)-NH—CH₂CH₂CH₂—C(=O)—,
—C(=O)-cyc.Hex(1,4)-CH₂—(N-ly-3-diminiccuS)-S—CH₂CH₂—C(=O)-KGGF (SEQ ID NO: 35)-NH—CH₂—O—CH₂—C(=O)—,
—C(=O)-cyc.Hex(1,4)-CH₂—(N-ly-3-diminiccuS)-S—CH₂CH₂—C(=O)-KGGF (SEQ ID NO: 35)-NH—CH₂CH₂—O—CH₂—C(=O)—,
—C(=O)-cyc.Hex(1,4)-CH₂—(N-ly-3-diminiccuS)-S—CH₂CH₂—C(=O)-KGGFG (SEQ ID NO: 38)-NH—CH₂CH₂CH₂—C(=O)—,
—C(=O)-cyc.Hex(1,4)-CH₂—(N-ly-3-diminiccuS)-S—CH₂CH₂—C(=O)-KGGFG (SEQ ID NO: 38)-NH—CH₂—O—CH₂—C(=O)—,
—C(=O)-cyc.Hex(1,4)-CH₂—(N-ly-3-diminiccuS)-S—CH₂CH₂—C(=O)-KGGFG (SEQ ID NO: 38)-NH—CH₂CH₂—O—CH₂—C(=O)—.

[110] The linker according to [108], which is selected from the following group, provided that the left terminal is the connecting position to the antibody and the right terminal is the connecting position to the antitumor compound:
-(Succinimid-3-yl-N)—CH₂CH₂CH₂CH₂CH₂—C(=O)-DGGF (SEQ ID NO: 34)-NH—CH₂CH₂CH₂—C(=O)—,
-(Succinimid-3-yl-N)—CH₂CH₂CH₂CH₂CH₂—C(=O)-DGGFG (SEQ ID NO: 37)-NH—CH₂CH₂CH₂—C(=O)—,
-(Succinimid-3-yl-N)—CH₂CH₂CH₂CH₂CH₂—C(=O)-KGGF (SEQ ID NO: 35)-NH—CH₂CH₂CH₂—C(=O)—,
-(Succinimid-3-yl-N)—CH₂CH₂CH₂CH₂CH₂—C(=O)-KGGFG (SEQ ID NO: 38)-NH—CH₂CH₂CH₂—C(=O)—.

[111] The linker according to [108], which is any of the followings, provided that the left terminal is the connecting position to the antibody and the right terminal is the connecting position to the antitumor compound:
-(Succinimid-3-yl-N)—CH₂CH₂CH₂CH₂CH₂—C(=O)-DGGF (SEQ ID NO: 34)-NH—CH₂CH₂CH₂—C(=O)—, and
-(Succinimid-3-yl-N)—CH₂CH₂CH₂CH₂CH₂—C(=O)-DGGFG (SEQ ID NO: 37)-NH—CH₂CH₂CH₂—C(=O)—.

[112] The linker according to [108], which is selected from the following group, provided that the left terminal is the connecting position to the antibody and the right terminal is the connecting position to the antitumor compound:
—CH₂—C(=O)—NH—CH₂CH₂—C(=O)-DGGF (SEQ ID NO: 34)-NH—CH₂CH₂CH₂—C(=O)—,
—CH₂—C(=O)—NH—CH₂CH₂—C(=O)-DGGFG (SEQ ID NO: 37)-NH—CH₂CH₂CH₂—C(=O)—,
—CH₂—C(=O)—NH—CH₂CH₂—C(=O)-KGGF (SEQ ID NO: 35)-NH—CH₂CH₂CH₂—C(=O)—,
—CH₂—C(=O)—NH—CH₂CH₂—C(=O)-KGGFG (SEQ ID NO: 38)-NH—CH₂CH₂CH₂—C(=O)—.

[113] The linker according to [108], which is any of the followings, provided that the left terminal is the connecting position to the antibody and the right terminal is the connecting position to the antitumor compound:
—CH₂—C(=O)—NH—CH₂CH₂—C(=O)-DGGF (SEQ ID NO: 34)-NH—CH₂CH₂CH₂—C(=O)—, and
—CH₂—C(=O)—NH—CH₂CH₂—C(=O)-DGGFG (SEQ ID NO: 37)-NH—CH₂CH₂CH₂—C(=O)—.

[114] The linker according to [108], which is selected from the following group, provided that the left terminal is the connecting position to the antibody and the right terminal is the connecting position to the antitumor compound:
—C(=O)-cyc.Hex(1,4)-CH₂—(N-ly-3-diminiccuS)-S—CH₂CH₂—C(=O)-DGGF (SEQ ID NO: 34)-NH—CH₂CH₂CH₂—C(=O)—,
—C(=O)-cyc.Hex(1,4)-CH₂—(N-ly-3-diminiccuS)-S—CH₂CH₂—C(=O)-DGGFG (SEQ ID NO: 37)-NH—CH₂CH₂CH₂—C(=O)—,
—C(=O)-cyc.Hex(1,4)-CH₂—(N-ly-3-diminiccuS)-S—CH₂CH₂—C(=O)-KGGF (SEQ ID NO: 35)-NH—CH₂CH₂CH₂—C(=O)—,
—C(=O)-cyc.Hex(1,4)-CH₂—(N-ly-3-diminiccuS)-S—CH₂CH₂—C(=O)-KGGFG (SEQ ID NO: 38)-NH—CH₂CH₂CH₂—C(=O)—.

[115] The linker according to [108], which is any of the followings, provided that the left terminal is the connecting position to the antibody and the right terminal is the connecting position to the antitumor compound:
—C(=O)-cyc.Hex(1,4)-CH₂—(N-ly-3-diminiccuS)-S—CH₂CH₂—C(=O)-DGGF (SEQ ID NO: 34)-NH—CH₂CH₂CH₂—C(=O)—, and
—C(=O)-cyc.Hex(1,4)-CH₂—(N-ly-3-diminiccuS)-S—CH₂CH₂—C(=O)-DGGFG (SEQ ID NO: 37)-NH—CH₂CH₂CH₂—C(=O)—.

[116] The linker according to [108], which is selected from the following group, provided that the left terminal is the connecting position to the antibody and the right terminal is the connecting position to the antitumor compound:
-(Succinimid-3-yl-N)—CH₂CH₂CH₂CH₂CH₂—C(=O)-DGGF (SEQ ID NO: 34)-,
-(Succinimid-3-yl-N)—CH₂CH₂CH₂CH₂CH₂—C(=O)-KGGF (SEQ ID NO: 35)-,
-(Succinimid-3-yl-N)—CH₂CH₂CH₂CH₂CH₂—C(=O)-DGGFG (SEQ ID NO: 37)-,
-(Succinimid-3-yl-N)—CH₂CH₂CH₂CH₂CH₂—C(=O)-KGGFG (SEQ ID NO: 38)-,
—CH₂—C(=O)—NH—CH₂CH₂—C(=O)-DGGF (SEQ ID NO: 34)-,
—CH₂—C(=O)—NH—CH₂CH₂—C(=O)-KGGF (SEQ ID NO: 35)-,
—CH₂—C(=O)—NH—CH₂CH₂—C(=O)-DGGFG (SEQ ID NO: 37)-,
—CH₂—C(=O)—NH—CH₂CH₂—C(=O)-KGGFG (SEQ ID NO: 38)-,
—C(=O)-cyc.Hex(1,4)-CH₂—(N-ly-3-diminiccuS)-S—CH₂CH₂—C(=O)-DGGF (SEQ ID NO: 34)-,
—C(=O)-cyc.Hex(1,4)-CH₂—(N-ly-3-diminiccuS)-S—CH₂CH₂—C(=O)-KGGF (SEQ ID NO: 35)-,
—C(=O)-cyc.Hex(1,4)-CH₂—(N-ly-3-diminiccuS)-S—CH₂CH₂—C(=O)-DGGFG (SEQ ID NO: 37)-,
—C(=O)-cyc.Hex(1,4)-CH₂—(N-ly-3-diminiccuS)-S—CH₂CH₂—C(=O)-KGGFG (SEQ ID NO: 38)-,
—C(=O)—CH₂CH₂CH₂CH₂CH₂—C(=O)-DGGF (SEQ ID NO: 34)-,
—C(=O)—CH₂CH₂CH₂CH₂CH₂—C(=O)-KGGF (SEQ ID NO: 35)-,
—C(=O)—CH₂CH₂CH₂CH₂CH₂—C(=O)-DGGFG (SEQ ID NO: 37)-,
—C(=O)—CH₂CH₂CH₂CH₂CH₂—C(=O)-KGGFG (SEQ ID NO: 38)-.

[117] The linker according to [108], which is selected from the following group, provided that the left terminal is the connecting position to the antibody and the right terminal is the connecting position to the antitumor compound:
-(Succinimid-3-yl-N)—CH₂CH₂CH₂CH₂CH₂—C(=O)-DGGF (SEQ ID NO: 34)-,
-(Succinimid-3-yl-N)—CH₂CH₂CH₂CH₂CH₂—C(=O)-DGGFG (SEQ ID NO: 37)-,
-(Succinimid-3-yl-N)—CH₂CH₂CH₂CH₂CH₂—C(=O)-KGGFG (SEQ ID NO: 38)-.

[118] The linker according to [108], which is any of the followings, provided that the left terminal is the connecting position to the antibody and the right terminal is the connecting position to the antitumor compound:
-(Succinimid-3-yl-N)—CH₂CH₂CH₂CH₂CH₂—C(=O)-DGGFG (SEQ ID NO: 37)-, and
-(Succinimid-3-yl-N)—CH₂CH₂CH₂CH₂CH₂—C(=O)-KGGFG (SEQ ID NO: 38)-.

[119] The linker according to [108], which has the following structure, provided that the left terminal is the connecting position to the antibody and the right terminal is the connecting position to the antitumor compound:
-(Succinimid-3-yl-N)—CH₂CH₂CH₂CH₂CH₂—C(=O)-DGGFG (SEQ ID NO: 37)-.

[120] The linker according to [108], which is any of the followings, provided that the left terminal is the connecting position to the antibody and the right terminal is the connecting position to the antitumor compound:
—CH₂—C(=O)—NH—CH₂CH₂—C(=O)-DGGFG (SEQ ID NO: 37)-, and
—CH₂—C(=O)—NH—CH₂CH₂—C(=O)-KGGFG (SEQ ID NO: 38)-.

[121] The linker according to [108], which has the following structure, provided that the left terminal is the connecting position to the antibody and the right terminal is the connecting position to the antitumor compound:
—CH₂—C(=O)—NH—CH₂CH₂—C(=O)-DGGFG (SEQ ID NO: 37)-.

[122] The linker according to [108], which is any of the followings, provided that the left terminal is the connecting position to the antibody and the right terminal is the connecting position to the antitumor compound:
—C(=O)-cyc.Hex(1,4)-CH₂—(N-ly-3-diminiccuS)-S—CH₂CH₂—C(=O)-DGGFG (SEQ ID NO: 37)-, and
—C(=O)-cyc.Hex(1,4)-CH₂—(N-ly-3-diminiccuS)-S—CH₂CH₂—C(=O)-KGGFG (SEQ ID NO: 38)-.

[123] The linker according to [108], which has the following structure, provided that the left terminal is the connecting position to the antibody and the right terminal is the connecting position to the antitumor compound:
—C(=O)-cyc.Hex(1,4)-CH₂—(N-ly-3-diminiccuS)-S—CH₂CH₂—C(=O)-DGGFG (SEQ ID NO: 37)-.

[124] The linker according to [108], which is selected from the following group, provided that the left terminal is the connecting position to the antibody and the right terminal is the connecting position to the antitumor compound:
-(Succinimid-3-yl-N)—CH(CH₂CH₂—COOH)—C(=O)—NH—CH₂CH₂—C(=O)-GGFG (SEQ ID NO: 33)-NH—CH₂CH₂—C(=O)—,
-(Succinimid-3-yl-N)—CH(CH₂CH₂—COOH)—C(=O)—NH—CH₂CH₂—C(=O)-GGFG (SEQ ID NO: 33)-NH—CH₂CH₂CH₂—C(=O)—,
-(Succinimid-3-yl-N)—CH(CH₂CH₂—COOH)—C(=O)—NH—CH₂CH₂—C(=O)-GGFG (SEQ ID NO: 33)-NH—CH₂—O—CH₂—C(=O)—,
-(Succinimid-3-yl-N)—CH(CH₂CH₂—COOH)—C(=O)—NH—CH₂CH₂—C(=O)-GGFG (SEQ ID NO: 33)-NH—CH₂CH₂—O—CH₂—C(=O)—.

[125] The linker according to [108], which is selected from the following group, provided that the left terminal is the connecting position to the antibody and the right terminal is the connecting position to the antitumor compound:
-(Succinimid-3-yl-N)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—C(=O)—,
-(Succinimid-3-yl-N)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂CH₂—C(=O)—,
-(Succinimid-3-yl-N)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂—O—CH₂—C(=O)—,
-(Succinimid-3-yl-N)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—O—CH₂—C(=O)—.

[126] The linker according to [108], which is selected from the following group, provided that the left terminal is the connecting position to the antibody and the right terminal is the connecting position to the antitumor compound:
—CH₂—C(=O)—NH—CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—C(=O)—,
—CH₂—C(=O)—NH—CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂CH₂—C(=O)—,
—CH₂—C(=O)—NH—CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂—O—CH₂—C(=O)—,
—CH₂—C(=O)—NH—CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—O—CH₂—C(=O)—.

[127] The linker according to [108], which is selected from the following group, provided that the left terminal is the connecting position to the antibody and the right terminal is the connecting position to the antitumor compound:
—C(=O)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—C(=O)—,
—C(=O)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂CH₂—C(=O)—,
—C(=O)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂—O—CH₂—C(=O)—,
—C(=O)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-NH—CH₂CH₂—O—CH₂—C(=O)—.

[128] The linker according to [108], which has the following structure, provided that the left terminal is the connecting position to the antibody and the right terminal is the connecting position to the antitumor compound:
-(Succinimid-3-yl-N)—CH(CH₂CH₂—COOH)—C(=O)—NH—CH₂CH₂—C(=O)-GGFG (SEQ ID NO: 33)-.

[129] The linker according to [108], which has the following structure, provided that the left terminal is the connecting position to the antibody and the right terminal is the connecting position to the antitumor compound:
-(Succinimid-3-yl-N)—CH₂CH₂CH₂CH₂CH₂—C(=O)—N(—CH₂CH₂—O—CH₂CH₂—O—CH₂CH₂—O—CH₂CH₂—OH)—CH₂—C(=O)-GGFG (SEQ ID NO: 33)-.

[130] The linker according to [108], which has the following structure, provided that the left terminal is the connecting position to the antibody and the right terminal is the connecting position to the antitumor compound:

—CH$_2$—C(=O)—NH—CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-.

[131] The linker according to [108], which has the following structure, provided that the left terminal is the connecting position to the antibody and the right terminal is the connecting position to the antitumor compound:

—C(=O)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-.

[132] The linker according to [108], which is any of the followings, provided that the left terminal is the connecting position to the antibody and the right terminal is the connecting position to the antitumor compound:

-(Succinimid-3-yl-N)—CH$_2$CH$_2$CH$_2$CH$_2$CH$_2$—C(=O)-GGFGG (SEQ ID NO: 40)-, and -(Succinimid-3-yl-N)—CH$_2$CH$_2$CH$_2$CH$_2$CH$_2$—C(=O)-GGFGGG (SEQ ID NO: 41)-.

[133] The linker according to [108], which is any of the followings, provided that the left terminal is the connecting position to the antibody and the right terminal is the connecting position to the antitumor compound:

—CH$_2$—C(=O)—NH—CH$_2$CH$_2$—C(=O)-GGFGG (SEQ ID NO: 40)-, and

—CH$_2$—C(=O)—NH—CH$_2$CH$_2$—C(=O)-GGFGGG (SEQ ID NO: 41)-.

[134] The linker according to [108], which is any of the followings, provided that the left terminal is the connecting position to the antibody and the right terminal is the connecting position to the antitumor compound:

—C(=O)-cyc.Hex(1,4)-CH$_2$—(N-ly-3-diminiccuS)-S—CH$_2$CH$_2$—C(=O)-GGFGG (SEQ ID NO: 40)-, and —C(=O)-cyc.Hex(1,4)-CH$_2$—(N-ly-3-diminiccuS)-S—CH$_2$CH$_2$—C(=O)-GGFGGG (SEQ ID NO: 41)-.

[135] The linker according to [108], which is any of the followings, provided that the left terminal is the connecting position to the antibody and the right terminal is the connecting position to the antitumor compound:

—C(=O)—CH$_2$CH$_2$CH$_2$CH$_2$CH$_2$—C(=O)-GGFGG (SEQ ID NO: 40)-, and

—C(=O)—CH$_2$CH$_2$CH$_2$CH$_2$CH$_2$—C(=O)-GGFGGG (SEQ ID NO: 41)-.

Here, in the linker according to any one of [109] to [135], —(N-ly-3-diminiccuS)- has a structure represented by the following formula:

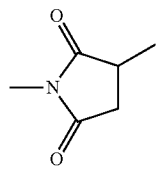

[Formula 23]

which is connected to L$^2$ at position 3 thereof and is connected to a methylene group in the linker structure containing this structure on the nitrogen atom at position 1, —(N-ly-3-diminiccuS)- has a structure represented by the following formula:

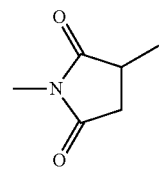

[Formula 24]

which is connected to L$^2$ at position 3 thereof and is connected to a methylene group in the linker structure containing this structure on the nitrogen atom at position 1, and cyc.Hex(1,4) represents a 1,4-cyclohexylene group.

[136] A method for producing an antibody-drug conjugate comprising reacting a compound represented by the following formula:

Q-L$^{1a}$-(CH$_2$)n$^Q$-C(=O)-L$^{2a}$-L$^P$-NH—(CH$_2$)n$^1$-L$^a$-L$^b$-L$^c$-(NH-DX), or

Q-L$^{1a}$-(CH$_2$)n$^Q$-C(=O)-L$^{2a}$-L$^P$-(NH-DX)

with an antibody or a reactive derivative thereof and conjugating a drug-linker moiety to the antibody by a method for forming a thioether bond at a disulfide bond moiety present in a hinge part of the antibody, or by a method for forming an amide bond at an amino group present on a side chain of an amino acid constituting the antibody or at the terminal amino group.

In the formula, Q represents (maleimid-N-yl)-, HS—, X—CH$_2$—C(=O)—NH—, or (Pyrrolidine-2,5-dione-N-yl)-O—C(=O)—, X represents a bromine atom or an iodine atom, L$^{1a}$ represents —CH[—(CH$_2$)n$^3$-COOH]— or a single bond, n$^Q$ represents an integer of 0 to 8, L$^{2a}$ represents —NH—(CH$_2$—CH$_2$—O)n$^6$-CH$_2$—CH$_2$—C(=O)—, —N[—(CH$_2$CH$_2$—O)n$^7$-CH$_2$CH$_2$—OH]—CH$_2$—H$_2$—C(=O)—, or a single bond, wherein n$^6$ represents an integer of 0 to 6, n$^7$ represents an integer of 1 to 4, L$^P$ represents a peptide residue consisting of 3 to 8 amino acids, n$^1$ represents an integer of 0 to 6, L$^a$ represents —C(=O)—NH—, —NR$^1$—(CH$_2$)n$^9$-, —O—, or a single bond, wherein n$^9$ represents an integer of 1 to 6, R$^1$ represents a hydrogen atom, an alkyl group having 1 to 6 carbon atoms, —(CH$_2$)n$^a$-COOH, or —(CH$_2$)n$^b$-OH, n$^a$ represents an integer of 1 to 4, n$^b$ represents an integer of 1 to 6, L$^b$ represents —CR$^2$(—R$^3$)—, —O—, —NR$^4$—, or a single bond, wherein R$^2$ and R$^3$ each independently represent a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ represents a hydrogen atom or an alkyl group having 1 to 6 carbon atoms, n$^c$ represents an integer of 0 to 6, n$^d$ represents an integer of 1 to 4, n$^e$ represents an integer of 1 to 4, provided that when $n^c$ is 0, $R^2$ and $R^3$ are not the same as each other,
$L^c$ represents —CH$_2$— or —C(=O)—,
(maleimid-N-yl)- is a group represented by the following formula:

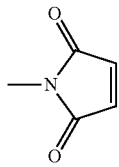

[Formula 25]

wherein the nitrogen atom is the connecting position,
(Pyrrolidine-2,5-dione-N-yl) is a group represented by the following formula:

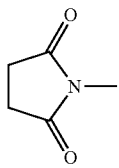

[Formula 26]

wherein the nitrogen atom is the connecting position,
—(NH-DX) is a group represented by the following formula:

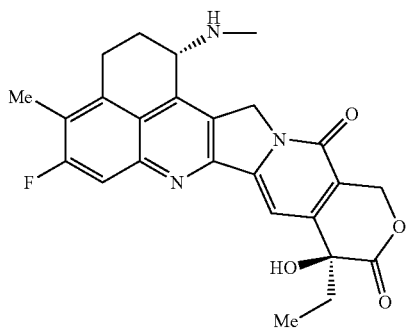

[Formula 27]

wherein the nitrogen atom of the amino group at position 1 is the connecting position,
provided that any one or two or more of linkers of $L^{1a}$-(CH$_2$)n$^Q$-C(=O)—, $L^2$, and $L^P$ have a structure containing a hydrophilic structure,
said hydrophilic structure means,
when $L^P$ has this structure,
$L^P$ is a peptide residue having a hydrophilic amino acid other than glycine at the N terminal, or
$L^P$ is a peptide residue in which the C terminal is an oligopeptide consisting of 2 or 3 or more glycines and is connected to the drug, and the even in case that a hydrophilic amino acid is present at N terminal, no other hydrophilic amino acid than glycine is present thereat,
as for linker $L^{1a}$-(CH$_2$)n$^Q$-C(=O)—, the case in which $L^{1a}$-(CH$_2$)n$^Q$-C(=O)— is —CH[—(CH$_2$)n$^3$-COOH]—C(=O)—, or
as for linker $L^{2a}$, the case in which $L^{2a}$ is —N[—(CH$_2$CH$_2$—O)n$^7$-CH$_2$CH$_2$—OH]—CH$_2$—C(=O)—.

[137] The method for producing an antibody-drug conjugate according to [136], wherein the method for conjugating a drug-linker moiety to an antibody is
a method of reducing the antibody and thereafter forming a thioether bond by the reaction of the antibody with the compound in which Q is a maleimidyl group or X—CH$_2$—C(=O)—NH—,
a method of forming an amide bond by the reaction of the antibody with the compound in which Q is (Pyrrolidine-2,5-dione-N-yl)-O—C(=O)—, or
a method of reacting the antibody with a compound represented by the formula Q$^1$-L$^{1a}$-(CH$_2$)n$^Q$-C(=O)-Q$^2$
wherein Q$^1$ represents (Pyrrolidine-2,5-dione-N-yl)-O—C(=O)—, (3-Sulfo-pyrrolidine-2,5-dione-N-yl)-O—C(=O)—, R$^Q$—O—C(=N)—, or O=C=N—,
L$^{1a}$ represents -cyc.Hex(1,4)-CH$_2$—, an alkylene group having 1 to 10 carbon atoms, a phenylene group, —(CH$_2$)n$^4$-C(=O)—, —(CH$_2$)n$^{4a}$-NH—C(=O)—(CH$_2$)n$^{4b}$-, or —(CH$_2$)n$^{4a}$-NH—C(=O)-cyc.Hex(1,4)-CH$_2$—,
Q$^2$ represents (maleimid-N-yl), a halogen atom, or —S—S-(2-Pyridyl),
R$^Q$ represents an alkyl group having 1 to 6 carbon atoms, n$^4$ represents an integer of 1 to 8, n$^{4a}$ represents an integer of 0 to 6, n$^{4b}$ represents an integer of 1 to 6, (3-Sulfo-pyrrolidine-2,5-dione-N-yl)- is a group represented by the following formula:

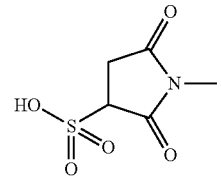

[Formula 28]

wherein the nitrogen atom is the connecting position, this sulfonic acid is capable of forming a lithium salt, sodium salt, or potassium salt, cyc.Hex(1,4) represents a 1,4-cyclohexylene group, and (2-Pyridyl) represents a 2-pyridyl group
and thereafter reacting the antibody with the compound in which Q is SH to form a drug-linker structure by an amide bond.
[138] The method for producing an antibody-drug conjugate according to [136] or [137], wherein the compound represented by the following formula:
Q-L$^{1a}$-(CH$_2$)n$^Q$-C(=O)-L$^{2a}$-L$^P$-NH—(CH$_2$)n$^1$-L$^a$-L$^b$-L$^c$-(NH-DX), or Q-L$^{1a}$-(CH$_2$)n$^Q$-C(=O)-L$^{2a}$-L$^P$-(NH-DX)
is a compound according to any one of [87] to [107].
[139] A method for producing an antibody-drug conjugate produced by a production method according to any one of [136] to [138].

Advantageous Effects of Invention

With an antibody-drug conjugate having an antitumor compound exatecan conjugated via a linker with a specific structure, an excellent antitumor effect can be achieved.

BRIEF DESCRIPTION OF DRAWINGS

FIG. 1 shows an amino acid sequence of B7-H3 variant 1 (SEQ ID NO: 1).
FIG. 2 shows an amino acid sequence of B7-H3 variant 2 (SEQ ID NO: 2).

FIG. 3 shows an amino acid sequence of an M30-H1-type heavy chain (SEQ ID NO: 9).

FIG. 4 shows an amino acid sequence of an M30-H2-type heavy chain (SEQ ID NO: 10)

FIG. 5 shows an amino acid sequence of an M30-H3-type heavy chain (SEQ ID NO: 11)

FIG. 6 shows an amino acid sequence of an M30-H4-type heavy chain (SEQ ID NO: 12)

FIG. 7 shows an amino acid sequence of an M30-L1-type light chain (SEQ ID NO: 13)

FIG. 8 shows an amino acid sequence of an M30-L2-type light chain (SEQ ID NO: 14)

FIG. 9 shows an amino acid sequence of an M30-L3-type light chain (SEQ ID NO: 15)

FIG. 10 shows an amino acid sequence of an M30-L4-type light chain (SEQ ID NO: 16)

FIG. 11 shows an amino acid sequence of an M30-L5-type light chain (SEQ ID NO: 17)

FIG. 12 shows an amino acid sequence of an M30-L6-type light chain (SEQ ID NO: 18)

FIG. 13 shows an amino acid sequence of an M30-L7-type light chain (SEQ ID NO: 19).

FIG. 14 shows an amino acid sequence of an M30 antibody heavy chain (SEQ ID NO: 20).

FIG. 15 shows an amino acid sequence of an M30 antibody light chain (SEQ ID NO: 21).

FIG. 16 shows a nucleotide sequence of B7-H3 variant 1 (SEQ ID NO: 26).

DESCRIPTION OF EMBODIMENTS

Figure 17:
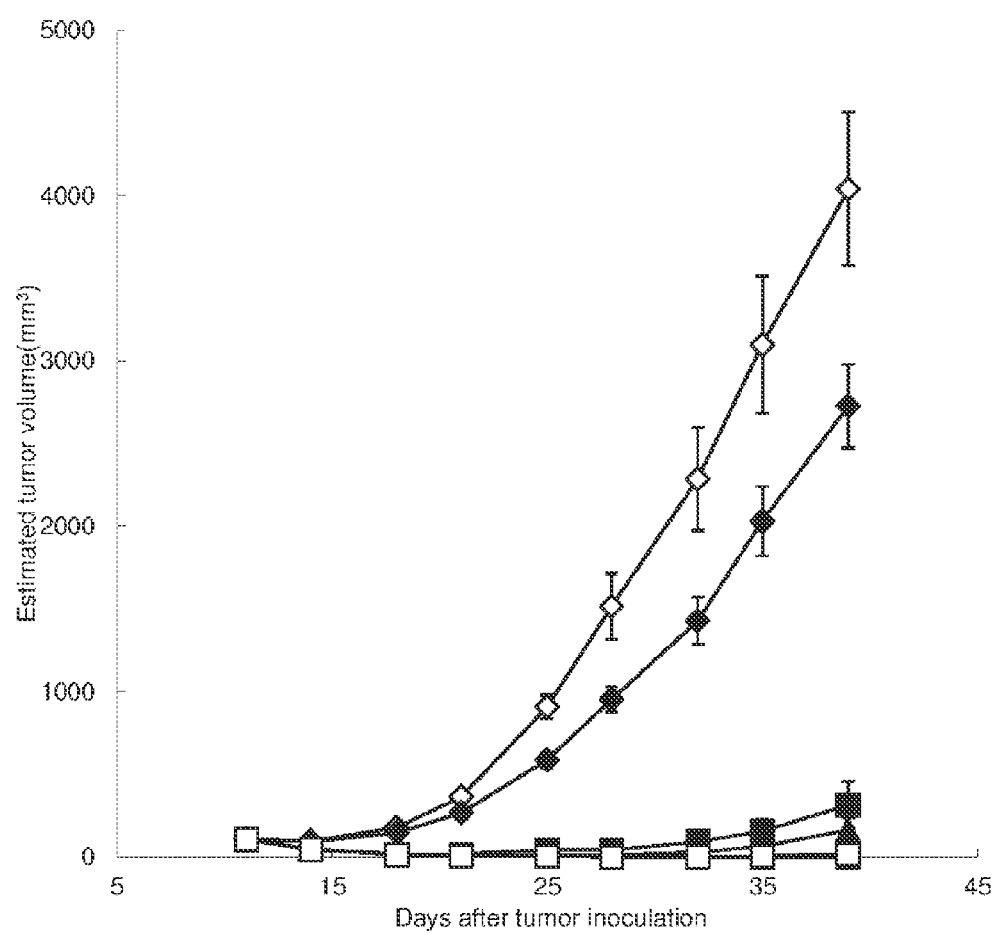
FIG. 17 shows the effects of an M30-H1-L4P antibody and antibody-drug conjugates (1), (2), (18), and (19) administered at 10 mg/kg on human melanoma line A375 cells transplanted in mice. The line with open rhombuses depicts results about untreated tumor, the line with filled rhombuses depicts the effect of the M30-H1-L4P antibody, the line with filled squares depicts the effect of the antibody-drug conjugate (1), the line with open squares depicts the effect of the antibody-drug conjugate (2), the line with filled triangles depicts the effect of the antibody-drug conjugate (18), and the line with open triangles depicts the effect of the antibody-drug conjugate (19).

The antibody-drug conjugate of the present invention is an antitumor drug in which an antitumor antibody is conjugated to an antitumor compound via a linker structure moiety and explained in detail hereinbelow.

[Antibody]

The antibody used in the antibody-drug conjugate of the present invention means an immunoglobulin and is a molecule containing an antigen-binding site immunospecifically binding to an antigen. The class of the antibody of the present invention may be any of IgG, IgE, IgM, IgD, IgA, and IgY and is preferably IgG. The subclass of the antibody of the present invention may be any of IgG1, IgG2, IgG3, IgG4, IgA1, and IgA2 and is preferably IgG1 or IgG2. The antibody may be derived from any species, and preferred examples of the species can include humans, rats, mice, and rabbits. In case when derived from other than human species, it is preferably chimerized or humanized using a well known technique. The antibody of the present invention may be a polyclonal antibody or a monoclonal antibody and is preferably a monoclonal antibody.

The antibody of the present invention may be those which is capable of targeting tumor cells. Since the antibody of the present invention is conjugated with a drug having antitumor activity via a linker, the antibody preferably possesses one or more of a property of recognizing a tumor cell, a property of binding to a tumor cell, a property of internalizing in a tumor cell, and a property of damaging a tumor cell.

The binding activity of the antibody against tumor cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring the amount of fluorescence incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000).

The antitumor activity of the antibody refers to a cytotoxic activity or cytocidal effect against tumor cells and can be confirmed in vitro by determining inhibitory activity against cell growth. For example, a cancer cell line overexpressing a target protein for the antibody is cultured, and the antibody is added at varying concentrations into the culture system to determine an inhibitory activity against focus formation, colony formation, and spheroid growth. The antitumor activity can be confirmed in vivo, for example, by administering the antibody to a nude mouse with a transplanted tumor cell line highly expressing the target protein, and determining change in the cancer cell. Since the drug conjugated in the antibody-drug conjugate exerts an antitumor effect, it is more preferred but not essential that the antibody itself should have an antitumor effect. For exerting the antitumor effect and also for specifically and selectively damaging tumor cells by the drug, it is important and also preferred that the antibody should have the property of internalizing to migrate into tumor cells.

Examples of such an antibody can include, but not limited to, an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-Cripto antibody, an anti-EphA2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, and an anti-mesothelin antibody.

The antibody of the present invention is preferably an anti-CD30 antibody, an anti-CD33 antibody, an anti-CD70 antibody, or an anti-B7-H3 antibody, and more preferably an anti-B7-H3 antibody.

The antibody of the present invention can be yielded using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the yielded heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be yielded.

The antigen can be yielded by genetically engineering host cells to produce a gene encoding the antigenic protein. Specifically, vectors that permit expression of the antigen gene are prepared and transferred to host cells so that the gene is expressed. The antigen thus expressed can be purified.

The anti-CD30 antibody, the anti-CD33 antibody, and the anti-CD70 antibody can yielded by an approach known in the art with reference to WO2002/043661, U.S. Pat. No. 5,773,001, and WO2006/113909, respectively.

The B7-H3 antibody used in the present invention is preferably those having properties as described below.
(1) An antibody having the following properties:
  (a) specifically binding to B7-H3,
  (b) having antibody-dependent cell-mediated phagocytosis (ADCP) activity, and
  (c) having antitumor activity in vivo.
(2) The antibody according to (1), wherein B7-H3 is a molecule comprising the amino acid sequence represented by SEQ ID NO: 1 or 2.
(3) The antibody according to (1) or (2), wherein the antibody has CDRH1 comprising the amino acid sequence represented by SEQ ID NO: 3, CDRH2 comprising the amino acid sequence represented by SEQ ID NO: 4, and CDRH3 comprising the amino acid sequence represented by SEQ ID NO: 5 as heavy chain complementarity determining regions, and CDRL1 comprising the amino acid sequence represented by SEQ ID NO: 6, CDRL2 comprising the amino acid sequence represented by SEQ ID NO: 7, and CDRL3 comprising the amino acid sequence represented by SEQ ID NO: 8 as light chain complementarity determining regions.
(4) The antibody according to any of (1) to (3), wherein the constant region thereof is a human-derived constant region.
(5) The antibody according to any of (1) to (4), wherein the antibody is a humanized antibody.
(6) The antibody according to (5), wherein the antibody has a heavy chain variable region comprising an amino acid sequence selected from the group consisting of (a) an amino acid sequence described in amino acid positions 20 to 141 in SEQ ID NO: 9, (b) an amino acid sequence described in amino acid positions 20 to 141 in SEQ ID NO: 10, (c) an amino acid sequence described in amino acid positions 20 to 141 in SEQ ID NO: 11, (d) an amino acid sequence described in amino acid positions 20 to 141 in SEQ ID NO: 12, (e) an amino acid sequence having at least 95% or higher homology to any of the sequences (a) to (d), and (f) an amino acid sequence derived from any of the sequences (a) to (d) by the deletions, replacements, or additions of at least one amino acid, and a light chain variable region comprising an amino acid sequence selected from the group consisting of (g) an amino acid sequence described in amino acid positions 21 to 128 in SEQ ID NO: 13, (h) an amino acid sequence described in amino acid positions 21 to 128 in SEQ ID NO: 14, (i) an amino acid sequence described in amino acid positions 21 to 128 in SEQ ID NO: 15, (j) an amino acid sequence described in amino acid positions 21 to 128 in SEQ ID NO: 16, (k) an amino acid sequence described in amino acid positions 21 to 128 in SEQ ID NO: 17, (l) an amino acid sequence described in amino acid positions 21 to 128 in SEQ ID NO: 18, (m) an amino acid sequence described in amino acid positions 21 to 128 in SEQ ID NO: 19, (n) an amino acid sequence having at least 95% or higher homology to any of the sequences (g) to (m), and (o) an amino acid sequence derived from any of the sequences (g) to (m) by the deletions, replacements, or additions of at least one amino acid.
(7) The antibody according to (6), wherein the antibody has a heavy chain variable region and a light chain variable region selected from the group consisting of a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 13, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 14, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 15, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 16, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 17, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 18, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 19, a heavy chain variable region comprising an amino acid sequence described in amino acid positions 20 to 141 in SEQ ID NO: 12 and a light chain variable region comprising an amino acid sequence described in amino acid positions 21 to 128 in SEQ ID NO: 13, a heavy chain variable region comprising an amino acid sequence described in amino acid positions 20 to 141 in SEQ ID NO: 12 and a light chain variable region comprising an amino acid sequence described in amino acid positions 21 to 128 in SEQ ID NO: 14, a heavy chain variable region comprising an amino acid sequence described in amino acid positions 20 to 141 in SEQ ID NO: 12 and a light chain variable region comprising an amino acid sequence described in amino acid positions 21 to 128 in SEQ ID NO: 15, and a heavy chain variable region comprising an amino acid sequence described in amino acid positions 20 to 141 in SEQ ID NO: 12 and a light chain variable region comprising an amino acid sequence described in amino acid positions 21 to 128 in SEQ ID NO: 16.

(8) The antibody according to (6) or (7), wherein the antibody comprises a heavy chain and a light chain selected from the group consisting of a heavy chain comprising an amino acid sequence described in amino acid positions 20 to 471 in SEQ ID NO: 9 and a light chain comprising an amino acid sequence described in amino acid positions 21 to 233 in SEQ ID NO: 13, a heavy chain comprising an amino acid sequence described in amino acid positions 20 to 471 in SEQ ID NO: 9 and a light chain comprising an amino acid sequence described in amino acid positions 21 to 233 in SEQ ID NO: 14, a heavy chain comprising an amino acid sequence described in amino acid positions 20 to 471 in SEQ ID NO: 9 and a light chain comprising an amino acid sequence described in amino acid positions 21 to 233 in SEQ ID NO: 15, a heavy chain comprising an amino acid sequence described in amino acid positions 20 to 471 in SEQ ID NO: 9 and a light chain comprising an amino acid sequence described in amino acid positions 21 to 233 in SEQ ID NO: 16, a heavy chain comprising an amino acid sequence described in amino acid positions 20 to 471 in SEQ ID NO: 9 and a light chain comprising an amino acid sequence described in amino acid positions 21 to 233 in SEQ ID NO: 17, a heavy chain comprising an amino acid sequence described in amino acid positions 20 to 471 in SEQ ID NO: 9 and a light chain comprising an amino acid sequence described in amino acid positions 21 to 233 in SEQ ID NO: 18, a heavy chain comprising an amino acid sequence described in amino acid positions 20 to 471 in SEQ ID NO: 9 and a light chain comprising an amino acid sequence described in amino acid positions 21 to 233 in SEQ ID NO: 19, a heavy chain comprising an amino acid sequence described in amino acid positions 20 to 471 in SEQ ID NO: 12 and a light chain comprising an amino acid sequence described in amino acid positions 21 to 233 in SEQ ID NO: 13, a heavy chain comprising an amino acid sequence described in amino acid positions 20 to 471 in SEQ ID NO: 12 and a light chain comprising an amino acid sequence described in amino acid positions 21 to 233 in SEQ ID NO: 14, a heavy chain comprising an amino acid sequence described in amino acid positions 20 to 471 in SEQ ID NO: 12 and a light chain comprising an amino acid sequence described in amino acid positions 21 to 233 in SEQ ID NO: 15, and a heavy chain comprising an amino acid sequence described in amino acid positions 20 to 471 in SEQ ID NO: 12 and a light chain comprising an amino acid sequence described in amino acid positions 21 to 233 in SEQ ID NO: 16.

(9) The antibody according to any of (6) to (8), wherein the antibody comprises a heavy chain and a light chain selected from the group consisting of a heavy chain comprising the amino acid sequence represented by SEQ ID NO: 9 and a light chain comprising the amino acid sequence represented by SEQ ID NO: 13, a heavy chain comprising the amino acid sequence represented by SEQ ID NO: 9 and a light chain comprising the amino acid sequence represented by SEQ ID NO: 14, a heavy chain comprising the amino acid sequence represented by SEQ ID NO: 9 and a light chain comprising the amino acid sequence represented by SEQ ID NO: 15, a heavy chain comprising the amino acid sequence represented by SEQ ID NO: 9 and a light chain comprising the amino acid sequence represented by SEQ ID NO: 16, a heavy chain comprising the amino acid sequence represented by SEQ ID NO: 9 and a light chain comprising the amino acid sequence represented by SEQ ID NO: 17, a heavy chain comprising the amino acid sequence represented by SEQ ID NO: 9 and a light chain comprising the amino acid sequence represented by SEQ ID NO: 18, a heavy chain comprising the amino acid sequence represented by SEQ ID NO: 9 and a light chain comprising the amino acid sequence represented by SEQ ID NO: 19, a heavy chain comprising the amino acid sequence represented by SEQ ID NO: 12 and a light chain comprising the amino acid sequence represented by SEQ ID NO: 13, a heavy chain comprising the amino acid sequence represented by SEQ ID NO: 12 and a light chain comprising the amino acid sequence represented by SEQ ID NO: 14, a heavy chain comprising the amino acid sequence represented by SEQ ID NO: 12 and a light chain comprising the amino acid sequence represented by SEQ ID NO: 15, and a heavy chain comprising the amino acid sequence represented by SEQ ID NO: 12 and a light chain comprising the amino acid sequence represented by SEQ ID NO: 16.

(10) The antibody according to (8) or (9), wherein the antibody lacks an amino acid at the carboxy terminus of the amino acid sequence represented by SEQ ID NO: 9 or 12 in the heavy chain.

(11) An antibody yielded by a method for producing the antibody according to any of (1) to (10), the method comprising the steps of: culturing a host cell transformed with an expression vector containing a polynucleotide encoding the antibody; and collecting the antibody of interest from the cultures yielded in the preceding step.

(12) The antibody according to any of (1) to (11), wherein the modification of a glycan is regulated in order to enhance antibody-dependent cytotoxic activity.

Hereinafter, the B7-H3 antibody used in the invention is described.

The terms "cancer" and "tumor" as used herein are used with the same meaning.

The term "gene" as used herein includes not only DNA, but also mRNA thereof, cDNA thereof and cRNA thereof.

The term "polynucleotide" as used herein is used with the same meaning as a nucleic acid and also includes DNA, RNA, probes, oligonucleotides, and primers.

The terms "polypeptide" and "protein" as used herein are used without distinction.

The term "cell" as used herein also includes cells in an animal individual and cultured cells.

The term "B7-H3" as used herein is used in the same meaning as B7-H3 protein, and also refers to B7-H3 variant 1 and/or B7-H3 variant 2.

The term "CDR" as used herein refers to a complementarity determining region (CDR), and it is known that each heavy and light chain of an antibody molecule has three complementarity determining regions (CDRs). The CDR is also called the hypervariable region, and is present in a variable region of each heavy and light chain of an antibody. It is a site which has unusually high variability in its primary structure, and there are three separate CDRs in the primary structure of each heavy and light polypeptide chain. In this specification, as for the CDRs of an antibody, the CDRs of the heavy chain are represented by CDRH1, CDRH2, and CDRH3 from the amino-terminal side of the amino acid sequence of the heavy chain, and the CDRs of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The phrase "hybridization is performed under stringent conditions" as used herein refers to a process in which hybridization is performed under conditions under which identification can be achieved by performing hybridization at 68° C. in a commercially available hybridization solution ExpressHyb Hybridization Solution (manufactured by Clontech, Inc.) or by performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. B7-H3

B7-H3 is a member of the B7 family expressed on antigen-presenting cells as a co-stimulatory molecule, and is considered to act on a receptor on T cells to enhance or suppress immune activity.

B7-H3 is a protein having a single-pass transmembrane structure, and the N-terminal extracellular domain of B7-H3 contains two variants. The B7-H3 variant 1 (4Ig-B7-H3) contains a V-like or C-like Ig domain at two sites, respectively, and the B7-H3 variant 2 (2Ig-B7-H3) contains a V-like or C-like Ig domain at one site, respectively.

As for B7-H3 to be used in the invention, B7-H3 can be directly purified from B7-H3-expressing cells of a human or a non-human mammal (such as a rat or a mouse) and used, or a cell membrane fraction of the above-described cells can be prepared and used. Further, B7-H3 can be yielded by in vitro synthesis thereof or production thereof in a host cell through genetic engineering. In the genetic engineering, specifically, after B7-H3 cDNA is integrated into a vector capable of expressing B7-H3 cDNA, B7-H3 can be yielded by synthesizing it in a solution containing an enzyme, a substrate and an energy substance required for transcription and translation, or by expressing B7-H3 in another prokaryotic or eucaryotic transformed host cell.

The amino acid sequence of an open reading frame (ORF) of a human B7-H3 variant 1 gene is represented by SEQ ID NO: 1 in the Sequence Listing. Further, the sequence of SEQ ID NO: 1 is shown in FIG. 1.

The amino acid sequence of an ORF of a human B7-H3 variant 2 gene is represented by SEQ ID NO: 2 in the Sequence Listing. Further, the sequence of SEQ ID NO: 2 is shown in FIG. 2.

Further, a protein which consists of an amino acid sequence wherein one or several amino acids are substituted, deleted and/or added in any of the above-described amino acid sequences of B7-H3 and also has a biological activity equivalent to that of the protein is also included in B7-H3.

Mature human B7-H3 variant 1 from which the signal sequence has been removed corresponds to an amino acid sequence consisting of amino acid residues 27 to 534 of the amino acid sequence represented by SEQ ID NO: 1. Further, mature human B7-H3 variant 2 from which the signal sequence has been removed corresponds to an amino acid sequence consisting of amino acid residues 27 to 316 of the amino acid sequence represented by SEQ ID NO: 2.

2. Production of Anti-B7-H3 Antibody

The antibody against B7-H3 of the invention can be yielded by immunizing an animal with B7-H3 or an arbitrary polypeptide selected from the amino acid sequence of B7-H3, and collecting and purifying the antibody produced in vivo according to a common procedure. The biological species of B7-H3 to be used as an antigen is not limited to being human, and an animal can be immunized with B7-H3 derived from an animal other than humans such as a mouse or a rat. In this case, by examining the cross-reactivity between an antibody binding to the yielded heterologous B7-H3 and human B7-H3, an antibody applicable to a human disease can be selected.

Further, a monoclonal antibody can be yielded from a hybridoma established by fusing antibody-producing cells which produce an antibody against B7-H3 with myeloma cells according to a known method (for example, Kohler and Milstein, Nature, (1975) 256, pp. 495-497; Kennet, R. ed., Monoclonal Antibodies, pp. 365-367, Plenum Press, N.Y. (1980)).

B7-H3 to be used as an antigen can be yielded by expressing B7-H3 gene in a host cell using genetic engineering.

Specifically, a vector capable of expressing B7-H3 gene is produced, and the resulting vector is transfected into a host cell to express the gene, and then, the expressed B7-H3 is purified. Hereinafter, a method of yielding an antibody against B7-H3 is specifically described.

(1) Preparation of Antigen

Examples of the antigen to be used for producing the anti-B7-H3 antibody include B7-H3, a polypeptide consisting of a partial amino acid sequence comprising at least 6 consecutive amino acids of B7-H3, and a derivative yielded by adding a given amino acid sequence or carrier thereto.

B7-H3 can be purified directly from human tumor tissues or tumor cells and used. Further, B7-H3 can be yielded by synthesizing it in vitro or by producing it in a host cell by genetic engineering.

With respect to the genetic engineering, specifically, after B7-H3 cDNA is integrated into a vector capable of expressing B7-H3 cDNA, B7-H3 can be yielded by synthesizing it in a solution containing an enzyme, a substrate and an energy substance required for transcription and translation, or by expressing B7-H3 in another prokaryotic or eucaryotic transformed host cell.

Further, the antigen can also be yielded as a secretory protein by expressing a fusion protein yielded by ligating the extracellular domain of B7-H3, which is a membrane protein, to the constant region of an antibody in an appropriate host-vector system.

B7-H3 cDNA can be yielded by, for example, a so-called PCR method in which a polymerase chain reaction (hereinafter referred to as "PCR") is performed using a cDNA library expressing B7-H3 cDNA as a template and primers which specifically amplify B7-H3 cDNA (see Saiki, R. K., et al., Science, (1988) 239, pp. 487-489).

As the in vitro synthesis of the polypeptide, for example, Rapid Translation System (RTS) manufactured by Roche Diagnostics, Inc. can be exemplified, but it is not limited thereto.

Examples of the prokaryotic host cells include *Escherichia coli* and *Bacillus subtilis*. In order to transform the host cells with a target gene, the host cells are transformed by a plasmid vector comprising a replicon, i.e., a replication origin derived from a species compatible with the host, and a regulatory sequence. Further, the vector preferably has a sequence capable of imposing phenotypic selectivity on the transformed cell.

Examples of the eucaryotic host cells include vertebrate cells, insect cells, and yeast cells. As the vertebrate cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61); and the like are often used, however, the cells are not limited thereto.

The thus yielded transformant can be cultured according to a common procedure, and by the culturing of the transformant, a target polypeptide is produced intracellularly or extracellularly.

A suitable medium to be used for the culturing can be selected from various commonly used culture media depending on the employed host cells. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues (SEQ ID NO: 42) to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-described methods, a large amount of a target polypeptide can be easily produced in high yield and high purity.

(2) Production of Anti-B7-H3 Monoclonal Antibody

Examples of the antibody specific binding to B7-H3 include a monoclonal antibody specific binding to B7-H3, and a method of yielding the antibody is as described below.

The production of a monoclonal antibody generally requires the following operational steps of:

(a) purifying a biopolymer to be used as an antigen;

(b) preparing antibody-producing cells by immunizing an animal by injection of the antigen, collecting the blood, assaying its antibody titer to determine when the spleen is excised;

(c) preparing myeloma cells (hereinafter referred to as "myeloma");

(d) fusing the antibody-producing cells with the myeloma;

(e) screening a group of hybridomas producing a desired antibody;

(f) dividing the hybridomas into single cell clones (cloning);

(g) optionally, culturing the hybridoma or rearing an animal implanted with the hybridoma for producing a large amount of a monoclonal antibody;

(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, B7-H3 prepared by the method as described above or a partial peptide thereof can be used.

Further, a membrane fraction prepared from recombinant cells expressing B7-H3 or the recombinant cells expressing B7-H3 themselves, and also a partial peptide of the protein of the invention chemically synthesized by a method known to those skilled in the art can also be used as the antigen.

(b) Preparation of Antibody-Producing Cells

The antigen yielded in the step (a) is mixed with an adjuvant such as Freund's complete or incomplete adjuvant or aluminum potassium sulfate and the resulting mixture is used as an immunogen to immunize an experimental animal. As the experimental animal, any animal used in a known hybridoma production method can be used without any trouble. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of a mouse or a rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 and the like can be used, and in the case of a rat, for example, Wistar, Low, Lewis, Sprague, Dawley, ACI, BN, Fischer and the like can be used.

These mice and rats are commercially available from breeders/distributors of experimental animals, for example, CLEA Japan, Inc. and Charles River Laboratories Japan, Inc.

Among these, in consideration of compatibility of fusing with myeloma cells described below, in the case of a mouse, BALB/c strain, and in the case of a rat, Wistar and Low strains are particularly preferred as the animal to be immunized.

Further, in consideration of antigenic homology between humans and mice, it is also preferred to use a mouse having decreased biological function to remove auto-antibodies, that is, a mouse with an autoimmune disease.

The age of such mouse or rat at the time of immunization is preferably 5 to 12 weeks of age, more preferably 6 to 8 weeks of age.

In order to immunize an animal with B7-H3 or a recombinant thereof, for example, a known method described in detail in, for example, Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Springfield, Ill. (1964) or the like can be used.

Among these immunization methods, a preferred specific method in the invention is, for example, as follows.

That is, first, a membrane protein fraction serving as the antigen or cells caused to express the antigen is/are intradermally or intraperitoneally administrated to an animal.

However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual difference or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal, individual differences or the like, however, the dose is generally set to 0.05 to 5 mg, preferably about 0.1 to 0.5 mg.

A booster immunization is performed 1 to 6 weeks, preferably 2 to 4 weeks, more preferably 2 to 3 weeks after the administration of the antigen as described above.

The dose of the antigen at the time of performing the booster immunization varies depending on the type or size of animal or the like, however, in the case of, for example, a mouse, the dose is generally set to 0.05 to 5 mg, preferably 0.1 to 0.5 mg, more preferably about 0.1 to 0.2 mg.

Spleen cells or lymphocytes including antibody-producing cells are aseptically removed from the immunized animal 1 to 10 days, preferably 2 to 5 days, more preferably 2 to 3 days after the booster immunization. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto.

For example, if an ELISA method is employed, the measurement of the antibody titer in the invention can be carried out according to the procedures as described below.

First, a purified or partially purified antigen is adsorbed to the surface of a solid phase such as a 96-well plate for ELISA, and the surface of the solid phase having no antigen adsorbed thereto is covered with a protein unrelated to the antigen such as bovine serum albumin (hereinafter referred to as "BSA"). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody. After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495). For example, in the case of spleen cells, a general method in which the antibody-producing cells are separated by homogenizing the spleen to yield the cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1(P3U1), X63-Ag8.653(X63.653), SP2/0-Ag14(SP2/0), MPC11-45.6TG1.7(45.6TG), FO, S149/5XXO, and BU.1 derived from mice; 210.RSY3.Ag.1.2.3(Y3) derived from rats; and U266AR(SKO-007), GM1500.GTG-A12 (GM1500), UC729-6, LICR-LOW-HMy2(HMy2) and 8226AR/NIP4-1(NP41) derived from humans. These HGPRT-deficient strains are available from, for example, the American Type Culture Collection (ATCC) or the like.

These cell strains are subcultured in an appropriate medium such as an 8-azaguanine medium [a medium yielded by adding 8-azaguanine to an RPMI 1640 medium supplemented with glutamine, 2-mercaptoethanol, gentamicin, and fetal calf serum (hereinafter referred to as "FCS")], Iscove's Modified Dulbecco's Medium (hereinafter referred to as "IMDM"), or Dulbecco's Modified Eagle Medium (hereinafter referred to as "DMEM"). In this case, 3 to 4 days before performing cell fusion, the cells are subcultured in a normal medium [for example, an ASF104 medium (manufactured by Ajinomoto Co., Ltd.) containing 10% FCS] to ensure not less than $2 \times 10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987), Kabat, E. A. and Mayer, M. M., Experimental Immunochemistry, Charles C Thomas Publisher, Springfield, Ill. (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used. Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40° C., preferably from 35 to 38° C. for 1 to 10 minutes, preferably 5 to 8 minutes.

(e) Selection of a Group of Hybridomas

The method of selecting hybridomas yielded by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are yielded using the myeloma cells of an HGPRT-deficient strain which cannot survive in the presence of aminopterin.

That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell-HY Selection Medium D (manufactured by StemCell Technologies, inc., #03804) and cultured. Then, the formed hybridoma colonies are collected, whereby monoclonal hybridomas can be yielded. The collected respective hybridoma colonies are cultured, and a hybridoma which has been confirmed to have a stable antibody titer in an yielded hybridoma culture supernatant is selected as a B7-H3 monoclonal antibody-producing hybridoma strain.

Examples of the thus established hybridoma strain include B7-H3 hybridoma M30. In this specification, an antibody produced by the B7-H3 hybridoma M30 is referred to as "M30 antibody" or simply "M30".

The heavy chain of the M30 antibody has an amino acid sequence represented by SEQ ID NO: 20 in the Sequence Listing. Further, the light chain of the M30 antibody has an amino acid sequence represented by SEQ ID NO: 21 in the Sequence Listing. In the heavy chain amino acid sequence represented by SEQ ID NO: 20 in the Sequence Listing, an amino acid sequence consisting of amino acid residues 1 to 19 is a signal sequence, an amino acid sequence consisting of amino acid residues 20 to 141 is a variable region, and an amino acid sequence consisting of amino acid residues 142 to 471 is a constant region. Further, in the light chain amino acid sequence represented by SEQ ID NO: 21 in the Sequence Listing, an amino acid sequence consisting of amino acid residues 1 to 22 is a signal sequence, an amino acid sequence consisting of amino acid residues 23 to 130 is a variable region, and an amino acid sequence consisting of amino acid residues 131 to 235 is a constant region.

(g) Preparation of Monoclonal Antibody by Culturing Hybridoma

By culturing the thus selected hybridoma, a monoclonal antibody can be efficiently yielded. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma yielded by the method described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture. From the supernatant yielded by the large-scale culture, a monoclonal antibody which specifically binds to the protein of the invention can be yielded by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be yielded.

In the case where the hybridoma is administrated in the abdominal cavity, if a mineral oil such as 2,6,10,14-tetramethyl pentadecane (pristane) is administrated 3 to 7 days prior thereto, a larger amount of the ascites can be yielded.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is administrated in the abdominal cavity of the mouse. In general, when the abdomen is expanded and filled with the ascites, the ascites is collected from the mouse. By this method, the monoclonal antibody can be yielded at a concentration which is about 100 times or much higher than that in the culture solution.

The monoclonal antibody yielded by the above-described method can be purified by a method described in, for example, Weir, D. M.: Handbook of Experimental Immunology Vol. I, II, III, Blackwell Scientific Publications, Oxford (1978).

The thus yielded monoclonal antibody has high antigen specificity for B7-H3.

(h) Assay of Monoclonal Antibody

The isotype and subclass of the thus yielded monoclonal antibody can be determined as follows.

First, examples of the identification method include an Ouchterlony method, an ELISA method, and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm [1.4 (OD 280)=Immunoglobulin 1 mg/ml].

Further, even when the monoclonal antibody is separately and independently yielded by performing again the steps of (a) to (h) in (2), it is possible to yield an antibody having a cytotoxic activity equivalent to that of the M30 antibody. As one example of such an antibody, an antibody which binds to the same epitope as the M30 antibody can be exemplified. The M30 recognizes an epitope in the IgC1 or IgC2 domain, which is a domain in the B7-H3 extracellular domain, and binds to the IgC1 domain or the IgC2 domain or both. Therefore, as the epitope for the antibody of the invention, particularly, an epitope present in the IgC1 or IgC2 domain of B7-H3 can be exemplified. If a newly produced monoclonal antibody binds to a partial peptide or a partial tertiary structure to which the M30 antibody binds, it can be determined that the monoclonal antibody binds to the same epitope as the M30 antibody. Further, by confirming that the monoclonal antibody competes with the M30 antibody for the binding to B7-H3 (that is, the monoclonal antibody inhibits the binding between the M30 antibody and B7-H3), it can be determined that the monoclonal antibody binds to the same epitope as the M30 antibody even if the specific epitope sequence or structure has not been determined. When it is confirmed that the monoclonal antibody binds to the same epitope as the M30 antibody, the monoclonal antibody is strongly expected to have a cytotoxic activity equivalent to that of the M30 antibody.

(3) Other Antibodies

The antibody of the invention includes not only the above-described monoclonal antibody against B7-H3 but also a recombinant antibody yielded by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (see Proc. Natl. Acad. Sci. USA, 81, 6851-6855, (1984)).

As the humanized antibody, an antibody yielded by integrating only a complementarity determining region (CDR) into a human-derived antibody (see Nature (1986) 321, pp. 522-525), and an antibody yielded by grafting a part of the amino acid residues of the framework as well as the CDR sequence to a human antibody by a CDR-grafting method (WO 90/07861) can be exemplified.

However, the humanized antibody derived from the M30 antibody is not limited to a specific humanized antibody as long as the humanized antibody has all 6 types of CDR sequences of the M30 antibody and has an antitumor activity. The heavy chain variable region of the M30 antibody has CDRH1 (NYVMH) consisting of an amino acid sequence represented by SEQ ID NO: 3 in the Sequence Listing, CDRH2 (YINPYNDDVKYNEKFKG) consisting of an amino acid sequence represented by SEQ ID NO: 4 in the Sequence Listing, and CDRH3 (WGYYGSPLYYFDY) consisting of an amino acid sequence represented by SEQ ID NO: 5 in the Sequence Listing. Further, the light chain variable region of the M30 antibody has CDRL1 (RASSR-LIYMH) consisting of an amino acid sequence represented by SEQ ID NO: 6 in the Sequence Listing, CDRL2 (ATSN-LAS) consisting of an amino acid sequence represented by SEQ ID NO: 7 in the Sequence Listing, and CDRL3 (QQWNSNPPT) consisting of an amino acid sequence represented by SEQ ID NO: 8 in the Sequence Listing.

As an example of the humanized antibody of a mouse antibody M30, an arbitrary combination of a heavy chain comprising a heavy chain variable region consisting of any one of (1) an amino acid sequence consisting of amino acid residues 20 to 141 of SEQ ID NO: 9, 10, 11, or 12 in the Sequence Listing, (2) an amino acid sequence having a homology of at least 95% or more with the amino acid sequence (1) described above, and (3) an amino acid sequence wherein one or several amino acids in the amino acid sequence (1) described above are deleted, substituted or added and a light chain comprising a light chain variable region consisting of any one of (4) an amino acid sequence consisting of amino acid residues 21 to 128 of SEQ ID NO: 13, 14, 15, 16, 17, 18, or 19 in the Sequence Listing, (5) an amino acid sequence having a homology of at least 95% or more with the amino acid sequence (4) described above, and (6) an amino acid sequence wherein one or several amino acids in the amino acid sequence (4) described above are deleted, substituted or added can be exemplified.

The term "several" as used herein refers to 1 to 10, 1 to 9, 1 to 8, 1 to 7, 1 to 6, 1 to 5, 1 to 4, 1 to 3, or 1 or 2.

As the amino acid substitution in this specification, a conservative amino acid substitution is preferred. The conservative amino acid substitution refers to a substitution occurring within a group of amino acids related to amino acid side chains. Preferred amino acid groups are as follows: an acidic group (aspartic acid and glutamic acid); a basic group (lysine, arginine, and histidine); a non-polar group (alanine, valine, leucine, isoleucine, proline, phenylalanine, methionine, and tryptophan); and an uncharged polar family (glycine, asparagine, glutamine, cysteine, serine, threonine, and tyrosine). More preferred amino acid groups are as follows: an aliphatic hydroxy group (serine and threonine); an amide-containing group (asparagine and glutamine); an aliphatic group (alanine, valine, leucine, and isoleucine); and an aromatic group (phenylalanine, tryptophan, and tyrosine). Such an amino acid substitution is preferably performed within a range which does not impair the properties of a substance having the original amino acid sequence.

As an antibody which has a preferred combination of a heavy chain and a light chain described above, an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 13; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 14; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 15; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 16; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 17; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 18; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 19; an antibody consisting of a heavy chain comprising a heavy chain variable region consisting of an amino acid sequence consisting of amino acid residues 20 to 141 of SEQ ID NO: 12 and a light chain comprising a light chain variable region consisting of an amino acid sequence consisting of amino acid residues 21 to 128 of SEQ ID NO: 13; an antibody consisting of a heavy chain comprising a heavy chain variable region consisting of an amino acid sequence consisting of amino acid residues 20 to 141 of SEQ ID NO: 12 and a light chain comprising a light chain variable region consisting of an amino acid sequence consisting of amino acid residues 21 to 128 of SEQ ID NO: 14; an antibody consisting of a heavy chain comprising a heavy chain variable region consisting of an amino acid sequence consisting of amino acid residues 20 to 141 of SEQ ID NO: 12 and a light chain comprising a light chain variable region consisting of an amino acid sequence consisting of amino acid residues 21 to 128 of SEQ ID NO: 15; and an antibody consisting of a heavy chain comprising a heavy chain variable region consisting of an amino acid sequence consisting of amino acid residues 20 to 141 of SEQ ID NO: 12 and a light chain comprising a light chain variable region consisting of an amino acid sequence consisting of amino acid residues 21 to 128 of SEQ ID NO: 16 can be exemplified.

Further, as an antibody which has a more preferred combination of a heavy chain and a light chain described above, an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 13; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 14; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 15; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 16; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 17; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 18; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 19; an antibody consisting of a heavy chain consisting of an amino acid sequence consisting of amino acid residues 20 to 471 of SEQ ID NO: 12 and a light chain consisting of an amino acid sequence consisting of amino acid residues 21 to 233 of SEQ ID NO: 13; an antibody consisting of a heavy chain consisting of an amino acid sequence consisting of amino acid residues 20 to 471 of SEQ ID NO: 12 and a light chain consisting of an amino acid sequence consisting of amino acid residues 21 to 233 of SEQ ID NO: 14; an antibody consisting of a heavy chain consisting of an amino acid sequence consisting of amino acid residues 20 to 471 of SEQ ID NO: 12 and a light chain consisting of an amino acid sequence consisting of amino acid residues 21 to 233 of SEQ ID NO: 15; and an antibody consisting of a heavy chain consisting of an amino acid sequence consisting of amino acid residues 20 to 471 of SEQ ID NO: 12 and a light chain consisting of an amino acid sequence consisting of amino acid residues 21 to 233 of SEQ ID NO: 16 can be exemplified.

Furthermore, as an antibody which has another more preferred combination of a heavy chain and a light chain described above, an antibody consisting of a heavy chain consisting of an amino acid sequence of SEQ ID NO: 9 and a light chain consisting of an amino acid sequence of SEQ ID NO: 13; an antibody consisting of a heavy chain consisting of an amino acid sequence of SEQ ID NO: 9 and a light chain consisting of an amino acid sequence of SEQ ID NO: 14; an antibody consisting of a heavy chain consisting of an amino acid sequence of SEQ ID NO: 9 and a light chain consisting of an amino acid sequence of SEQ ID NO: 15; an antibody consisting of a heavy chain consisting of an amino acid sequence of SEQ ID NO: 9 and a light chain consisting of an amino acid sequence of SEQ ID NO: 16; an antibody consisting of a heavy chain consisting of an amino acid sequence of SEQ ID NO: 9 and a light chain consisting of an amino acid sequence of SEQ ID NO: 17; an antibody consisting of a heavy chain consisting of an amino acid sequence of SEQ ID NO: 9 and a light chain consisting of an amino acid sequence of SEQ ID NO: 18; an antibody consisting of a heavy chain consisting of an amino acid sequence of SEQ ID NO: 9 and a light chain consisting of an amino acid sequence of SEQ ID NO: 19; an antibody consisting of a heavy chain consisting of an amino acid sequence of SEQ ID NO: 12 and a light chain consisting of an amino acid sequence of SEQ ID NO: 13; an antibody consisting of a heavy chain consisting of an amino acid sequence of SEQ ID NO: 12 and a light chain consisting of an amino acid sequence of SEQ ID NO: 14; an antibody consisting of a heavy chain consisting of an amino acid sequence of SEQ ID NO: 12 and a light chain consisting of an amino acid sequence of SEQ ID NO: 15; and an antibody consisting of a heavy chain consisting of an amino acid sequence of SEQ ID NO: 12 and a light chain consisting of an amino acid sequence of SEQ ID NO: 16 can be exemplified.

By combining a sequence having a high homology with the above-described heavy chain amino acid sequence with a sequence having a high homology with the above-described light chain amino acid sequence, it is possible to select an antibody having a cytotoxic activity equivalent to that of each of the above-described antibodies. Such a homology is generally a homology of 80% or more, preferably a homology of 90% or more, more preferably a homology of 95% or more, most preferably a homology of 99% or more. Further, by combining an amino acid sequence wherein one to several amino acid residues are substituted, deleted or added in the heavy chain or light chain amino acid sequence, it is also possible to select an antibody having a cytotoxic activity equivalent to that of each of the above-described antibodies.

The homology between two amino acid sequences can be determined using default parameters of Blast algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can be used also through the Internet by accessing the site www.ncbi.nlm.nih.gov/blast.

In the heavy chain amino acid sequence represented by SEQ ID NO: 9, 10, 11 or 12 in the Sequence Listing, an amino acid sequence consisting of amino acid residues 1 to 19 is a signal sequence, an amino acid sequence consisting of amino acid residues 20 to 141 is a variable region, and an amino acid sequence consisting of amino acid residues 142 to 471 is a constant region. The sequence of SEQ ID NO: 9, 10, 11 and 12 are shown in FIGS. 3, 4, 5 and 6 respectively. Further, in the light chain amino acid sequence represented by SEQ ID NO: 13, 14, 15, 16, 17, 18 or 19 in the Sequence Listing, an amino acid sequence consisting of amino acid residues 1 to 20 is a signal sequence, an amino acid sequence consisting of amino acid residues 21 to 128 is a variable region, and an amino acid sequence consisting of amino acid residues 129 to 233 is a constant region. The sequence of SEQ ID NO: 13, 14, 15, 16, 17, 18 and 19 are shown in FIGS. 7, 8, 9, 10, 11, 12 and 13 respectively.

Further, the antibody of the invention includes a human antibody which binds to the same epitope as the M30 antibody. An anti-B7-H3 human antibody refers to a human antibody having only a sequence of an antibody derived from a human chromosome. The anti-B7-H3 human antibody can be yielded by a method using a human antibody-producing mouse having a human chromosome fragment comprising heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a recombinant DNA technique, by using cDNAs encoding each of such a heavy chain and a light chain of a human antibody, and preferably a vector comprising such cDNAs, eukaryotic cells are transformed, and a transformant cell which produces a recombinant human monoclonal antibody is cultured, whereby the antibody can also be yielded from the culture supernatant.

Here, as the host, for example, eukaryotic cells, preferably mammalian cells such as CHO cells, lymphocytes, or myeloma cells can be used.

Further, a method of yielding a phage display-derived human antibody selected from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Ophthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be yielded by preparing an expression vector comprising the sequence and introducing the vector into an appropriate host to express it (WO 92/01047, WO 92/20791, WO 93/06213, WO 93/11236, WO 93/19172, WO 95/01438, WO 95/15388, Annu. Rev. Immunol. (1994) 12, pp. 433-455, Nature Biotechnology (2005) 23 (9), pp. 1105-1116).

If a newly produced human antibody binds to a partial peptide or a partial tertiary structure to which the M30 antibody binds, it can be determined that the human antibody binds to the same epitope as the M30 antibody. Further, by confirming that the human antibody competes with the M30 antibody for the binding to B7-H3 (that is, the human antibody inhibits the binding between the M30 antibody and B7-H3), it can be determined that the human antibody binds to the same epitope as the M30 antibody even if the specific epitope sequence or structure has not been determined. When it is confirmed that the human antibody binds to the same epitope as the M30 antibody, the human antibody is strongly expected to have a cytotoxic activity equivalent to that of the M30 antibody.

The chimeric antibodies, humanized antibodies, or human antibodies yielded by the above-described method are evaluated for the binding property to an antigen by a known method or the like, and a preferred antibody can be selected.

As one example of another index for use in the comparison of the properties of antibodies, the stability of antibodies can be exemplified. The differential scanning calorimetry (DSC) is a device capable of quickly and accurately measuring a thermal denaturation midpoint temperature (Tm) to be used as a favorable index of the relative conformational stability of proteins. By measuring the Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following features: the yield in an appropriate host cell is high; and the aggregability in an aqueous solution is low. For example, an antibody which shows the highest yield does not always show the highest thermal stability, and therefore, it is necessary to select an antibody most suitable for the administration to humans by making comprehensive evaluation based on the above-described indices.

In the invention, a modified variant of the antibody is also included. The modified variant refers to a variant yielded by subjecting the antibody of the invention to chemical or biological modification. Examples of the chemically modified variant include variants chemically modified by linking a chemical moiety to an amino acid skeleton, variants chemically modified with an N-linked or O-linked carbohydrate chain, etc. Examples of the biologically modified variant include variants yielded by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell.

Further, an antibody labeled so as to enable the detection or isolation of the antibody or an antigen of the invention, for example, an enzyme-labeled antibody, a fluorescence-labeled antibody, and an affinity-labeled antibody are also included in the meaning of the modified variant. Such a modified variant of the antibody of the invention is useful for improving the stability and blood retention of the original antibody of the invention, reducing the antigenicity thereof, detecting or isolating such an antibody or an antigen, and so on.

Further, by regulating the modification of a glycan which is linked to the antibody of the invention (glycosylation, defucosylation, etc.), it is possible to enhance an antibody-dependent cellular cytotoxic activity. As the technique for regulating the modification of a glycan of antibodies, WO 99/54342, WO 00/61739, WO 02/31140, etc. are known. However, the technique is not limited thereto. In the antibody of the invention, an antibody in which the modification of a glycan is regulated is also included.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately.

In the case where eukaryotic cells are used as the host, animal cells, plant cells, and eukaryotic microorganisms can be used. As the animal cells, mammalian cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61) can be exemplified.

In the case where prokaryotic cells are used, for example, *Escherichia coli* and *Bacillus subtilis* can be exemplified.

By introducing a desired antibody gene into these cells through transformation, and culturing the thus transformed cells in vitro, the antibody can be yielded. In the above-described culture method, the yield may sometimes vary depending on the sequence of the antibody, and therefore, it is possible to select an antibody which is easily produced as a pharmaceutical by using the yield as an index among the antibodies having an equivalent binding activity. Therefore, in the antibody of the invention, an antibody yielded by a method of producing an antibody, characterized by including a step of culturing the transformed host cell and a step of collecting a desired antibody from a cultured product yielded in the culturing step is also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of a complement, the antibody-dependent cellular cytotoxicity, etc.) of the antibody. Therefore, in the invention, an antibody subjected to such modification is also included, and a deletion variant in which one or two amino acids have been deleted at the carboxyl terminus of the heavy chain, a variant yielded by amidation of the deletion variant (for example, a heavy chain in which the carboxyl terminal proline residue has been amidated), and the like can be exemplified. The type of deletion variant having a deletion at the carboxyl terminus of the heavy chain of the antibody according to the invention is not limited to the above variants as long as the antigen-binding affinity and the effector function are conserved. The two heavy chains constituting the antibody according to the invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the invention and the culture conditions, however, a case where one amino acid residue at the carboxyl terminus has been deleted in both of the two heavy chains contained as main components in the antibody according to the invention can be exemplified.

As isotype of the antibody of the invention, for example, IgG (IgG1, IgG2, IgG3, IgG4) can be exemplified, and IgG1 or IgG2 can be exemplified preferably.

As the function of the antibody, generally an antigen-binding activity, an activity of neutralizing the activity of an antigen, an activity of enhancing the activity of an antigen, an antibody-dependent cellular cytotoxicity (ADCC) activity and a complement-dependent cytotoxicity (CDC) activity can be exemplified. The function of the antibody of the invention is a binding activity to B7-H3, preferably an antibody-dependent cell-mediated phagocytosis (ADCP) activity, more preferably a cytotoxicity activity (antitumor activity) to tumor cell mediated by an ADCP activity. Further, the antibody of the invention may have an ADCC activity and/or a CDC activity in addition to an ADCP activity.

The yielded antibody can be purified to homogeneity. The separation and purification of the antibody may be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified. For example, as a column using a Protein A column, Hyper D, POROS, Sepharose FF (Pharmacia) and the like can be exemplified.

Further, by using a carrier having an antigen immobilized thereon, the antibody can also be purified utilizing the binding property of the antibody to the antigen.

[Antitumor Compound]

The antitumor compound to be conjugated to the antibody-drug conjugate of the present invention is explained.

The antitumor compound is not particularly limited if it is a compound having an antitumor effect and a substituent group or a partial structure allowing connecting to a linker structure. When a part or whole linker is cleaved in tumor cells, the antitumor compound moiety is released to exhibit the antitumor effect of the antitumor compound. As the linker is cleaved at a connecting position to drug, the antitumor compound is released in its intrinsic structure to exhibit its intrinsic antitumor effect.

Examples of the antitumor compound can include doxorubicin, daunorubicin, mitomycin C, bleomycin, cyclocytidine, vincristine, vinblastine, methotrexate, platinum-based antitumor agent (cisplatin or derivatives thereof), taxol or derivatives thereof, and camptothecin or derivatives thereof (antitumor agent described in Japanese Patent Laid-Open No. 6-87746). In the antibody-drug conjugate of the present invention, exatecan as a camptothecin derivative (((1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione; shown in the following formula) can be preferably used.

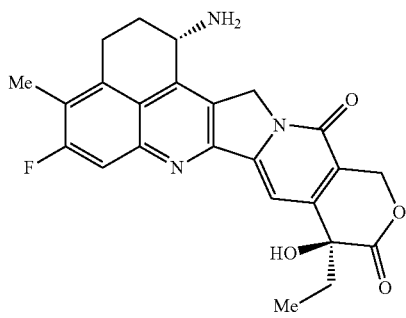

[Formula 29]

Although having an excellent antitumor effect, exatecan has not been commercialized as an antitumor drug. The compound can be easily obtained by a known method and the amino group at position 1 can be preferably used as a connecting position to the linker structure. Further, although exatecan can be also released in tumor cells while part of the linker is still attached thereto, it is an excellent compound exhibiting an excellent antitumor effect even in such case.

With regard to the antibody-drug conjugate, the number of conjugated drug molecules per antibody molecule is a key factor having an influence on the efficacy and safety. Production of the antibody-drug conjugate is performed by defining the reaction condition including the amounts of use of raw materials and reagents for reaction so as to have a constant number of conjugated drug molecules, a mixture containing different numbers of conjugated drug molecules is generally obtained unlike the chemical reaction of a low-molecular-weight compound. The number of drugs conjugated in an antibody molecule is expressed or specified by the average value, that is, the average number of conjugated drug molecules. Unless specifically described otherwise as a principle, the number of conjugated drug molecules means an average value except in a case in which it represents an antibody-drug conjugate having a specific number of conjugated drug molecules that is included in an antibody-drug conjugate mixture having different number of conjugated drug molecules. The number of exatecan molecules conjugated to an antibody molecule is controllable, and as an average number of conjugated drug molecules per antibody, about 1 to 10 exatecans can be bound. Preferably, it is 2 to 8, and more preferably 3 to 8. Meanwhile, a person skilled in the art can design a reaction for conjugating a required number of drug molecules to an antibody molecule based on the description of the Examples of the present application and can obtain an antibody conjugated with a controlled number of exatecan molecules.

Because exatecan has a camptothecin structure, it is known that the equilibrium shifts to a structure with a closed lactone ring (closed ring) in an aqueous acidic medium (for example, pH 3 or so) but it shifts to a structure with an open lactone ring (open ring) in an aqueous basic medium (for example, pH 10 or so). A drug conjugate being introduced with an exatecan residue corresponding to the closed ring structure and the open ring structure is also expected to have the same antitumor effect and it is needless to say that any of them is within the scope of the present invention.

[Linker Structure]

1. Linker Having Hydrophilic Structure

The antibody-drug conjugate of the present invention is characterized by a linker structure in which a hydrophilic structure moiety is formed. This hydrophilic structure moiety is present in the $L^P$ moiety, $L^1$ moiety, or $L^2$ moiety of the linker and pulural of them may have the hydrophilic structure. This hydrophilic structure corresponds to the following cases. In case of linker $L^P$, either of the two following forms corresponds to, i.e., $L^P$ is a peptide residue having a hydrophilic amino acid other than glycin at its N terminal, or $L^P$ is a peptide residue in which the C terminal is an oligopeptide consisting of 2 or 3 or more glycines and is connected to the drug, and further, even in case that a hydrophilic amino acid is present at N terminal, no other hydrophilic amino acid than glycine is present thereat, in case of $L^1$, $L^1$ corresponds to the form of -(Succinimid-3-yl-N)—CH[—(CH$_2$)n$^3$-COOH]—C(=O)—, in case of $L^2$, $L^2$ corresponds to the form of —N[—(CH$_2$CH$_2$—O)n$^7$-CH$_2$CH$_2$—OH]—CH$_2$—C(=O)—.

Hereinbelow, the linker of the present invention is described. The linker of the present invention has a structure represented by the following formula:

-$L^1$-$L^2$-$L^P$-NH—(CH$_2$)n$^1$-$L^a$-$L^b$-$L^c$- or -$L^1$-$L^2$-$L^P$-

The antibody is connected to the terminal of $L^1$, terminal opposite to the connecting position to $L^2$. The antitumor drug is connected to the terminal of $L^c$, terminal opposite to the connecting position to $L^b$, or the terminal of $L^P$, terminal opposite to the connecting position to $L^2$.

n$^1$ represents an integer of 0 to 6 and is preferably an integer of 1 to 5, and more preferably 1 to 3.

2. Hydrophilic Structure in $L^P$

The hydrophilic structure of each moiety in the linker is described. As for linker $L^P$, two forms are present as the hydrophilic structure. One of them is a structure in which the peptide residue $L^P$ is a peptide residue having a hydrophilic amino acid at its N terminal and, also, this N-terminal hydrophilic amino acid is a hydrophilic amino acid other than glycine.

The total number of amino acids constituting such a peptide linker can be in a range of from 3 to 8. The hydrophilic amino acid other than glycine can be aspartic acid, glutamic acid, lysine, serine, threonine, glutamine, asparagine, histidine, tyrosine, or arginine. Among them, glutamic acid, aspartic acid, or lysine is preferred, and aspartic acid is more preferred. The number of this hydrophilic amino acid can be 1 or more and is preferably 1 or 2, and more preferably 1.

A peptide following this hydrophilic amino acid can be in a range of from 2 to 7 in total and more preferably consists of 3 or 4 amino acids. This peptide can be a peptide consisting of amino acids selected from phenylalanine (Phe; F), tyrosine (Tyr; Y), leucine (Leu; L), glycine (Gly; G), alanine (Ala; A), valine (Val; V), lysine (Lys; K), citrulline (Cit), serine (Ser; S), glutamic acid (Glu; E), aspartic acid (Asp; D), and the like. Further, the amino acids constituting the peptide can be any of L- and D-amino acids and are preferably L-amino acids. Further, the amino acids may be amino acids having a structure such as β-alanine, ε-aminocaproic acid, or γ-aminobutyric acid in addition to α-amino acids. Further, they can be non-natural type amino acids such as N-methylated amino acids. Among them, preferred examples can include phenylalanine, glycine, valine, lysine, citrulline, serine, glutamic acid, and aspartic acid. The peptide after the second amino acid counted from the N terminal in the peptide residue of the linker is preferably GGF or GGFG (SEQ ID NO: 33).

The peptide residue $L^P$ of the linker having a hydrophilic amino acid at the N terminal is preferably DGGF (SEQ ID NO: 34), KGGF (SEQ ID NO: 35), EGGF (SEQ ID NO: 36), DGGFG (SEQ ID NO: 37), KGGFG (SEQ ID NO: 38), or EGGFG (SEQ ID NO: 39), more preferably DGGF (SEQ ID NO: 34), KGGF (SEQ ID NO: 35), DGGFG (SEQ ID NO: 37), or KGGFG (SEQ ID NO: 38), and further preferably DGGF (SEQ ID NO: 34) or DGGFG (SEQ ID NO: 37).

Another form in which $L^P$ becomes a hydrophilic linker can include a case in which the C terminal is an oligopeptide consisting of 2 or 3 or more glycines and is connected to the drug, and also, even in case that a hydrophilic amino acid is present at N terminal, no other hydrophilic amino acid than glycine is present thereat. Although glycine is also classified as a hydrophilic amino acid, it is preferable that a plurality of glycines are connected to the C terminal when glycine is selected as the hydrophilic amino acid in the peptide linker. Such a glycine oligopeptide can consist of 2 or 3 or more glycines and is preferably glycine di- or tri-peptide.

When linker $L^P$ has the hydrophilic structure containing the glycine oligopeptide, preferred examples thereof can include GGFGG (SEQ ID NO: 40) and GGFGGG (SEQ ID NO: 41).

Also, when $L^P$ has the hydrophilic structure containing the glycine oligopeptide at the C terminal, a further feature of this peptide residue of the linker is that $L^P$ having this structure is directly connected to the drug.

When oligopeptide consisting of 2 or 3 or more glycines is present at the C terminal and is connected to the drug, a peptide sequence other than this moiety in the peptide linker $L^P$ can be a peptide consisting of amino acids selected from phenylalanine, glycine, valine, lysine, citrulline, serine, glutamic acid, and aspartic acid. However, in this case, the N terminal of the peptide residue of the linker is not aspartic acid, glutamic acid, lysine, serine, threonine, glutamine, asparagine, histidine, tyrosine, or arginine listed above as the hydrophilic amino acid.

The amino acids constituting the peptide can be any of L- and D-amino acids and are preferably L-amino acids. Further, the amino acids may be amino acids having a structure such as β-alanine, ε-aminocaproic acid, or γ-aminobutyric acid in addition to α-amino acids. Further, they can be non-natural type amino acids such as N-methylated amino acids. As for the number of the amino acids, the peptide can consist of 4 to 8 amino acids and more preferably consists of 4 to 6 amino acids.

3. $L^P$

The liner $L^P$ may be in a form that does not have the hydrophilic structure, as mentioned below. Specifically, even when linker $L^P$ does not have the hydrophilic structure, linker $L^P$ can consist of an oligopeptide residue in which 3 to 8 amino acids are linked by a peptide bonding. $L^P$ is connected to $L^2$ at its N terminal and is connected to the —NH—$(CH_2)n^1$-$L^a$-$L^b$-$L^c$- moiety of the linker at its C terminal or directly to the antitumor compound at its C terminal, in case of exatecan, it is connected to the amino group at position 1 thereof.

The amino acid constituting $L^P$ that does not have the hydrophilic linker is not particularly limited as long as it is not the amino acid constituting $L^P$ having the hydrophilic structure. The amino acid can be any of L- and D-amino acids and is preferably an L-amino acid. Further, it can be an amino acid having a structure such as β-alanine, ε-aminocaproic acid, or γ-aminobutyric acid in addition to an α-amino acid. Further, it can be a non-natural type amino acid such as N-methylated amino acid.

The amino acid sequence of such $L^P$ is not particularly limited, but examples of the constituting amino acid can include phenylalanine, tyrosine, leucine, glycine, alanine, valine, lysine, citrulline, serine, glutamic acid, and aspartic acid. Among them, preferred examples can include phenylalanine, glycine, valine, lysine, citrulline, serine, glutamic acid, and aspartic acid. Depending on the type of the amino acid, drug release pattern can be controlled. The number of the amino acid can be between 3 to 8.

Specific examples of $L^P$ that does not form the hydrophilic structure in the linker can include

-GGF-

-GGFG (SEQ ID NO: 33)-

-GFLG (SEQ ID NO: 43)-.

Among them, -GGF- or -GGFG (SEQ ID NO: 33)- can be preferably used.

In the structure moiety represented by —NH—$(CH_2)n^1$- in the linker, $n^1$ is an integer of 0 to 6 and is preferably an integer of 1 to 5, and more preferably 1 to 3. The amino group of this moiety is connected to the C terminal of $L^P$.

4. Hydrophilic structure in $L^1$ or $L^2$

When linker $L^1$ takes a form of -(Succinimid-3-yl-N)—CH[—$(CH_2)n^3$-COOH]—C(=O)—, this moiety corresponds to the hydrophilic linker according to the present invention. $n^3$ is an integer of 1 to 8 and is preferably 2 to 4, and more preferably 2. In —$(CH_2)n^3$-COOH of this hydrophilic structure moiety, the carboxy group may be a hydroxy group or an amino group. When $L^1$ in the linker is -(Succinimid-3-yl-N)—CH[—$(CH_2)n^3$-COOH]—C(=O)—, $L^2$ in the linker is —NH—$(CH_2$—$CH_2$—O$)n^6$-$CH_2$—$CH_2$—C(=O)— wherein $n^6$ is 0 to 4, preferably.

When linker $L^2$ takes a form of —N[—$(CH_2CH_2$—O$)n^7$-$CH_2CH_2$—OH]—$CH_2$—C(=O)—, this moiety corresponds to the hydrophilic structure according to the present invention. $n^7$ is an integer of 1 to 4 and is preferably 3 or 4. This linker is connected to $L^1$ at its terminal amino group and is connected to the N terminal of $L^P$ at its carbonyl group at the other terminal.

The presence of the linker having the hydrophilic structure described above can achieve the excellent release of the drug component having an antitumor effect.

5. $L^1$

The linker $L^1$ is the linker represented by the following structure of -(Succinimid-3-yl-N)—$(CH_2)n^2$-C(=O)—, -(Succinimid-3-yl-N)—CH[—$(CH_2)n^3$-COOH]—C(=O)—, —$CH_2$—C(=O)—NH—$(CH_2)n^4$-C(=O)—, —C(=O)-cyc.Hex (1,4)-$CH_2$—(N-ly-3-diminiccuS)-, or —C(=O)—$(CH_2)n^5$-C(=O)—. Wherein, $n^2$ is an integer of 2 to 8, $n^3$ is an integer of 1 to 8, and $n^4$ is an integer of 1 to 8, and $n^5$ is an integer of 1 to 8.

In the linker having a structure represented by -(Succinimid-3-yl-N)—(CH$_2$)n$^2$-C(=O)-m among L$^1$, "-(Succinimid-3-yl-N)—" has a structure represented by the following formula:

[Formula 30]

Position 3 of the above partial structure is a connecting position to the antibody. And further, the bond to the antibody at this position 3 is characterized by connecting with the formation of thioether at a disulfide bond moiety in a hinge part of the antibody. On the other hand, the nitrogen atom at position 1 of this structure moiety is connected to the carbon atom of methylene which is present within the linker including this structure. Specifically, -(Succinimid-3-yl-N)—(CH$_2$)n$^2$-C(=O)-L$^2$- is a structure represented by the following formula (herein, "antibody-S-" originates from an antibody).

[Formula 31]

Anibody-S—[structure]—N—(CH$_2$)n$^2$—C(=O)—L$^2$—

In the formula, n$^2$ is an integer of 2 to 8, and preferably 2 to 5.

Among L$^1$, -(Succinimid-3-yl-N)—CH[—(CH$_2$)n$^3$-COOH]—C(=O)— is the hydrophilic structure mentioned above.

In the linker having a structure represented by —CH$_2$—C(=O)—NH—(CH$_2$)n$^4$-C(=O)— among L$^1$, n$^4$ is an integer of 1 to 8, preferably 2 to 6. This linker is connected to the antibody at its carbon atom of terminal methylene and, as with the preceding, has the following structure for connection by forming thioether, (herein, "antibody-S-" originates from an antibody).

Antibody-S—CH$_2$—C(=O)—NH—(CH$_2$)n$^4$-C(=O)-L$^2$-.

In the linker having a structure represented by —C(=O)-cyc.Hex(1,4)-CH$_2$—(N-ly-3-diminiccuS)- among L$^1$, "(N-ly-3-diminiccuS)-" has a structure represented by the following formula:

[Formula 32]

In this structure moiety, the nitrogen atom at position 1 is connected to the carbon atom of methylene present in the linker structure containing this structure. The carbon atom at position 3 is connected to —S—(CH$_2$)n$^8$-C(=O)— among linker L$^2$ at its terminal sulfur atom. This —S—(CH$_2$)n$^8$-C(=O)— among linker L$^2$ forms a linker structure only combined with —C(=O)-cyc.Hex(1,4)-CH$_2$—(N-ly-3-diminiccuS)- among linker L$^1$. In the above, "-cyc.Hex(1,4)-" contained in the linker represents a 1,4-cyclohexylene group. The linker —C(=O)-cyc.Hex(1,4)-CH$_2$—(N-ly-3-diminiccuS)- is connected to the antibody by forming amide bond at its terminal carbonyl carbon (herein, "antibody-NH—" originates from an antibody).

[Formula 33]

Antibody-NH—[structure]—CH$_2$—N—S—(CH$_2$)n$^8$—C(=O)—L$^P$—

The amino group of the antibody forming this amide bond may be an amino group in a lysine residue in the antibody or that at the N terminal of the antibody. The linker can be conneted by amide bond as well as with ester bond formation with the hydroxy group carried by an amino acid in the antibody.

The structure moiety "-cyc.Hex(1,4)-" in the linker may be a divalent saturated cyclic alkylene group other than the 1,4-cyclohexylene group, i.e., a divalent cyclic saturated hydrocarbon group such as a cyclobutylene group, a cyclopentylene group, a cycloheptalene group, or a cyclooctalene group. The moiety may also be a divalent aromatic hydrocarbon group such as a phenylene group or a naphthylene group, or a 5- or 6-membered saturated, partially saturated, or aromatic divalent heterocyclic group containing 1 or 2 heteroatoms. Alternatively, this moiety may be a divalent alkylene group having 1 to 4 carbon atoms. The divalent group may be at adjacent positions or at distant positions.

In the linker having a structure represented by —C(=O)—(CH$_2$)n$^5$-C(=O)— among L$^1$, n$^5$ is an integer of 1 to 8, and preferably 2 to 6. This linker is also connected by forming amide bond at its terminal carbonyl group with an amino group of an amino acid in the antibody, as with the linker mentioned above (see the following formula; in the structure thereof, "antibody-NH—" originates from an antibody).

Antibody-NH—C(=O)—(CH$_2$)n$^5$-C(=O)-L$^2$-.

Specific examples of L$^1$ in the linker can include
-(Succinimid-3-yl-N)—CH$_2$CH$_2$—C(=O)—
-(Succinimid-3-yl-N)—CH$_2$CH$_2$CH$_2$—C(=O)—
-(Succinimid-3-yl-N)—CH$_2$CH$_2$CH$_2$CH$_2$—C(=O)—
-(Succinimid-3-yl-N)—CH$_2$CH$_2$CH$_2$CH$_2$CH$_2$—C(=O)—
-(Succinimid-3-yl-N)—CH(—CH$_2$—COOH)—C(=O)—
-(Succinimid-3-yl-N)—CH(—CH$_2$CH$_2$—COOH)—C(=O)—
-(Succinimid-3-yl-N)—CH(—CH$_2$CH$_2$CH$_2$—COOH)—C(=O)—
-(Succinimid-3-yl-N)—CH(—CH$_2$CH$_2$CH$_2$CH$_2$—COOH)—C(=O)—
-(Succinimid-3-yl-N)—CH(—CH$_2$CH$_2$CH$_2$CH$_2$CH$_2$—COOH)—C(=O)—
-(Succinimid-3-yl-N)—CH(—CH$_2$CH$_2$CH$_2$CH$_2$CH$_2$CH$_2$—COOH)—C(=O)—
-(Succinimid-3-yl-N)—CH(—CH$_2$CH$_2$CH$_2$CH$_2$CH$_2$CH$_2$CH$_2$—COOH)—C(=O)—
-(Succinimid-3-yl-N)—CH(—CH$_2$CH$_2$CH$_2$CH$_2$CH$_2$CH$_2$CH$_2$CH$_2$—COOH)—C(=O)—

—CH$_2$—C(=O)—NH—CH$_2$—C(=O)—
—CH$_2$—C(=O)NH—CH$_2$CH$_2$—C(=O)—
—CH$_2$—C(=O)NH—CH$_2$CH$_2$CH$_2$—C(=O)—
—CH$_2$—C(=O)NH—CH$_2$CH$_2$CH$_2$CH$_2$—C(=O)—
—CH$_2$—C(=O)NH—CH$_2$CH$_2$CH$_2$CH$_2$CH$_2$—C(=O)—
—C(=O)-cyc.Hex(1,4)-CH$_2$—(N-ly-3-diminiccuS)-
—C(=O)-Aryl-CH$_2$—(N-ly-3-diminiccuS)-
—C(=O)-cyc.Het-CH$_2$—(N-ly-3-diminiccuS)-
—C(=O)—CH$_2$—C(=O)—
—C(=O)—CH$_2$CH$_2$—C(=O)—
—C(=O)—CH$_2$CH$_2$CH$_2$—C(=O)—
—C(=O)—CH$_2$CH$_2$CH$_2$CH$_2$—C(=O)—
—C(=O)—CH$_2$CH$_2$CH$_2$CH$_2$CH$_2$—C(=O)—
—C(=O)—CH$_2$CH$_2$CH$_2$CH$_2$CH$_2$CH$_2$—C(=O)—.

(Aryl represents a divalent aromatic hydrocarbon group, and cyc.Het represents a divalent cyclic heterocyclic group).

6. $L^2$

Linker $L^2$ is a linker represented by the following structure: —NH—(CH$_2$—CH$_2$—O)n$^6$-CH$_2$—CH$_2$—C(=O)—, —N[—(CH$_2$CH$_2$—O)n$^7$-CH$_2$CH$_2$—OH]—CH$_2$—C(=O)—, or —S—(CH$_2$)n$^8$-C(=O)—, $L^2$ may not be present, and in such a case, $L^2$ is a single bond. And, n$^6$ is an integer of 0 to 6, n$^7$ is an integer of 1 to 4, and n$^8$ is an integer of 1 to 6.

In the linker having a structure represented by —NH—(CH$_2$CH$_2$O)n$^6$-CH$_2$—CH$_2$—C(=O)— among $L^2$, n$^6$ is an integer of 0 to 6, and preferably 2 to 4. Said linker is connected to $L^1$ at the nitrogen atom of its terminal amino group and is connected to the N terminal of $L^P$ at its carbonyl group at the other terminal. When $L^1$ is -(Succinimid-3-yl-N)—CH[—(CH$_2$)n$^3$-COOH]—C(=O)—, only —NH—(CH$_2$CH$_2$O)n$^6$-CH$_2$—CH$_2$—C(=O)— wintin $L^2$ is connected to this and also n$^6$ is 0.

Among $L^2$, the linker represented by —N[—(CH$_2$CH$_2$—O)n$^7$-CH$_2$CH$_2$—OH]—CH$_2$—(C(=O)— is the hydrophilic structure previously mentioned.

In the linker having a structure represented by —S—(CH$_2$)n$^8$-C(=O)— among $L^2$, n$^8$ is an integer of 1 to 6, and preferably 2 to 4.

Specific examples of $L^2$ in the linker can include
—NH—CH$_2$CH$_2$—C(=O)—
—NH—CH$_2$CH$_2$O—CH$_2$CH$_2$—C(=O)—
—NH—CH$_2$CH$_2$O—CH$_2$CH$_2$O—CH$_2$CH$_2$—C(=O)—
—NH—CH$_2$CH$_2$O—CH$_2$CH$_2$O—CH$_2$CH$_2$O—CH$_2$CH$_2$—C(=O)—
—NH—CH$_2$CH$_2$O—CH$_2$CH$_2$O—CH$_2$CH$_2$O—CH$_2$CH$_2$O—CH$_2$CH$_2$—C(=O)—
—NH—CH$_2$CH$_2$O—CH$_2$CH$_2$O—CH$_2$CH$_2$O—CH$_2$CH$_2$O—CH$_2$CH$_2$O—CH$_2$CH$_2$—C(=O)—
—NH—CH$_2$CH$_2$O—CH$_2$CH$_2$O—CH$_2$CH$_2$O—CH$_2$CH$_2$O—CH$_2$CH$_2$O—CH$_2$CH$_2$O—CH$_2$CH$_2$—C(=O)—
—N(—CH$_2$CH$_2$—O—CH$_2$CH$_2$—OH)—CH$_2$—C(=O)—
—N(—CH$_2$CH$_2$—O—CH$_2$CH$_2$—O—CH$_2$CH$_2$—OH)—CH$_2$—C(=O)—
—N(—CH$_2$CH$_2$—O—CH$_2$CH$_2$—O—CH$_2$CH$_2$—O—CH$_2$CH$_2$—OH)—CH$_2$—C(=O)—
—N(—CH$_2$CH$_2$—O—CH$_2$CH$_2$—O—CH$_2$CH$_2$—O—CH$_2$CH$_2$—O—CH$_2$CH$_2$—OH)—CH$_2$—C(=O)—.

When $L^2$ is —S—(CH$_2$)n$^8$-C(=O)—, $L^1$ to be combined therewith is —C(=O)-cyc.Hex(1,4)-CH$_2$—(N-ly-3-diminiccuS)-. So the specific examples of -$L^1$-$L^2$- in the linker can include
—C(=O)-cyc.Hex(1,4)-CH$_2$—(N-ly-3-diminiccuS)-S—CH$_2$—C(=O)—
—C(=O)-cyc.Hex(1,4)-CH$_2$—(N-ly-3-diminiccuS)-S—CH$_2$CH$_2$—C(=O)—
—C(=O)-cyc.Hex(1,4)-CH$_2$—(N-ly-3-diminiccuS)-S—CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$CH$_2$CH$_2$—C(=O)—.

7. $L^a$

The linker $L^a$ is any of structures —C(=O)—NH—, —NR$^1$—(CH$_2$)n$^9$-, and —O— or is a single bond, wherein, n$^9$ is an integer of 1 to 6, R$^1$ is a hydrogen atom, an alkyl group having 1 to 6 carbon atoms, —(CH$_2$)n$^a$-COOH, or —(CH$_2$)n$^b$-OH, n$^a$ is an integer of 1 to 4, and n$^b$ is an integer of 1 to 6.

The amide structure —C(=O)—NH— among linker $L^a$ is connected to $L^b$ at its nitrogen atom side. In the structure moiety —NR$^1$—(CH$_2$)n$^9$- among linker $L^a$, n$^9$ is an integer of 1 to 6, and preferably 1 to 3. This moiety is connected to $L^b$ at its methylene side. R$^1$ is a hydrogen atom or an alkyl group having 1 to 6 carbon atoms. The alkyl group having 1 to 6 carbon atoms may be linear or branched. Examples thereof can include a methyl group, an ethyl group, a propyl group, an isopropyl group, a butyl group, an isobutyl group, a sec-butyl group, a tert-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. Of them, a methyl group or an ethyl group is preferred. When R$^1$ has a structure represented by —(CH$_2$)n$^a$-COOH, n$^a$ is an integer of 1 to 4, and preferably 1 or 2. When R$^1$ has a structure represented by —(CH$_2$)n$^b$-OH, n$^9$ is an integer of 1 to 6, and preferably 1 or 2. R$^1$ is preferably a hydrogen atom, a methyl group, an ethyl group, —CH$_2$COOH, —CH$_2$CH$_2$—COOH, or —CH$_2$CH$_2$—OH, and more preferably a hydrogen atom, a methyl group, or —CH$_2$COOH. It is further preferably a hydrogen atom. The $L^a$ moiety of the linker may be —O— or a single bond.

8. $L^b$

The linker $L^b$ is any of structures —CR$^2$(—R$^3$)—, —O—, and —NR$^4$— or is a single bond. In the above, R$^2$ and R$^3$ each independently represents a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ is a hydrogen atom or an alkyl group having 1 to 6 carbon atoms, n$^c$ is an integer of 0 to 6, n$^d$ is an integer of 1 to 4, and n$^e$ is an integer of 0 to 4. When n$^c$ or n$^e$ is 0, R$^2$ and R$^3$ are not the same as each other.

When each of R$^2$ and R$^3$ is an alkyl group, this alkyl group is interpreted as defined in the alkyl group of R$^1$. When each of R$^2$ and R$^3$ has a structure of —(CH$_2$)n$^c$-NH$_2$, n$^c$ is an integer of 0 to 6, and preferably 0, or is 3 to 5. When n$^c$ is 0, R$^2$ and R$^3$ are not the same as each other. When each of R$^2$ and R$^3$ has a structure of —(CH$_2$)n$^d$-COOH, n$^d$ is an integer of 1 to 4, and preferably 1 or 2. When each of R$^2$ and R$^3$ has a structure of —(CH$_2$)n$^e$-OH, n$^e$ is an integer of 0 to 4, and preferably 1 or 2.

Each of R$^2$ and R$^3$ is preferably a hydrogen atom, a methyl group, an ethyl group, —NH$_2$, —CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$, —CH$_2$COOH, —CH$_2$CH$_2$—COOH, —CH$_2$OOH, or —CH$_2$CH$_2$—OH, and more preferably a hydrogen atom, a methyl group, —$NH_2$, —$CH_2CH_2CH_2CH_2NH_2$, —$CH_2COOH$, —$CH_2CH_2$—COOH, —$CH_2OH$, or —$CH_2CH_2$—OH. They are further preferably hydrogen atoms.

When $R^4$ is an alkyl group having 1 to 6 carbon atoms, this alkyl group is interpreted as defined in the alkyl group of $R^1$. $R^4$ is preferably a hydrogen atom or a methyl group, and more preferably a hydrogen atom.

Specific examples of the structure represented by linker —NH—$(CH_2)n^1$-$L^a$-$L^b$- include
—NH—$CH_2$—
—NH—CH(-Me)-
—NH—C(-Me)$_2$-
—NH—$CH_2$—CHMe-
—NH—CH(—$CH_2OH$)—
—NH—CH(—$CH_2COOH$)—
—NH—CH(—$CH_2CH_2COOH$)—
—NH—CH(—$CH_2CH_2CH_2CH_2NH_2$)—
—NH—$CH_2CH_2$—
—NH—$CH_2$—O—$CH_2$—
—NH—$CH_2CH_2$—O—
—NH—$CH_2CH_2$—O—$CH_2$—
—NH—$CH_2CH_2$C(-Me)$_2$-
—NH—$CH_2CH_2$NH—
—NH—$CH_2CH_2$NH—$CH_2$—
—NH—$CH_2CH_2$NMe-$CH_2$—
—NH—$CH_2CH_2$NH—$CH_2CH_2$—
—NH—$CH_2CH_2$NMe-$CH_2CH_2$—
—NH—$CH_2CH_2$N(—$CH_2COOH$)—$CH_2$—
—NH—$CH_2CH_2$N(—$CH_2CH_2OH$)—$CH_2$—
—NH—$CH_2CH_2$N(—$CH_2CH_2OH$)—$CH_2CH_2$—
—NH—$CH_2CH_2CH_2$C(=O)—NHCH(—$CH_2OH$)—
—NH—$CH_2CH_2CH_2$C(=O)—NHCH(—$CH_2COOH$)—
—NH—$CH_2CH_2CH_2$C(=O)—NHCH(—$CH_2CH_2CH_2CH_2NH_2$)—
—NH—$CH_2CH_2CH_2$—
—NH—$CH_2CH_2CH_2CH_2$—
—NH—$CH_2CH_2CH_2CH_2CH_2$—
—NH—$CH_2CH_2CH_2CH_2$CH($NH_2$)—.

Of them, preferred examples thereof can include
—NH—$CH_2$—
—NH—$CH_2$—CH(Me)-
—NH—CH(—$CH_2OH$)—
—NH—CH(—$CH_2CH_2COOH$)—
—NH—$CH_2CH_2$—
—NH—$CH_2$—O—$CH_2$—
—NH—$CH_2CH_2$—O—
—NH—$CH_2CH_2$—O—$CH_2$—
—NH—$CH_2CH_2$C(-Me)$_2$-
—NH—$CH_2CH_2$NH—
—NH—$CH_2CH_2$NH—$CH_2$—
—NH—$CH_2CH_2$NMe-$CH_2$—
—NH—$CH_2CH_2$NMe-$CH_2CH_2$—
—NH—$CH_2CH_2$N(—$CH_2COOH$)—$CH_2$—
—NH—$CH_2CH_2$N(—$CH_2CH_2OH$)—$CH_2$—
—NH—$CH_2CH_2$N(—$CH_2CH_2OH$)—$CH_2CH_2$—
—NH—$CH_2CH_2CH_2$C(=O)—NHCH(—$CH_2OH$)—
—NH—$CH_2CH_2CH_2$C(=O)—NHCH(—$CH_2COOH$)—
—NH—$CH_2CH_2CH_2$—
—NH—$CH_2CH_2CH_2CH_2$—
—NH—$CH_2CH_2CH_2CH_2CH_2$—.

More preferred examples thereof can include
—NH—$CH_2$—
—NH—$CH_2CH_2$—
—NH—$CH_2$—O—$CH_2$—
—NH—$CH_2CH_2$—O—
—NH—$CH_2CH_2$—O—$CH_2$—
—NH—$CH_2CH_2$NH—
—NH—$CH_2CH_2$NH—$CH_2$—
—NH—$CH_2CH_2$N(—$CH_2COOH$)—$CH_2$—
—NH—$CH_2CH_2$N(—$CH_2CH_2OH$)—$CH_2CH_2$—
—NH—$CH_2CH_2CH_2$C(=O)—NHCH(—$CH_2COOH$)—
—NH—$CH_2CH_2CH_2$—
—NH—$CH_2CH_2CH_2CH_2$—
—NH—$CH_2CH_2CH_2CH_2CH_2$—.

Further preferred examples thereof can include
—NH—$CH_2$—
—NH—$(CH_2)_2$—
—NH—$(CH_2)$—
—NH—$CH_2$—O—$CH_2$— and
—NH—$(CH_2)_2$—O—$CH_2$—.

9. $L^c$

The linker $L^c$ is —$CH_2$— or —C(=O)—. Said linker is connected to the antitumor compound. The linker $L^c$ is more preferably —C(=O)—.

The chain length of the linker —NH—$(CH_2)n^1$-$L^a$-$L^b$-$L^c$ moiety is preferably a chain length of 4 to 7 atoms, and more preferably a chain length of 5 or 6 atoms.

With regard to the antibody-drug conjugate of the present invention, when it is transferred to the inside of tumor cells, the linker moiety is cleaved and the drug derivative having a structure represented by $NH_2$—$(CH_2)n^1$-$L^a$-$L^b$-$L^c$-(NH-DX) is released to express an antitumor activity. Examples of the antitumor derivative exhibiting an antitumor effect by releasing from the antibody-drug conjugate of the present invention include an antitumor derivative having a structure moiety in which the structure represented by —NH—$(CH_2)n^1$-$L^a$-$L^b$- of the linker is bound with L and has a terminal amino group, and the particularly preferred include the followings.

$NH_2$—$CH_2$—C(=O)—(NH-DX)
$NH_2$—$CH_2CH_2$—C(=O)—(NH-DX)
$NH_2$—$CH_2CH_2CH_2$—C(=O)—(NH-DX)
$NH_2$—$CH_2$—O—$CH_2$—C(=O)—(NH-DX)
$NH_2$—CH$CH_2$—O—CH—$CH_2$—C(=O)—(NH-DX)

Meanwhile, in case of $NH_2$—$CH_2$—O—$CH_2$—C(=O)—(NH-DX), as the aminal structure in the molecule is unstable, it again undergoes a self-decomposition to release the following HO—$CH_2$—C(=O)—(NH-DX). Those compounds can be also preferably used as a production intermediate of the antibody-drug conjugate of the present invention.

For the antibody-drug conjugate of the present invention in which exatecan is used as a drug, it is preferable that the drug-linker structure moiety having the structure described below is connected to an antibody. The average connected number of the drug-linker structure moiety per antibody can be 1 to 10. Preferably, it is 2 to 8, and more preferably 3 to 8. Preferred examples of the drug-linker structure moiety can include the followings.

10. Specific Example when $L^P$ has Hydrophilic Structure

A drug-linker structure moiety in which $L^P$ is a peptide residue having a hydrophilic amino acid at the N terminal is present in the form of -$L^1$-$L^2$-$L^P$-NH—$(CH_2)n^1$-$L^a$-$L^b$-$L^c$-(NH-DX) or -$L^1$-$L^2$-$L^P$-(NH-DX). The combinations of each part of the linkers constituting this drug-linker structure moiety are the followings.

When the drug-linker structure moiety is connected to the antibody via a thioether bond, $L^1$ is -(Succinimid-3-yl-N)—$(CH_2)n^2$-C(=O)— or —$CH_2$—C(=O)—NH—$(CH_2)n^4$-C(=O)—. When the drug-linker structure moiety is connected to the antibody via an amide bond, it is —C(=O)-cyc.Hex(1,4)-$CH_2$—(N-ly-3-diminiccuS)- or —C(=O)—$(CH_2)n^5$-C(=O)—.

As for the linker $L^2$, when $L^1$ is -(Succinimid-3-yl-N)—$(CH_2)n^2$-C(=O)— or —$CH_2$—C(=O)—NH—$(CH_2)n^4$-C(=O)—, this can be a single bond, when linker $L^1$ is —C(=O)—$(CH_2)n^5$-C(=O)—, this is selected from —NH—$(CH_2$—$CH_2$—O$)n^6$-$CH_2$—$CH_2$—C(=O)— and a single bond. And the linker —S—$(CH_2)n^8$-C(=O)— is used in combination with —C(=O)-cyc.Hex(1,4)-$CH_2$—(N-ly-3-diminiccuS)- among $L^1$.

The linker —NH—$(CH_2)n^1$-$L^a$-$L^b$-$L^c$- moiety preferably has a chain length of 3 to 7 atoms. The moiety more preferably has a chain length of 4 to 7 atoms in the linker and further preferably has a chain length of 5 or 6 atoms. Specific examples of the linker —NH—$(CH_2)n^1$-$L^a$-$L^b$- are as described above, —NH—$CH_2CH_2$—C(=O)—, —NH—$CH_2CH_2CH_2$—C(=O)—, —NH—$CH_2$—O—$CH_2$—C(=O)—, or —NH—$CH_2CH_2$—O—$CH_2$—C(=O)— is particularly preferred one.

The linker -$L^c$- moiety is preferably —C(=O)—.

Specific examples of the drug-linker structure moiety containing the peptide having a hydrophilic amino acid at the N terminal can include the followings.

Examples of the drug-linker structure moiety for conjugating the drug-linker structure moiety to the antibody via a thioether bond can include the following formulas:
-(Succinimid-3-yl-N)—$(CH_2)n^2$-C(=O)-DGGF (SEQ ID NO: 34)-NH—$(CH_2)n^1$-$L^a$-$L^b$-$L^c$-(NH-DX)
-(Succinimid-3-yl-N)—$(CH_2)n^2$-C(=O)-KGGF (SEQ ID NO: 35)-NH—$(CH_2)n^1$-$L^a$-$L^b$-$L^c$-(NH-DX)
-(Succinimid-3-yl-N)—$(CH_2 n^2$-C(=O)-EGGF (SEQ ID NO: 36)-NH—$(CH_2)n^1$-$L^a$-$L^b$-$L^c$-(NH-DX)
-(Succinimid-3-yl-N)—$(CH_2)n^2$-C(=O)-DGGFG (SEQ ID NO: 37)-NH—$(CH_2)n^1$-$L^a$-$L^b$-$L^c$-(NH-DX)
-(Succinimid-3-yl-N)—$(CH_2 n^2$-C(=O)-KGGFG (SEQ ID NO: 38)-NH—$(CH_2)n^1$-$L^a$-$L^b$-$L^c$-(NH-DX)
-(Succinimid-3-yl-N)—$(CH_2)n^2$-C(=O)-EGGFG (SEQ ID NO: 39)-NH—$(CH_2)n^1$-$L^a$-$L^b$-$L^c$-(NH-DX)
In the above formula, preferably, $n^2$ is 2 to 5, and the —NH—$(CH_2)n^1$-$L^a$-$L^b$-$L^c$- moiety is —NH—$CH_2CH_2$—C(=O)—, —NH—$CH_2CH_2CH_2$—C(=O)—, —NH—$CH_2$—O—$CH_2$—C(=O)—, or —NH—$CH_2CH_2$—O—$CH_2$—C(=O)—. Also, those which $L^p$ is directly connected to the drug are preferable.

More specifically, it is preferably represented by the following formula:
-(Succinimid-3-yl-N)—$(CH_2)n^2$-C(=O)-DGGF (SEQ ID NO: 34)-NH—$CH_2CH_2$—C(=O)—(NH-DX)
-(Succinimid-3-yl-N)—$(CH_2)n^2$-C(=O)-DGGF (SEQ ID NO: 34)-NH—$CH_2CH_2CH_2$—C(=O)—(NH-DX)
-(Succinimid-3-yl-N)—$(CH_2)n^2$-C(=O)-DGGF (SEQ ID NO: 34)-NH—$CH_2$—O—$CH_2$—$H_2$—C(=O)—(NH-DX)
-(Succinimid-3-yl-N)—$(CH_2)n^2$-C(=O)-DGGF (SEQ ID NO: 34)-NH—$CH_2CH_2$—O—$CH_2$—C(=O)—(NH-DX)
-(Succinimid-3-yl-N)—$(CH_2)n^2$-C(=O)-KGGF (SEQ ID NO: 35)-NH—$CH_2CH_2$—C(=O)—(NH-DX)
-(Succinimid-3-yl-N)—$(CH_2)n^2$-C(=O)-KGGF (SEQ ID NO: 35)-NH—$CH_2CH_2CH_2$—C(=O)—(NH-DX)
-(Succinimid-3-yl-N)—$(CH_2)n^2$-C(=O)-KGGF (SEQ ID NO: 35)-NH—$CH_2$—O—$CH_2$—$H_2$—C(=O)—(NH-DX)
-(Succinimid-3-yl-N)—$(CH_2)n^2$-C(=O)-KGGF (SEQ ID NO: 35)-NH—$CH_2CH_2$—O—$CH_2$—C(=O)—(NH-DX)
-(Succinimid-3-yl-N)—$(CH_2)n^2$-C(=O)-DGGFG (SEQ ID NO: 37)-NH—$CH_2CH_2$—C(=O)—(NH-DX)
-(Succinimid-3-yl-N)—$(CH_2)n^2$-C(=O)-DGGFG (SEQ ID NO: 37)-NH—$CH_2CH_2CH_2$—C(=O)—(NH-DX)
-(Succinimid-3-yl-N)—$(CH_2)n^2$-C(=O)-DGGFG (SEQ ID NO: 37)-NH—$CH_2$—O—$CH_2$—$H_2$—C(=O)—(NH-DX)
-(Succinimid-3-yl-N)—$(CH_2)n^2$-C(=O)-DGGFG (SEQ ID NO: 37)-NH—$CH_2CH_2$—O—$CH_2$—C(=O)—(NH-DX)
-(Succinimid-3-yl-N)—$(CH_2)n^2$-C(=O)-KGGFG (SEQ ID NO: 38)-NH—$CH_2CH_2$—C(=O)—(NH-DX)
-(Succinimid-3-yl-N)—$(CH_2)n^2$-C(=O)-KGGFG (SEQ ID NO: 38)-NH—$CH_2CH_2CH_2$—C(=O)—(NH-DX)
-(Succinimid-3-yl-N)—$(CH_2)n^2$-C(=O)-KGGFG (SEQ ID NO: 38)-NH—$CH_2$—O—$CH_2$—C(=O)—(NH-DX)
-(Succinimid-3-yl-N)—$(CH_2)n^2$-C(=O)-KGGFG (SEQ ID NO: 38)-NH—$CH_2CH_2$—O—$CH_2$—C(=O)—(NH-DX)
or the following formulas:
-(Succinimid-3-yl-N)—$(CH_2)n^2$-C(=O)-DGGF (SEQ ID NO: 34)-(NH-DX)
-(Succinimid-3-yl-N)—$(CH_2)n^2$-C(=O)-KGGF (SEQ ID NO: 35)-(NH-DX)
-(Succinimid-3-yl-N)—$(CH_2)n^2$-C(=O)-DGGFG (SEQ ID NO: 37)-(NH-DX)
-(Succinimid-3-yl-N)—$(CH_2)n^2$-C(=O)-KGGFG (SEQ ID NO: 38)-(NH-DX)
More preferably, $n^2$ is 2 or 5.

Further preferably, $n^2$ is 5, and it is represented by the following formulas:
-(Succinimid-3-yl-N)—$CH_2CH_2CH_2CH_2CH_2$—C(=O)-DGGF (SEQ ID NO: 34)-NH—$CH_2CH_2$—C(=O)—(NH-DX)
-(Succinimid-3-yl-N)—$CH_2CH_2CH_2CH_2CH_2$—C(=O)-DGGF (SEQ ID NO: 34)-NH—$CH_2CH_2CH_2$—C(=O)—(NH-DX)
-(Succinimid-3-yl-N)—$CH_2CH_2CH_2CH_2CH_2$—C(=O)-DGGF (SEQ ID NO: 34)-NH—$CH_2$—O—$CH_2$—C(=O)—(NH-DX)
-(Succinimid-3-yl-N)—$CH_2CH_2CH_2CH_2CH_2$—C(=O)-DGGF (SEQ ID NO: 34)-NH—$CH_2CH_2$—O—$CH_2$—C(=O)—(NH-DX)
-(Succinimid-3-yl-N)—$CH_2CH_2CH_2CH_2CH_2$—C(=O)-KGGF (SEQ ID NO: 35)-NH—$CH_2CH_2$—C(=O)—(NH-DX)
-(Succinimid-3-yl-N)—$CH_2CH_2CH_2CH_2CH_2$—C(=O)-KGGF (SEQ ID NO: 35)-NH—$CH_2CH_2CH_2$—C(=O)—(NH-DX)
-(Succinimid-3-yl-N)—$CH_2CH_2CH_2CH_2CH_2$—C(=O)-KGGF (SEQ ID NO: 35)-NH—$CH_2$—O—$CH_2$—C(=O)—(NH-DX)
-(Succinimid-3-yl-N)—$CH_2CH_2CH_2CH_2CH_2$—C(=O)-DGGFG (SEQ ID NO: 37)-NH—$CH_2CH_2$—C(=O)—(NH-DX)
-(Succinimid-3-yl-N)—$CH_2CH_2CH_2CH_2CH_2$—C(=O)-DGGFG (SEQ ID NO: 37)-NH—$CH_2CH_2CH_2$—C(=O)—(NH-DX)
-(Succinimid-3-yl-N)—$CH_2CH_2CH_2CH_2CH_2$—C(=O)-DGGFG (SEQ ID NO: 37)-NH—$CH_2$—O—$CH_2$—C(=O)—(NH-DX)
-(Succinimid-3-yl-N)—$CH_2CH_2CH_2CH_2CH_2$—C(=O)-DGGFG (SEQ ID NO: 37)-NH—$CH_2CH_2$—O—$CH_2$—C(=O)—(NH-DX)
-(Succinimid-3-yl-N)—$CH_2CH_2CH_2CH_2CH_2$—C(=O)-KGGFG (SEQ ID NO: 38)-NH—$CH_2CH_2$—C(=O)—(NH-DX)
-(Succinimid-3-yl-N)—$CH_2CH_2CH_2CH_2CH_2$—C(=O)-KGGFG (SEQ ID NO: 38)-NH—$CH_2CH_2CH_2$—C(=O)—(NH-DX)
-(Succinimid-3-yl-N)—$CH_2CH_2CH_2CH_2CH_2$—C(=O)-KGGFG (SEQ ID NO: 38)-NH—$CH_2$—O—$C_2$-C(=O)—(NH-DX)

-(Succinimid-3-yl-N)—CH$_2$CH$_2$CH$_2$CH$_2$CH$_2$—C(=O)-KGGFG (SEQ ID NO: 38)-NH—CH$_2$CH$_2$—O—CH$_2$—C(=O)—(NH-DX)
or the following formulas:
-(Succinimid-3-yl-N)—CH$_2$CH$_2$CH$_2$CH$_2$CH$_2$—C(=O)-DGGF (SEQ ID NO: 34)-(NH-DX)
-(Succinimid-3-yl-N)—CH$_2$CH$_2$CH$_2$CH$_2$CH$_2$—C(=O)-KGGF (SEQ ID NO: 35)-(NH-DX)
-(Succinimid-3-yl-N)—CH$_2$CH$_2$CH$_2$CH$_2$CH$_2$—C(=O)-DGGFG (SEQ ID NO: 37)-(NH-DX)
-(Succinimid-3-yl-N)—CH$_2$CH$_2$CH$_2$CH$_2$CH$_2$—C(=O)-KGGFG (SEQ ID NO: 38)-(NH-DX)

Among them, it is further preferably represented by the following formulas:
-(Succinimid-3-yl-N)—CH$_2$CH$_2$CH$_2$CH$_2$CH$_2$—C(=O)-DGGF (SEQ ID NO: 34)-NH—CH$_2$CH$_2$—C(=O)—(NH-DX)
-(Succinimid-3-yl-N)—CH$_2$CH$_2$CH$_2$CH$_2$CH$_2$—C(=O)-DGGF (SEQ ID NO: 34)-NH—CH$_2$CH$_2$CH$_2$—C(=O)—(NH-DX)
-(Succinimid-3-yl-N)—CH$_2$CH$_2$CH$_2$CH$_2$CH$_2$—C(=O)-DGGF (SEQ ID NO: 34)-NH—CH$_2$—O—CH$_2$—C(=O)—(NH-DX)
-(Succinimid-3-yl-N)—CH$_2$CH$_2$CH$_2$CH$_2$CH$_2$—C(=O)-DGGF (SEQ ID NO: 34)-NH—CH$_2$CH$_2$—O—CH$_2$—C(=O)—(NH-DX)
-(Succinimid-3-yl-N)—CH$_2$CH$_2$CH$_2$CH$_2$CH$_2$—C(=O)-DGGFG (SEQ ID NO: 37)-NH—CH$_2$CH$_2$—C(=O)—(NH-DX)
-(Succinimid-3-yl-N)—CH$_2$CH$_2$CH$_2$CH$_2$CH$_2$—C(=O)-DGGFG (SEQ ID NO: 37)-NH—CH$_2$CH$_2$CH$_2$—C(=O)—(NH-DX)
-(Succinimid-3-yl-N)—CH$_2$CH$_2$CH$_2$CH$_2$CH$_2$—C(=O)-DGGFG (SEQ ID NO: 37)-NH—CH$_2$—O—CH$_2$—C(=O)—(NH-DX)
-(Succinimid-3-yl-N)—CH$_2$CH$_2$CH$_2$CH$_2$CH$_2$—C(=O)-DGGFG (SEQ ID NO: 37)-NH—CH$_2$CH$_2$—O—CH$_2$—C(=O)—(NH-DX)
or the following formulas:
-(Succinimid-3-yl-N)—CH$_2$CH$_2$CH$_2$CH$_2$CH$_2$—C(=O)-DGGF (SEQ ID NO: 34)-(NH-DX)
-(Succinimid-3-yl-N)—CH$_2$CH$_2$CH$_2$CH$_2$CH$_2$—C(=O)-DGGFG (SEQ ID NO: 37)-(NH-DX)

Examples of another form of the drug-linker structure moiety for conjugating the drug-linker structure moiety to the antibody via a thioether bond can include the following formulas:
—CH$_2$—C(=O)—NH—(CH$_2$)n$^4$-C(=O)-DGGF (SEQ ID NO: 34)-NH—(CH$_2$)n$^1$-L$^a$-L$^b$-L$^c$-(NH-DX)
—CH$_2$—C(=O)—NH—(CH$_2$)n$^4$-C(=O)-KGGF (SEQ ID NO: 35)-NH—(CH$_2$)n$^1$-L$^a$-L$^b$-L$^c$-(NH-DX)
—CH$_2$—C(=O)—NH—(CH$_2$)n$^4$-C(=O)-EGGF (SEQ ID NO: 36)-NH—(CH$_2$)n$^1$-L$^a$-L$^b$-L$^c$-(NH-DX)
—CH$_2$—C(=O)—NH—(CH$_2$)n$^4$-C(=O)-DGGFG (SEQ ID NO: 37)-NH—(CH$_2$)n$^1$-L$^a$-L$^b$-L$^c$-(NH-DX)
—CH$_2$—C(=O)—NH—(CH$_2$)n$^4$-C(=O)-KGGFG (SEQ ID NO: 38)-NH—(CH$_2$)n$^1$-L$^a$-L$^b$-L$^c$-(NH-DX)
—CH$_2$—C(=O)—NH—(CH$_2$)n$^4$-C(=O)-EGGFG (SEQ ID NO: 39)-NH—(CH$_2$)n$^1$-L$^a$-L$^b$-L$^c$-(NH-DX)
In the above formula, preferably, n$^4$ is 2 to 5, and the —NH—(CH$_2$)n$^1$-L$^a$-L$^b$-L$^c$- moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^p$ is directly connected to the drug are preferable.

More specifically, it is preferably
—CH$_2$—C(=O)—NH—(CH$_2$)n$^4$-C(=O)-DGGF (SEQ ID NO: 34)-NH—CH$_2$CH$_2$—C(=O)—(NH-DX)
—CH$_2$—C(=O)—NH—(CH$_2$)n$^4$-C(=O)-DGGF (SEQ ID NO: 34)-NH—CH$_2$CH$_2$CH$_2$—C(=O)—(NH-DX)
—CH$_2$—C(=O)—NH—(CH$_2$)n$^4$-C(=O)-DGGF (SEQ ID NO: 34)-NH—CH$_2$—O—CH$_2$—C(=O)—(NH-DX)
—CH$_2$—C(=O)—NH—(CH$_2$)n$^4$-C(=O)-DGGF (SEQ ID NO: 34)-NH—CH$_2$CH$_2$—O—CH$_2$—C(=O)—(NH-DX)
—CH$_2$—C(=O)—NH—(CH$_2$)n$^4$-C(=O)-KGGF (SEQ ID NO: 35)-NH—CH$_2$CH$_2$—C(=O)—(NH-DX)
—CH$_2$—C(=O)—NH—(CH$_2$)n$^4$-C(=O)-KGGF (SEQ ID NO: 35)-NH—CH$_2$CH$_2$CH$_2$—C(=O)—(NH-DX)
—CH$_2$—C(=O)—NH—(CH$_2$)n$^4$-C(=O)-KGGF (SEQ ID NO: 35)-NH—CH$_2$—O—CH$_2$—C(=O)—(NH-DX)
—CH$_2$—C(=O)—NH—(CH$_2$)n$^4$-C(=O)-KGGF (SEQ ID NO: 35)-NH—CH$_2$CH$_2$—O—CH$_2$—C(=O)—(NH-DX)
—CH$_2$—C(=O)—NH—(CH$_2$)n$^4$-C(=O)-DGGFG (SEQ ID NO: 37)-NH—CH$_2$CH$_2$—C(=O)—(NH-DX)
—CH$_2$—C(=O)—NH—(CH$_2$)n$^4$-C(=O)-DGGFG (SEQ ID NO: 37)-NH—CH$_2$CH$_2$CH$_2$—C(=O)—(NH-DX)
—CH$_2$—C(=O)—NH—(CH$_2$)n$^4$-C(=O)-DGGFG (SEQ ID NO: 37)-NH—CH$_2$—O—CH$_2$—C(=O)—(NH-DX)
—CH$_2$—C(=O)—NH—(CH$_2$)n$^4$-C(=O)-DGGFG (SEQ ID NO: 37)-NH—CH$_2$CH$_2$—O—CH$_2$—C(=O)—(NH-DX)
—CH$_2$—C(=O)—NH—(CH$_2$)n$^4$-C(=O)-KGGFG (SEQ ID NO: 38)-NH—CH$_2$CH$_2$—C(=O)—(NH-DX)
—CH$_2$—C(=O)—NH—(CH$_2$)n$^4$-C(=O)-KGGFG (SEQ ID NO: 38)-NH—CH$_2$CH$_2$CH$_2$—C(=O)—(NH-DX)
—CH$_2$—C(=O)—NH—(CH$_2$)n$^4$-C(=O)-KGGFG (SEQ ID NO: 38)-NH—CH$_2$—O—CH$_2$—C(=O)—(NH-DX)
—CH$_2$—C(=O)—NH—(CH$_2$)n$^4$-C(=O)-KGGFG (SEQ ID NO: 38)-NH—CH$_2$CH$_2$—O—CH$_2$—C(=O)—(NH-DX)
or the following formulas:
—CH$_2$—C(=O)—NH—(CH$_2$)n$^4$-C(=O)-DGGF (SEQ ID NO: 34)-(NH-DX)
—CH$_2$—C(=O)—NH—(CH$_2$)n$^4$-C(=O)-KGGF (SEQ ID NO: 35)-(NH-DX)
—CH$_2$—C(=O)—NH—(CH$_2$)n$^4$-C(=O)-DGGFG (SEQ ID NO: 37)-(NH-DX)
—CH$_2$—C(=O)—NH—(CH$_2$)n$^4$-C(=O)-KGGFG (SEQ ID NO: 38)-NH—(NH-DX)

More preferably, n$^4$ is 2, and it is represented by
—CH$_2$—C(=O)—NH—CH$_2$CH$_2$—C(=O)-DGGF (SEQ ID NO: 34)-NH—CH$_2$CH$_2$—C(=O)—(NH-DX)
—CH$_2$—C(=O)—NH—CH$_2$CH$_2$—C(=O)-DGGF (SEQ ID NO: 34)-NH—CH$_2$CH$_2$CH$_2$—C(=O)—(NH-DX)
—CH$_2$—C(=O)—NH—CH$_2$CH$_2$—C(=O)-DGGF (SEQ ID NO: 34)-NH—CH$_2$—O—CH$_2$—C(=O)—(NH-DX)
—CH$_2$—C(=O)—NH—CH$_2$CH$_2$—C(=O)-DGGF (SEQ ID NO: 34)-NH—CH$_2$CH$_2$—O—CH$_2$—C(=O)—(NH-DX)
—CH$_2$—C(=O)—NH—CH$_2$CH$_2$—C(=O)-KGGF (SEQ ID NO: 35)-NH—CH$_2$CH$_2$—C(=O)—(NH-DX)
—CH$_2$—C(=O)—NH—CH$_2$CH$_2$—C(=O)-KGGF (SEQ ID NO: 35)-NH—CH$_2$CH$_2$CH$_2$—C(=O)—(NH-DX)
—CH$_2$—C(=O)—NH—CH$_2$CH$_2$—C(=O)-KGGF (SEQ ID NO: 35)-NH—CH$_2$—O—CH$_2$—C(=O)—(NH-DX)
—CH$_2$—C(=O)—NH—CH$_2$CH$_2$—C(=O)-KGGF (SEQ ID NO: 35)-NH—CH$_2$CH$_2$—O—CH$_2$—C(=O)—(NH-DX)
—CH$_2$—C(=O)—NH—CH$_2$CH$_2$—C(=O)-DGGFG (SEQ ID NO: 37)-NH—CH$_2$CH$_2$—C(=O)—(NH-DX)
—CH$_2$—C(=O)—NH—CH$_2$CH$_2$—C(=O)-DGGFG (SEQ ID NO: 37)-NH—CH$_2$CH$_2$CH$_2$—C(=O)—(NH-DX)

—CH$_2$—C(=O)—NH—CH$_2$CH$_2$—C(=O)-DGGFG (SEQ ID NO: 37)-NH—CH$_2$—O—CH$_2$—C(=O)—(NH-DX)
—CH$_2$—C(=O)—NH—CH$_2$CH$_2$—C(=O)-DGGFG (SEQ ID NO: 37)-NH—CH$_2$CH$_2$—O—CH$_2$—C(=O)—(NH-DX)
—CH$_2$—C(=O)—NH—CH$_2$CH$_2$—C(=O)-KGGFG (SEQ ID NO: 38)-NH—CH$_2$CH$_2$—C(=O)—(NH-DX)
—CH$_2$—C(=O)—NH—CH$_2$CH$_2$—C(=O)-KGGFG (SEQ ID NO: 38)-NH—CH$_2$CH$_2$CH$_2$—C(=O)—(NH-DX)
—CH$_2$—C(=O)—NH—CH$_2$CH$_2$—C(=O)-KGGFG (SEQ ID NO: 38)-NH—CH$_2$—O—CH$_2$—C(=O)—(NH-DX)
—CH$_2$—C(=O)—NH—CH$_2$CH$_2$—C(=O)-KGGFG (SEQ ID NO: 38)-NH—CH$_2$CH$_2$—O—CH$_2$—C(=O)—(NH-DX)
or the following formulas:
—CH$_2$—C(=O)—NH—CH$_2$CH$_2$—C(=O)-DGGF (SEQ ID NO: 34)-(NH-DX)
—CH$_2$—C(=O)—NH—CH$_2$CH$_2$—C(=O)-KGGF (SEQ ID NO: 35)-(NH-DX)
—CH$_2$—C(=O)—NH—CH$_2$CH$_2$—C(=O)-DGGFG (SEQ ID NO: 37)-(NH-DX)
—CH$_2$—C(=O)—NH—CH$_2$CH$_2$—C(=O)-KGGFG (SEQ ID NO: 38)-(NH-DX)

Further preferably, it is
—CH$_2$—C(=O)—NH—CH$_2$CH$_2$—C(=O)-DGGF (SEQ ID NO: 34)-NH—CH$_2$CH$_2$—C(=O)—(NH-DX)
—CH$_2$—C(=O)—NH—CH$_2$CH$_2$—C(=O)-DGGF (SEQ ID NO: 34)-NH—CH$_2$CH$_2$CH$_2$—C(=O)—(NH-DX)
—CH$_2$—C(=O)—NH—CH$_2$CH$_2$—C(=O)-DGGF (SEQ ID NO: 34)-NH—CH$_2$—O—CH$_2$—C(=O)—(NH-DX)
—CH$_2$—C(=O)—NH—CH$_2$CH$_2$—C(=O)-DGGF (SEQ ID NO: 34)-NH—CH$_2$CH$_2$—O—CH$_2$—C(=O)—(NH-DX)
—CH$_2$—C(=O)—NH—CH$_2$CH$_2$—C(=O)-DGGFG (SEQ ID NO: 37)-NH—CH$_2$CH$_2$—C(=O)—(NH-DX)
—CH$_2$—C(=O)—NH—CH$_2$CH$_2$—C(=O)-DGGFG (SEQ ID NO: 37)-NH—CH$_2$CH$_2$CH$_2$—C(=O)—(NH-DX)
—CH$_2$—C(=O)—NH—CH$_2$CH$_2$—C(=O)-DGGFG (SEQ ID NO: 37)-NH—CH$_2$—O—CH$_2$—C(=O)—(NH-DX)
—CH$_2$—C(=O)—NH—CH$_2$CH$_2$—C(=O)-DGGFG (SEQ ID NO: 37)-NH—CH$_2$CH$_2$—O—CH$_2$—C(=O)—(NH-DX)
or the following formulas:
—CH$_2$—C(=O)—NH—CH$_2$CH$_2$—C(=O)-DGGF (SEQ ID NO: 34)-(NH-DX)
—CH$_2$—C(=O)—NH—CH$_2$CH$_2$—C(=O)-DGGFG (SEQ ID NO: 37)-(NH-DX)

Alternatively, examples of the drug-linker structure moiety for conjugating the drug-linker structure moiety to the antibody via an amide bond can include the following formulas:
—C(=O)-cyc.Hex(1,4)-CH$_2$—(N-ly-3-diminiccuS)-S—(CH$_2$)n$^8$-C(=O)-DGGF (SEQ ID NO: 34)-NH—(CH$_2$)n$^1$-L$^a$-L$^b$-L$^c$-(NH-DX)
—C(=O)-cyc.Hex(1,4)-CH$_2$—(N-ly-3-diminiccuS)-S—(CH$_2$)n$^8$-C(=O)-KGGF (SEQ ID NO: 35)-NH—(CH$_2$)n$^1$-L$^a$-L$^b$-L$^c$-(NH-DX)
—C(=O)-cyc.Hex(1,4)-CH$_2$—(N-ly-3-diminiccuS)-S—(CH$_2$)n$^8$-C(=O)-EGGF (SEQ ID NO: 36)-NH—(CH$_2$)n$^1$-L$^a$-L$^b$-L$^c$-(NH-DX)
—C(=O)-cyc.Hex(1,4)-CH$_2$—(N-ly-3-diminiccuS)-S—(CH$_2$)n$^8$-C(=O)-DGGFG (SEQ ID NO: 37)-NH—(CH$_2$)n$^1$-L$^a$-L$^b$-L$^c$-(NH-DX)
—C(=O)-cyc.Hex(1,4)-CH$_2$—(N-ly-3-diminiccuS)-S—(CH$_2$)n$^8$-C(=O)-KGGFG (SEQ ID NO: 38)-NH—(CH$_2$)n$^1$-L$^a$-L$^b$-L$^c$-(NH-DX)
—C(=O)-cyc.Hex(1,4)-CH$_2$—(N-ly-3-diminiccuS)-S—(CH$_2$)n$^8$-C(=O)-EGGFG (SEQ ID NO: 39)-NH—(CH$_2$)n$^1$-L$^a$-L$^b$-L$^c$-(NH-DX)

In the above formula, n$^8$ is preferably 1 to 6, and more preferably 2. The —NH—(CH$_2$)n$^1$-L$^a$-L$^b$-L$^c$- moiety is preferably —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^P$ is directly connected to the drug are preferable.

More specifically, it is more preferably
—C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-KGGF (SEQ ID NO: 35)-NH—CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-KGGF (SEQ ID NO: 35)-NH—CH$_2$CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-KGGF (SEQ ID NO: 35)-NH—CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-KGGF (SEQ ID NO: 35)-NH—CH$_2$CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-KGGFG (SEQ ID NO: 38)-NH—CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-KGGFG (SEQ ID NO: 38)-NH—CH$_2$CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-KGGFG (SEQ ID NO: 38)-NH—CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-KGGFG (SEQ ID NO: 38)-NH—CH$_2$CH$_2$—O—CH$_2$—C(=O)—(NH-DX)
or the following formulas:
—C(=O)-cyc.Hex(1,4)-CH$_2$—(N-ly-3-diminiccuS)-S—CH$_2$CH$_2$—C(=O)-DGGF (SEQ ID NO: 34)-(NH-DX)
—C(=O)-cyc.Hex(1,4)-CH$_2$—(N-ly-3-diminiccuS)-S—CH$_2$CH$_2$—C(=O)-KGGF (SEQ ID NO: 35)-(NH-DX)

—C(=O)-cyc.Hex(1,4)-CH$_2$—(N-ly-3-diminiccuS)-S—CH$_2$CH$_2$—C(=O)-DGGFG (SEQ ID NO: 37)-(NH-DX)
—C(=O)-cyc.Hex(1,4)-CH$_2$—(N-ly-3-diminiccuS)-S—CH$_2$CH$_2$—C(=O)-KGGFG (SEQ ID NO: 38)-(NH-DX)

Among them, it is further preferably represented by the following formula:
—C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-DGGF (SEQ ID NO: 34)-NH—CH$_2$CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$CH$_2$CH$_2$—C(=O)—(NH-DX)
—C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$—O—CH$_2$—C(=O)—(NH-DX)
—C(=O)-cyc.Hex(1,4)-CH$_2$—(N-ly-3-diminiccuS)-S—CH$_2$CH$_2$—C(=O)-DGGFG (SEQ ID NO: 37)-NH—CH$_2$CH$_2$—O—CH$_2$—C(=O)—(NH-DX)
or the following formulas:
—C(=O)-cyc.Hex(1,4)-CH$_2$—(N-ly-3-diminiccuS)-S—CH$_2$CH$_2$—C(=O)-DGGF (SEQ ID NO: 34)-(NH-DX)
—C(=O)-cyc.Hex(1,4)-CH$_2$—(N-ly-3-diminiccuS)-S—CH$_2$CH$_2$—C(=O)-DGGFG (SEQ ID NO: 37)-(NH-DX)

Examples of another form of the drug-linker structure moiety for conjugating the drug-linker structure moiety to the antibody via an amide bond can include the following formulas:
—C(=O)—(CH$_2$)n$^5$-C(=O)-L$^2$-DGGF (SEQ ID NO: 34)-NH—(CH$_2$)n$^1$-L$^a$-L$^b$-L$^c$-(NH-DX)
—C(=O)—(CH$_2$)n$^5$-C(=O)-L$^2$-KGGF (SEQ ID NO: 35)-NH—(CH$_2$)n$^1$-L$^a$-L$^b$-L$^c$-(NH-DX)
—C(=O)—(CH$_2$)n$^5$-C(=O)-L$^2$-EGGF (SEQ ID NO: 36)-NH—(CH$_2$)n$^1$-L$^a$-L$^b$-L$^c$-(NH-DX)
—C(=O)—(CH$_2$)n$^5$-C(=O)-L$^2$-DGGFG (SEQ ID NO: 37)-NH—(CH$_2$)n$^1$-L$^a$-L$^b$-L$^c$-(NH-DX)
—C(=O)—(CH$_2$)n$^5$-C(=O)-L$^2$-KGGFG (SEQ ID NO: 38)-NH—(CH$_2$)n$^1$-L$^a$-L$^b$-L$^c$-(NH-DX)
—C(=O)—(CH$_2$)n$^5$-C(=O)-L$^2$-EGGFG (SEQ ID NO: 39)-NH—(CH$_2$)n$^1$-L$^a$-L$^b$-L$^c$-(NH-DX)

In the above formula, n$^5$ is preferably 6, and L$^2$ is —NH—(CH$_2$—CH$_2$—O)n$^6$-CH$_2$—CH$_2$—C(=O)— or a single bond and is preferably a single bond. n$^6$ is preferably 0, 2, or 4, and more preferably 0. The —NH—(CH$_2$)n$^1$-L$^a$-L$^b$-L$^c$- moiety is preferably —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^P$ is directly connected to the drug are preferable.

More specifically, it is preferably
—C(=O)—CH$_2$CH$_2$CH$_2$CH$_2$CH$_2$CH$_2$—C(=O)-DGGF (SEQ ID NO: 34)-NH—CH$_2$CH$_2$—C(=O)—(NH-DX)
—C(=O)—CH$_2$CH$_2$CH$_2$CH$_2$CH$_2$CH$_2$—C(=O)-DGGF (SEQ ID NO: 34)-NH—CH$_2$CH$_2$CH$_2$—C(=O)—(NH-DX)
—C(=O)—CH$_2$CH$_2$CH$_2$CH$_2$CH$_2$CH$_2$—C(=O)-DGGF (SEQ ID NO: 34)-NH—CH$_2$—O—CH$_2$—C(=O)—(NH-DX)
—C(=O)—CH$_2$CH$_2$CH$_2$CH$_2$CH$_2$CH$_2$—C(=O)-DGGF (SEQ ID NO: 34)-NH—CH$_2$CH$_2$—O—CH$_2$—C(=O)—(NH-DX)
—C(=O)—CH$_2$CH$_2$CH$_2$CH$_2$CH$_2$CH$_2$—C(=O)-KGGF (SEQ ID NO: 35)-NH—CH$_2$CH$_2$—C(=O)—(NH-DX)
—C(=O)—CH$_2$CH$_2$CH$_2$CH$_2$CH$_2$CH$_2$—C(=O)-KGGF (SEQ ID NO: 35)-NH—CH$_2$CH$_2$CH$_2$—C(=O)—(NH-DX)
—C(=O)—CH$_2$CH$_2$CH$_2$CH$_2$CH$_2$CH$_2$—C(=O)-KGGF (SEQ ID NO: 35)-NH—CH$_2$—O—CH$_2$—C(=O)—(NH-DX)
—C(=O)—CH$_2$CH$_2$CH$_2$CH$_2$CH$_2$CH$_2$—C(=O)-KGGF (SEQ ID NO: 35)-NH—CH$_2$CH$_2$—O—CH$_2$—C(=O)—(NH-DX)
—C(=O)—CH$_2$CH$_2$CH$_2$CH$_2$CH$_2$CH$_2$—C(=O)-DGGFG (SEQ ID NO: 37)-NH—CH$_2$CH$_2$—C(=O)—(NH-DX)
—C(=O)—CH$_2$CH$_2$CH$_2$CH$_2$CH$_2$CH$_2$—C(=O)-DGGFG (SEQ ID NO: 37)-NH—CH$_2$CH$_2$CH$_2$—C(=O)—(NH-DX)
—C(=O)—CH$_2$CH$_2$CH$_2$CH$_2$CH$_2$CH$_2$—C(=O)-DGGFG (SEQ ID NO: 37)-NH—CH$_2$—O—CH$_2$—C(=O)—(NH-DX)
—C(=O)—CH$_2$CH$_2$CH$_2$CH$_2$CH$_2$CH$_2$—C(=O)-DGGFG (SEQ ID NO: 37)-NH—CH$_2$CH$_2$—O—CH$_2$—C(=O)—(NH-DX)
—C(=O)—CH$_2$CH$_2$CH$_2$CH$_2$CH$_2$CH$_2$—C(=O)-KGGFG (SEQ ID NO: 38)-NH—CH$_2$CH$_2$—C(=O)—(NH-DX)
—C(=O)—CH$_2$CH$_2$CH$_2$CH$_2$CH$_2$CH$_2$—C(=O)-KGGFG (SEQ ID NO: 38)-NH—CH$_2$CH$_2$CH$_2$—C(=O)—(NH-DX)
—C(=O)—CH$_2$CH$_2$CH$_2$CH$_2$CH$_2$CH$_2$—C(=O)-KGGFG (SEQ ID NO: 38)-NH—CH$_2$—O—CH$_2$—C(=O)—(NH-DX)
—C(=O)—CH$_2$CH$_2$CH$_2$CH$_2$CH$_2$CH$_2$—C(=O)-KGGFG (SEQ ID NO: 38)-NH—CH$_2$CH$_2$—O—CH$_2$—C(=O)—(NH-DX)
or the following formulas:
—C(=O)—CH$_2$CH$_2$CH$_2$CH$_2$CH$_2$CH$_2$—C(=O)-DGGF (SEQ ID NO: 34)-(NH-DX)
—C(=O)—CH$_2$CH$_2$CH$_2$CH$_2$CH$_2$CH$_2$—C(=O)-KGGF (SEQ ID NO: 35)-(NH-DX)
—C(=O)—CH$_2$CH$_2$CH$_2$CH$_2$CH$_2$CH$_2$—C(=O)-DGGFG (SEQ ID NO: 37)-(NH-DX)
—C(=O)—CH$_2$CH$_2$CH$_2$CH$_2$CH$_2$CH$_2$—C(=O)-KGGFG (SEQ ID NO: 38)-(NH-DX)

When the linker L$^P$ is a peptide residue having a glycine oligopeptide at the C terminal, the drug-linker structure moiety is present in a form in which L$^P$ is directly connected to the drug, as in -L$^1$-L$^2$-L$^P$-(NH-DX) When L$^P$ in the linker is a peptide residue having a glycine oligopeptide at the C terminal, the combinations of each linker moiety constituting the drug-linker structure moiety are as follows.

When the drug-linker structure moiety is connected to the antibody via a thioether bond, the linker L is -(Succinimid-3-yl-N)—(CH$_2$)n$^2$-C(=O)— or —CH$_2$—C(=O)—NH—(CH$_2$)n$^4$-C(=O)— and when the drug-linker structure moiety is connected to the antibody via an amide bond, is selected from —C(=O)-cyc.Hex(1,4)-CH$_2$—(N-ly-3-diminiccuS)- or —C(=O)— (CH$_2$)n$^5$-C(=O)—.

As for the linker L$^2$, when linker L$^1$ is -(Succinimid-3-yl-N)—(CH$_2$)n$^2$-C(=O)— or —CH$_2$—C(=O)—NH—(CH$_2$)n$^4$-C(=O)—, it can be —NH—(CH$_2$—CH$_2$—O)n$^6$-CH$_2$—CH$_2$—C(=O)— or a single bond, and when linker L$^1$ in —C(=O)—(CH$_2$)n$^5$-C(=O)—, it is selected from single bonds. And the linker —S—(CH$_2$)n$^8$-C(=O)— is used in combination with —C(=O)-cyc.Hex(1,4)-CH$_2$—(N-ly-3-diminiccuS)- among L$^1$.

Specific examples of the drug-linker structure moiety containing the peptide having a glycine oligopeptide at the C terminal can include the followings.

Examples of the drug-linker structure moiety for conjugating the drug-linker structure moiety to the antibody via a thioether bond can include following formulas:
-(Succinimid-3-yl-N)—(CH$_2$)n$^2$-C(=O)-GGFGG (SEQ ID NO: 40)-(NH-DX)

-(Succinimid-3-yl-N)—(CH$_2$)n$^2$-C(=O)-GGFGGG (SEQ ID NO: 41)-(NH-DX)

In the above formula, preferably, n$^2$ is 2 or 5.

More preferably, n$^2$ is 5, and it is represented by the following formula:

-(Succinimid-3-yl-N)—CH$_2$CH$_2$CH$_2$CH$_2$CH$_2$—C(=O)-GGFGG (SEQ ID NO: 40)-(NH-DX)

-(Succinimid-3-yl-N)—CH$_2$CH$_2$CH$_2$CH$_2$CH$_2$—C(=O)-GGFGGG (SEQ ID NO: 41)-(NH-DX)

Examples of the drug-linker structure moiety in another form for conjugating the drug-linker structure moiety to the antibody via a thioether bond can include the following formulas:

—CH$_2$—C(=O)—NH—(CH$_2$)n$^4$-C(=O)-GGFGG (SEQ ID NO: 40)-(NH-DX)

—CH$_2$—C(=O)—NH—(CH$_2$)n$^4$-C(=O)-GGFGGG (SEQ ID NO: 41)-(NH-DX)

In the above formula, more preferably, n$^4$ is 2 or 5.

Among them, more preferably, n$^4$ is 2, and it is preferably represented by the following formula:

—CH$_2$—C(=O)—NH—CH$_2$CH$_2$—C(=O)-GGFGG (SEQ ID NO: 40)-(NH-DX)

—CH$_2$—C(=O)—NH—CH$_2$CH$_2$—C(=O)-GGFGGG (SEQ ID NO: 41)-(NH-DX)

Alternatively, examples of the drug-linker structure moiety for conjugating the drug-linker structure moiety to the antibody via an amide bond or an ester bond can include the following formulas:

—C(=O)-cyc.Hex(1,4)-CH$_2$—(N-ly-3-diminiccuS)-S—(CH$_2$)n$^8$-C(=O)-GGFGG (SEQ ID NO: 40)-(NH-DX)

—C(=O)-cyc.Hex(1,4)-CH$_2$—(N-ly-3-diminiccuS)-S—(CH$_2$)n$^8$-C(=O)-GGFGGG (SEQ ID NO: 41)-(NH-DX)

In the above formula, n$^8$ is preferably 2.

Specifically, it is

—C(=O)-cyc.Hex(1,4)-CH$_2$—(N-ly-3-diminiccuS)-S—CH$_2$CH$_2$—C(=O)-GGFGG (SEQ ID NO: 40)-(NH-DX)

—C(=O)-cyc.Hex(1,4)-CH$_2$—(N-ly-3-diminiccuS)-S—CH$_2$CH$_2$—C(=O)-GGFGGG (SEQ ID NO: 41)-(NH-DX)

Examples of the drug-linker structure moiety in another form for conjugating the drug-linker structure moiety to the antibody via an amide bond can include the following formulas:

—C(=O)—(CH$_2$)n$^5$-C(=O)-L$^2$-GGFGG (SEQ ID NO: 40)-(NH-DX)

—C(=O)—(CH$_2$)n$^5$-C(=O)-L$^2$-GGFGGG (SEQ ID NO: 41)-(NH-DX)

In the above formula, n$^5$ is preferably 6, and L$^2$ is —NH—(CH$_2$—CH$_2$—O)n$^6$-CH$_2$—CH$_2$—C(=O)— or a single bond and is preferably a single bond. n$^6$ is preferably 0, 2, or 4, and more preferably 0.

More specifically, it is

—C(=O)—CH$_2$CH$_2$CH$_2$CH$_2$CH$_2$—C(=O)-GGFGG (SEQ ID NO: 40)-(NH-DX)

—C(=O)—CH$_2$CH$_2$CH$_2$CH$_2$CH$_2$—C(=O)-GGFGGG (SEQ ID NO: 41)-(NH-DX)

11. Specific Example when L$^1$ has Hydrophilic Structure

When linker L$^1$ is -(Succinimid-3-yl-N)—CH[—(CH$_2$)n$^3$-COOH]—C(=O)—, the drug-linker structure moiety is connected to the antibody via a thioether bond, and is present in the form of -L$^1$-L$^2$-L$^P$-NH—(CH$_2$)n$^1$-L$^a$-L$^b$-L$^c$-(NH-DX) or -L$^1$-L$^2$-L$^P$-(NH-DX). The combinations of each linker moiety constituting this drug-linker structure are as follows.

The linker L$^2$ in is NH—(CH$_2$—CH$_2$—O)n$^6$-CH$_2$—CH$_2$—C(=O)— or a single bond and is preferably a single bond. n$^6$ is preferably 0, 2, or 4, and more preferably 0.

The amino acid sequence of linker L$^P$ is not particularly limited, but examples of the constituting amino acid include phenylalanine, tyrosine, leucine, glycine, alanine, valine, lysine, citrulline, serine, glutamic acid, and aspartic acid. Among them, preferred examples include phenylalanine, glycine, valine, lysine, citrulline, serine, glutamic acid, and aspartic acid. Depending on the type of the amino acid, drug release pattern can be controlled. The number of the amino acid can be between 3 to 8. Specific examples thereof are as listed above, and GGFG (SEQ ID NO: 33) is particularly preferred.

The linker —NH—(CH$_2$)n$^1$-L$^a$-L$^b$-L$^c$- moiety preferably has a chain length of 4 to 7 atoms. The moiety more preferably has a chain length of 5 or 6 atoms in the linker. Specific examples of the —NH—(CH$_2$)n$^1$-L$^a$-L$^b$- moiety in the linker are as described above.

The —NH—(CH$_2$)n$^1$-L$^a$-L$^b$-L$^c$- moiety may be a single bond.

The linker -L$^c$- moiety is preferably —C(=O)—.

The drug-linker structure moiety in which linker L is -(Succinimid-3-yl-N)—CH[—(CH$_2$)n$^3$-COOH]—C(=O)— is connected to the antibody via a thioether bond and has a structure represented by the following formula:

-(Succinimid-3-yl-N)—CH[—(CH$_2$)n$^3$-COOH]—C(=O)—NH—(CH$_2$—CH$_2$—O)n$^6$-CH$_2$—CH$_2$—C(=O)-GGFG (SEQ ID NO: 33)-NH—(CH$_2$)n$^1$-L$^a$-L$^b$-L$^c$-(NH-DX)

In the above formula, n$^6$ is 0. Preferably, n$^3$ is 2 to 4, and the —NH—(CH$_2$)n$^1$-L$^a$-L$^b$-L$^c$- moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^P$ is directly connected to the drug are preferable.

More specifically, it is represented by the following formula:

-(Succinimid-3-yl-N)—CH[—(CH$_2$)n$^3$-COOH]—C(=O)—NH—CH$_2$CH$_2$—C(=O)-GGFG (SEQ ID NO: 33)-NH—CH$_2$CH$_2$—C(=O)—(NH-DX)

-(Succinimid-3-yl-N)—CH[—(CH$_2$)n$^3$-COOH]—C(=O)—NH—CH$_2$CH$_2$—C(=O)-GGFG (SEQ ID NO: 33)-NH—CH$_2$CH$_2$CH$_2$—C(=O)—(NH-DX)

-(Succinimid-3-yl-N)—CH[—(CH$_2$)n$^3$-COOH]—C(=O)—NH—CH$_2$CH$_2$—C(=O)-GGFG (SEQ ID NO: 33)-NH—CH$_2$—O—CH$_2$—C(=O)—(NH-DX)

-(Succinimid-3-yl-N)—CH[—(CH$_2$)n$^3$-COOH]—C(=O)—NH—CH$_2$CH$_2$—C(=O)-GGFG (SEQ ID NO: 33)-NH—CH$_2$CH$_2$—O—CH$_2$—C(=O)—(NH-DX)

or the following formula:

-(Succinimid-3-yl-N)—CH[—(CH$_2$)n$^3$-COOH]—C(=O)—NH—CH$_2$CH$_2$—C(=O)-GGFG (SEQ ID NO: 33)-(NH-DX)

In the above formula, n$^3$ is preferably 2, and it is preferably represented by the following formula:

-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$CH$_2$—C(=O)—(NH-DX)

-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$CH$_2$CH$_2$—C(=O)—(NH-DX)

-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$—O—CH$_2$—C(=O)—(NH-DX)

-(Succinimid-3-yl-N)—CH(CH$_2$CH$_2$—COOH)—C(=O)—NH—CH$_2$CH$_2$—C(=O)-GGFG (SEQ ID NO: 33)-NH—CH$_2$CH$_2$—O—CH$_2$—C(=O)—(NH-DX)

or the following formula:
-(Succinimid-3-yl-N)—CH(CH$_2$CH$_2$—COOH)—C(=O)—NH—CH$_2$CH$_2$—C(=O)-GGFG (SEQ ID NO: 33)-(NH-DX)

12. Specific Example when L$^2$ has Hydrophilic Structure

When linker L$^2$ is —N[—(CH$_2$CH$_2$—O)n$^7$-CH$_2$CH$_2$—OH]—CH$_2$—C(=O)—, the drug-linker structure moiety is present in the form of -L$^1$-L$^2$-L$^P$-NH—(CH$_2$)n$^1$-L$^a$-L$^b$-L$^c$-(NH-DX) or -L$^1$-L$^2$-L$^P$-(NH-DX). The combinations of each linker moiety constituting this drug-linker structure moiety are as follows.

When the drug-linker structure moiety is connected to the antibody via a thioether bond, linker L$^1$ is -(Succinimid-3-yl-N)—(CH$_2$)n$^2$-C(=O)— or —CH$_2$—C(=O)—NH—(CH$_2$)n$^4$-C(=O)—, and when the drug-linker structure moiety is connected to the antibody via an amide bond, it is selected from —C(=O)—(CH$_2$)n$^5$-C(=O)—.

The amino acid sequence of linker L$^P$ is not particularly limited, but examples of the constituting amino acid can include phenylalanine, tyrosine, leucine, glycine, alanine, valine, lysine, citrulline, serine, glutamic acid, and aspartic acid. Among them, preferred examples can include phenylalanine, glycine, valine, lysine, citrulline, serine, glutamic acid, and aspartic acid. Depending on the type of the amino acid, drug release pattern can be controlled. The number of the amino acid can be between 3 to 8. Specific examples thereof are as listed above. GGFG (SEQ ID NO: 33) is particularly preferred.

The linker —NH—(CH$_2$)n$^1$-L$^a$-L$^b$-L$^c$- moiety preferably has a chain length of 4 to 7 atoms. The moiety more preferably has a chain length of 5 or 6 atoms in the linker. Specific examples of the —NH—(CH$_2$)n$^1$-L$^a$-L$^b$- moiety in the linker are as described above.

The —NH—(CH$_2$)n$^1$-L$^a$-L$^b$-L$^c$- moiety may be a single bond.

The linker -L$^c$- moiety is preferably —C(=O)—.

The drug-linker structure moiety in which linker L$^2$ is —N[—(CH$_2$CH$_2$—O)n$^7$-CH$_2$CH$_2$—OH]—CH$_2$—C(=O)— is preferably represented by the following formula:
-L$^1$-N[—(CH$_2$CH$_2$—O)n$^7$-CH$_2$CH$_2$—OH]—CH$_2$—C(=O)-L$^P$-NH—(CH$_2$)n$^1$-L$^a$-L$^b$-L$^c$-(NH-DX)

The drug-linker structure moiety for conjugating the drug-linker structure moiety to the antibody via a thioether bond is represented by the following formula:
-(Succinimid-3-yl-N)—(CH$_2$)n$^2$-C(=O)—N[—(CH$_2$CH$_2$—O)n$^7$-CH$_2$CH$_2$—OH]—CH$_2$—C(=O)-GGFG (SEQ ID NO: 33)-NH—(CH$_2$)n$^1$-L$^a$-L$^b$-L$^c$-(NH-DX)

In the above formula, preferably, n$^2$ is 2 or 5, n$^7$ is 3 or 4, and the —NH—(CH$_2$)n$^1$-L$^a$-L$^b$-L$^c$- moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^P$ is directly connected to the drug are preferable.

More specifically, it is represented by the following formula:
-(Succinimid-3-yl-N)—(CH$_2$)n$^2$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$—C(=O)—(NH-DX)
-(Succinimid-3-yl-N)—(CH$_2$)n$^2$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$CH$_2$—C(=O)—(NH-DX)
-(Succinimid-3-yl-N)—(CH$_2$)n$^2$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$—O—CH$_2$—C(=O)—(NH-DX)
-(Succinimid-3-yl-N)—(CH$_2$)n$^2$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$—O—CH$_2$—C(=O)—(NH-DX)
or the following formula:
-(Succinimid-3-yl-N)—(CH$_2$)n$^2$-C(=O)—N[—(CH$_2$CH$_2$—O)n$^7$-CH$_2$CH$_2$—OH]—CH$_2$—C(=O)-GGFG (SEQ ID NO: 33)-(NH-DX)

Further preferably, n$^2$ is 5, n$^7$ is 3 or 4, and more preferably 3, and it is preferably represented by the following formulas:
-(Succinimid-3-yl-N)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—C(=O)—(NH-DX)
-(Succinimid-3-yl-N)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$CH$_2$—C(=O)—(NH-DX)
-(Succinimid-3-yl-N)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$—O—CH$_2$—C(=O)—(NH-DX)
-(Succinimid-3-yl-N)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—O—CH$_2$—C(=O)—(NH-DX)
or the following formula:
-(Succinimid-3-yl-N)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-(NH-DX)

Examples of the drug-linker structure moiety as another form for conjugating the drug-linker structure moiety to the antibody via a thioether bond can include the following formula:
—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—(CH$_2$)n$^1$-L$^a$-L$^b$-L$^c$-(NH-DX)

In the above formula, preferably, n$^4$ is 2 or 5, n$^7$ is 3 or 4, and the —NH—(CH$_2$)n$^1$-L$^a$-L$^b$-L$^c$- moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^P$ is directly connected to the drug are preferable.

Specifically, it is represented by the following formula:
—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$—C(=O)—(NH-DX)
—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$CH$_2$—C(=O)—(NH-DX)
—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$—O—CH$_2$—C(=O)—(NH-DX)
—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$—O—CH$_2$—C(=O)—(NH-DX)
or the following formula:
—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-(NH-DX)

In the above formula, preferably, n$^4$ is 2, n$^7$ is 3 or 4, and more preferably 3, and it is represented by the following formulas:

—CH$_2$—C(=O)—NH—CH$_2$CH$_2$—C(=O)—N(—CH$_2$CH$_2$—O—CH$_2$CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—C(=O)—(NH-DX)
—CH$_2$—C(=O)—NH—CH$_2$CH$_2$—C(=O)—N(—CH$_2$CH$_2$OCH$_2$CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$CH$_2$—C(=O)—(NH-DX)
—CH$_2$—C(=O)—NH—CH$_2$CH$_2$—C(=O)—N(—CH$_2$CH$_2$OCH$_2$CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$—O—CH$_2$—C(=O)—(NH-DX)
—CH$_2$—C(=O)—NH—CH$_2$CH$_2$—C(=O)—N(—CH$_2$CH$_2$OCH$_2$CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—O—CH$_2$—C(=O)—(NH-DX)
or the following formula:
—CH$_2$—C(=O)—NH—CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-(NH-DX)

Alternatively, the drug-linker structure moiety for conjugating the drug-linker structure moiety to the antibody via an amide bond is represented by the following formula:
—C(=O)—(CH$_2$)n$^5$-C(=O)—N[—(CH$_2$CH$_2$—O)n$^7$-CH$_2$CH$_2$—OH]—CH$_2$—C(=O)-GGFG (SEQ ID NO: 33)-NH—(CH$_2$)n$^1$-L$^a$-L$^b$-L$^c$-(NH-DX)
In the above formula, preferably, n$^5$ is an integer of 1 to 8 and is more preferably 2 to 6, n$^7$ is 3 or 4, and the —NH—(CH$_2$)n$^1$-L$^a$-L$^b$-L$^c$- moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^P$ is directly connected to the drug are preferable.

More specifically, it is represented by the following formula:
—C(=O)—(CH$_2$)n$^5$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$—C(=O)—(NH-DX)
—C(=O)—(CH$_2$)n$^5$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$CH$_2$—C(=O)—(NH-DX)
—C(=O)—(CH$_2$)n$^5$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$—O—CH$_2$—C(=O)—(NH-DX)
—C(=O)—(CH$_2$)n$^5$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$—O—CH$_2$—C(=O)—(NH-DX)
or the following formula:
—C(=O)—(CH$_2$)n$^5$-C(=O)—N[—(CH$_2$CH$_2$—O)n$^7$-CH$_2$CH$_2$—OH]—CH$_2$—C(=O)-GGFG (SEQ ID NO: 33)-(NH-DX)

Further preferably, n$^5$ is 6, n$^7$ is 3 or 4, and more preferably 3, and it is represented by the following formulas:
—C(=O)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—C(=O)—(NH-DX)
—C(=O)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$CH$_2$—C(=O)—(NH-DX)
—C(=O)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$—O—CH$_2$—C(=O)—(NH-DX)
—C(=O)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—O—CH$_2$—C(=O)—(NH-DX)
Further preferably, it is represented by the following formula:
—C(=O)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—C(=O)—(NH-DX)
—C(=O)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$CH$_2$—C(=O)—(NH-DX)
or the following formula:
—C(=O)—CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-(NH-DX)

[Production Method]

Next, explanations are given for the representative method for producing the antibody-drug conjugate of the present invention or a production intermediate thereof. Meanwhile, the compounds are hereinbelow described with the number shown in each reaction formula. Specifically, they are referred to as a "compound of the formula (1)", a "compound (1)", or the like. The compounds with numbers other than those are also described similarly.

1. Production Method 1

The antibody-drug conjugate represented by the formula (1) in which the antibody is connected to the linker structure via thioether can be produced by the following method, for example.

[Formula 34]

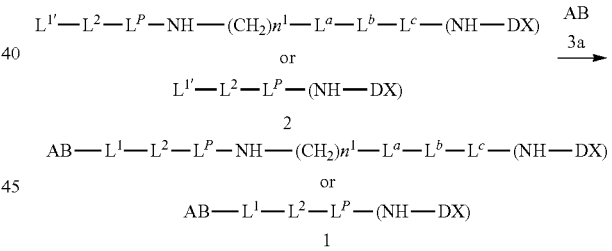

In the formula, AB represents an antibody with a sulfhydryl group, and L$^{1'}$ represents an L$^1$ linker structure in which the linker terminal has a maleimidyl group (formula shown below) (in the formula, the nitrogen atom is the connecting position)

[Formula 35]

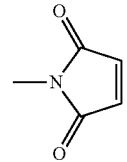

or the terminal has a halogen, and represents a group in which the -(Succinimid-3-yl-N)— moiety in -(Succinimid-3-yl-N)—(CH$_2$)n$^2$-C(=O)— among L$^1$ is a maleimidyl group or a halogen-CH$_2$C(=O)NH—(CH$_2$)n$^3$-C(=O)— group in which terminal methylene in —CH$_2$C(=O)NH—(CH$_2$)n$^4$-C(=O)— among L$^1$ is halogenated to form haloacetamide. Further, the —(NH-DX) represents a structure represented by the following formula:

[Formula 36]

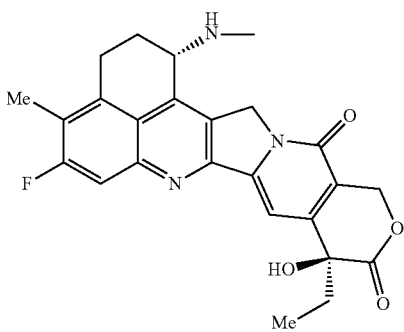

and it represents a group that is produced by removing one hydrogen atom of the amino group at position 1 of the antitumor drug. Meanwhile, the compound of the formula (1) in the above reaction formula is described as a structure in which one structure moiety from drug to the linker terminal is connected to one antibody. However, it is only the description given for the sake of convenience, and there are actually many cases in which a plurality of the structure moieties are connected to one antibody molecule. The same also applies to the explanation of the production method described below.

Specifically, the antibody-drug conjugate (1) can be produced by reacting the compound (2), which is obtainable by the method described below, with the antibody (3a) having a sulfhydryl group.

The antibody (3a) having a sulfhydryl group can be obtained by a method well known in the art (Hermanson, G. T, Bioconjugate Techniques, pp. 56-136, pp. 456-493, Academic Press (1996)). Examples include: Traut's reagent is reacted with the amino group of the antibody; N-succinimidyl S-acetylthioalkanoates are reacted with the amino group of the antibody followed by reaction with hydroxylamine; after reacting with N-succinimidyl 3-(pyridyldithio)propionate, it is reacted with a reducing agent; the antibody is reacted with a reducing agent such as dithiothreitol, 2-mercaptoethanol, and tris(2-carboxyethyl)phosphine hydrochloride (TCEP) to reduce the disulfide bond at a hinge part in the antibody, but it is not limited thereto.

Specifically, the antibody-drug conjugate (1) can be produced by adding dimethyl sulfoxide solution of the compound (2) into a phosphate-buffered sodium chloride aqueous solution (pH 7.2) containing the antibody (3a) having a sulfhydryl group. Then, as is ordinary used in the reaction for the production of antibody-drug bond formation, unreacted compound (2) was deactivated by the addition of N-acetyl-L-cysteine (NAC). The produced antibody-drug conjugate (1) can be subjected to the following procedures such as, concentration, buffer exchange, conducting purification, measurement of antibody concentration and average number of conjugated drug molecules per antibody molecule, and calculation of aggregate content, identification of the antibody-drug conjugate (1)

Common Procedure A: Concentration of Aqueous Solution of Antibody or Antibody-Drug Conjugate To a Amicon Ultra (50,000 MWCO, Millipore Corporation) container, a solution of antibody or antibody-drug conjugate was added and the solution of the antibody or antibody-drug conjugate was concentrated by centrifugation (centrifuge for 5 to 20 minutes at 2000 G to 3800 G) using a centrifuge (Allegra X-15R, Beckman Coulter, Inc.).

Common Procedure B: Measurement of Antibody Concentration

Using a UV detector (Nanodrop 1000, Thermo Fisher Scientific Inc), measurement of the antibody concentration was performed according to the method defined by the manufacturer. At that time, 280 nm absorption coefficient different for each antibody was used (1.3 to 1.8/mg/mL).

Common procedure C-1: NAP-25 column (Cat. No. 17-0852-02, GE Healthcare Japan Corporation) using Sephadex G-25 carrier was equilibrated with phosphate buffer (10 mM, pH 6.0) (it is referred to as PBS6.0/EDTA in the specification) containing sodium chloride (137 mM) and ethylene diamine tetraacetic acid (EDTA, 5 mM) according to the method defined by the manufacturer's instruction manual. Aqueous solution of the antibody was applied in an amount of 2.5 mL to single NAP-25 column, and then the fraction (3.5 mL) eluted with 3.5 mL of PBS6.0/EDTA was collected. The resulting fraction was concentrated by the Common procedure A. After measuring the concentration of the antibody using the Common procedure B, the antibody concentration was adjusted to 10 mg/mL using PBS6.0/EDTA.

Common Procedure C-2: Buffer Exchange for Antibody

NAP-25 column (Cat. No. 17-0852-02, GE Healthcare Japan Corporation) using Sephadex G-25 carrier was equilibrated with phosphate buffer (50 mM, pH 6.5) (it is referred to as PBS6.5/EDTA in the specification) containing sodium chloride (50 mM) and EDTA (2 mM) according to the method defined by the manufacturer. Aqueous solution of the antibody was applied in an amount of 2.5 mL to single NAP-25 column, and then the fraction (3.5 mL) eluted with 3.5 mL of PBS6.5/EDTA was collected. The resulting fraction was concentrated by the Common procedure A. After measuring the concentration of the antibody using the Common procedure B, the antibody concentration was adjusted to 20 mg/mL using PBS6.5/EDTA.

Common Procedure D-1: Purification of Antibody-Drug Conjugate

NAP-25 column was equilibrated with any buffer selected from commercially available phosphate buffer (PBS7.4, Cat. No. 10010-023, Invitrogen), sodium phosphate buffer (10 mM, pH 6.0; it is referred to as PBS6.0) containing sodium chloride (137 mM), and acetate buffer containing sorbitol (5%) (10 mM, pH 5.5; it is referred to as ABS in the specification). Aqueous solution of the antibody-drug conjugate reaction was applied in an amount of about 1.5 mL to the NAP-25 column, and then eluted with the buffer in an amount defined by the manufacturer to collect the antibody fraction. The collected fraction was again applied to the NAP-25 column and, by repeating 2 to 3 times in total the gel filtration purification process for eluting with buffer, the antibody-drug conjugate excluding non-conjugated drug linker and a low-molecular-weight compound (tris(2-carboxyethyl)phosphine hydrochloride (TCEP), N-acetyl-L-cysteine (NAC), and dimethyl sulfoxide) was obtained.

Common Procedure D-2: Purification of Succinimidyl 4-(N-Maleimidylmethyl)-Cyclohexane-1-Carboxylate (SMCC)-Derivatized Antibody NAP-25 column was equilibrated with PBS6.5/EDTA. To the NAP-25 column, reaction solution (about 0.5 mL) containing the succinimidyl 4-(N-maleimidylmethyl)-cyclohexane-1-carboxylate (herein, referred to as SMCC)-derivatized antibody was applied, and then eluted with the buffer in an amount defined by the manufacturer to collect the antibody fraction for purification.

Common Procedure E: Measurement of Antibody Concentration in Antibody-Drug Conjugate and Average Number of Conjugated Drug Molecules Per Antibody Molecule.

The conjugated drug concentration in the antibody-drug conjugate can be calculated by measuring UV absorbance of an aqueous solution of the antibody-drug conjugate at two wavelengths of 280 nm and 370 nm, followed by performing the calculation shown below.

Because the total absorbance at any wavelength is equal to the sum of the absorbance of every light-absorbing chemical species that are present in a system [additivity of absorbance], when the molar absorption coefficients of the antibody and the drug remain the same before and after conjugation between the antibody and the drug, the antibody concentration and the drug concentration in the antibody-drug conjugate are expressed with the following equations.

$$A_{280} = A_{D,280} + A_{A,280} = \epsilon_{D,280} C_D + \epsilon_{A,280} C_A \quad \text{Equation (1)}$$

$$A_{370} = A_{D,370} + A_{A,370} = \epsilon_{D,370} C_D + \epsilon_{A,370} C_A \quad \text{Equation (2)}$$

In the above, $A_{280}$ represents the absorbance of an aqueous solution of the antibody-drug conjugate at 280 nm; $A_{370}$ represents the absorbance of an aqueous solution of the antibody-drug conjugate at 370 nm; $A_{A,280}$ represents the absorbance of an antibody at 280 nm; $A_{A,370}$ represents the absorbance of an antibody at 370 nm; $A_{D,280}$ represents the absorbance of a conjugate precursor at 280 nm; $A_{D,370}$ represents the absorbance of a conjugate precursor at 370 nm; $\epsilon_{A,280}$ represents the molar absorption coefficient of an antibody at 280 nm; $\epsilon_{A,370}$ represents the molar absorption coefficient of an antibody at 370 nm; $\epsilon_{D,280}$ represents the molar absorption coefficient of a conjugate precursor at 280 nm; $\epsilon_{D,370}$ represents the molar absorption coefficient of a conjugate precursor at 370 nm; $C_A$ represents the antibody concentration in an antibody-drug conjugate; and $C_D$ represent the drug concentration in an antibody-drug conjugate.

$\epsilon_{A,280}$, $\epsilon_{A,370}$, $\epsilon_{D,280}$, and $\epsilon_{D,370}$ in the above are known from the previous measurements By measuring $A_{280}$ and $A_{370}$ of an aqueous solution of the antibody-drug conjugate and solving the simultaneous equations (1) and (2) using the values, $C_A$ and $C_D$ can be obtained. Further, by diving $C_D$ by $C_A$, the average drug conjugated number per antibody can be obtained.

The compound represented by the formula (2) in Production method 1 is any compound represented by the following formula:

[Formula 37]

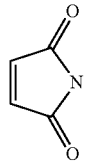

(CH$_2$)$n^2$—C(=O)—NH—[(CH$_2$CH$_2$—O)$n^7$—CH$_2$CH$_2$—OH]—CH$_2$—C(=O)—L$^p$—(NH—DX)

Halogen-CH$_2$C(=O)NH—(CH$_2$)$n^4$—C(=O)—L$^2$—L$^p$—(NH—DX)

Halogen-CH$_2$C(=O)NH—(CH$_2$)$n^4$—C(=O)—NH—[(CH$_2$CH$_2$—O)$n^7$—CH$_2$CH$_2$-OH]—CH$_2$-C(=O)—L$^p$—(NH—DX)

In the formula, $n^1$, $n^2$, $n^3$, $n^4$, $n^7$, $L^2$, $L^P$, $L^a$, $L^b$, and $L^c$ are as already defined, and $L^P$ or $L^c$ is a connecting position to the drug.

In an intermediate useful in producing such an antibody-drug conjugate of the present invention, preferably,
$n^2$ is an integer of 2 to 5,
when $L^1$ in the linker is not -(Succinimid-3-yl-N)—CH[—(CH$_2$)$n^3$-COOH]—C(=O)—, $L^2$ is —N[(—CH$_2$CH$_2$—O)$n^7$-CH$_2$CH$_2$—OH]—CH$_2$—C(=O)—, and $n^7$ is 3 or 4, or a single bond,
what is preferable for $L^P$,
when this is a peptide residue having a hydrophilic amino acid at the N terminal, is DGGF (SEQ ID NO: 34), KGGF (SEQ ID NO: 35), EGGF (SEQ ID NO: 36), DGGFG (SEQ ID NO: 37), KGGFG (SEQ ID NO: 38), or EGGFG (SEQ ID NO: 39), or
when this is a peptide linker having a glycine oligopeptide at the C terminal, is GGFGG (SEQ ID NO: 40) or GGFGGG (SEQ ID NO: 41) and
the —NH—(CH$_2$)$n^1$-L$^a$-L$^b$-L$^c$- moiety is a partial structure of —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—.

And, those which $L^P$ is directly connected to the drug are preferable, in case the peptide linker has a glycine oligopeptide at its C terminal, this C terminal is directly connected to the drug.

Specific examples of these compounds can include the followings [herein, (maleimid-N-yl) represents a maleimidyl group (2,5-dioxo-2,5-dihydro-1H-pyrrol-1-yl group)].

When linker $L^P$ is a peptide linker which has a hydrophilic amino acid at the N terminal, a compound having a structure represented by the following formula can be preferably used as a production intermediate:
(maleimid-N-yl)-(CH$_2$)$n^2$-C(=O)-DGGF (SEQ ID NO: 34)-NH—(CH$_2$)$n^1$-L$^a$-L$^b$-L$^c$-(NH-DX)
(maleimid-N-yl)-(CH$_2$)$n^2$-C(=O)-KGGF (SEQ ID NO: 35)-NH—(CH$_2$)$n^1$-L$^a$-L$^b$-L$^c$-(NH-DX)
(maleimid-N-yl)-(CH$_2$)$n^2$-C(=O)-DGGFG (SEQ ID NO: 37)-NH—(CH$_2$)$n^1$-L$^a$-L$^b$-L$^c$-(NH-DX)
(maleimid-N-yl)-(CH$_2$)$n^2$-C(=O)-KGGFG (SEQ ID NO: 38)-NH—(CH$_2$)$n^1$-L$^a$-L$^b$-L$^c$-(NH-DX)

In the above formula, preferably, $n^2$ is 2 to 5, and the —NH—(CH$_2$)$n^1$-L$^a$-L$^b$-L$^c$- moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which $L^P$ is directly connected to the drug are preferable.

More specifically, it is represented by the following formula:
(maleimid-N-yl)-(CH$_2$)$n^2$-C(=O)-DGGF (SEQ ID NO: 34)-NH—CH$_2$CH$_2$—C(=O)—(NH-DX)
(maleimid-N-yl)-(CH$_2$)$n^2$-C(=O)-DGGF (SEQ ID NO: 34)-NH—CH$_2$CH$_2$CH$_2$—C(=O)—(NH-DX)
(maleimid-N-yl)-(CH$_2$)$n^2$-C(=O)-DGGF (SEQ ID NO: 34)-NH—CH$_2$—O—CH$_2$—C(=O)—(NH-DX)
(maleimid-N-yl)-(CH$_2$)$n^2$-C(=O)-DGGF (SEQ ID NO: 34)-NH—CH$_2$CH$_2$—O—CH$_2$—C(=O)—(NH-DX)
(maleimid-N-yl)-(CH$_2$)$n^2$-C(=O)-KGGF (SEQ ID NO: 35)-NH—CH$_2$CH$_2$—C(=O)—(NH-DX)
(maleimid-N-yl)-(CH$_2$)$n^2$-C(=O)-KGGF (SEQ ID NO: 35)-NH—CH$_2$CH$_2$CH$_2$—C(=O)—(NH-DX)
(maleimid-N-yl)-(CH$_2$)$n^2$-C(=O)-KGGF (SEQ ID NO: 35)-NH—CH$_2$—O—CH$_2$—C(=O)—(NH-DX)
(maleimid-N-yl)-(CH$_2$)$n^2$-C(=O)-KGGF (SEQ ID NO: 35)-NH—CH$_2$CH$_2$—O—CH$_2$—C(=O)—(NH-DX)
(maleimid-N-yl)-(CH$_2$)$n^2$-C(=O)-DGGFG (SEQ ID NO: 37)-NH—CH$_2$CH$_2$—C(=O)—(NH-DX)
(maleimid-N-yl)-(CH$_2$)$n^2$-C(=O)-DGGFG (SEQ ID NO: 37)-NH—CH$_2$CH$_2$CH$_2$—C(=O)—(NH-DX)
(maleimid-N-yl)-(CH$_2$)$n^2$-C(=O)-DGGFG (SEQ ID NO: 37)-NH—CH$_2$—O—CH$_2$—C(=O)—(NH-DX)
(maleimid-N-yl)-(CH$_2$)$n^2$-C(=O)-DGGFG (SEQ ID NO: 37)-NH—CH$_2$CH$_2$—O—CH$_2$—C(=O)—(NH-DX)
(maleimid-N-yl)-(CH$_2$)$n^2$-C(=O)-KGGFG (SEQ ID NO: 38)-NH—CH$_2$CH$_2$—C(=O)—(NH-DX)
(maleimid-N-yl)-(CH$_2$)$n^2$-C(=O)-KGGFG (SEQ ID NO: 38)-NH—CH$_2$CH$_2$CH$_2$—C(=O)—(NH-DX)
(maleimid-N-yl)-(CH$_2$)$n^2$-C(=O)-KGGFG (SEQ ID NO: 38)-NH—CH$_2$—O—CH$_2$—C(=O)—(NH-DX)
(maleimid-N-yl)-(CH$_2$)$n^2$-C(=O)-KGGFG (SEQ ID NO: 38)-NH—CH$_2$CH$_2$—O—CH$_2$—C(=O)—(NH-DX)
or the following formulas:
(maleimid-N-yl)-(CH$_2$)$n^2$-C(=O)-DGGF (SEQ ID NO: 34)-(NH-DX)
(maleimid-N-yl)-(CH$_2$)$n^2$-C(=O)-KGGF (SEQ ID NO: 35)-(NH-DX)
(maleimid-N-yl)-(CH$_2$)$n^2$-C(=O)-DGGFG (SEQ ID NO: 37)-(NH-DX)
(maleimid-N-yl)-(CH$_2$)$n^2$-C(=O)-KGGFG (SEQ ID NO: 38)-(NH-DX)

In the above formula, preferably, $n^2$ is 2 or 5.

Among them, further preferably, $n^2$ is 5, and it is represented by the following formulas:
(maleimid-N-yl)-CH$_2$CH$_2$CH$_2$CH$_2$CH$_2$—C(=O)-DGGF (SEQ ID NO: 34)-NH—CH$_2$CH$_2$—C(=O)—(NH-DX)
(maleimid-N-yl)-CH$_2$CH$_2$CH$_2$CH$_2$CH$_2$—C(=O)-DGGF (SEQ ID NO: 34)-NH—CH$_2$CH$_2$CH$_2$—C(=O)—(NH-DX)
(maleimid-N-yl)-CH$_2$CH$_2$CH$_2$CH$_2$CH$_2$—C(=O)-DGGF (SEQ ID NO: 34)-NH—CH$_2$—O—CH$_2$—C(=O)—(NH-DX)
(maleimid-N-yl)-CH$_2$CH$_2$CH$_2$CH$_2$CH$_2$—C(=O)-DGGF (SEQ ID NO: 34)-NH—CH$_2$CH$_2$—O—CH$_2$—C(=O)—(NH-DX)
(maleimid-N-yl)-CH$_2$CH$_2$CH$_2$CH$_2$CH$_2$—C(=O)-KGGF (SEQ ID NO: 35)-NH—CH$_2$CH$_2$—C(=O)—(NH-DX)
(maleimid-N-yl)-CH$_2$CH$_2$CH$_2$CH$_2$CH$_2$—C(=O)-KGGF (SEQ ID NO: 35)-NH—CH$_2$CH$_2$CH$_2$—C(=O)—(NH-DX)

(maleimid-N-yl)-CH₂CH₂CH₂CH₂CH₂—C(=O)-KGGF (SEQ ID NO: 35)-NH—CH₂—O—CH₂—C(=O)—(NH-DX)
(maleimid-N-yl)-CH₂CH₂CH₂CH₂CH₂—C(=O)-KGGF (SEQ ID NO: 35)-NH—CH₂CH₂—O—CH₂—C(=O)—(NH-DX)
(maleimid-N-yl)-CH₂CH₂CH₂CH₂CH₂—C(=O)-DGGFG (SEQ ID NO: 37)-NH—CH₂CH₂—C(=O)—(NH-DX)
(maleimid-N-yl)-CH₂CH₂CH₂CH₂CH₂—C(=O)-DGGFG (SEQ ID NO: 37)-NH—CH₂CH₂CH₂—C(=O)—(NH-DX)
(maleimid-N-yl)-CH₂CH₂CH₂CH₂CH₂—C(=O)-DGGFG (SEQ ID NO: 37)-NH—CH₂—O—CH₂—C(=O)—(NH-DX)
(maleimid-N-yl)-CH₂CH₂CH₂CH₂CH₂—C(=O)-DGGFG (SEQ ID NO: 37)-NH—CH₂CH₂—O—CH₂—C(=O)—(NH-DX)
(maleimid-N-yl)-CH₂CH₂CH₂CH₂CH₂—C(=O)-KGGFG (SEQ ID NO: 38)-NH—CH₂CH₂—C(=O)—(NH-DX)
(maleimid-N-yl)-CH₂CH₂CH₂CH₂CH₂—C(=O)-KGGFG (SEQ ID NO: 38)-NH—CH₂CH₂CH₂—C(=O)—(NH-DX)
(maleimid-N-yl)-CH₂CH₂CH₂CH₂CH₂—C(=O)-KGGFG (SEQ ID NO: 38)-NH—CH₂—O—CH₂—C(=O)—(NH-DX)
(maleimid-N-yl)-CH₂CH₂CH₂CH₂CH₂—C(=O)-KGGFG (SEQ ID NO: 38)-NH—CH₂CH₂—O—CH₂—C(=O)—(NH-DX)

or the following formulas:
(maleimid-N-yl)-CH₂CH₂CH₂CH₂CH₂—C(=O)-DGGF (SEQ ID NO: 34)-(NH-DX)
(maleimid-N-yl)-CH₂CH₂CH₂CH₂CH₂—C(=O)-KGGF (SEQ ID NO: 35)-(NH-DX)
(maleimid-N-yl)-CH₂CH₂CH₂CH₂CH₂—C(=O)-DGGFG (SEQ ID NO: 37)-(NH-DX)
(maleimid-N-yl)-CH₂CH₂CH₂CH₂CH₂—C(=O)-KGGFG (SEQ ID NO: 38)-(NH-DX)

When linker $L^P$ is a peptide linker which has a glycine oligopeptide at the C terminal, a compound having a structure represented by the following formula can be preferably used as a production intermediate:
(maleimid-N-yl)-(CH₂)n²-C(=O)-GGFGG (SEQ ID NO: 40)-(NH-DX)
(maleimid-N-yl)-(CH₂)n²-C(=O)-GGFGGG (SEQ ID NO: 41)-(NH-DX)

In the above formula, $n^2$ is preferably 2 to 5.

Among them, further preferably, $n^2$ is 5, and it is represented by the following formula:
(maleimid-N-yl)-CH₂CH₂CH₂CH₂CH₂—C(=O)-GGFGG (SEQ ID NO: 40)-(NH-DX)
(maleimid-N-yl)-CH₂CH₂CH₂CH₂CH₂—C(=O)-GGFGGG (SEQ ID NO: 41)-(NH-DX)

When linker $L^1$ in -(Succinimid-3-yl-N)—CH[—(CH₂)n³-COOH]—C(=O)—, a compound having a structure represented by the following formula can be preferably used as a production intermediate:
(maleimid-N-yl)-CH [—(CH₂)n³-COOH]—C(=O)—NH—(CH₂—CH₂—O)n⁶-CH₂—CH₂—C(=O)-$L^P$-NH—(CH₂)n¹-$L^a$-$L^b$-$L^c$-(NH-DX)

In the above formula, $n^6$ is 0. Preferably, $n^3$ is 2 to 4, and the —NH—(CH₂)n¹-$L^a$-$L^b$-$L^c$- moiety is —NH—CH₂CH₂—C(=O)—, —NH—CH₂CH₂CH₂—C(=O)—, —NH—CH₂—O—CH₂—C(=O)—, or —NH—CH₂CH₂—O—CH₂—C(=O)—. Also, those which $L^P$ is directly connected to the drug are preferable. $L^P$ is preferably GGFG (SEQ ID NO: 33).

More specifically, it is represented by the following formula:
(maleimid-N-yl)-CH[—(CH₂)n³-COOH]—C(=O)—NH—CH₂CH₂—C(=O)-GGFG (SEQ ID NO: 33)-NH—CH₂CH₂—C(=O)—(NH-DX)
(maleimid-N-yl)-CH[—(CH₂)n³-COOH]—C(=O)—NH—CH₂CH₂—C(=O)-GGFG (SEQ ID NO: 33)-NH—CH₂CH₂CH₂—C(=O)—(NH-DX)
(maleimid-N-yl)-CH [—(CH₂)n³-COOH]—C(=O)—NH—CH₂CH₂—C(=O)-GGFG (SEQ ID NO: 33)-NH—CH₂—O—CH₂—C(=O)—(NH-DX)
(maleimid-N-yl)-CH [—(CH₂)n³-COOH]—C(=O)—NH—CH₂CH₂—C(=O)-GGFG (SEQ ID NO: 33)-NH—CH₂CH₂—O—CH₂—C(=O)—(NH-DX)
or the following formula:
(maleimid-N-yl)-CH [—(CH₂)n³-COOH]—C(=O)—NH—CH₂CH₂—C(=O)-GGFG (SEQ ID NO: 33)-(NH-DX)

In the above formula, $n^3$ is preferably 2, and it is preferably represented by the following formula:
(maleimid-N-yl)-CH(CH₂CH₂—COOH)—C(=O)—NH—CH₂CH₂—C(=O)-GGFG (SEQ ID NO: 33)-NH—CH₂CH₂—C(=O)— (NH-DX)
(maleimid-N-yl)-CH(CH₂CH₂—COOH)—C(=O)—NH—CH₂CH₂—C(=O)-GGFG (SEQ ID NO: 33)-NH—CH₂CH₂CH₂—C(=O)—(NH-DX)
(maleimid-N-yl)-CH(CH₂CH₂—COOH)—C(=O)—NH—CH₂CH₂—C(=O)-GGFG (SEQ ID NO: 33)-NH—CH₂—O—CH₂—C(=O)—(NH-DX)
(maleimid-N-yl)-CH(CH₂CH₂—COOH)—C(=O)—NH—CH₂CH₂—C(=O)-GGFG (SEQ ID NO: 33)-NH—CH₂CH₂—O—CH₂—C(=O)—(NH-DX)
or the following formula:
(maleimid-N-yl)-CH(CH₂CH₂—COOH)—C(=O)—NH—CH₂CH₂—C(=O)-GGFG (SEQ ID NO: 33)-(NH-DX)

When linker $L^2$ is —N[—(CH₂CH₂—O)n⁷-CH₂CH₂—OH]—CH₂—C(=O)—, a compound having a structure represented by the following formula can be preferably used as production intermediate:
(maleimid-N-yl)-(CH₂)n²-C(=O)—N[—(CH₂CH₂—O)n⁷-CH₂CH₂—OH]—CH₂—C(=O)-$L^P$-NH—(CH₂)n¹-$L^a$-$L^b$-$L^c$-(NH-DX)

In the above formula, preferably, $n^2$ is 2 to 5, $n^7$ is 3 or 4, and the —NH—(CH₂)n¹-$L^a$-$L^b$-$L^c$- moiety is —NH—CH₂CH₂—C(=O)—, —NH—CH₂CH₂CH₂—C(=O)—, —NH—CH₂—O—CH₂—C(=O)—, or —NH—CH₂CH₂—O—CH₂—C(=O)—. Also those which $L^P$ is directly connected to the drug are preferable. $L^P$ is preferably GGFG (SEQ ID NO: 33).

More specifically, it is represented by the following formulas:
(maleimid-N-yl)-(CH₂)n²-C(=O)—N[—(CH₂CH₂—O)n⁷-CH₂CH₂—OH]—CH₂—C(=O)-GGFG (SEQ ID NO: 33)-NH—CH₂CH₂—C(=O)—(NH-DX)
(maleimid-N-yl)-(CH₂)n²-C(=O)—N[—(CH₂CH₂—O)n⁷-CH₂CH₂—OH]—CH₂—C(=O)-GGFG (SEQ ID NO: 33)-NH—CH₂CH₂CH₂—C(=O)—(NH-DX)
(maleimid-N-yl)-(CH₂)n²-C(=O)—N[—(CH₂CH₂—O)n⁷-CH₂CH₂—OH]—CH₂—C(=O)-GGFG (SEQ ID NO: 33)-NH—CH₂—O—CH₂—C(=O)—(NH-DX)
(maleimid-N-yl)-(CH₂)n²-C(=O)—N[—(CH₂CH₂—O)n⁷-CH₂CH₂—OH]—CH₂—C(=O)-GGFG (SEQ ID NO: 33)-NH—CH₂CH₂—O—CH₂—C(=O)—(NH-DX)
or the following formula:
(maleimid-N-yl)-(CH₂)n²-C(=O)—N[—(CH₂CH₂—O)n⁷-CH₂CH₂—OH]—CH₂—C(=O)-GGFG (SEQ ID NO: 33)-(NH-DX)

Further preferably, $n^2$ is 5, $n^7$ is 3 or 4, and more preferably 3, and it is represented by the following formulas;

(maleimid-N-yl)-CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—C(=O)—(NH-DX)

(maleimid-N-yl)-CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$CH$_2$—C(=O)—(NH-DX)

(maleimid-N-yl)-CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$—O—CH$_2$—C(=O)—(NH-DX)

(maleimid-N-yl)-CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—O—CH$_2$—C(=O)—(NH-DX)

or the following formula:

(maleimid-N-yl)-CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-(NH-DX)

In case when a halogenoacetyl group is present and peptide linker has a hydrophilic amino acid at the N terminal, a compound having a structure represented by the following formula can be preferably used as a production intermediate:

X—CH$_2$—C(=O)—NH—(CH$_2$)n$^4$-C(=O)-DGGF (SEQ ID NO: 34)-NH—(CH$_2$)n$^1$-L$^a$-L$^b$-L$^c$-(NH-DX)

X—CH$_2$—C(=O)—NH—(CH$_2$)n$^4$-C(=O)-KGGF (SEQ ID NO: 35)-NH—(CH$_2$)n$^1$-L$^a$-L$^b$-L$^c$-(NH-DX)

X—CH$_2$—C(=O)—NH—(CH$_2$)n$^4$-C(=O)-EGGF (SEQ ID NO: 36)-NH—(CH$_2$)n$^1$-L$^a$-L$^b$-L$^c$-(NH-DX)

X—CH$_2$—C(=O)—NH—(CH$_2$)n$^4$-C(=O)-DGGFG (SEQ ID NO: 37)-NH—(CH$_2$)n$^1$-L$^a$-L$^b$-L$^c$-(NH-DX)

X—CH$_2$—C(=O)—NH—(CH$_2$)n$^4$-C(=O)-KGGFG (SEQ ID NO: 38)-NH—(CH$_2$)n$^1$-L$^a$-L$^b$-L$^c$-(NH-DX)

X—CH$_2$—C(=O)—NH—(CH$_2$)n$^4$-C(=O)-EGGFG (SEQ ID NO: 39)-NH—(CH$_2$)n$^1$-L$^a$-L$^b$-L$^c$-(NH-DX)

In the above formula, preferably, $n^4$ is 2 to 5, and the —NH—(CH$_2$)n$^1$-L$^a$-L$^b$-L$^c$- moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^p$ is directly connected to the drug are preferable. X is preferably bromine or iodine.

More specifically, it is more preferably represented by the following formulas:

X—CH$_2$—C(=O)—NH—(CH$_2$)n$^4$-C(=O)-DGGF (SEQ ID NO: 34)-NH—CH$_2$CH$_2$—C(=O)—(NH-DX)

X—CH$_2$—C(=O)—NH—(CH$_2$)n$^4$-C(=O)-DGGF (SEQ ID NO: 34)-NH—CH$_2$CH$_2$CH$_2$—C(=O)—(NH-DX)

X—CH$_2$—C(=O)—NH—(CH$_2$)n$^4$-C(=O)-DGGF (SEQ ID NO: 34)-NH—CH$_2$-O—CH$_2$—C(=O)—(NH-DX)

X—CH$_2$—C(=O)—NH—(CH$_2$)n$^4$-C(=O)-DGGF (SEQ ID NO: 34)-NH—CH$_2$CH$_2$—O—CH$_2$—C(=O)—(NH-DX)

X—CH$_2$—C(=O)—NH—(CH$_2$)n$^4$-C(=O)-KGGF (SEQ ID NO: 35)-NH—CH$_2$CH$_2$—C(=O)—(NH-DX)

X—CH$_2$—C(=O)—NH—(CH$_2$)n$^4$-C(=O)-KGGF (SEQ ID NO: 35)-NH—CH$_2$CH$_2$CH$_2$—C(=O)—(NH-DX)

X—CH$_2$—C(=O)—NH—(CH$_2$)n$^4$-C(=O)-KGGF (SEQ ID NO: 35)-NH—CH$_2$-O—CH$_2$—C(=O)—(NH-DX)

X—CH$_2$—C(=O)—NH—(CH$_2$)n$^4$-C(=O)-KGGF (SEQ ID NO: 35)-NH—CH$_2$CH$_2$—O—CH$_2$—C(=O)—(NH-DX)

X—CH$_2$—C(=O)—NH—(CH$_2$)n$^4$-C(=O)-DGGFG (SEQ ID NO: 37)-NH—CH$_2$CH$_2$—C(=O)—(NH-DX)

X—CH$_2$—C(=O)—NH—(CH$_2$)n$^4$-C(=O)-DGGFG (SEQ ID NO: 37)-NH—CH$_2$CH$_2$CH$_2$—C(=O)—(NH-DX)

X—CH$_2$—C(=O)—NH—(CH$_2$)n$^4$-C(=O)-DGGFG (SEQ ID NO: 37)-NH—CH$_2$-O—CH$_2$—C(=O)—(NH-DX)

X—CH$_2$—C(=O)—NH—(CH$_2$)n$^4$-C(=O)-DGGFG (SEQ ID NO: 37)-NH—CH$_2$CH$_2$—O—CH$_2$—C(=O)—(NH-DX)

X—CH$_2$—C(=O)—NH—(CH$_2$)n$^4$-C(=O)-KGGFG (SEQ ID NO: 38)-NH—CH$_2$CH$_2$—C(=O)—(NH-DX)

X—CH$_2$—C(=O)—NH—(CH$_2$)n$^4$-C(=O)-KGGFG (SEQ ID NO: 38)-NH—CH$_2$CH$_2$CH$_2$—C(=O)—(NH-DX)

X—CH$_2$—C(=O)—NH—(CH$_2$)n$^4$-C(=O)-KGGFG (SEQ ID NO: 38)-NH—CH$_2$-O—CH$_2$—C(=O)—(NH-DX)

X—CH$_2$—C(=O)—NH—(CH$_2$)n$^4$-C(=O)-KGGFG (SEQ ID NO: 38)-NH—CH$_2$CH$_2$—O—CH$_2$—C(=O)—(NH-DX)

or the following formulas:

X—CH$_2$—C(=O)—NH—(CH$_2$)n$^4$-C(=O)-DGGF (SEQ ID NO: 34)-(NH-DX)

X—CH$_2$—C(=O)—NH—(CH$_2$)n$^4$-C(=O)-KGGF (SEQ ID NO: 35)-(NH-DX)

X—CH$_2$—C(=O)—NH—(CH$_2$)n$^4$-C(=O)-DGGFG (SEQ ID NO: 37)-(NH-DX)

X—CH$_2$—C(=O)—NH—(CH$_2$)n$^4$-C(=O)-KGGFG (SEQ ID NO: 38)-(NH-DX)

Further preferably, $n^4$ is 2, and it is represented by the following formulas:

X—CH$_2$—C(=O)—NH—CH$_2$CH$_2$—C(=O)-DGGF (SEQ ID NO: 34)-NH—CH$_2$CH$_2$—C(=O)—(NH-DX)

X—CH$_2$—C(=O)—NH—CH$_2$CH$_2$—C(=O)-DGGF (SEQ ID NO: 34)-NH—CH$_2$CH$_2$CH$_2$—C(=O)—(NH-DX)

X—CH$_2$—C(=O)—NH—CH$_2$CH$_2$—C(=O)-DGGF (SEQ ID NO: 34)-NH—CH$_2$—O—CH$_2$—C(=O)—(NH-DX)

X—CH$_2$—C(=O)—NH—CH$_2$CH$_2$—C(=O)-DGGF (SEQ ID NO: 34)-NH—CH$_2$CH$_2$—O—CH$_2$—C(=O)—(NH-DX)

X—CH$_2$—C(=O)—NH—CH$_2$CH$_2$—C(=O)-KGGF (SEQ ID NO: 35)-NH—CH$_2$CH$_2$—C(=O)—(NH-DX)

X—CH$_2$—C(=O)—NH—CH$_2$CH$_2$—C(=O)-KGGF (SEQ ID NO: 35)-NH—CH$_2$CH$_2$CH$_2$—C(=O)—(NH-DX)

X—CH$_2$—C(=O)—NH—CH$_2$CH$_2$—C(=O)-KGGF (SEQ ID NO: 35)-NH—CH$_2$—O—CH$_2$—C(=O)—(NH-DX)

X—CH$_2$—C(=O)—NH—CH$_2$CH$_2$—C(=O)-KGGF (SEQ ID NO: 35)-NH—CH$_2$CH$_2$—O—CH$_2$—C(=O)—(NH-DX)

X—CH$_2$—C(=O)—NH—CH$_2$CH$_2$—C(=O)-DGGFG (SEQ ID NO: 37)-NH—CH$_2$CH$_2$—C(=O)—(NH-DX)

X—CH$_2$—C(=O)—NH—CH$_2$CH$_2$—C(=O)-DGGFG (SEQ ID NO: 37)-NH—CH$_2$CH$_2$CH$_2$—C(=O)—(NH-DX)

X—CH$_2$—C(=O)—NH—CH$_2$CH$_2$—C(=O)-DGGFG (SEQ ID NO: 37)-NH—CH$_2$-O—CH$_2$—C(=O)—(NH-DX)

X—CH$_2$—C(=O)—NH—CH$_2$CH$_2$—C(=O)-DGGFG (SEQ ID NO: 37)-NH—CH$_2$CH$_2$—O—CH$_2$—C(=O)—(NH-DX)

X—CH$_2$—C(=O)—NH—CH$_2$CH$_2$—C(=O)-KGGFG (SEQ ID NO: 38)-NH—CH$_2$CH$_2$—C(=O)—(NH-DX)

X—CH$_2$—C(=O)—NH—CH$_2$CH$_2$—C(=O)-KGGFG (SEQ ID NO: 38)-NH—CH$_2$CH$_2$CH$_2$—C(=O)—(NH-DX)

X—CH$_2$—C(=O)—NH—CH$_2$CH$_2$—C(=O)-KGGFG (SEQ ID NO: 38)-NH—CH$_2$—O—CH$_2$—C(=O)—(NH-DX)

X—CH$_2$—C(=O)—NH—CH$_2$CH$_2$—C(=O)-KGGFG (SEQ ID NO: 38)-NH—CH$_2$CH$_2$—O—CH$_2$—C(=O)—(NH-DX)

or the following formulas:

X—CH$_2$—C(=O)—NH—CH$_2$CH$_2$—C(=O)-DGGF (SEQ ID NO: 34)-(NH-DX)

X—CH$_2$—C(=O)—NH—CH$_2$CH$_2$—C(=O)-KGGF (SEQ ID NO: 35)-(NH-DX)

X—CH$_2$—C(=O)—NH—CH$_2$CH$_2$—C(=O)-DGGFG (SEQ ID NO: 37)-(NH-DX)

X—CH$_2$—C(=O)—NH—CH$_2$CH$_2$—C(=O)-KGGFG (SEQ ID NO: 38)-(NH-DX)

In the above formula, X represents a bromine atom or an iodine atom. All of these bromine and iodine compounds can be preferably used as production intermediates.

In case when halogenoacetyl group is present and the peptide linker has a glycine oligopeptide at the C terminal, a compound having a structure represented by the following formula can be preferably used as a production intermediate:

X—CH$_2$—C(=O)—NH—(CH$_2$)n$^4$-C(=O)-GGFGG (SEQ ID NO: 40)-(NH-DX)

X—CH$_2$—C(=O)—NH—(CH$_2$)n$^4$-C(=O)-GGFGGG (SEQ ID NO: 41)-(NH-DX)

Preferably, n$^4$ is 2 or 5, and more preferably 2, and it is represented by the following formula:

X—CH$_2$—C(=O)—NH—CH$_2$CH$_2$—C(=O)-GGGFG-(NH-DX)

X—CH$_2$—C(=O)—NH—CH$_2$CH$_2$—C(=O)-GGFGGG (SEQ ID NO: 41)-(NH-DX)

In the above formula, X represents a bromine atom or an iodine atom. All of these bromine and iodine compounds can be preferably used as production intermediates.

When linker L$^2$ is —N[—(CH$_2$CH$_2$—O)n$^7$-CH$_2$CH$_2$—OH]—CH$_2$—C(=O)—, a compound having a structure represented by the following formula can be preferably used as a production intermediate:

X—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-L$^P$-NH—(CH$_2$) n$^1$-L$^a$-L$^b$-L$^c$-(NH-DX)

In the above formula, preferably, n$^4$ is 2 to 5, n$^7$ is 3 or 4, and the —NH—(CH$_2$)n$^1$-L$^a$-L$^b$-L$^c$- moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—. Also, those which L$^P$ is directly connected to the drug are preferable. L$^P$ is preferably GGFG (SEQ ID NO: 33).

Specifically, it is represented by the following formula:

X—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$—C(=O)—(NH-DX)

X—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$CH$_2$—C(=O)—(NH-DX)

X—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$—O—CH$_2$—C(=O)—(NH-DX)

X—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-NH—CH$_2$CH$_2$—O—CH$_2$—C(=O)—(NH-DX)

or the following formula:

X—CH$_2$—C(=O)—NH—(CH$_2$)n$^4$-C(=O)—N[—(CH$_2$CH$_2$—O)n$^7$-CH$_2$CH$_2$—OH]—CH$_2$—C(=O)-GGFG (SEQ ID NO: 33)-(NH-DX)

Further preferably, n$^4$ is 2, n$^7$ is 3 or 4, and more preferably 3, and it is represented by the following formulas:

X—CH$_2$—C(=O)—NH—(CH$_2$)n$^4$-C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—C(=O)—(NH-DX)

X—CH$_2$—C(=O)—NH—(CH$_2$)n$^4$-C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$CH$_2$—C(=O)—(NH-DX)

X—CH$_2$—C(=O)—NH—(CH$_2$)n$^4$-C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$—O—CH$_2$—C(=O)—(NH-DX)

X—CH$_2$—C(=O)—NH—(CH$_2$)n$^4$-C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-NH—CH$_2$CH$_2$—O—CH$_2$—C(=O)—(NH-DX)

or the following formula:

X—CH$_2$—C(=O)—NH—(CH$_2$)n$^4$-C(=O)—N(—CH$_2$CH$_2$—O—CH$_2$CH$_2$—O—CH$_2$CH$_2$—O—CH$_2$CH$_2$—OH)—CH$_2$—C(=O)-GGFG (SEQ ID NO: 33)-(NH-DX)

In order to secure the amount of the conjugate, a plurality of conjugates obtained under similar production conditions to have an equivalent number of drugs (e.g., about ±1) can be mixed to prepare new lots. In this case, the average number of drugs falls between the average numbers of drugs in the conjugates before the mixing.

2. Production Method 2

The antibody-drug conjugate represented by the formula (1) or a pharmacologically acceptable salt thereof, in which the bond to the antibody is amide group and has thioether bond within the linker, specifically, a structure in which -L$^1$-L$^2$- is —C(=O)-cyc.Hex(1,4)-CH$_2$—(N-ly-3-dimiccuS)-S—(CH$_2$)n$^8$-C(=O)—, can be also produced by the following method.

[Formula 38]

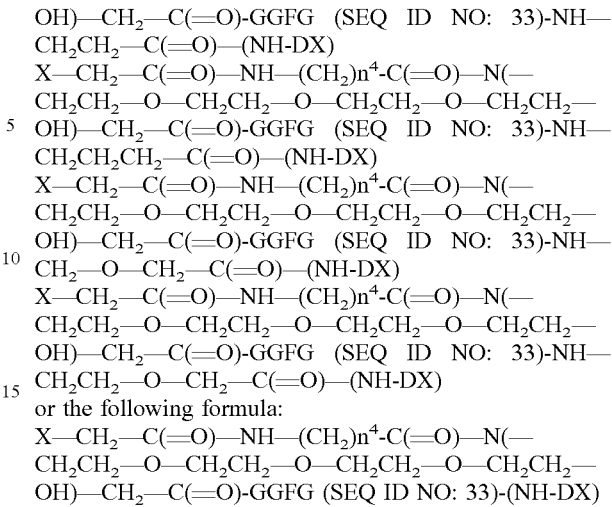

[In the formula, AB-L$^{1'}$ represents that the antibody is connected to linker L$^1$, and the terminal of L$^1$ is converted to a N-maleimidyl group. This group specifically has a structure in which —(N-ly-3-dimiccuS)- in AB—C(=O)-cyc.Hex(1,4)-CH$_2$—(N-ly-3-dimiccuS)- is converted to a maleimidyl group. L$^{2'}$ represents a HS—(CH$_2$)n$^8$-C(=O)— group in which the terminal is a mercapto group, and AB represents the antibody.]

Specifically, the antibody-drug conjugate (1) can be produced by reacting the compound (2a), which is obtainable by the method described below, with the antibody (3b) to which the linker having a maleimidyl group is connected.

The antibody (3b) having a maleimidyl group can be also obtained by a method well known in the art (Hermanson, G. T, Bioconjugate Techniques, pp. 56-136, pp. 456-493, Academic Press (1996)). Example includes a method in which a bifunctional linker such as succinimidyl-4-(N-maleimidomethyl)cyclohexane-1-carboxylate (SMCC), which is capable of connecting to an amino group or a hydroxyl group, is allowed to act on the amino group of the antibody so as to introduce a maleimidyl group, but it is not limited thereto.

For example, a compound having an amino group-reactive moiety and a thiol group-reactive moiety are connected via a linker can be preferably used. Here, the amino group-reactive moiety can be active ester, imide ester, or the like, and the thiol-reactive moiety can be maleimidyl, halogenated acetyl, halogenated alkyl, dithiopyridyl, or the like.

As a method for constructing the linker via an amide bond with the amino group or hydroxy group, particularly, the amino group, of an amino acid constituting antibody, the compound to be first reacted with the antibody can be a compound represented by the following formula: $Q^1$-$L^{1a}$-$Q^2$.

In the formula, $Q^1$ represents (Pyrrolidine-2,5-dione-N-yl)-O—C(=O)—, (3-Sulfo-pyrrolidine-2,5-dione-N-yl)-O—C(=O)—, $R^Q$—O—C(=N)—, or O=C=N—, $L^{1a}$- represents -cyc.Hex(1,4)-CH$_2$—, an alkylene group having 1 to 10 carbon atoms, a phenylene group, —(CH$_2$)n$^4$-C(=O)—, —(CH$_2$)n$^{4a}$-NH—C(=O)—(CH$_2$)n$^{4b}$-, or —(CH$_2$)n$^{4a}$-NH—C(=O)-cyc.Hex(1,4)-CH$_2$—, $Q^2$ represents (maleimid-N-yl), a halogen atom, or —S—S-(2-Pyridyl), $R^Q$ represents an alkyl group having 1 to 6 carbon atoms, n$^4$ represents an integer of 1 to 8, n$^{4a}$ represents an integer of 0 to 6, and n$^{4b}$ represents an integer of 1 to 6.

In the above, $R^Q$ is an alkyl group having 1 to 6 carbon atoms, and more preferably a methyl group or an ethyl group.

The alkylene group of $L^{1a}$ may be those having 1 to 10 carbon atoms. The phenylene group may be any of ortho, meta, and para and is more preferably a para- or meta-phenylene group.

Preferred examples of $L^{1a}$ can include -cyc.Hex(1,4)-CH$_2$—, —(CH$_2$)$_5$—NH—C(=O)-cyc.Hex(1,4)-CH$_2$—, —(CH$_2$)$_2$—NH—C(=O)—CH$_2$—, —(CH$_2$)$_5$—NH—C(=O)—(CH$_2$)$_2$—, —CH$_2$—, —(CH$_2$)$_2$—, —(CH$_2$)$_3$—, —(CH$_2$)$_5$—, —(CH$_2$)$_{10}$—, -(para-Ph)-, -(meta-Ph)-, -(para-Ph)-CH(—CH$_3$)—, —(CH$_2$)$_3$-(meta-Ph)-, and -(meta-Ph)-NH—C(=O)—CH$_2$—.

Q1 is preferably (Pyrrolidine-2,5-dione-N-yl)-O—C(=O)— and $Q^2$ is preferably (maleimid-N-yl), or —S—S-(2-Pyridyl) can be used when a disulfide bond is to be formed.

In the above, (Pyrrolidine-2,5-dione-N-yl)- is a group represented by the following formula:

[Formula 39]

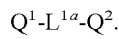

wherein the nitrogen atom is the connecting position, (3-Sulfo-pyrrolidine-2,5-dione-N-yl)- is a group represented by the following formula:

[Formula 40]

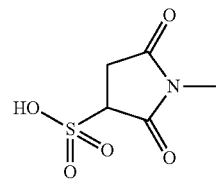

wherein the nitrogen atom is the connecting position, and this sulfonic acid is capable of forming a lithium salt, sodium salt, or potassium salt, and preferably sodium salt, cyc.Hex(1,4) represents a 1,4-cyclohexylene group, (maleimid-N-yl) is a group represented by the following formula:

[Formula 41]

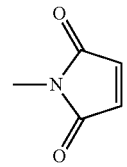

wherein the nitrogen atom is the connecting position, (2-Pyridyl) represents a 2-pyridyl group, (para-Ph) represents a para-phenylene group, and (meta-Ph) represents a meta-phenylene group.

As for such a compound other than the compounds described above, sulfosuccinimidyl-4-(N-maleimidylmethyl)cyclohexane-1-carboxylate (sulfo-SMCC), N-succinimidyl-4-(N-maleimidylmethyl)-cyclohexane-1-carboxy-(6-amidocaproate) (LC-SMCC), κ-maleimidyl undecanoic acid N-succinimidyl ester (KMUA), γ-maleimidyl butyric acid N-succinimidyl ester (GMBS), ε-maleimidyl caproic acid N-hydroxysuccinimide ester (EMCS), m-maleimidyl-benzoyl-N-hydroxysuccinimide ester (MBS), N-(α-maleimidylacetoxy)-succinimide ester [AMAS], succinimidyl-6-(β-maleimidylpropionamide)hexanoate (SMPH), N-succinimidyl 4-(p-maleimidylphenyl)-butyrate (SMPB), N-(p-maleimidylphenyl)isocyanate (PMPI), N-succinimidyl-4-(iodoacetyl)-aminobenzoate (SIAB), N-succinimidyl iodoacetate (SIA), N-succinimidyl bromoacetate (SBA), N-succinimidyl 3-(bromoacetamide)propionate (SBAP), N-succinimidyl-3-(2-pyridodithio)propionate (SPDP), and succinimidyloxycarbonyl-α-methyl-α-(2-pyridyldithio) toluene (SMPT) can be used.

Specifically, for example, by reacting 2 to 6 equivalents of SMCC with the antibody (3) in a phosphate buffer of pH 6 to 7 at room temperature for 1 to 6 hours, the active ester of SMCC can react with the antibody to yield the antibody (3b) having a maleimidyl group. The obtained antibody (3b) can be purified by Common procedure D-2 described below, and used for the next reaction with the compound (2).

The amino group and hydroxyl group of the antibody refer to, for example, a N-terminal amino group carried by the antibody and/or an amino group carried by a lysine residue and a hydroxy group carried by a serine residue, respectively, but they are not limited thereto.

For the produced antibody-drug conjugate (1), concentration, buffer exchange, purification, and identification of the antibody-drug conjugate (1) by the measurement of antibody concentration and an average number of conjugated drug molecules per antibody molecule and calculation of aggregate content can be performed in the same manner as Production method 1.

The compound represented by the formula (3b) in Production method 2 has the following structure (see the following formula; in the structure thereof, "antibody-NH—" originates from an antibody).

[Formula 42]

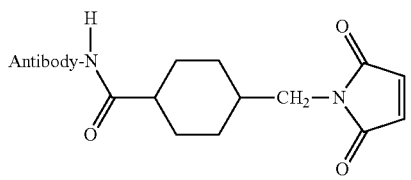

A compound which is an intermediate for producing the antibody-drug conjugate of the present invention and has the above structure is as described below (in the formula, n is an integer of 1 to 10, preferably 2 to 8, and more preferably 3 to 7).

[Formula 43]

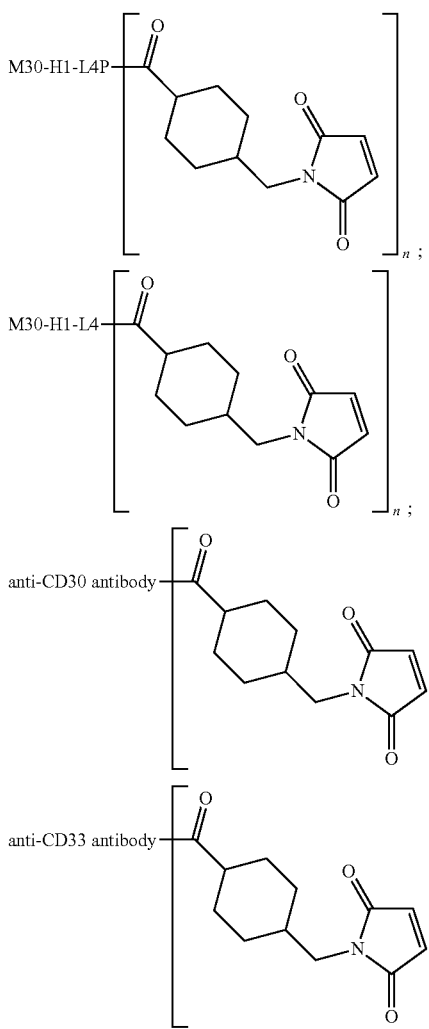

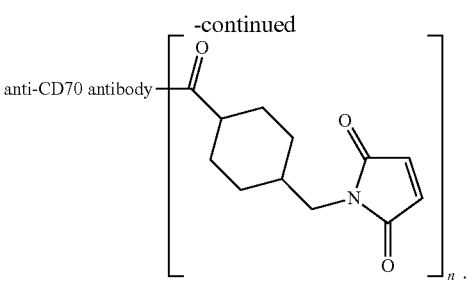

Further, examples of the compound of the present invention in which the terminal is a mercapto group can include the followings.

When the peptide linker has a hydrophilic amino acid at the N terminal, a compound having a structure represented by the following formula can be preferably used as a production intermediate:

HS—$(CH_2)n^8$-C(=O)-DGGF (SEQ ID NO: 34)-NH—$(CH_2)n^1$-$L^a$-$L^b$-$L^c$-(NH-DX)
HS—$(CH_2)n^8$-C(=O)-KGGF (SEQ ID NO: 35)-NH—$(CH_2)n^1$-$L^a$-$L^b$-$L^c$-(NH-DX)
HS—$(CH_2)n^8$-C(=O)-DGGFG (SEQ ID NO: 37)-NH—$(CH_2)n^1$-$L^a$-$L^b$-$L^c$-(NH-DX)
HS—$(CH_2)n^8$-C(=O)-KGGFG (SEQ ID NO: 38)-NH—$(CH_2)n^1$-$L^a$-$L^b$-$L^c$-(NH-DX)

In the above formula, preferably, $n^8$ is 2 to 5, and the —NH—$(CH_2)n^1$-$L^a$-$L^b$-$L^c$- moiety is —NH—$CH_2CH_2$—C(=O)—, —NH—$CH_2CH_2CH_2$—C(=O)—, —NH—$CH_2$—O—$CH_2$—C(=O)—, or —NH—$CH_2CH_2$—O—$CH_2$—C(=O)—. Also, those which $L^P$ is directly connected to the drug are preferable.

More specifically, $n^8$ is preferably 2, and it is represented by the following formula:

HS—$CH_2CH_2$—C(=O)-DGGF (SEQ ID NO: 34)-NH—$CH_2CH_2$—C(=O)—(NH-DX)
HS—$CH_2CH_2$—C(=O)-DGGF (SEQ ID NO: 34)-NH—$CH_2CH_2CH_2$—C(=O)—(NH-DX)
HS—$CH_2CH_2$—C(=O)-DGGF (SEQ ID NO: 34)-NH—$CH_2$—O—$CH_2$—C(=O)—(NH-DX)
HS—$CH_2CH_2$—C(=O)-DGGF (SEQ ID NO: 34)-NH—$CH_2CH_2$—O—$CH_2$—C(=O)—(NH-DX)
HS—$CH_2CH_2$—C(=O)-KGGF (SEQ ID NO: 35)-NH—$CH_2CH_2$—C(=O)—(NH-DX)
HS—$CH_2CH_2$—C(=O)-KGGF (SEQ ID NO: 35)-NH—$CH_2CH_2CH_2$—C(=O)—(NH-DX)
HS—$CH_2CH_2$—C(=O)-KGGF (SEQ ID NO: 35)-NH—$CH_2$—O—$CH_2$—C(=O)—(NH-DX)
HS—$CH_2CH_2$—C(=O)-KGGF (SEQ ID NO: 35)-NH—$CH_2CH_2$—O—$CH_2$—C(=O)—(NH-DX)
HS—$CH_2CH_2$—C(=O)-DGGFG (SEQ ID NO: 37)-NH—$CH_2CH_2$—C(=O)—(NH-DX)
HS—$CH_2CH_2$—C(=O)-DGGFG (SEQ ID NO: 37)-NH—$CH_2CH_2CH_2$—C(=O)—(NH-DX)
HS—$CH_2CH_2$—C(=O)-DGGFG (SEQ ID NO: 37)-NH—$CH_2$—O—$CH_2$—C(=O)—(NH-DX)
HS—$CH_2CH_2$—C(=O)-DGGFG (SEQ ID NO: 37)-NH—$CH_2CH_2$—O—$CH_2$—C(=O)—(NH-DX)
HS—$CH_2CH_2$—C(=O)-KGGFG (SEQ ID NO: 38)-NH—$CH_2CH_2$—C(=O)—(NH-DX)
HS—$CH_2CH_2$—C(=O)-KGGFG (SEQ ID NO: 38)-NH—$CH_2CH_2CH_2$—C(=O)—(NH-DX)
HS—$CH_2CH_2$—C(=O)-KGGFG (SEQ ID NO: 38)-NH—$CH_2$—O—$CH_2$—C(=O)—(NH-DX)

HS—CH$_2$CH$_2$—C(=O)-KGGFG (SEQ ID NO: 38)-NH—CH$_2$CH$_2$—O—CH$_2$—C(=O)—(NH-DX)
or the following formulas:
HS—CH$_2$CH$_2$—C(=O)-DGGF (SEQ ID NO: 34)-(NH-DX)
HS—CH$_2$CH$_2$—C(=O)-KGGF (SEQ ID NO: 35)-(NH-DX)
HS—CH$_2$CH$_2$—C(=O)-DGGFG (SEQ ID NO: 37)-(NH-DX)
HS—CH$_2$CH$_2$—C(=O)-KGGFG (SEQ ID NO: 38)-(NH-DX)

When the peptide residue of the linker has a glycine oligopeptide at the C terminal, a compound having a structure represented by the following formula can be preferably used as a production intermediate:
HS—(CH$_2$)n$^8$-C(=O)-GGFGG (SEQ ID NO: 40)-(NH-DX)
HS—(CH$_2$)n$^8$-C(=O)-GGFGGG (SEQ ID NO: 41)-(NH-DX)

In the above formula, n$^8$ is preferably 2 or 5.

More preferably, n$^8$ is 2, and it is represented by the following formula:
HS—CH$_2$CH$_2$—C(=O)-GGFGG (SEQ ID NO: 40)-(NH-DX)
HS—CH$_2$CH$_2$—C(=O)-GGFGGG (SEQ ID NO: 41)-(NH-DX)

3. Production Method 3

The antibody-drug conjugate represented by the formula (1) or a pharmacologically acceptable salt thereof in which the antibody is conjugated to the drug linker moiety via an amide bond can be produced by a method described below. For example, L$^{1\prime}$ in which L$^1$ is —C(=O)—(CH$_2$)n$^5$-C(=O)—, and this is converted to active ester, for example, (Pyrrolidine-2,5-dione-N-yl)-O—C(=O)—(CH$_2$)n$^5$-C(=O)—, can be preferably used. Further, when L$^2$ is a single bond, the antibody-drug conjugate (1) can be produced by the following method, for example.

[Formula 44]

L$^{1\prime}$—L$^2$—L$^p$—NH—(CH$_2$)n$^1$—L$^a$—L$^b$—L$^c$—(NH—DX)

or

L$^{1\prime}$—L$^2$—L$^p$—(NH—DX)

2b $\xrightarrow{AB\ 3}$

AB—L$^1$—L$^2$—L$^p$—NH—(CH$_2$)n$^1$—L$^a$—L$^b$—L$^c$—(NH—DX)

or

AB—L$^1$—L$^2$—L$^p$—(NH—DX)

1

Specifically, the antibody-drug conjugate (1) can be produced by reacting the compound (2b), which is obtainable by the method described below, with the antibody (3).

The compound (2b) has a property capable of connecting to the amino group or hydroxyl group of the antibody. The amino group and hydroxyl group of the antibody refer to, as described in Production method 2, for example, a N-terminal amino group carried by the antibody and/or an amino group carried by a lysine residue and a hydroxy group carried by a serine residue, respectively, but they are not limited thereto.

The compound (2b) is an active ester composed of a N-hydroxysuccinimidyl ester group, and alternatively, other active esters, for example, a sulfosuccinimidyl ester group, N-hydroxyphthalimidyl ester, N-hydroxysulfophthalimidyl ester, ortho-nitrophenyl ester, para-nitrophenyl ester, 2,4-dinitrophenyl ester, 3-sulfonyl-4-nitrophenyl ester, 3-carboxy-4-nitrophenyl ester, and pentafluorophenyl ester, may be used.

As the reaction between compound (2b) and antibody (3), using 2 to 20 molar equivalents of the compound (2b) per the antibody (3) in the reaction of the compound (2b) with the antibody (3), the antibody-drug conjugate (1) in which 1 to 10 drug molecules are conjugated per antibody can be produced. Specifically, the solution containing the compound (2b) dissolved therein can be added to a buffer solution containing the antibody (3) for the reaction to produce the antibody-drug conjugate (1). Herein, examples of the buffer solution which may be used include sodium acetate solution, sodium phosphate, and sodium borate. pH for the reaction can be 5 to 9, and more preferably the reaction is performed near pH 7. Examples of the solvent for dissolving the compound (2b) include an organic solvent such as dimethyl sulfoxide (DMSO), dimethylformamide (DMF), dimethylacetamide (DMA), and N-methyl-2-pyridone (NMP). It is sufficient that the organic solvent solution containing the compound (2b) dissolved therein is added at 1 to 20% v/v to a buffer solution containing the antibody (3) for the reaction. The reaction temperature is 0 to 37° C., more preferably 10 to 25° C., and the reaction time is 0.5 to 20 hours.

For the produced antibody-drug conjugate (1), concentration, buffer exchange, purification, and identification of the antibody-drug conjugate (1) by the measurement of antibody concentration and an average number of conjugated drug molecules per antibody molecule can be performed in the same manner as Production method 1.

In Production method 3, (Pyrrolidine-2,5-dione-N-yl)-O—C(=O)—(CH$_2$)n$^4$-C(=O)— has the following structure.

[Formula 45]

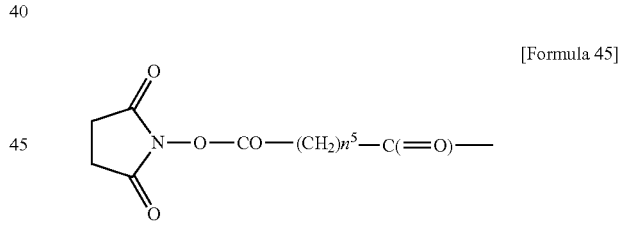

Examples of the compound having the above partial structure and having the peptide linker having a hydrophilic amino acid at the N terminal can include the followings.
(Pyrrolidine-2,5-dione-N-yl)-O—C(=O)—CH$_2$CH$_2$CH$_2$CH$_2$CH$_2$—C(=O)-DGGF (SEQ ID NO: 34)-NH—CH$_2$CH$_2$—C(=O)—(NH-DX),
(Pyrrolidine-2,5-dione-N-yl)-O—C(=O)—CH$_2$CH$_2$CH$_2$CH$_2$CH$_2$—C(=O)-DGGF (SEQ ID NO: 34)-NH—CH$_2$CH$_2$CH$_2$—C(=O)—(NH-DX),
(Pyrrolidine-2,5-dione-N-yl)-O—C(=O)—CH$_2$CH$_2$CH$_2$CH$_2$CH$_2$—C(=O)-DGGF (SEQ ID NO: 34)-NH—CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$—C(=O)-DGGF (SEQ ID NO: 34)-NH—CH$_2$CH$_2$—O—CH$_2$—C(=O)—(NH-DX),
(Pyrrolidine-2,5-dione-N-yl)-O—C(=O)—CH$_2$CH$_2$CH$_2$CH$_2$CH$_2$—C(=O)-KGGF (SEQ ID NO: 35)-NH—CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$—O—CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$—O—CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$—O—CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$—O—CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$—O—CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$—O—CH$_2$—C(=O)—(NH-DX).

Among them, the followings are more preferred.

(Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-NH—CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-NH—CH$_2$CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-NH—CH$_2$CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-NH—CH$_2$CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-NH—CH$_2$CH$_2$—C(=O)—(NH-DX).

Examples of the compound having the above partial structure and having the peptide linker having a hydrophilic amino acid at the N terminal, which is directly connected to the drug can include the followings.

(Pyrrolidine-2,5-dione-N-yl)-O—C(=O)—CH$_2$CH$_2$CH$_2$CH$_2$CH$_2$CH$_2$—C(=O)-DGGF (SEQ ID NO: 34)-(NH-DX), (Pyrrolidine-2,5-dione-N-yl)-O—C(=O)—CH$_2$CH$_2$CH$_2$CH$_2$CH$_2$CH$_2$—C(=O)-KGGF (SEQ ID NO: 35)-(NH-DX), (Pyrrolidine-2,5-dione-N-yl)-O—C(=O)—CH$_2$CH$_2$CH$_2$CH$_2$CH$_2$CH$_2$—C(=O)-DGGFG (SEQ ID NO: 37)-(NH-DX), (Pyrrolidine-2,5-dione-N-yl)-O—C(=O)—CH$_2$CH$_2$CH$_2$CH$_2$CH$_2$CH$_2$—C(=O)-KGGFG (SEQ ID NO: 38)-(NH-DX).

Examples of the compound having the above partial structure and having the peptide linker having a glycine oligopeptide at the C terminal, which is directly connected to the drug can include the followings.

(Pyrrolidine-2,5-dione-N-yl)-O—C(=O)—CH$_2$CH$_2$CH$_2$CH$_2$CH$_2$CH$_2$—C(=O)-GGFGG (SEQ ID NO: 40)-(NH-DX), (Pyrrolidine-2,5-dione-N-yl)-O—C(=O)—CH$_2$CH$_2$CH$_2$CH$_2$CH$_2$CH$_2$—C(=O)-GGFGGG (SEQ ID NO: 41)-(NH-DX).

Examples of the compound having the above partial structure and having the hydrophilic structure in $L^1$ can include the followings.

(Pyrrolidine-2,5-dione-N-yl)-O—C(=O)—CH(CH$_2$CH$_2$—COOH)—CH$_2$—C(=O)-GGFG (SEQ ID NO: 33)-NH—CH$_2$CH$_2$—C(=O)—(NH-DX), (Pyrrolidine-2,5-dione-N-yl)-O—C(=O)—CH(CH$_2$CH$_2$—COOH)—CH$_2$—C(=O)-GGFG (SEQ ID NO: 33)-NH—CH$_2$CH$_2$CH$_2$—C(=O)—(NH-DX), (Pyrrolidine-2,5-dione-N-yl)-O—C(=O)—CH(CH$_2$CH$_2$—COOH)—CH$_2$—C(=O)-GGFG (SEQ ID NO: 33)-NH—CH$_2$—O—CH$_2$—C(=O)—(NH-DX), (Pyrrolidine-2,5-dione-N-yl)-O—C(=O)—CH(CH$_2$CH$_2$—COOH)—CH$_2$—C(=O)-GGFG (SEQ ID NO: 33)-NH—CH$_2$CH$_2$—O—CH$_2$—C(=O)—(NH-DX).

Examples of the compound having the above partial structure, having the hydrophilic structure in $L^1$, and having the peptide linker directly connected to the drug can include the followings.

(Pyrrolidine-2,5-dione-N-yl)-O—C(=O)—CH(CH$_2$CH$_2$—COOH)—CH$_2$—C(=O)-GGFG (SEQ ID NO: 33)-(NH-DX).

Examples of the compound having the above partial structure and having the hydrophilic structure in $L^2$ can include the followings.

(Pyrrolidine-2,5-dione-N-yl)-O—C(=O)—CH$_2$CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$—C(=O)-GGFG (SEQ ID NO: 33)-NH—CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$—C(=O)-GGFG (SEQ ID NO: 33)-NH—CH$_2$CH$_2$CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$—C(=O)-GGFG (SEQ ID NO: 33)-NH—CH$_2$—O—CH$_2$—C(=O)—(NH-DX), (Pyrrolidine-2,5-dione-N-yl)-O—C(=O)—CH$_2$CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$—C(=O)-GGFG (SEQ ID NO: 33)-NH—CH$_2$CH$_2$—O—CH$_2$—C(=O)—(NH-DX).

Examples of the compound having the above partial structure, having the hydrophilic structure in $L^2$, and the peptide linker directly connected to the drug can include the followings.

(Pyrrolidine-2,5-dione-N-yl)-O—C(=O)—CH$_2$CH$_2$CH$_2$CH$_2$CH$_2$CH$_2$—C(=O)—N(—CH$_2$CH$_2$—O—CH$_2$CH$_2$—O—CH$_2$CH$_2$—O—CH$_2$—C(=O)-GGFG (SEQ ID NO: 33)-(NH-DX).

4. Production Method 4

Among the compound represented by the formula (2) or (2b) used as an intermediate in the previous production method and a pharmacologically acceptable salt thereof, those in which the linker has a structure represented by -$L^1$-$L^2$-$L^P$-NH—(CH$_2$)n$^1$-$L^a$-$L^b$-$L^c$-, and $L^P$ has a hydrophilic amino acid other than glycine at the N terminal, for example, can be produced by the following method.

[Formula 46-1]

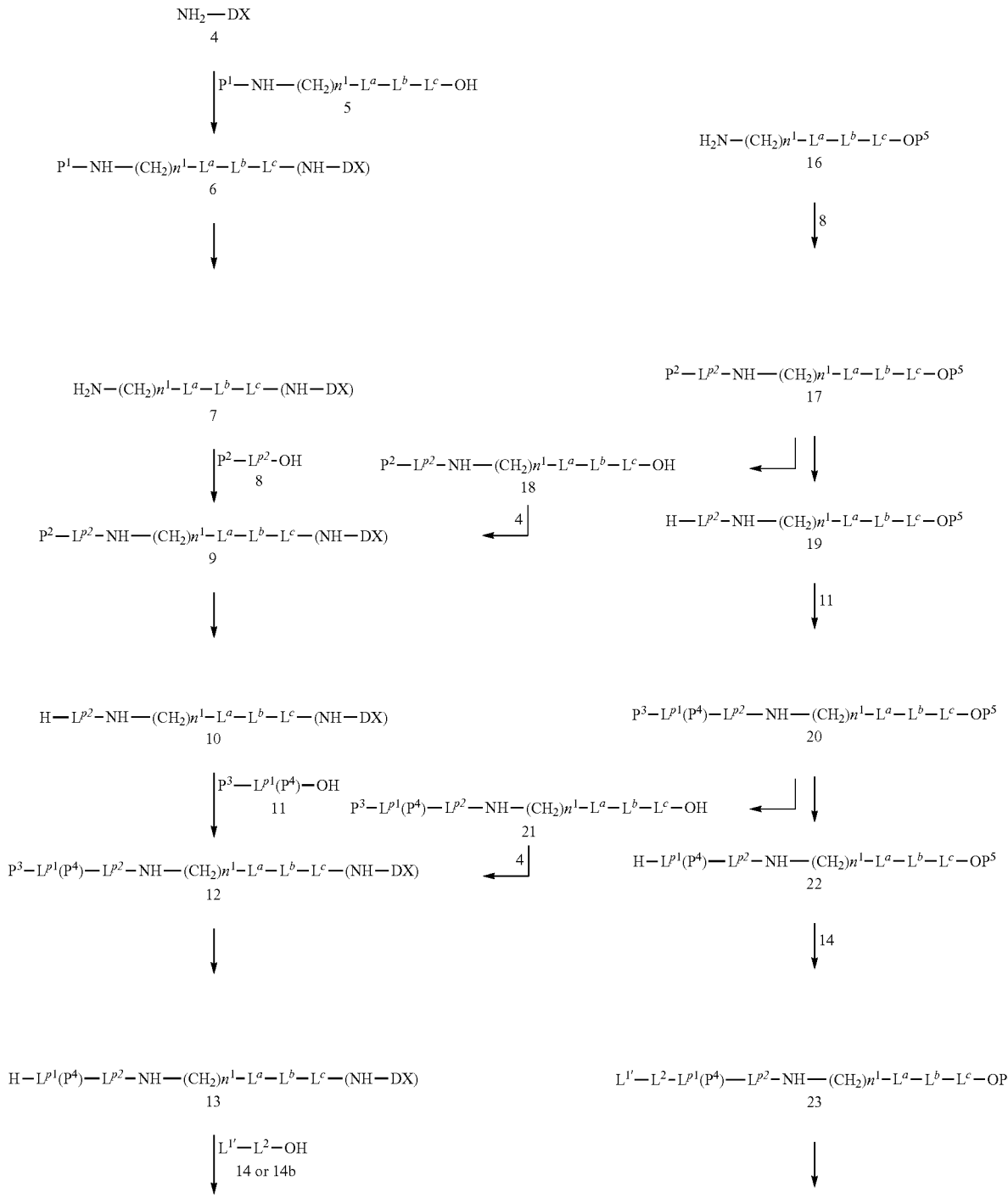

-continued

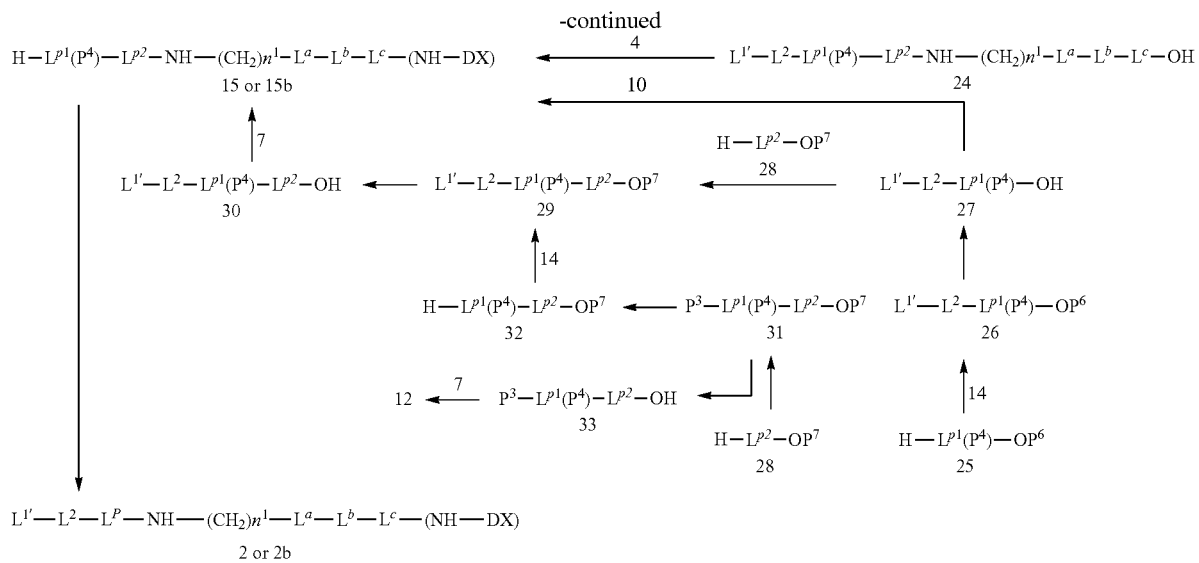

In the formula, $L^c$ is a —C(=O)— group, $L^{1'}$ represents $L^1$ structure in which the terminal is a maleimidyl group or a haloacetyl group, or $L^1$ is converted to (Pyrrolidine-2,5-dione-N-yl)-O—C(=O)—(CH$_2$)n$^5$-C(=O)—, $L^P$ represents a structure of -$L^{p1}$-$L^{p2}$-, and $P^1$, $P^2$, $P^3$, $P^4$, $P^5$, $P^6$, and $P^7$ each represent a protecting group.

Since $L^P$ is formed by connecting $L^{p1}$ and $L^{p2}$, the N-terminal hydrophilic amino acid of $L^P$ is derived from $L^{p1}$, therefore, $L^{p1}$ having a hydrophilic amino acid at the N terminal can be used. A plurality of hydrophilic amino acids may be present therein. If $L^{p2}$ having a hydrophilic amino acid is used, according to its position, $L^P$ can be produced so as to contain a plurality of hydrophilic amino acids at the N terminal of $L^P$ or at the N terminal and other positions.

The compound (6) can be produced by derivatizing the carboxylic acid compound (5) having the terminal amino group protected with $P^1$ into active ester, mixed acid anhydride, acid halide, or the like and reacting it with NH$_2$-DX [which represents exatecan; chemical name: (1S,9S)-1-amino-9-ethyl-5-fluoro-2,3-dihydro-9-hydroxy-4-methyl-1H,12H-benzo[de]pyrano[3',4':6,7]indolidino[1,2-b]quinoline-10,13(9H,15H)-dione] (that is, the pharmaceutical compound described in claim 2 of Japanese Patent Laid-Open No. 6-87746) (4) or a pharmacologically acceptable salt thereof in the presence of a base.

For this reaction, reagents and conditions commonly used for amidation and peptide synthesis can be employed There are various kinds of active ester, for example, it can be produced by reacting phenols such as p-nitrophenol, N-hydroxy benzotriazole, N-hydroxy succinimide, or the like, with the carboxylic acid compound (5) using a condensation agent such as N,N'-dicyclohexylcarbodiimide or 1-ethyl-3-(3-dimethylaminopropyl)carbodiimide hydrochloride. Further, the active ester can be also produced by a reaction of the carboxylic acid compound (5) with pentafluorophenyl trifluoroacetate or the like; a reaction of the carboxylic acid compound (5) with 1-benzotriazolyl oxytripyrrolidinophosphonium hexafluorophosphite; a reaction of the carboxylic acid compound (5) with diethyl cyanophosphonate (Shioiri method); a reaction of the carboxylic acid compound (5) with triphenylphosphine and 2,2'-dipyridyl disulfide (Mukaiyama's method); a reaction of the carboxylic acid compound (5) with a triazine derivative such as 4-(4,6-dimethoxy-1,3,5-triazin-2-yl)-4-methylmorpholinium chloride (DMTMM); or the like. Further, the reaction can be also performed by, e.g., an acid halide method by which the carboxylic acid compound (5) is treated with acid halide such as thionyl chloride or oxalyl chloride in the presence of a base. By reacting the active ester, mixed acid anhydride, or acid halide of the carboxylic acid compound (5) obtained above with the compound (4) in the presence of a suitable base in an solvent which does not inhibit a reaction at −78° C. to 150° C., the compound (6) can be produced.

Specific examples of the base used for each step described above include carbonate of an alkali metal or an alkali earth metal, an alkali metal alkoxide, hydroxide or hydride of an alkali metal including sodium carbonate, potassium carbonate, sodium ethoxide, potassium butoxide, sodium hydroxide, potassium hydroxide, sodium hydride, and potassium hydride, organometallic base represented by an alkyl lithium including n-butyl lithium, dialkylamino lithium including lithium diisopropylamide; organometallic base of bissilylamine including lithium bis(trimethylsilyl)amide; and organic base including pyridine, 2,6-lutidine, collidine, 4-dimethylaminopyridine, triethylamine, N-methylmorpholine, diisopropylethylamine, and diazabicyclo[5.4.0]undec-7-ene (DBU).

Examples of the solvent, which is used for the reaction of the present invention and does not inhibit the reaction, include a halogenated hydrocarbon solvent such as dichloromethane, chloroform, and carbon tetrachloride; an ether solvent such as tetrahydrofuran, 1,2-dimethoxyethane, and dioxane; an aromatic solvent such as benzene and toluene; and an amide solvent such as N,N-dimethylformamide, N,N-dimethylacetamide, and N-methylpyrrolidin-2-one. In addition to them, a sulfoxide solvent such as dimethyl sulfoxide and sulfolane; an alcohol solvent such as methanol and ethanol; and a ketone solvent such as acetone and methyl ethyl ketone may be used depending on a case.

The hydroxy group, carboxy group, amino group, or the like of $L^a$ and $L^b$ in the compound (6) may be protected by a protecting group which is commonly used in organic compound synthesis, as mentioned later. Specifically, examples of the protecting group for a hydroxyl group include an alkoxymethyl group such as methoxymethyl group; an arylmethyl group such as benzyl group, 4-methoxybenzyl group, and triphenylmethyl group; an alkanoyl group such as acetyl group; an aroyl group such as benzoyl group; and a silyl group such as tert-butyl diphenylsilyl group. Carboxy group can be protected, e.g., as an ester with an alkyl group such as methyl group, ethyl group, and tert-butyl group, an allyl group, or an arylmethyl group such as benzyl group. Amino group can be protected with a protecting group for an amino group which is generally used for peptide synthesis, for example, an alkyloxy carbonyl group such as tert-butyloxy carbonyl group, methoxycarbonyl group, ethoxycarbonyl group, and 2-(trimethylsilyl) ethoxycarbonyl group; an arylmethyl group such as allyloxycarbonyl, 9-fluorenylmethyloxy carbonyl group, benzyloxy carbonyl group, paramethoxybenzyloxy carbonyl group, and para (or ortho)nitroybenzyloxy carbonyl group; an alkanoyl group such as acetyl group; an arylmethyl group such as benzyl group and triphenyl methyl group; an aroyl group such as benzoyl group; and an aryl sulfonyl group such as 2,4-dinitrobenzene sulfonyl group or orthonitrobenzene sulfonyl group. Protection with and deprotection of the protecting group can be performed according to a method commonly carried out in the art.

As for the protecting group $P^1$ for the terminal amino group of the compound (6), a protecting group for an amino group which is generally used for peptide synthesis, for example, tert-butyloxy carbonyl group, 9-fluorenylmethyloxy carbonyl group, and benzyloxy carbonyl group, can be used. Examples of the other protecting group for an amino group include an alkanoyl group such as acetyl group; an alkoxycarbonyl group such as methoxycarbonyl group and ethoxycarbonyl group; an arylmethoxy carbonyl group such as paramethoxybenzyloxy carbonyl group, and para (or ortho)nitrobenzyloxy carbonyl group; an arylmethyl group such as benzyl group and triphenyl methyl group; an aroyl group such as benzoyl group; and an aryl sulfonyl group such as 2,4-dinitrobenzene sulfonyl group and orthonitrobenzene sulfonyl group. The protecting group $P^1$ can be selected depending on, e.g., properties of a compound having an amino group to be protected.

By deprotecting the protecting group $P^1$ for the terminal amino group of the compound (6) obtained, the compound (7) can be produced. Reagents and conditions can be selected depending on the protecting group.

By derivatizing the peptide or amino acid (8), which is protected by $P^2$ at its N terminal, into an active ester, mixed acid anhydride, or the like and reacting it with the compound (7) obtained, the compound (9) can be produced. The reaction conditions, reagents, base, and solvent used for forming a amide bond between the peptide or amino acid (8) and the compound (7) are not limited as long as they do not inhibit a reaction, and can be suitably selected from those described for the synthesis of the compound (6). The protecting group $P^2$ for an amino group can be suitably selected from those described for the protecting group of the compound (6), and the selection can be made based on, e.g., the properties of the compound. As it is generally used for peptide synthesis, by repeating sequentially the reaction and deprotection of the amino acid or peptide constituting the peptide or amino acid (8) for elongation, the compound (9) can be also produced.

By deprotecting $P^2$ as the protecting group for the amino group of the compound (9) obtained, the compound (10) can be produced. Reagents and conditions can be selected depending on the protecting group.

By derivatizing the amino acid or peptide (11) having the N terminal protected with $P^3$ and a side chain carboxy group, hydroxy group, or amino group protected with $P^4$ into an active ester, mixed acid anhydride, or the like and reacting it with the compound (10) obtained, the compound (12) can be produced. The reaction conditions, reagents, base, and solvent used for forming a peptide bond between the amino acid or peptide (11) and the compound (10) can be suitably selected from those described for the synthesis of the compound (6). The protecting groups $P^3$ and $P^4$ can be suitably selected from those described for the protecting group for the amino group, carboxy group, or hydroxy group of the compound (6). However, in such case, it is necessary that the protecting group $P^3$ for an amino group and the protecting group $P^4$ for a side chain functional group can be removed by a different method or different conditions. For example, a representative example includes a combination in which $P^3$ is a 9-fluorenylmethyloxycarbonyl group and $P^4$ is a tert-butyl group or the like for a carboxy group, a methoxymethyl group or the like for a hydroxy group, or a tert-butyloxycarbonyl group or the like for an amino group. The protecting group $P^4$ for a side chain functional group is preferably a protecting group that can be deprotected under acidic conditions, but it is not limited thereto, and can be selected from the aforementioned ones depending on, e.g., the properties of the compound having an amino group, carboxy group, or hydroxy group to be protected. For removal of the protecting groups, reagents and conditions can be selected depending on the protecting group. As it is generally used for peptide synthesis, by repeating sequentially the reaction and deprotection of the constituting amino acid or peptide for elongation, the compound (12) can be also produced.

By deprotecting $P^3$ as the protecting group for the terminal amino group of the compound (12) obtained, the compound (13) can be produced. Reagents and conditions can be selected depending on the protecting group.

By derivatizing the carboxylic acid derivative (14) or (14b) into an active ester, mixed acid anhydride, acid halide, or the like and reacting it with the compound (13) obtained, the compound (15) or (15b) can be produced. Here, the carboxylic acid derivative (14) is a compound having a structure of $L^{1'}$ in which the linker terminal is a maleimidyl group or a haloacetyl group, and the carboxylic acid derivative (14b) is a compound having a structure of $L^{1'}$ in which the linker terminal has (Pyrrolidine-2,5-dione-N-yl)-O—C(=O)—.

The reaction conditions, reagents, base, and solvent used for a peptide bond formation between the carboxylic acid derivative (14) or (14b) and the compound (13) can be suitably selected from those described for the synthesis of the compound (6).

By deprotecting $P^4$ as the protecting group for the amino acid side chain carboxy group, hydroxy group or amino group of the peptide moiety of the compound (15) or (15b) obtained, the compound (2) or (2b) can be produced. Reagents and conditions can be selected depending on the protecting group.

The compound (9) can be also produced by the following method, for example.

By derivatizing the peptide or amino acid (8) having the N terminal protected with $P^2$ into active ester, mixed acid anhydride, or the like and reacting it with the amine compound (16) having the terminal carboxy group protected with $P^5$ in the presence of a base, the compound (17) can be produced. The reaction conditions, reagents, base, and solvent used for forming a peptide bond between the peptide or amino acid (8) and the compound (16) can be suitably selected from those described for the synthesis of the compound (6). The protecting group $P^2$ for the amino group of the compound (17) can be suitably selected from those described for the protecting group of the compound (6). As for the protecting group P5 for a carboxy group, a protecting group commonly used as a protecting group for a carboxy group in organic synthetic chemistry, in particular, peptide synthesis can be used. Specifically, it can be suitably selected from those described for the protecting group of the compound (6), for example, esters with an alkyl group such as a methyl group, an ethyl group, or a tert-butyl, allyl esters, and benzyl esters. In such case, it is necessary that the protecting group $P^2$ for an amino group and the protecting group $P^5$ for a carboxy group can be removed by a different method or different conditions. For example, a representative example includes a combination in which $P^2$ is a tert-butyloxy carbonyl group and $P^5$ is a benzyl group. The protecting groups can be selected from the aforementioned ones depending on, e.g., the properties of a compound having an amino group and a carboxy group to be protected. For removal of the protecting groups, reagents and conditions can be selected depending on the protecting group.

By deprotecting the protecting group $P^5$ for the carboxy group of the compound (17) obtained, the compound (18) can be produced. Reagents and conditions are selected depending on the protecting group.

By derivatizing the compound (18) obtained into active ester, mixed acid anhydride, acid halide, or the like and reacting with the compound (4) in the presence of a base, the compound (9) can be produced. For the reaction, reaction reagents and conditions that are generally used for peptide synthesis can be also used, and the reaction conditions, reagents, base, and solvent used for the reaction can be suitably selected from those described for the synthesis of the compound (6).

The compound (12) can be also produced by the following method, for example.

By deprotecting the protecting group $P^2$ for the amino group of the compound (17), the compound (19) can be produced. Reagents and conditions can be selected depending on the protecting group.

By derivatizing the amino acid or peptide (11) into active ester, mixed acid anhydride, acid halide, or the like and reacting it with the compound (19) obtained in the presence of a base, the compound (20) can be produced. The reaction conditions, reagents, base, and solvent used for forming an amide bond between the amino acid or peptide (11) and the compound (19) can be suitably selected from those described for the synthesis of the compound (6). Here, it is necessary that the protecting groups $P^3$ and $P^4$ of the amino acid or peptide (11) and the protecting group $P^5$ of the compound (19) can be removed by a different method or different conditions. For example, a representative example includes a combination in which $P^3$ is a 9-fluorenylmethyloxycarbonyl group, $P^4$ is a tert-butyloxycarbonyl group, tert-butyl group, or methoxymethyl group, and $P^5$ is a benzyl group. As mentioned above, the protecting group $P^4$ for a side chain functional group is preferably a protecting group that can be deprotected under acidic conditions, but it is not limited thereto, and can be selected from the aforementioned ones depending on, e.g., the properties of the compound having an amino group, carboxy group, or hydroxy group to be protected. For removal of the protecting groups, reagents and conditions can be selected depending on the protecting group.

By deprotecting the protecting group $P^5$ for the carboxy group of the compound (20) obtained, the compound (21) can be produced. Reagents and conditions can be selected depending on the protecting group.

By derivatizing the compound (21) into active ester, mixed acid anhydride, acid halide, or the like and reacting it with the compound (4) in the presence of a base, the compound (12) can be produced. For the reaction, reaction reagents and conditions that are generally used for peptide synthesis can be also used, and the reaction conditions, reagents, base, and solvent used for the reaction can be suitably selected from those described for the synthesis of the compound (6).

The compound (15) can be also produced by the following method, for example.

By deprotecting the protecting group $P^3$ for the amino group of the compound (20), the compound (22) can be produced. Reagents and conditions can be selected depending on the protecting group.

By derivatizing the carboxylic acid derivative (14) into active ester, mixed acid anhydride, acid halide, or the like and reacting it with the compound (22) obtained in the presence of a base, the compound (23) can be produced. The reaction conditions, reagents, base, and solvent used for forming an amide bond between the carboxylic acid derivative (14) and the compound (22) can be suitably selected from those described for the synthesis of the compound (6).

By deprotecting the protecting group $P^5$ for the carboxy group of the compound (23) obtained, the compound (24) can be produced. Reagents and conditions can be selected depending on the protecting group.

The compound (15) can be produced by derivatizing the compound (24) into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (15) can be also produced by the following method, for example.

By derivatizing the carboxylic acid derivative (14) into active ester, mixed acid anhydride, acid halide, or the like and reacting it with the amino acid or peptide (25) having a carboxy group protected with $P^6$ and a side chain carboxy group, hydroxy group, or amino group protected with $P^4$ in the presence of a base, the compound (26) can be produced. The reaction conditions, reagents, base, and solvent used for forming an amide bond between the carboxylic acid derivative (14) and the compound (25) can be suitably selected from those described for the synthesis of the compound (6). Here, the protecting groups $P^4$ and $P^6$ of the compound (26) can be suitably selected from those described for the protecting group for the carboxy group, hydroxy group, or amino group of the compound (6). However, in such case, it is necessary that the protecting group $P^6$ for a carboxy group and the protecting group $P^4$ for a side chain functional group can be removed by a different method or different conditions. For example, a representative example includes a combination in which $P^6$ is a benzyl group and $P^4$ is a tert-butyl group or the like for a carboxy group, a methoxymethyl group or the like for a hydroxy group, or a tert-butyloxycarbonyl group or the like for an amino group. The protecting group $P^4$ for a side chain functional group is preferably a protecting group that can be deprotected under acidic conditions, but it is not limited thereto, and can be selected from the aforementioned ones depending on, e.g., the properties of the compound having an amino group, carboxy group, or hydroxy group to be protected. For removal of the protecting groups, reagents and conditions can be selected depending on the protecting group.

By deprotecting the protecting group $P^6$ for the carboxy group of the compound (26) obtained, the compound (27) can be produced. Reagents and conditions can be selected depending on the protecting group.

By derivatizing the compound (27) into active ester, mixed acid anhydride, acid halide, or the like and reacting it with the compound (10) in the presence of a base, the compound (15) can be produced. For the reaction, reaction reagents and conditions that are generally used for peptide synthesis can be also used, and the reaction conditions, reagents, base, and solvent used for the reaction can be suitably selected from those described for the synthesis of the compound (6).

By derivatizing the compound (27) into active ester, mixed acid anhydride, acid halide, or the like and reacting it with the amino acid or peptide (28) having a carboxy group protected with $P^7$ in the presence of a base, the compound (29) can be produced. For the reaction, reaction reagents and conditions that are generally used for peptide synthesis can be also used, and the reaction conditions, reagents, base, and solvent used for the reaction can be suitably selected from those described for the synthesis of the compound (6). Here, the protecting groups $P^4$ and $P^7$ of the compound (29) can be suitably selected from those described for the protecting group for the carboxy group, hydroxy group, or amino group of the compound (6). However, in such case, it is necessary that the protecting group $P^7$ for a carboxy group and the protecting group $P^4$ for a side chain functional group can be removed by a different method or different conditions. For example, a representative example includes a combination in which $P^7$ is a benzyl group and $P^4$ is a tert-butyl group or the like for a carboxy group, a methoxymethyl group or the like for a hydroxy group, or a tert-butyloxycarbonyl group or the like for an amino group. The protecting group $P^4$ for a side chain functional group is preferably a protecting group that can be deprotected under acidic conditions, but it is not limited thereto, and can be selected from the aforementioned ones depending on, e.g., the properties of the compound having an amino group, carboxy group, or hydroxy group to be protected. For removal of the protecting groups, reagents and conditions can be selected depending on the protecting group. By repeating sequentially the reaction and deprotection of the constituting amino acid or peptide for elongation, the compound (29) can be also produced.

By deprotecting the protecting group $P^7$ for the carboxy group of the compound (29) obtained, the compound (30) can be produced. Reagents and conditions can be selected depending on the protecting group.

By derivatizing the compound (30) into active ester, mixed acid anhydride, acid halide, or the like and reacting it with the compound (7) in the presence of a base, the compound (15) can be produced. For the reaction, reaction reagents and conditions that are generally used for peptide synthesis can be also used, and the reaction conditions, reagents, base, and solvent used for the reaction can be suitably selected from those described for the synthesis of the compound (6).

The compound (29) can be also produced by the following method, for example.

By derivatizing the amino acid or peptide (28) into active ester, mixed acid anhydride, acid halide, or the like and reacting it with the amino acid or peptide (11) having the N terminal protected with $P^3$ and a side chain carboxy group, hydroxy group, or amino group protected with $P^4$ in the presence of a base, the peptide (31) can be produced. The reaction conditions, reagents, base, and solvent used for forming a peptide bond between the amino acid or peptide (28) and the amino acid or peptide (11) can be suitably selected from those described for the synthesis of the compound (6). Here, as mentioned above, it is necessary that the protecting group $P^7$ for the carboxy group of the amino acid or peptide (28) and the protecting groups $P^3$ and $P^4$ of the amino acid or peptide (11) can be removed by a different method or different conditions. For example, a representative example includes a combination in which $P^3$ is a 9-fluorenylmethyloxycarbonyl group, $P^4$ is a tert-butyl group or the like for a carboxy group, a methoxymethyl group or the like for a hydroxy group, or a tert-butyloxycarbonyl group or the like for an amino group, and $P^7$ is a benzyl group. The protecting group $P^4$ for a side chain functional group is preferably a protecting group that can be deprotected under acidic conditions, but it is not limited thereto, and can be selected from the aforementioned ones depending on, e.g., the properties of the compound having an amino group, carboxy group, or hydroxy group to be protected. For removal of the protecting groups, reagents and conditions can be selected depending on the protecting group.

By deprotecting $P^3$ as the protecting group for the N-terminal of the peptide (31) obtained, the peptide (32) can be produced. Reagents and conditions can be selected depending on the protecting group.

By derivatizing the carboxylic acid derivative (14) into active ester, mixed acid anhydride, acid halide, or the like and reacting it with the peptide (32) obtained in the presence of a base, the compound (29) can be produced. The reaction conditions, reagents, base, and solvent used for forming an amide bond between the carboxylic acid derivative (14) and the peptide (32) can be suitably selected from those described for the synthesis of the compound (6).

The compound (12) can be also produced by the following method, for example.

By deprotecting $P^7$ as the protecting group for the C terminal of the peptide (31), the peptide (33) can be produced. Reagents and conditions can be selected depending on the protecting group.

By derivatizing the peptide (33) obtained into active ester, mixed acid anhydride, acid halide, or the like and reacting it with the compound (7) in the presence of a base, the compound (12) can be produced. The reaction conditions, reagents, base, and solvent used for forming an amide bond between the peptide (33) and the compound (7) can be suitably selected from those described for the synthesis of the compound (6).

5. Production Method 5

Among the production intermediate represented by the formula (2) or (2b) in which the linker has a structure represented by $-L^1-L^2-L^P-$, and $L^P$ is a peptide residue having a hydrophilic amino acid other than glycine at the N terminal can be also produced by the following method.

[Formula 46-2]

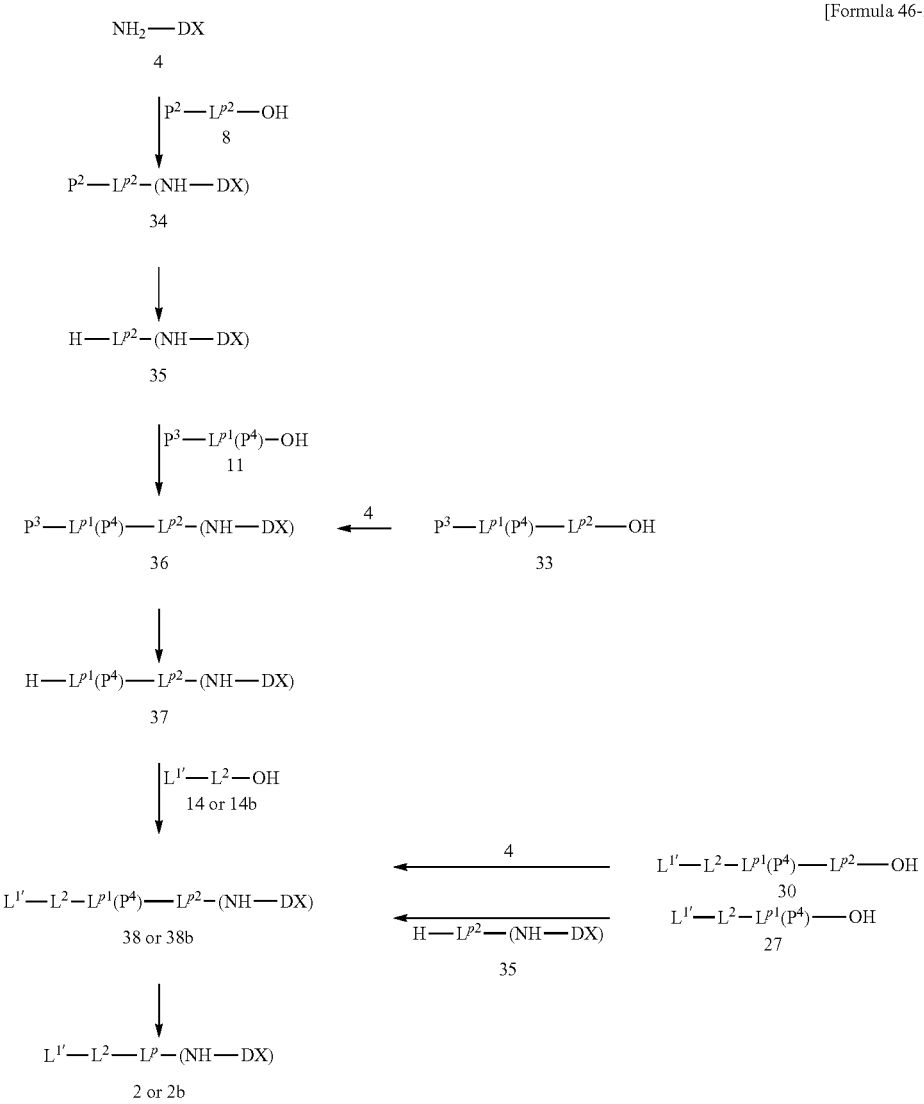

In the formula, $L^{1\prime}$ represents $L^1$ structure in which the terminal is a maleimidyl group or a haloacetyl group, or $L^1$ is converted to (Pyrrolidine-2,5-dione-N-yl)-O—C(=O)—(CH$_2$)n$^5$-C(=O)—, $L^P$ represents a structure of -L$^{p1}$-L$^{p2}$-, and P$^2$, P$^3$, P$^4$, and P$^7$ each represent a protecting group.

Since $L^P$ is formed by connecting $L^{p1}$ and $L^{p2}$, the N-terminal hydrophilic amino acid of $L^P$ is derived from $L^{p1}$, therefore, $L^{p1}$ having a hydrophilic amino acid at the N terminal can be employed. $L^P$ may have a plurality of hydrophilic amino acids. If $L^{p2}$ having a hydrophilic amino acid is used, according to the position thereof, $L^P$ can be produced so as to contain hydrophilic amino acids at the N terminal of $L^P$ or at the N terminal and other positions.

By derivatizing the peptide or amino acid (8) described in Production method 4 having the N terminal protected with P$^2$ into an active ester, mixed acid anhydride, or the like and reacting it with the compound (4) or a salt thereof, the compound (34) can be produced. The reaction conditions, reagents, base, and solvent used for forming a peptide bond between the peptide or amino acid (8) and the compound (4) are not limited as long as they do not inhibit a reaction, and can be suitably selected from those described for the synthesis of the compound (6). The protecting group P$^2$ can be suitably selected from those described for the protecting group of the compound (6), and the selection can be made based on, e.g., the properties of the compound having an amino group to be protected. As it is generally used for peptide synthesis, by repeating sequentially the reaction and deprotection of the amino acid or peptide constituting the peptide or amino acid (8) for elongation, the compound (34) can be also produced.

By deprotecting P$^2$ as the protecting group for the amino group of the compound (34) obtained, the compound (35) can be produced. Reagents and conditions can be selected depending on the protecting group.

By derivatizing the amino acid or peptide (11) described in Production method 4 having the N terminal protected with P$^3$ and a side chain carboxy group, hydroxy group, or amino group protected with P$^4$ into an active ester, mixed acid anhydride, or the like and reacting it with the compound (35) obtained, the compound (36) can be produced. The reaction conditions, reagents, base, and solvent used for forming a peptide bond between the amino acid or peptide (11) and the compound (35) can be suitably selected from those described for the synthesis of the compound (6). The protecting groups $P^3$ and $P^4$ are as described in Production method 4. As it is generally used for peptide synthesis, by repeating sequentially the reaction and deprotection of the constituting amino acid or peptide for elongation, the compound (36) can be also produced.

By deprotecting $P^3$ as the protecting group for the amino group of the compound (36) obtained, the compound (37)

base, and solvent used for forming a peptide bond can be suitably selected from those described for the synthesis of the compound (6).

6. Production Method 6

Among the production intermediate represented by the formula (2), those which have a structure of $-L^1-L^2-L^P-$NH$-(CH_2)n^1-L^a-L^b-L^c-$ or $-L^1-L^2-L^P-$, and $L^P$ is a peptide residue having a hydrophilic amino acid other than glycine at the N terminal can be also produced by the following method, for example.

[Formula 47]

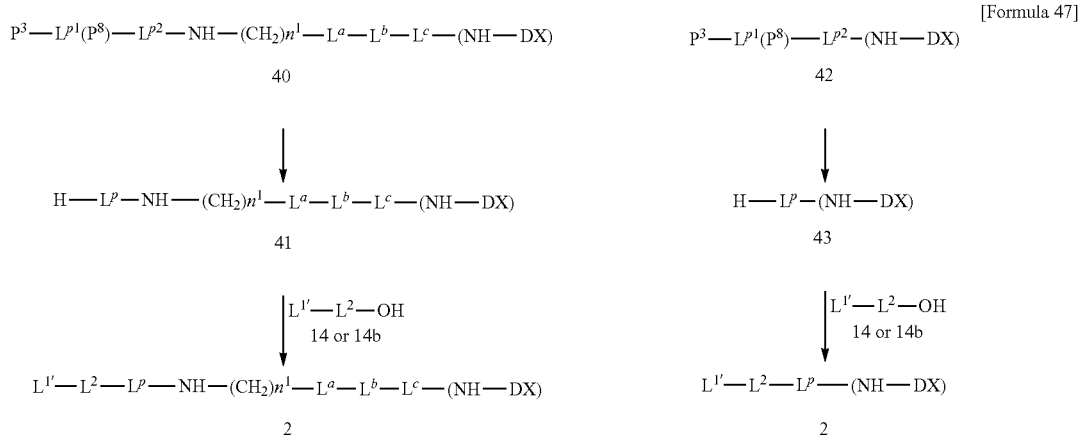

can be produced. Reagents and conditions can be selected depending on the protecting group.

By derivatizing the carboxylic acid derivative (14) or (14b) into active ester, mixed acid anhydride, acid halide, or the like and reacting it with the compound (37) obtained, the compound (38) or (38b) can be produced. The reaction conditions, reagents, base, and solvent used for forming a peptide bond between the carboxylic acid derivative (14) or (14b) and the compound (37) can be suitably selected from those described for the synthesis of the compound (6).

By deprotecting $P^4$ as the protecting group for the carboxy group or hydroxy group, or amino group of the compound (38) or (38b) obtained, the compound (2) or (2b) can be produced. Reagents and conditions can be selected depending on the protecting group.

The compound (36) can be also produced by the following method, for example.

By derivatizing the peptide (33) described in Production method 4 into active ester, mixed acid anhydride, acid halide, or the like and reacting it with the compound (4) or a salt thereof, the compound (36) can be produced. The reaction conditions, reagents, base, and solvent used for forming a peptide bond between the peptide (33) and the compound (4) can be suitably selected from those described for the synthesis of the compound (6).

The compound (38) can be also produced by the following method, for example.

The compound (38) can be produced by derivatizing the compound (30) described in Production method 4 into an active ester, mixed acid anhydride, or the like and reacting it with the compound (4) in the presence of a base, or by derivatizing the amino acid or peptide (27) described in Production method 4 into an active ester, mixed acid anhydride, or the like and reacting it with the compound (35) in the presence of a base. The reaction conditions, reagents, In the formula, $L^{1'}$ represents $L^1$ structure in which the terminal is a maleimidyl group or a haloacetyl group, or $L^1$ is converted to (Pyrrolidine-2,5-dione-N-yl)-O—C(=O)—(CH$_2$)n$^5$-C(=O)—, $L^P$ represents a structure of $-L^{P1}-L^{P2}-$, and $P^3$ and $P^8$ each represent a protecting group.

The production intermediate represented by the formula (2) has two forms of the linker: a structure represented by $-L^1-L^2-L^P-$NH$-(CH_2)n^1-L^a-L^b-L^c-$ and a structure represented by $-L^1-L^2-L^P-$.

The compound (2) in which the linker has the structure represented by $-L^1-L^2-L^P-$NH$-(CH_2)n^1-L^a-L^b-L^c-$ can be produced as follows.

The compound (40) can be synthesized in the same manner as in the compound (12) described in Production method 4. Unlike the compound (12), it may be unnecessary that the protecting group $P^3$ for an amino group and the protecting group $P^8$ for a side chain functional group can be removed by a different method or different conditions. The functional group of the side chain is a carboxy group or a hydroxy group, and the protecting group $P^3$ for an amino group and the protecting group $P^8$ for a side chain carboxy group or hydroxy group can be deprotected simultaneously. For example, a representative example includes a combination in which $P^3$ is a tert-butyloxycarbonyl group, and $P^8$ is a tert-butyl group or a trityl group, or $P^3$ is a benzyloxycarbonyl group, and $P^8$ is a benzyl group. These protecting groups can be suitably selected from those described for the protecting group of the compound (6) depending on, e.g., the properties of the compound having an amino group, carboxy group, or hydroxy group to be protected. For removal of the protecting groups, reagents and conditions can be selected depending on the protecting group. The compound (40) can be synthesized in the same manner as Production method 4 by using the protected amino acid or peptide that satisfies the properties described above.

By sequentially or simultaneously deprotecting the protecting groups P³ and P⁸ of the compound (40), the compound (41) can be produced. Reagents and conditions can be selected depending on the protecting group.

Although the functional group in the hydrophilic side chain of $L^P$ in the compound (41) is not particularly protected, the compound (2) can be produced by reacting it with the compound (14) or (14b) derivatized into an active ester, mixed acid anhydride, or the like in the presence of a base. The reaction conditions, reagents, base, and solvent used for a peptide bond formation can be suitably selected from those described for the synthesis of the compound (6).

The compound (2) in which the linker has the structure represented by -L¹-L²-$L^P$- can be produced as follows.

The compound (42) can be also synthesized as in the same manner as the compound (36) described in Production method 5. Unlike the compound (36), it may be unnecessary that the protecting group P³ for an amino group and the protecting group P⁸ for the functional group of the side chain can be removed by a different method or different conditions. The functional group of the side chain is a carboxy group or a hydroxy group, and the protecting group P³ for an amino group and the protecting group P⁸ for a side chain carboxy group or hydroxy group can be also deprotected simultaneously. For example, a representative example includes a combination in which P³ is a tert-butyloxycarbonyl group, and P⁸ is a tert-butyl group or a trityl group, or P³ is a benzyloxycarbonyl group, and P⁸ is a benzyl group. These protecting groups can be suitably selected from those described for the protecting group of the compound (6) depending on, e.g., the properties of the compound having an amino group, carboxy group, or hydroxy group to be protected. For removal of the protecting groups, reagents and conditions can be selected depending on the protecting group. The compound (42) can be synthesized in the same manner as Production method 5 by using the protected amino acid or peptide that satisfies the properties described above.

By sequentially or simultaneously deprotecting the protecting groups P³ and P⁸ of the compound (42), the compound (43) can be produced. Reagents and conditions can be selected depending on the protecting group.

Although the functional group in the hydrophilic side chain of $L^P$ in the compound (43) is not particularly protected, the compound (2) can be produced by reacting it with the compound (14) or (14b) derivatized into an active ester, mixed acid anhydride, or the like in the presence of a base. The reaction conditions, reagents, base, and solvent used for forming a peptide bond can be suitably selected from those described for the synthesis of the compound (6).

7. Production Method 7

The compound (36) shown in Production method 5 in which linker -$L^P$- has a structure of -$L^{p1}$-Gly-Gly-Phe-Gly- (SEQ ID NO: 33) can be also produced by the following method.

[Formula 48] ("Gly-Gly-Phe-Gly" disclosed as SEQ ID NO: 33)

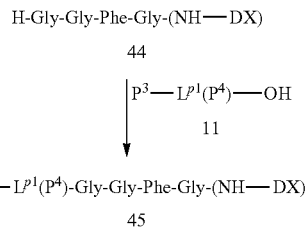

In the formula, $L^{1'}$ represents L¹ structure in which the terminal is a maleimidyl group or a haloacetyl group, or L¹ is converted to (Pyrrolidine-2,5-dione-N-yl)-O—C(=O)—(CH₂)n⁵-C(=O)—, -$L^P$- represents a structure of -$L^{p1}$-Gly-Gly-Phe-Gly- (SEQ ID NO: 33), and P³ and P⁴ each represent a protecting group.

The compound (45) can be produced by derivatizing the amino acid or peptide (11) described in Production method 4 into active ester, mixed acid anhydride, acid halide, or the like and reacting it with glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolidino[1,2-b]quinolin-1-yl]glycineamide (that is, a free form of the pharmaceutical compound described in WO97/46260) (44) or a salt thereof in the presence of a base. The reaction conditions, reagents, base, and solvent used for forming a peptide bond between the amino acid or peptide (11) and the compound (44) can be suitably selected from those described for the synthesis of the compound (6). The protecting group P³ for the N-terminal and the protecting group P⁴ for a side chain functional group are as mentioned above in Production method 4. The protecting group P⁴ for a side chain functional group may be absent, and the compound (45) can be obtained by the reaction using the amino acid or peptide (11) protected only at the N-terminal.

8. Production Method 8

Among the compound represented by the formula (2) or (2b), those which have the linker structure represented by -L¹-L²-$L^P$-, and $L^P$ is a peptide residue in which the C terminal is an oligopeptide consisting of 2 or 3 or more glycines and is connected to the drug, and even in case that a hydrophilic amino acid is present at N terminal, no other hydrophilic amino acid than glycine is present thereat, can be also produced by the following method, for example.

[Formula 49]

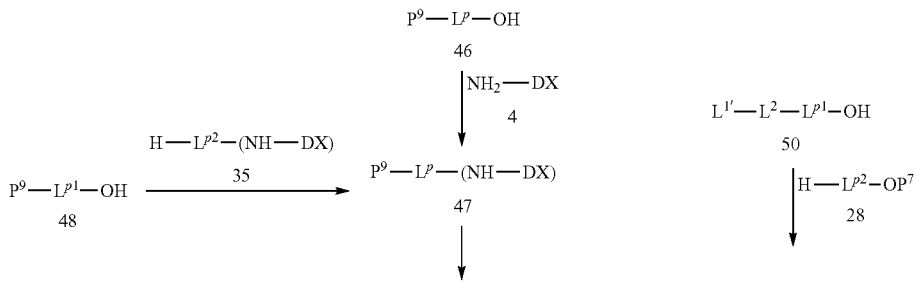

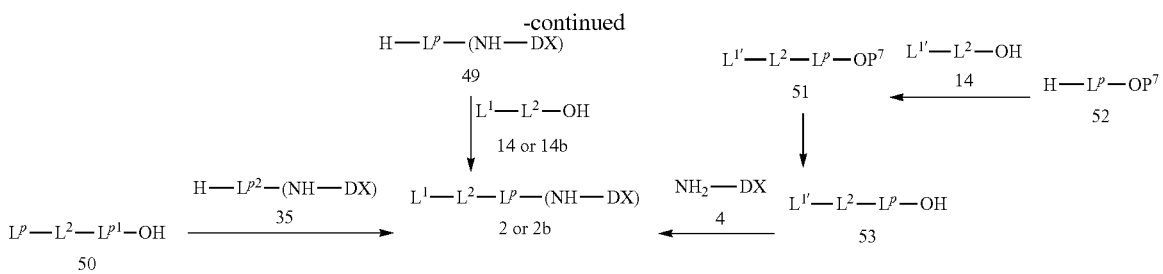

In the formula, $L^{1'}$ represents $L^1$ structure in which the terminal is a maleimidyl group or a haloacetyl group, or $L^1$ is converted to (Pyrrolidine-2,5-dione-N-yl)-O—C(=O)—(CH$_2$)n$^5$-C(=O)—, $L^P$ represents a structure of -$L^{p1}$-$L^{p2}$-, and $P^7$ and $P^9$ each represent a protecting group.

Since $L^P$ is formed by connecting $L^{p1}$ and $L^{p2}$, the number of glycines contained therein for constituting the C terminal of $L^P$ can be determined by considering the number of C-terminal glycines of $L^P$ and further, the number of repetitive uses thereof for the reaction.

The peptide (46) is an oligopeptide in which the C terminal is consisting of 2 or 3 or more glycines, and in case when the N terminal is optionally a hydrophilic amino acid but it is not a hydrophilic amino acid other than glycine, and this N terminal is protected with $P^9$. The peptide (46) can be synthesized by repeating sequentially the condensation reaction and deprotection of the amino acid or peptide constituting it, as it is generally used for peptide synthesis.

By derivatizing the peptide (46) into an active ester, mixed acid anhydride, or the like and reacting it with the compound (4) or a salt thereof, the compound (47) can be produced. The reaction conditions, reagents, base, and solvent used for forming a peptide bond between the peptide (46) and the compound (4) can be suitably selected from those described for the synthesis of the compound (6). The protecting group $P^9$ can be suitably selected from those described for the synthesis of the compound (6).

The compound (47) can be also produced by derivatizing the amino acid or peptide (48) having the N terminal protected with $P^9$ into an active ester, mixed acid anhydride, or the like and reacting it with the compound (35) described in Production method 5. The reaction conditions, reagents, base, and solvent used for forming a peptide bond between the amino acid or peptide (48) and the compound (35) can be suitably selected from those described for the synthesis of the compound (6). The protecting group $P^9$ can be suitably selected from those described for the synthesis of the compound (6).

By deprotecting the protecting group $P^9$ for the amino group of the compound (47) obtained, the compound (49) can be produced. Reagents and conditions can be selected depending on the protecting group.

By derivatizing the carboxylic acid derivative (14) or (14b) into active ester, mixed acid anhydride, acid halide, or the like and reacting it with the compound (49) obtained, the compound (2) or (2b) can be produced. The reaction conditions, reagents, base, and solvent used for forming an amide bond between the carboxylic acid derivative (14) or (14b) and the compound (49) can be suitably selected from those described for the synthesis of the compound (6).

The compound (2) can be also produced by the following method.

The compound (50) in which the N-terminal glycine of $L^{p1}$ is connected to $L^2$ can be synthesized as in the same manner as the compound (27) described in Production method 4. By derivatizing the amino acid or peptide (28) described in Production method 4 into active ester, mixed acid anhydride, acid halide, or the like and reacting it with the compound (50), the compound (51) can be produced. Here, the amino acid or peptide (28) is glycine or an oligopeptide having the C-terminal consisting of 2 or 3 or more glycines, and its C terminal is protected with $P^7$. The reaction conditions, reagents, base, and solvent used for forming an amide bond between the amino acid or peptide (28) and the compound (50) can be suitably selected from those described for the synthesis of the compound (6).

The compound (51) can be also produced by derivatizing the compound (14) into an active ester, mixed acid anhydride, or the like and reacting it with the peptide (52) having the C terminal protected with $P^7$. Here, the peptide (52) is an oligopeptide in which the C terminal is consisting of 2 or 3 or more glycines, and the N terminal is optionally a hydrophilic amino acid but no other hydrophilic amino acid than glycine is present thereat. The peptide (52) can be synthesized by repeating sequentially the condensation reaction and deprotection of the amino acid or peptide constituting it, as it is generally used for peptide synthesis. The reaction conditions, reagents, base, and solvent used for forming a peptide bond between the peptide (52) and the compound (14) can be suitably selected from those described for the synthesis of the compound (6). The protecting group $P^7$ is preferably a protecting group that can be deprotected under acidic conditions, but it is not limited thereto, and can be suitably selected from those described for the synthesis of the compound (6).

By deprotecting the protecting group $P^7$ for the carboxy group of the compound (51) obtained, the compound (53) can be produced. Reagents and conditions can be selected depending on the protecting group.

The compound (2) can be produced by derivatizing the compound (53) into an active ester, mixed acid anhydride, or the like and reacting it with the compound (4) or a salt thereof. The reaction conditions, reagents, base, and solvent used for forming a peptide bond between the compound (53) and the compound (4) can be suitably selected from those described for the synthesis of the compound (6).

Alternatively, the compound (2) can be also produced by the following method.

The compound (2) can be produced by derivatizing the compound (35) described in Production method 5 into an active ester, mixed acid anhydride, or the like and reacting it with the compound (50) in the presence of a base. The reaction conditions, reagents, base, and solvent used for forming a peptide bond between the compound (50) and the compound (35) can be suitably selected from those described for the synthesis of the compound (6).

9. Production Method 9

The production intermediate represented by the formula (2a) described in Production method 2 in which $L^{2'}$ corresponds to $L^2$ having a structure in which the terminal is converted to a mercaptoalkanoyl group can be produced by the following method.

The compound (2a) in which the linker has the structure represented by $-L^1-L^2-L^P-NH-(CH_2)n^1-L^a-L^b-L^c-$ can be produced as follows.

The compound (55) can be produced by derivatizing the carboxylic acid compound (54) having a terminal mercapto group protected with $P^{10}$ into an active ester, mixed acid

[Formula 50]

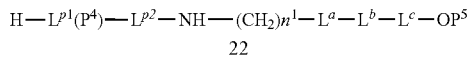

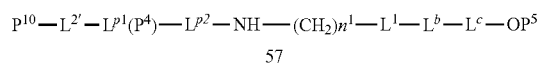

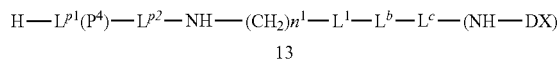

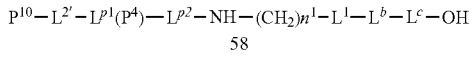

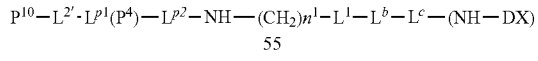

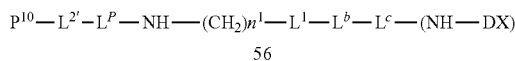

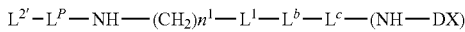

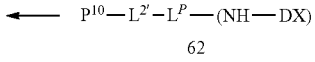

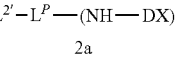

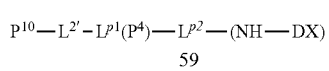

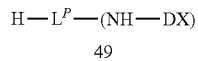

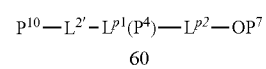

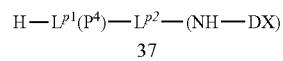

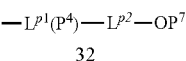

In the formula, $L^P$ represents a structure of $L^{p1}$-$L^{p2}$, and $P^4$, $P^5$, $P^7$, and $P^{10}$ each represents a protecting group.

The production intermediate represented by the formula (2a) has two forms of the linker: a structure represented by $-L^1-L^2-L^P-NH-(CH_2)n^1-L^a-L^b-L^c-$ and a structure represented by $-L^1-L^2-L^P-$.

anhydride, or the like and reacting it with the compound (13) described in Production method 4. For the reaction, reaction reagents and conditions that are generally used for peptide synthesis can be also used, and the reaction conditions, reagents, base, and solvent used for the reaction can be suitably selected from those described for the synthesis of the compound (6). As for the protecting group P10 for a mercapto group, a protecting group commonly used as a protecting group for a mercapto group in organic synthetic chemistry can be used. Specifically, it can be suitably selected from sulfide groups such as a S-methyl sulfide group, a S-ethyl sulfide group, and a S-2-pyridyl sulfide group, ester groups such as an acetyl group, aryl methyl ether groups such as a benzyl group, a 9-fluorenylmethyl group, and a trityl group, ethyl ether groups such as a S-2-cyanoethyl group, and the like. In this case, the protecting group $P^4$ for the side chain amino group, carboxy group, or hydroxy group of $L^{P1}$ is preferably a protecting group that can be deprotected under acidic conditions, but it is not limited thereto, and can be selected from the aforementioned ones depending on, e.g., the properties of the compound having an amino group, carboxy group, or hydroxy group to be protected. However, it is necessary that the protecting group $P^{10}$ for a mercapto group and the protecting group $P^4$ for the side chain carboxy group, hydroxy group, or amino group of $L^{P1}$ can be removed by a different method or different conditions. For example, a representative example includes a combination in which the protecting group $P^4$ is a tert-butyl group for a carboxy group, and the protecting group $P^{10}$ is a S-methyl sulfide group. The protecting group $P^{10}$ may be absent. In this case, the mercapto group of the compound (55) is unprotected.

By deprotecting the protecting group $P^4$ for the side chain carboxy group, hydroxy group, or amino group of $L^{P1}$ in the compound (55) obtained, the compound (56) can be produced. Reagents and conditions can be selected depending on the protecting group.

By deprotecting the protecting group $P^{10}$ for the mercapto group of the compound (56) obtained, the compound (2a) can be produced. Reagents and conditions can be selected depending on the protecting group.

The compound (55) can be also produced by the following method.

The compound (57) can be produced by derivatizing the carboxylic acid compound (54) having a mercapto group protected with $p^{10}$ into active ester, mixed acid anhydride, acid halide, or the like and reacting it with the compound (22) described in Production method 4. For the reaction, reaction reagents and conditions that are generally used for peptide synthesis can be also used, and the reaction conditions, reagents, base, and solvent used for the reaction can be suitably selected from those described for the synthesis of the compound (6). The protecting groups $P^4$ and $P^{10}$ are as mentioned above. The protecting group $P^5$ for a carboxy group can be suitably selected from those described for the protecting group of the compound (6). However, it is necessary that the protecting group $P^{10}$ for a mercapto group and the protecting group $P^4$ for a side chain functional group can be removed by a different method or different conditions from those for the protecting group $P^5$ for a carboxy group. For example, a representative example includes a combination in which $P^4$ is a tert-butyl group for a carboxy group, $P^{10}$ is a S-methyl sulfide group, and $P^5$ is an allyl group. The protecting group $P^{10}$ may be absent. In this case, the mercapto group of the compound (57) is unprotected.

The compound (58) can be produced by deprotecting the protecting group $P^5$ for the carboxy group of the compound (57) obtained. Reagents and conditions can be selected depending on the protecting group.

The compound (55) can be produced by derivatizing the compound (58) into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (2a) in which the linker has the structure represented by -$L^1$-$L^2$-$L^P$-, and $L^P$ is a peptide residue having a hydrophilic amino acid other than glycine at the N terminal can be produced as follows.

The compound (59) can be produced by derivatizing the carboxylic acid compound (54) having a mercapto group protected with $P^{10}$ into active ester, mixed acid anhydride, acid halide, or the like and reacting it with the compound (37) described in Production method 5. For the reaction, reaction reagents and conditions that are generally used for peptide synthesis can be also used, and the reaction conditions, reagents, base, and solvent used for the reaction can be suitably selected from those described for the synthesis of the compound (6). The protecting groups $P^4$ and $P^{10}$ are as mentioned above.

The compound (59) can be also produced by the following method, for example.

The compound (60) can be produced by derivatizing the carboxylic acid compound (54) having a mercapto group protected with $P^{10}$ into active ester, mixed acid anhydride, or the like and reacting it with the compound (32) described in Production method 4. For the reaction, reaction reagents and conditions that are generally used for peptide synthesis can be also used, and the reaction conditions, reagents, base, and solvent used for the reaction can be suitably selected from those described for the synthesis. The protecting groups $P^4$, $P^7$, and $P^{10}$ are as mentioned above and can be suitably selected from those described for the protecting group of the compound (6). However, it is necessary that the protecting group $P^{10}$ for a mercapto group and the protecting group $P^4$ for a side chain functional group can be removed by a different method or different conditions from those for the protecting group $P^7$ for a carboxy group. For example, a representative example includes a combination in which $P^4$ is a tert-butyl group for a carboxy group, $P^{10}$ is a S-methyl sulfide group, and $P^7$ is an allyl group. The protecting group $P^{10}$ may be absent. In this case, the mercapto group of the compound (60) is unprotected.

By deprotecting the protecting group $P^7$ for the carboxy group of the peptide in the compound (60) obtained, the compound (61) can be produced. Reagents and conditions can be selected depending on the protecting group.

The compound (59) can be produced by derivatizing the compound (61) obtained into active ester, mixed acid anhydride, acid halide, or the like and reacting it with the compound (4) or a salt thereof in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

By deprotecting the protecting group $P^4$ for the carboxy group of $L^{P1}$ in the compound (59) obtained, the compound (62) can be produced. Reagents and conditions can be selected depending on the protecting group.

By deprotecting the protecting group $P^{10}$ for the mercapto group of the compound (62) obtained, the compound (2a) can be produced. Reagents and conditions can be selected depending on the protecting group.

The compound (2a) in which the linker has the structure represented by -$L^1$-$L^2$-$L^P$-, and $L^P$ is a peptide residue in which the C terminal is an oligopeptide consisting of 2 or 3 or more glycines and is connected to the drug, and even in case when a hydrophilic amino acid is present at N terminal, no other hydrophilic amino acid than glycine is present thereat, can be produced as follows.

The compound (2a) can be produced by derivatizing the carboxylic acid compound (54) into active ester, mixed acid anhydride, or the like and reacting it with the compound (49) described in Production method 8. Here, the mercapto group may not be protected with $P^{10}$. For the reaction, reaction reagents and conditions that are generally used for peptide synthesis can be also used, and the reaction conditions, reagents, base, and solvent used for the reaction can be suitably selected from those described for the synthesis of the compound (6).

10. Production Method 10

Among the production intermediate represented by the formula (2), $L^{1'}$ in which $L^1$ is converted to have a structure of terminal (maleimid-N-yl)-CH[—(CH$_2$)n$^3$-COOH]—C(=O)— can be produced by the following method.

The compound (2) in which the linker has the structure represented by -$L^1$-$L^2$-$L^P$-NH—(CH$_2$)n$^1$-$L^a$-$L^b$-$L^c$- can be produced as follows.

The (maleimid-N-yl)- compound (65) can be produced by reacting the amino acid (63) having a protected side chain carboxy group by $P^{11}$ with the N-methoxycarbonylmaleimide (64) at $-40°$ C. to $100°$ C. in the presence of a base such as sodium bicarbonate in water. The maleimidyl compound can be synthesized from a compound having an amino group by a method known in the art using N-methoxycarbonylmaleimide (e.g., Keller, O.; Rudinger, J. Helv. Chem. Acta 1975, 58 (2), 531-541) or a method equivalent thereto. As for the protecting group $P^{11}$ for a carboxy group, a protecting group commonly used as a protecting group for a carboxy group in organic synthetic chemistry can be used. It is preferably a protecting group that can be deprotected under acidic conditions, but it is not limited thereto.

[Formula 51]

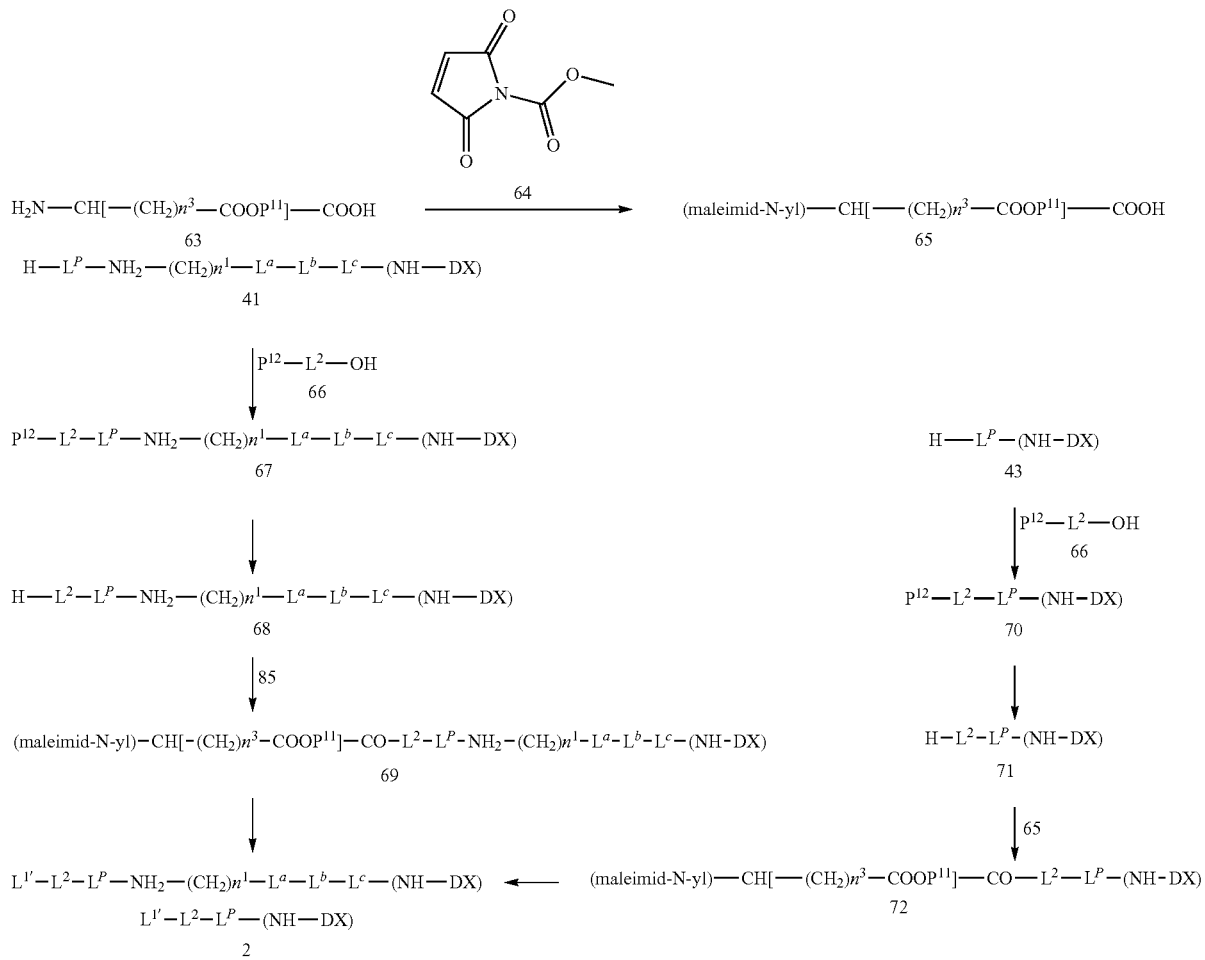

In the formula, $P^{11}$ and $P^{12}$ each represents a protecting group.

The production intermediate represented by the formula (2) has two forms of the linker: a structure represented by -$L^1$-$L^2$-$L^P$-NH—(CH$_2$)n$^1$-$L^a$-$L^b$-$L^c$- and a structure represented by -$L^1$-$L^2$-$L^P$-.

The compound (67) can be produced by derivatizing the compound (66) having a terminal amino group protected by $P^{12}$ into an active ester, mixed acid anhydride, or the like and reacting it with the compound (41) described in Production method 6 in the presence of a base. The reaction conditions, reagents, base, and solvent used for forming an amide bond between the compound (67) and the compound (41) can be suitably selected from those described for the synthesis of the compound (6). The protecting group $P^{12}$ for the amino group of the compound (66) can be suitably selected from those described for the protecting group of the compound (6).

By deprotecting the protecting group $P^{12}$ for the amino group of the compound (67) obtained, the compound (68) can be produced. Reagents and conditions can be selected depending on the protecting group.

The compound (69) can be produced by derivatizing the compound (65) into an active ester, mixed acid anhydride, or the like and reacting it with the compound (68) obtained in the presence of a base. The reaction conditions, reagents, base, and solvent used for forming an amide bond between the compound (65) and the compound (68) can be suitably selected from those described for the synthesis of the compound (6).

By deprotecting the protecting group $P^{11}$ for the carboxy group of the compound (69) obtained, the compound (2) can be produced. Reagents and conditions can be selected depending on the protecting group.

The compound (2) in which the linker has the structure represented by $-L^1-L^2-L^P-$ can be produced as follows.

The compound (72) can be produced by derivatizing the compound (65) into an active ester, mixed acid anhydride, or the like and reacting it with the compound (71) obtained in the presence of a base. The reaction conditions, reagents, base, and solvent used for forming an amide bond between the compound (65) and the compound (71) can be suitably selected from those described for the synthesis of the compound (6).

By deprotecting the protecting group $P^{11}$ for the carboxy group of the compound (72) obtained, the compound (2) can be produced. Reagents and conditions can be selected depending on the protecting group.

11. Production Method 11

Among the production intermediate represented by the formula (2), those having $L^{1'}$ in which $L^1$ is converted to have a structure of terminal maleimidyl group or terminal haloacetyl group, and $L^2$ is $-N[-(CH_2CH_2-O)n^7-CH_2CH_2-OH]-CH_2-C(=O)-$ can be produced by the following method.

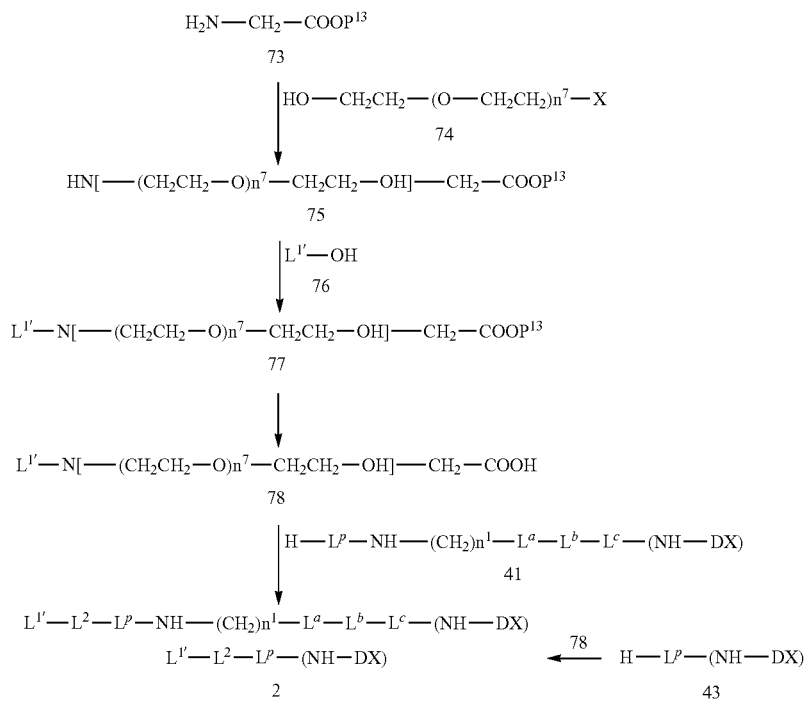

[Formula 52]

Similarly, the compound (70) can be produced by derivatizing the compound (66) having a protected terminal amino group by $P^{12}$ into an active ester, mixed acid anhydride, or the like and reacting it with the compound (43) described in Production method 6 in the presence of a base. The reaction conditions, reagents, base, and solvent used for forming an amide bond between the compound (66) and the compound (43) can be suitably selected from those described for the synthesis of the compound (6). The protecting group $P^{12}$ is as mentioned above.

By deprotecting the protecting group $P^{12}$ for the amino group of the compound (70) obtained, the compound (71) can be produced. Reagents and conditions can be selected depending on the protecting group.

In the formula, $P^{13}$ represents a protecting group, and X represents a leaving group.

The production intermediate represented by the formula (2) has two forms as the linker: a structure represented by $-L^1-L^2-L^P-NH-(CH_2)n^1-L^a-L^b-L^c-$ and a structure represented by $-L^1-L^2-L^P-$.

The compound (2) in which the linker has the structure represented by $-L^1-L^2-L^P-NH-(CH_2)n^1-L^a-L^b-L^c-$ can be produced as follows.

The compound (75) can be produced by reacting the glycine derivative (73) having the protected C terminal by $P^{13}$ with the compound (74) in the presence of a base. The protecting group $P^{13}$ for a carboxy group is preferably a protecting group that can be deprotected under acidic conditions, but it is not limited thereto. Examples of the leaving group X of the compound (74) can include sulfonic acid esters such as p-toluene sulfonate, methyl sulfonate, and trifluoromethyl sulfonate as well as halides such as iodide, bromide, and chloride. For this reaction, reaction conditions that are generally used for N-alkylation can be also used, and the base and solvent used for the reaction can be selected from those described for the synthesis of the compound (6).

The compound (77) can be produced by derivatizing the carboxylic acid derivative (76) into active ester, mixed acid anhydride, acid halide, or the like and reacting it with the compound (75) obtained. The reaction conditions, reagents, base, and solvent used for forming a peptide bond between the carboxylic acid derivative (76) and the compound (75) can be suitably selected from those described for the synthesis of the compound (6).

By deprotecting the protecting group $P^{13}$ for the carboxy group of the compound (77) obtained, the compound (78) can be produced. Reagents and conditions can be selected depending on the protecting group.

The compound (2) can be produced by derivatizing the compound (78) obtained into active ester, mixed acid anhydride, acid halide, or the like and reacting it with the compound (41) described in Production method 6. The reaction conditions, reagents, base, and solvent used for forming an amide bond between the carboxylic acid derivative (78) and the compound (41) can be suitably selected from those described for the synthesis of the compound (6).

The compound (2) in which the linker has the structure represented by $-L^1-L^2-L^P-$ can be produced as follows.

Similarly, the compound (2) can be produced by derivatizing the compound (78) into active ester, mixed acid anhydride, acid halide, or the like and reacting it with the compound (43) described in Production method 6. The reaction conditions, reagents, base, and solvent used for forming an amide bond between the carboxylic acid derivative (78) and the compound (43) can be suitably selected from those described for the synthesis of the compound (6).

All of the intermediate compounds of Production methods 1 to 11 may form salts.

Meanwhile, the antibody-drug conjugate of the present invention, when it is left in air or recrystallized, may absorb moisture to have adsorption water or turn into a hydrate, and such a compound and a salt containing water are also included in the present invention.

A compound labeled with various radioactive or non-radioactive isotopes is also included in the present invention. One or more atoms constituting the antibody-drug conjugate of the present invention may contain an atomic isotope at non-natural ratio. Examples of the atomic isotope include deuterium ($^2H$), tritium ($^3H$), iodine-125 ($^{125}I$), and carbon-13 ($^{13}C$). Further, the compound of the present invention may be radioactive-labeled with a radioactive isotope such as tritium ($^3H$), iodine-125 ($^{125}I$), carbon-14 ($^{14}C$), copper-64 ($^{64}Cu$), zirconium-89 ($^{89}Zr$), iodine-124 ($^{124}I$), fluorine-18 (18F), indium-111 ($^{111}I$), carbon-11 ($^{11}C$) and iodine-131 ($^{131}I$) The compound labeled with a radioactive isotope is useful as a therapeutic or prophylactic agent, a reagent for research such as an assay reagent and an agent for diagnosis such as an in vivo diagnostic imaging agent. Without being related to radioactivity, any isotope variant type of the antibody-drug conjugate of the present invention is within the scope of the present invention.

[Drugs]

The antibody-drug conjugate of the present invention exhibits a cytotoxic activity against cancer cells, and thus, it can be used as a drug, particularly as a therapeutic agent and/or prophylactic agent for cancer.

Examples of the cancer type to which the antibody-drug conjugate of the present invention is applied include lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer, however, it is not limited to them as long as it is a cancer cell expressing, in a cancer cell as a treatment subject, a protein which the antibody within the antibody-drug conjugate can recognize.

The antibody-drug conjugate of the present invention can be preferably administered to a mammal, but it is more preferably administered to a human.

Substances used in a pharmaceutical composition containing antibody-drug conjugate of the present invention can be suitably selected and applied from formulation additives or the like that are generally used in the art, in view of the dosage or administration concentration.

The antibody-drug conjugate of the present invention can be administered as a pharmaceutical composition containing at least one pharmaceutically suitable ingredient. For example, the pharmaceutical composition above typically contains at least one pharmaceutical carrier (for example, sterilized liquid). for example, water and oil (petroleum oil and oil of animal origin, plant origin, or synthetic origin (the oil may be, for example, peanut oil, soybean oil, mineral oil, sesame oil or the like)). Water is a more typical carrier when the pharmaceutical composition above is intravenously administered. Saline solution, an aqueous dextrose solution, and an aqueous glycerol solution can be also used as a liquid carrier, in particular, for an injection solution. A suitable pharmaceutical vehicle is known in the art. If desired, the composition above may also contain a trace amount of a moisturizing agent, an emulsifying agent, or a pH buffering agent. Examples of suitable pharmaceutical carrier are disclosed in "Remington's Pharmaceutical Sciences" by E. W. Martin. The formulations correspond to an administration mode.

Various delivery systems are known and they can be used for administering the antibody-drug conjugate of the present invention. Examples of the administration route include intradermal, intramuscular, intraperitoneal, intravenous, and subcutaneous routes, but not limited thereto. The administration can be made by injection or bolus injection, for example. According to a specific preferred embodiment, the administration of the antibody-drug conjugate is performed by injection. Parenteral administration is a preferred administration route.

According to a representative embodiment, the pharmaceutical composition is prescribed, as a pharmaceutical composition suitable for intravenous administration to human, according to the conventional procedures. The composition for intravenous administration is typically a solution in a sterile and isotonic aqueous buffer solution. If necessary, the drug may contain a solubilizing agent and local anesthetics to alleviate pain at injection site (for example, lignocaine). Generally, the ingredient above is provided individually as any one of lyophilized powder or an anhydrous concentrate contained in a container which is yielded by sealing in an ampoule or a sachet having an amount of the active agent or as a mixture in a unit dosage form. When the drug is to be administered by injection, it may be administered from an injection bottle containing water or saline of sterile pharmaceutical grade. When the drug is administered by injection, an ampoule of sterile water or saline for injection may be provided such that the aforementioned ingredients are admixed with each other before administration.

The pharmaceutical composition of the present invention may be a pharmaceutical composition containing only the antibody-drug conjugate of the present invention or a pharmaceutical composition containing the antibody-drug conjugate and at least one cancer treating agent other than the conjugate. The antibody-drug conjugate of the present invention can be administered with other cancer treating agent. The anti-cancer effect may be enhanced accordingly. Another anti-cancer agent used for such purpose may be administered to an individual simultaneously with, separately from, or subsequently to the antibody-drug conjugate, and it may be administered while varying the administration interval for each. Examples of the cancer treating agent include abraxane, carboplatin, cisplatin, gemcitabine, irinotecan (CPT-11), paclitaxel, pemetrexed, sorafenib, vinorelbine, drugs described in International Publication No. WO 2003/038043, LH-RH analogues (leuprorelin, goserelin, or the like), estramustine phosphate, estrogen antagonist (tamoxifen, raloxifene, or the like), and an aromatase inhibitor (anastrozole, letrozole, exemestane, or the like), but it is not limited as long as it is a drug having an antitumor activity.

The pharmaceutical composition can be formulated into a lyophilization formulation or a liquid formulation as a formulation having desired composition and required purity. When formulated as a lyophilization formulation, it may be a formulation containing suitable formulation additives that are used in the art. Also for a liquid formulation, it can be formulated as a liquid formulation containing various formulation additives that are used in the art.

Composition and concentration of the pharmaceutical composition may vary depending on administration method. However, the antibody-drug conjugate contained in the pharmaceutical composition of the present invention can exhibit the pharmaceutical effect even at a small dosage when the antibody-drug conjugate has higher affinity for an antigen, that is, higher affinity (=lower Kd value) in terms of the dissociation constant (that is, Kd value) for the antigen. Thus, for determining dosage of the antibody-drug conjugate, the dosage can be determined in view of a situation relating to the affinity between the antibody-drug conjugate and antigen. When the antibody-drug conjugate of the present invention is administered to a human, for example, about 0.001 to 100 mg/kg can be administered once or administered several times with an interval of one time for 1 to 180 days.

EXAMPLES

The present invention is specifically described in view of the examples shown below, however, the present invention is not limited to them, and further, it is by no means interpreted in a limited sense. Further, unless specifically described otherwise, the reagent, solvent, and starting material described in the specification can be easily obtained from a commercial supplier.

Reference Example 1 M30-H1-L4 Antibody

Among humanized antibodies of an anti-B7-H3 antibody, an antibody composed of a heavy chain consisting of an amino acid sequence described in amino acid positions 20 to 471 in SEQ ID NO: 9 and a light chain consisting of an amino acid sequence described in amino acid positions 21 to 233 in SEQ ID NO: 16 was produced in accordance with a method known in the art. The obtained humanized anti-B7-H3 antibody was designated as an M30-H1-L4 antibody.

Reference Example 2 M30-H1-L4P Antibody

The modification of a glycan linked to the M30-H1-L4 antibody obtained above was regulated by defucosylation in accordance with a method known in the art. The obtained antibody with the regulated modification of a glycan was designated as an M30-H1-L4P antibody.

Reference Example 3 Anti-CD30 Antibody

An anti-CD30 antibody was produced with reference to National Publication of International Patent Application No. 2005-506035. Its sequence is shown in SEQ ID NOs: 27 and 28.

Reference Example 4 Anti-CD33 Antibody

An anti-CD33 antibody was produced with reference to Japanese Patent Laid-Open No. 8-48637. Its sequence is shown in SEQ ID NOs: 29 and 30.

Reference Example 5 Anti-CD70 Antibody

An anti-CD70 antibody was produced with reference to National Publication of International Patent Application No. 2008-538292. Its sequence is shown in SEQ ID NOs: 31 and 32.

Example 1: 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butanamide

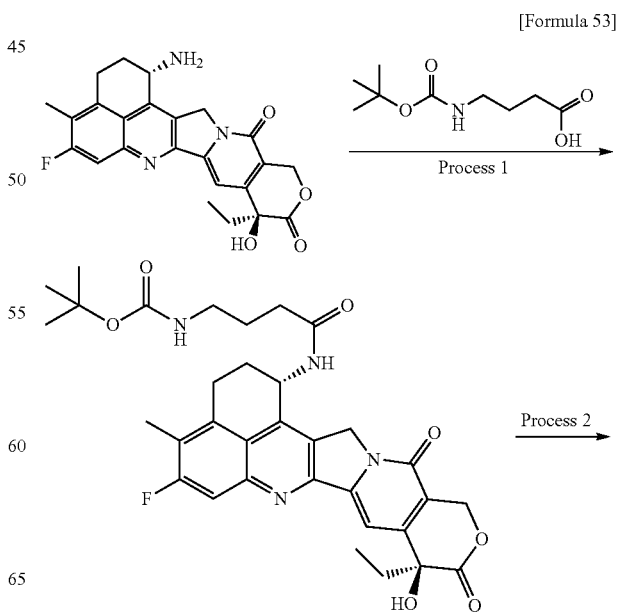

[Formula 53]

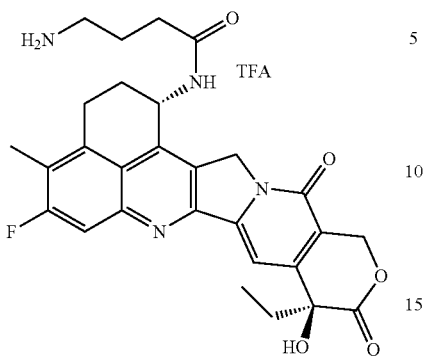

Process 1: tert-Butyl (4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl) carbamate 4-(tert-Butoxycarbonylamino)butanoic acid (0.237 g, 1.13 mmol) was dissolved in dichloromethane (10 mL), charged with N-hydroxysuccinimide (0.130 g, 1.13 mmol) and 1-(3-dimethylaminopropyl)-3-ethylcarbodiimide hydrochloride (0.216 g, 1.13 mmol), and stirred for 1 hour. The reaction solution was added dropwise to an N,N'-dimethylformamide solution (10.0 mL) charged with methanesulfonate of the compound (4) (0.500 g, 0.941 mmol) and triethylamine (0.157 mL, 1.13 mmol), and stirred at room temperature for 1 day. The solvent was removed under reduced pressure and the obtained residues were purified by silica gel column chromatography [chloroform-chloroform: methanol=8:2 (v/v)] to yield the titled compound as a deep yellow solid (0.595 g, quantitative).

$^1$H-NMR (400 MHz, DMSO-$d_6$) δ: 0.87 (3H, t, J=7.2 Hz), 1.31 (9H, s), 1.58 (1H, t, J=7.2 Hz), 1.66 (2H, t, J=7.2 Hz), 1.82-1.89 (2H, m), 2.12-2.21 (3H, m), 2.39 (3H, s), 2.92 (2H, t, J=6.5 Hz), 3.17 (2H, s), 5.16 (1H, d, J=18.8 Hz), 5.24 (1H, d, J=18.8 Hz), 5.42 (2H, s), 5.55-5.59 (1H, m), 6.53 (1H, s), 6.78 (1H, t, J=6.3 Hz), 7.30 (1H, s), 7.79 (1H, d, J=11.0 Hz), 8.40 (1H, d, J=8.6 Hz).

MS (APCI) m/z: 621 (M+H)$^+$

Process 2: 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butanamide The compound (0.388 g, 0.626 mmol) obtained in Process 1 above was dissolved in dichloromethane (9.00 mL). Trifluoroacetic acid (9.00 mL) was added to be stirred for 4 hours. The solvent was removed under reduced pressure and the obtained residue was purified by silica gel column chromatography [chloroform-partitioned organic layer of chloroform:methanol water=7:3:1 (v/v/v)] to yield trifluoroacetate of the titled compound as a yellow solid (0.343 g, quantitative).

$^1$H-NMR (400 MHz, DMSO-$d_6$) δ: 0.87 (3H, t, J=7.2 Hz), 1.79-1.92 (4H, m), 2.10-2.17 (2H, m), 2.27 (2H, t, J=7.0 Hz), 2.40 (3H, s), 2.80-2.86 (2H, m), 3.15-3.20 (2H, m), 5.15 (1H, d, J=18.8 Hz), 5.26 (1H, d, J=18.8 Hz), 5.42 (2H, s), 5.54-5.61 (1H, m), 6.55 (1H, s), 7.32 (1H, s), 7.72 (3H, brs), 7.82 (1H, d, J=11.0 Hz), 8.54 (1H, d, J=8.6 Hz).

MS (APCI) m/z: 521 (M+H)$^+$

Example 2: Antibody-Drug Conjugate (1)

[Formula 54]

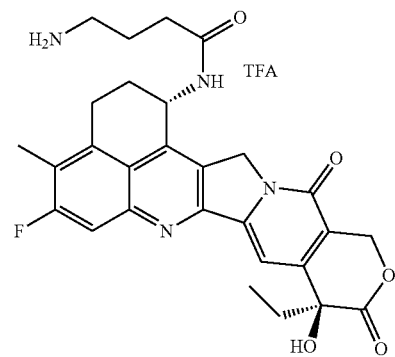
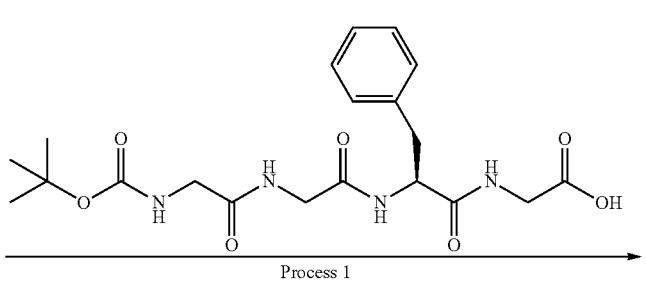

-continued
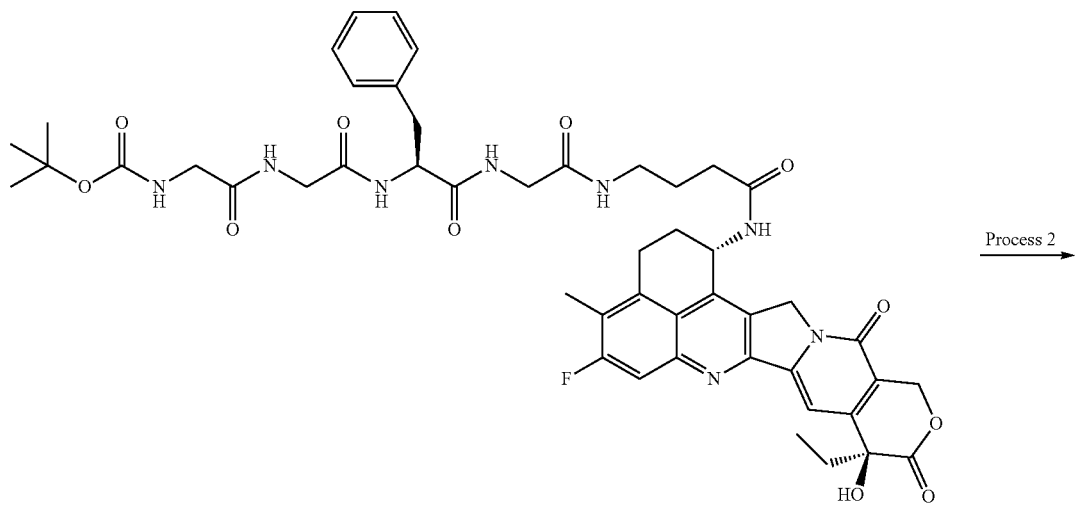
Process 2 →
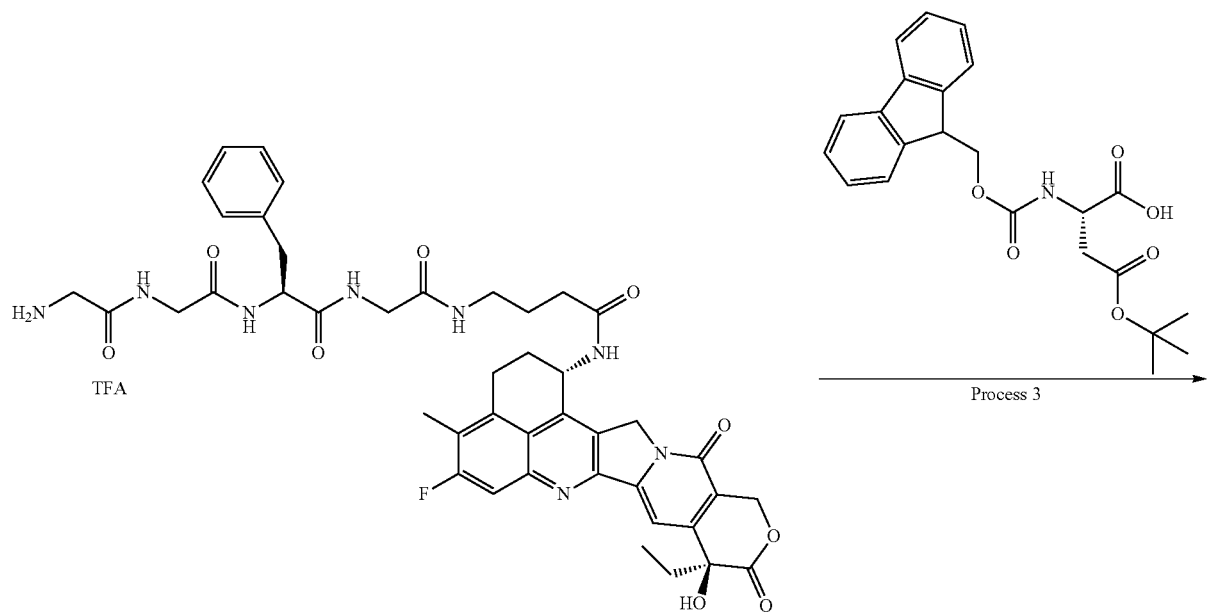
Process 3 →
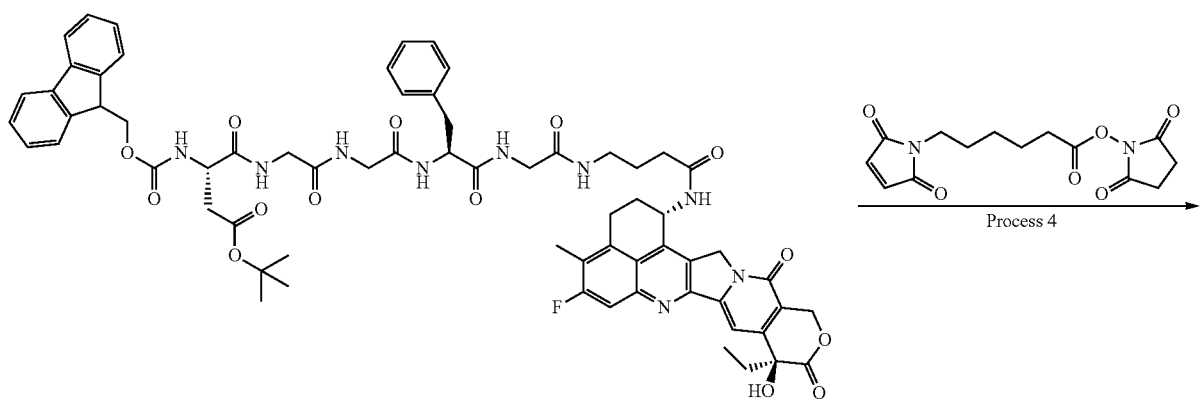
Process 4 →

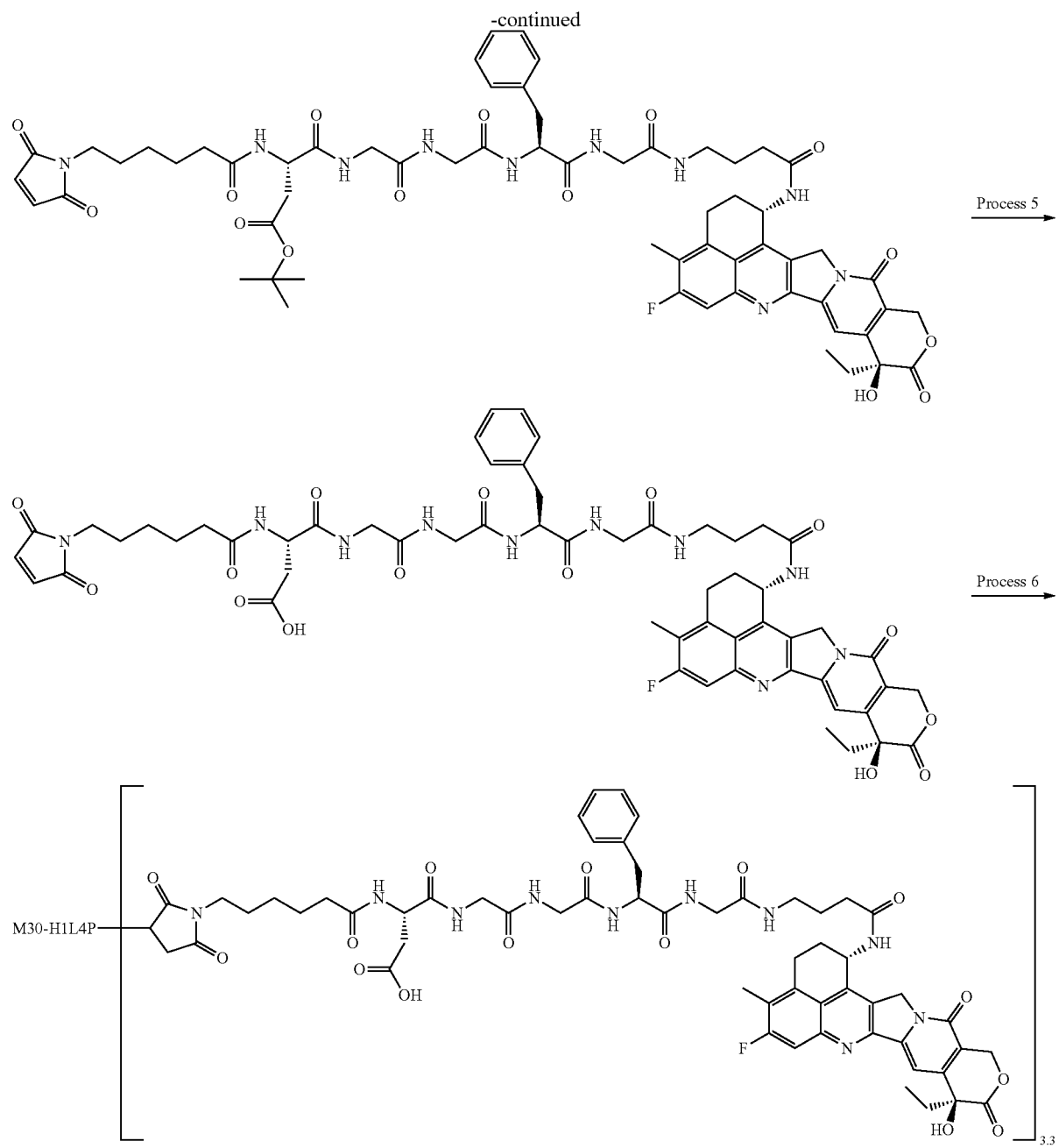

Process 1: N-(tert-butoxycarbonyl)glycylglycyl-L-phenylalanyl-N-(4-{[(S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide N-(tert-butoxycarbonyl)glycylglycyl-L-phenylalanylglycine (80.9 g, 0.185 mmol) was dissolved in dichloromethane (3.00 mL), charged with N-hydroxysuccinimide (21.3 mg, 0.185 mmol) and 1-(3-dimethylaminopropyl)-3-ethylcarbodiimide hydrochloride (35.5 mg, 0.185 mmol), and stirred for 3.5 hours. The reaction solution was added dropwise to an N,N'-dimethylformamide solution (1.50 mL) charged with the compound (80.4 mg, 0.154 mmol) of Example 1, and stirred at room temperature for 4 hours. The solvent was removed under reduced pressure and the obtained residue was purified by silica gel column chromatography [chloroform-chloroform:methanol=8:2 (v/v)] to yield the titled compound as a pale yellow solid (0.106 g, 73%).

$^1$H-NMR (400 MHz, DMSO-d$_6$) δ: 0.87 (3H, t, J=7.4 Hz), 1.36 (9H, s), 1.71 (2H, m), 1.86 (2H, t, J=7.8 Hz), 2.15-2.19 (4H, m), 2.40 (3H, s), 2.77 (1H, dd, J=12.7, 8.8 Hz), 3.02 (1H, dd, J=14.1, 4.7 Hz), 3.08-3.11 (2H, m), 3.16-3.19 (2H, m), 3.54 (2H, d, J=5.9 Hz), 3.57-3.77 (4H, m), 4.46-4.48 (1H, m), 5.16 (1H, d, J=19.2 Hz), 5.25 (1H, d, J=18.8 Hz), 5.42 (2H, s), 5.55-5.60 (1H, m), 6.53 (1H, s), 7.00 (1H, t, J=6.3 Hz), 7.17-7.26 (5H, m), 7.31 (1H, s), 7.71 (1H, t, J=5.7 Hz), 7.80 (1H, d, J=11.0 Hz), 7.92 (1H, t, J=5.7 Hz), 8.15

(1H, d, J=8.2 Hz), 8.27 (1H, t, J=5.5 Hz), 8.46 (1H, d, J=8.2 Hz).
MS (APCI) m/z: 939 (M+H)$^+$

Process 2: Glycylglycyl-L-phenylalanyl-N-(4-{[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide trifluoroacetate The compound (72.6 mg, 77.3 μmol) obtained in Process 1 above was reacted in the same manner as Process 2 of Example 1 to yield the titled compound as a yellow solid (64.8 g, quantitative).
$^1$H-NMR (400 MHz, DMSO-d6) δ: 0.87 (3H, t, J=7.4 Hz), 1.71-1.73 (2H, m), 1.82-1.90 (2H, m), 2.12-2.20 (4H, m), 2.40 (3H, s), 2.75 (1H, dd, J=13.7, 9.4 Hz), 3.03-3.09 (3H, m), 3.18-3.19 (2H, m), 3.58-3.60 (2H, m), 3.64 (1H, d, J=5.9 Hz), 3.69 (1H, d, J=5.9 Hz), 3.72 (1H, d, J=5.5 Hz), 3.87 (1H, dd, J=16.8, 5.9 Hz), 4.50-4.56 (1H, m), 5.16 (1H, d, J=19.2 Hz), 5.25 (1H, d, J=18.8 Hz), 5.42 (2H, s), 5.55-5.60 (1H, m), 7.17-7.27 (5H, m), 7.32 (1H, s), 7.78-7.81 (2H, m), 7.95-7.97 (3H, m), 8.33-8.35 (2H, m), 8.48-8.51 (2H, m).
MS (APCI) m/z: 839 (M+H)

Process 3: tert-Butyl (3S,12S)-12-benzyl-21-{[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-{[(9H-fluoren-9-ylmethoxy)carbonyl]amino}-4,7,10,13,16,21-hexaoxo-5,8,11,14,17-pentaazaheneicosan-1-noate (2S)-4-tert-Butoxy-2-{[(9H-fluoren-9-ylmethoxy)carbonyl]amino}-4-oxobutanoic acid (0.625 g, 1.52 mmol) was dissolved in dichloromethane (10.0 mL), charged with N-hydroxysuccinimide (0.175 g, 1.52 mol) and 1-(3-dimethylaminopropyl)-3-ethylcarbodiimide hydrochloride (0.291 g, 1.52 mmol), and stirred for 1 hour. The reaction solution was added dropwise to an N,N'-dimethylformamide solution (10.0 mL) charged with the compound (1.00 g, 1.01 mmol) obtained in Process 2 above, and stirred at room temperature for 20 hours. The solvent was removed under reduced pressure and the obtained residue was purified by silica gel column chromatography [chloroform to chloroform:methanol=8:2 (v/v)] to yield the titled compound as a pale yellow solid (0.873 g, 70%).
$^1$H-NMR (400 MHz, DMSO-d$_6$) δ: 0.88 (3H, t, J=7.4 Hz), 1.37 (9H, s), 1.68-1.78 (2H, m), 1.81-1.93 (2H, m), 2.10-2.23 (4H, m), 2.41 (3H, s), 2.68-2.85 (3H, m), 2.99-3.22 (5H, m), 3.58-3.81 (6H, m), 4.19-4.36 (3H, m), 4.38-4.52 (2H, m), 5.17 (1H, d, J=19.2 Hz), 5.25 (1H, d, J=19.2 Hz), 5.43 (2H, s), 5.54-5.62 (1H, m), 6.55 (1H, s), 7.15-7.34 (8H, m), 7.41 (2H, t, J=7.2 Hz), 7.66-7.75 (4H, m), 7.81 (1H, d, J=11.0 Hz), 7.88 (2H, d, J=7.4 Hz), 8.01-8.06 (1H, m), 8.14 (1H, d, J=8.2 Hz), 8.17-8.22 (1H, m), 8.25-8.30 (1H, m), 8.47 (1H, d, J=8.6 Hz).
MS (APCI) m/z: 1232 (M+H)$^+$ Process 4: tert-Butyl (3S,12S)-12-benzyl-3-{[6-(2,5-dioxo-2,5-dihydro-1H-pyrrol-1-yl)hexanoyl]amino}-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,21-hexaoxo-5,8,11,14,17-pentaazaheneicosan-1-noate The compound (0.800 g, 0.649 mmol) obtained in Process 3 above was dissolved in N,N'-dimethylformamide (3.00 mL), charged with piperidine (0.643 mL, 6.49 mmol), and stirred for 1 hour. The solvent was removed by drying under reduced pressure, and the obtained residue was dissolved in N,N'-dimethylformamide (10 mL). N-Succinimidyl 6-maleimide hexanoate (0.300 g, 0.974 mmol) was added thereto and stirred for 20 hours. The solvent was removed under reduced pressure and the obtained residues were purified by silica gel column chromatography [chloroform to chloroform:methanol=8:2 (v/v)] to yield the titled compound as a pale yellow solid (0.224 g, 29%).
$^1$H-NMR (400 MHz, DMSO-d$_6$) δ: 0.87 (3H, t, J=7.6 Hz), 1.15-1.22 (2H, m), 1.35 (9H, s), 1.44-1.47 (4H, m), 1.71-1.73 (2H, m), 1.80-1.91 (2H, m), 2.08 (2H, t, J=7.6 Hz), 2.13-2.20 (4H, m), 2.40 (3H, s), 2.67 (1H, dt, J=11.1, 4.8 Hz), 2.78 (1H, dd, J=13.6, 9.4 Hz), 2.99-3.17 (6H, m), 3.31-3.36 (2H, m), 3.57-3.76 (6H, m), 4.45-4.47 (1H, m), 4.57-4.60 (1H, m), 5.16 (1H, d, J=18.7 Hz), 5.25 (1H, d, J=18.7 Hz), 5.42 (2H, s), 5.55-5.60 (1H, m), 6.53 (1H, s), 6.99 (2H, s), 7.15-7.27 (5H, m), 7.31 (1H, s), 7.70 (1H, t, J=5.4 Hz), 7.80 (1H, d, J=10.9 Hz), 7.99 (1H, t, J=5.7 Hz), 8.09-8.12 (3H, m), 8.25 (1H, t, J=6.0 Hz), 8.45 (1H, d, J=9.1 Hz).
MS (APCI) m/z: 1203 (M+H)$^+$ Process 5: N-[6-(2,5-dioxo-2,5-dihydro-1H-pyrrol-1-yl)hexanoyl]-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b]quinolin-1-yl]amino}-4-oxobutyl)glycinamide The compound (0.224 g, 0.186 mmol) obtained in Process 4 above was reacted in the same manner as Process 2 of Example 1 to yield the titled compound as a pale yellow solid (21.2 mg, 10%).
$^1$H-NMR (400 MHz, DMSO-d$_6$) δ: 0.87 (3H, t, J=7.2 Hz), 1.13-1.21 (2H, m), 1.42-1.45 (6H, m), 1.70-1.72 (2H, m), 1.85-1.88 (2H, m), 2.06-2.20 (6H, m), 2.39 (3H, s), 2.63-2.67 (1H, m), 2.78-2.81 (1H, m), 3.04-3.12 (6H, m), 3.63-3.70 (6H, m), 4.46-4.52 (2H, m), 5.16 (1H, d, J=18.8 Hz), 5.25 (1H, d, J=18.8 Hz), 5.42 (2H, s), 5.55-5.58 (1H, m), 6.53 (1H, s), 6.99 (2H, s), 7.18-7.23 (6H, m), 7.30 (1H, s), 7.71 (1H, t, J=5.5 Hz), 7.79 (1H, d, J=10.9 Hz), 7.99-8.02 (1H, m), 8.10-8.11 (3H, m), 8.27-8.30 (1H, m), 8.47-8.50 (1H, m).
MS (APCI) m/z: 1147 (M+H)$^+$ Process 6: Antibody-Drug Conjugate (1)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (8.0 mL) was collected into a 15 mL tube and charged with an aqueous solution of 10 mM TCEP (Tokyo Chemical Industry Co., Ltd.) (0.124 mL; 2.3 equivalents per antibody molecule) and an aqueous solution of 1 M dipotassium hydrogen phosphate (Nacalai Tesque, Inc.; 0.400 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.249 mL; 4.6 equivalents per antibody molecule) containing 10 mM of the compound obtained in Process 5 above was added thereto and incubated at 22° C. for 40 minutes for conjugating the drug linker to the antibody. Next, an aqueous solution (0.050 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 18.5 mL of a solution containing the titled antibody-drug conjugate.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 3.56 mg/mL, antibody yield: 66 mg (83%), and average number of conjugated drug molecules (n) per antibody molecule: 3.3.

Example 3: Antibody-Drug Conjugate (2)

antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (8.0 mL) was collected into a 15 mL tube and charged with an aqueous solution of 10 mM TCEP (Tokyo Chemical Industry Co., Ltd.) (0.187 mL; 3.5 equivalents per antibody molecule) and an aqueous solution of 1 M dipotassium hydrogen phosphate (Nacalai Tesque, Inc.; 0.400 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.373 mL; 6.9 equivalents per antibody molecule) containing 10 mM of the compound obtained in Process 5 of Example 2 was added thereto and incubated at 22° C. for 40 minutes for conjugating the drug linker to the antibody. Next, an aqueous solution (0.075 mL; 13.8 equivalents per antibody molecule) of 100 mM NAC (Sigma-Aldrich Co. LLC) was added thereto and incubated at 22° C. for another 20 minutes to terminate the reaction of drug linker.

[Formula 55]

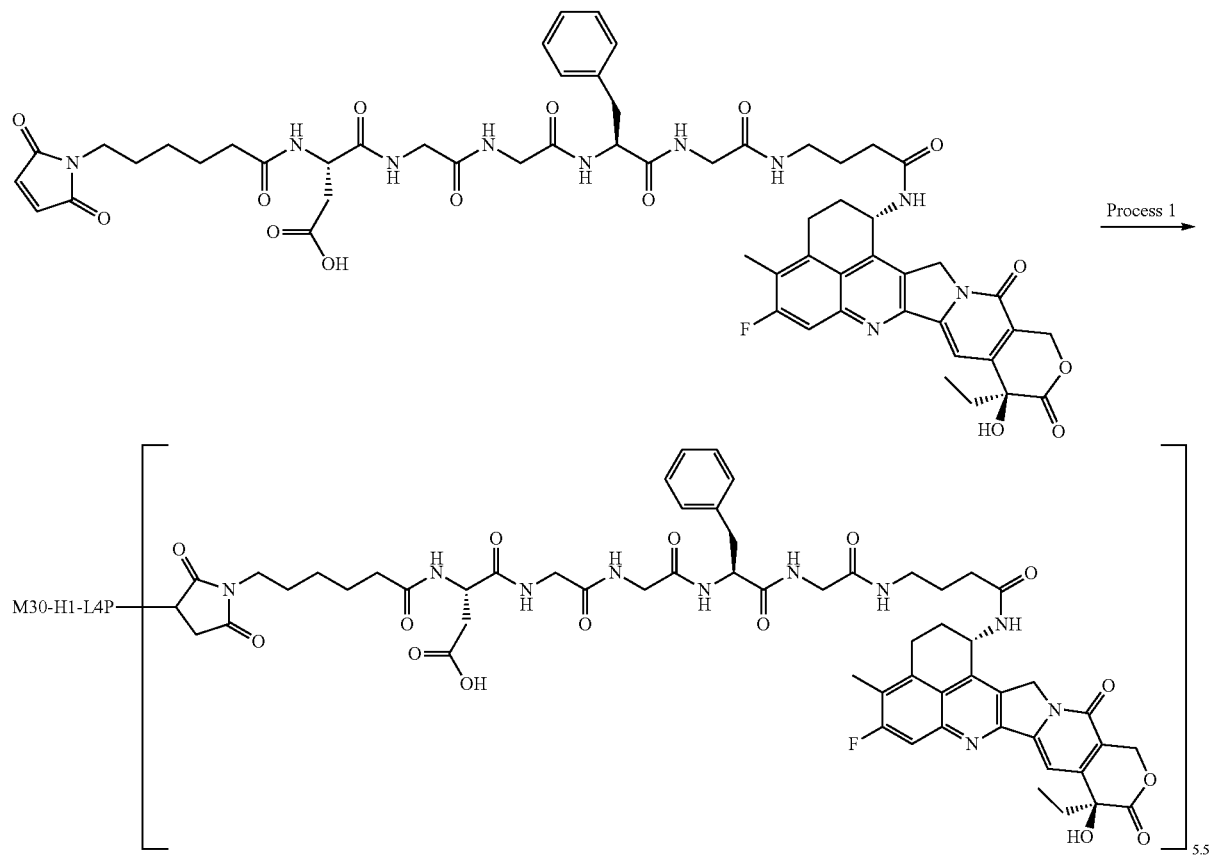

Process 1: Antibody-Drug Conjugate (2)

Reduction of the antibody: The M30-H1-L4P antibody produced in Reference Example 2 was prepared to have Purification: The above solution was subjected to purification using the Common procedure D-1 (ABS was used as buffer solution) described in Production method 1 to yield 16 mL of a solution containing the titled antibody-drug conjugate.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 3.55 mg/mL, antibody yield: 57 mg (71%), and average number of conjugated drug molecules (n) per antibody molecule: 5.5.

Example 4: Antibody-Drug Conjugate (3)

Conjugation between antibody and drug linker: After adding dimethyl sulfoxide (Sigma-Aldrich Co. LLC; 0.109 mL) and a dimethyl sulfoxide solution containing 10 mM (0.039 mL; 4.6 equivalents per antibody molecule) of the compound obtained in Process 5 of Example 2 to the above solution at room temperature, it was stirred by using a tube rotator (MTR-103, manufactured by AS ONE Corporation) at room temperature for 40 minutes for conjugating the drug linker to the antibody. Next, an aqueous solution (0.008 mL) of 100 mM NAC (Sigma-Aldrich Co. LLC) was added thereto and stirred at room temperature for another 20 minutes to terminate the reaction of drug linker.

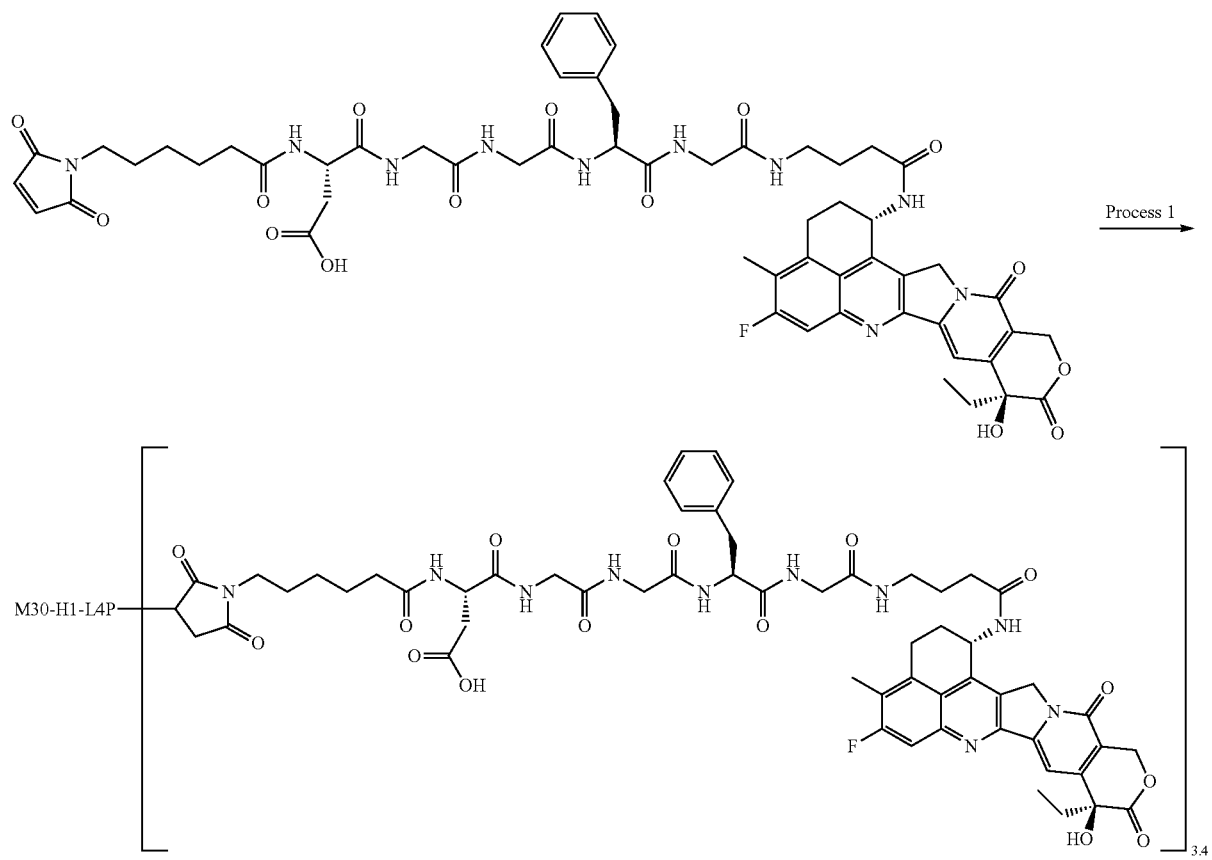

[Formula 56]

Process 1: Antibody-Drug Conjugate (3)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was added to a 1.5 mL polypropylene tube and charged with an aqueous solution of 10 mM TCEP (Tokyo Chemical Industry Co., Ltd.) (0.025 mL; 3.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 10.63 mg/mL, antibody yield: 7.4 mg (59%), and average number of conjugated drug molecules (n) per antibody molecule: 3.4.

Example 5: Antibody-Drug Conjugate (4)

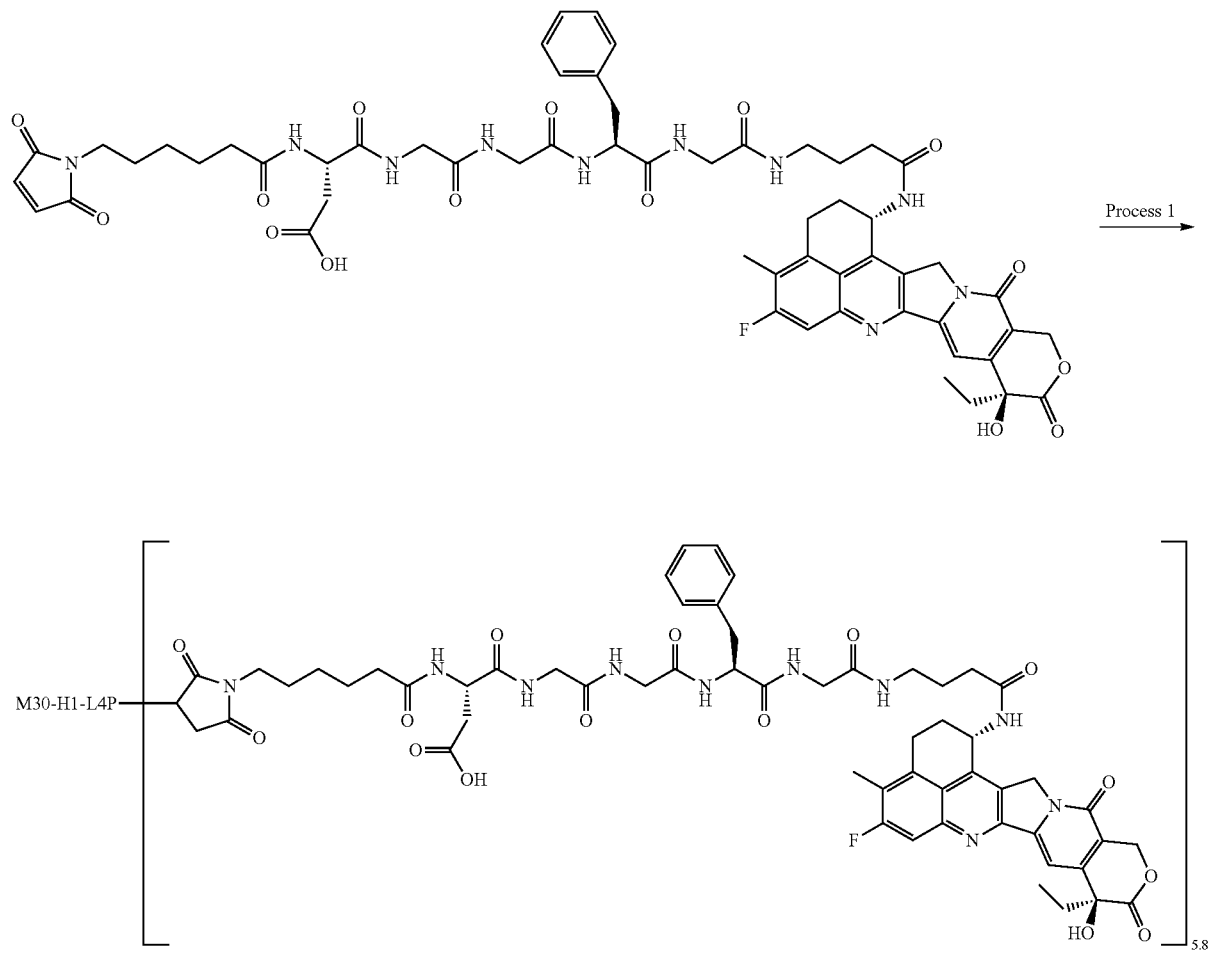

Process 1: Antibody-Drug Conjugate (4)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was added to a 1.5 mL polypropylene tube and charged with an aqueous solution of 10 mM TCEP (Tokyo Chemical Industry Co., Ltd.) (0.051 mL; 6.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.067 mL) and a dimethyl sulfoxide solution containing 10 mM of the compound obtained in Process 5 of Example 2 (0.085 mL; 10.0 equivalents per antibody molecule) to the above solution at room temperature, it was stirred by using a tube rotator (MTR-103, manufactured by AS ONE Corporation) at room temperature for 60 minutes for conjugating the drug linker to the antibody. Next, an aqueous solution (0.013 mL) of 100 mM NAC (Sigma-Aldrich Co. LLC) was added thereto and stirred at room temperature for another 20 minutes to terminate the reaction of drug linker.

Purification: The above solution was subjected to purification using the Common procedure D (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 1.48 mg/mL, antibody yield: 8.88 mg (71%), and average number of conjugated drug molecules (n) per antibody molecule: 5.8.

Example 6: Antibody-Drug Conjugate (5)

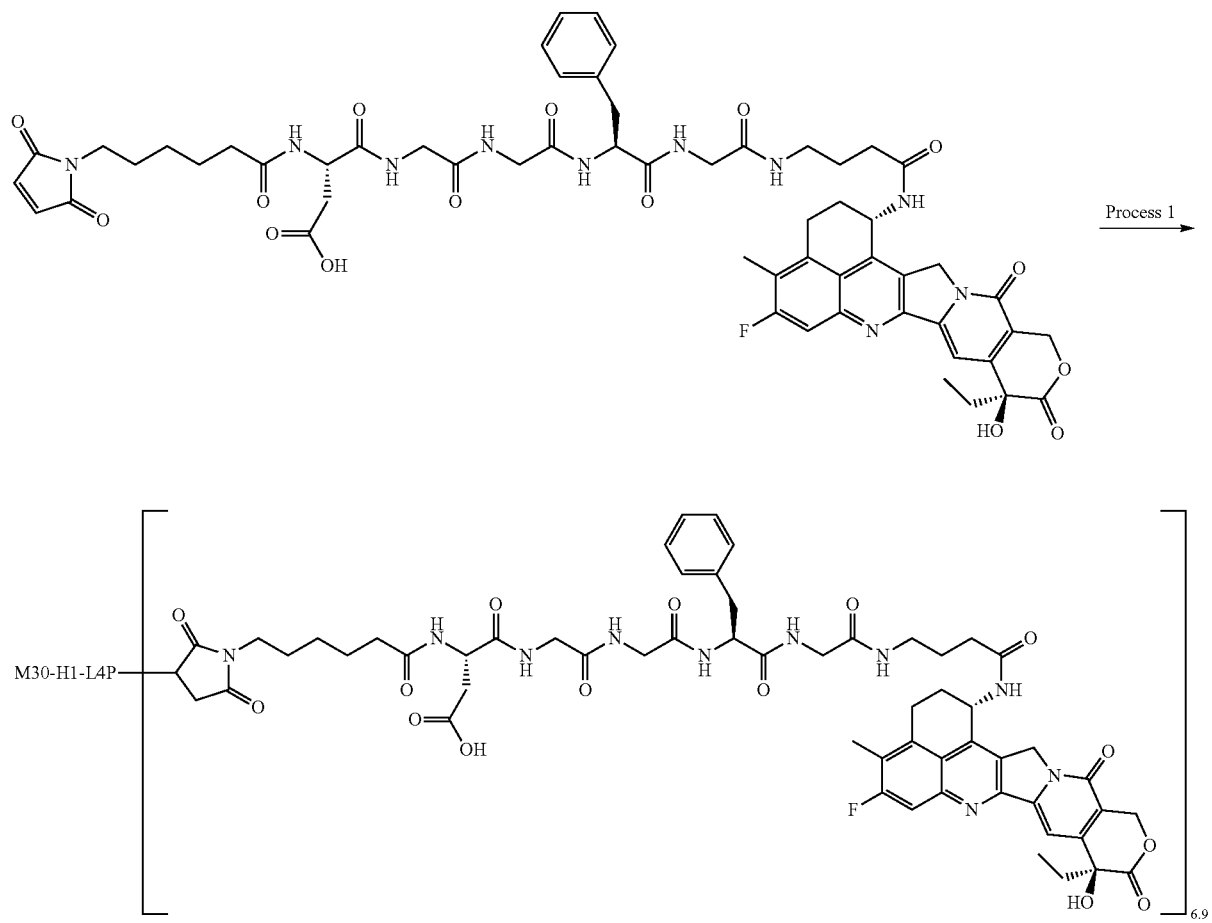

[Formula 58]

Process 1

Process 1: Antibody-Drug Conjugate (5)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was added to a 1.5 mL polypropylene tube and charged with an aqueous solution of 10 mM TCEP (Tokyo Chemical Industry Co., Ltd.) (0.051 mL; 6.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.025 mL) and a dimethyl sulfoxide solution containing 10 mM of the compound obtained in Process 5 of Example 2 (0.127 mL; 15.0 equivalents per antibody molecule) to the above solution at room temperature, it was stirred by using a tube rotator (MTR-103, manufactured by AS ONE Corporation) at room temperature for 60 minutes for conjugating the drug linker to the antibody. Next, an aqueous solution (0.019 mL) of 100 mM NAC (Sigma-Aldrich Co. LLC) was added thereto and stirred at room temperature for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 0.99 mg/mL, antibody yield: 5.94 mg (48%), and average number of conjugated drug molecules (n) per antibody molecule: 6.9.

Example 7: Antibody-Drug Conjugate (6)

[Formula 59]

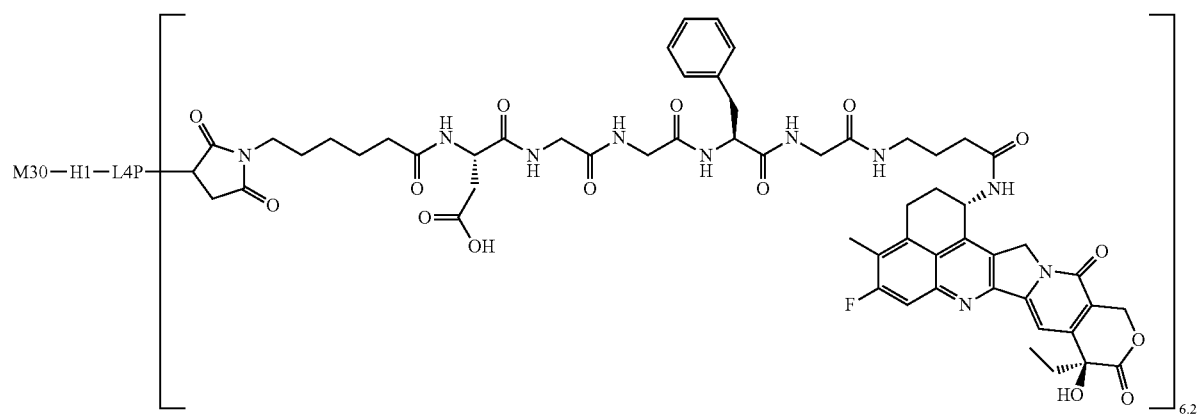

Almost the whole amounts of the antibody-drug conjugates of Examples 5 and 6 were mixed and the solution was concentrated by the Common procedure A to yield the titled antibody-drug conjugate.

Antibody concentration: 10.0 mg/mL, antibody yield: 14.36 mg, and average number of conjugated drug molecules (n) per antibody molecule: 6.2.

Example 8: Antibody-Drug Conjugate (7)

[Formula 60]

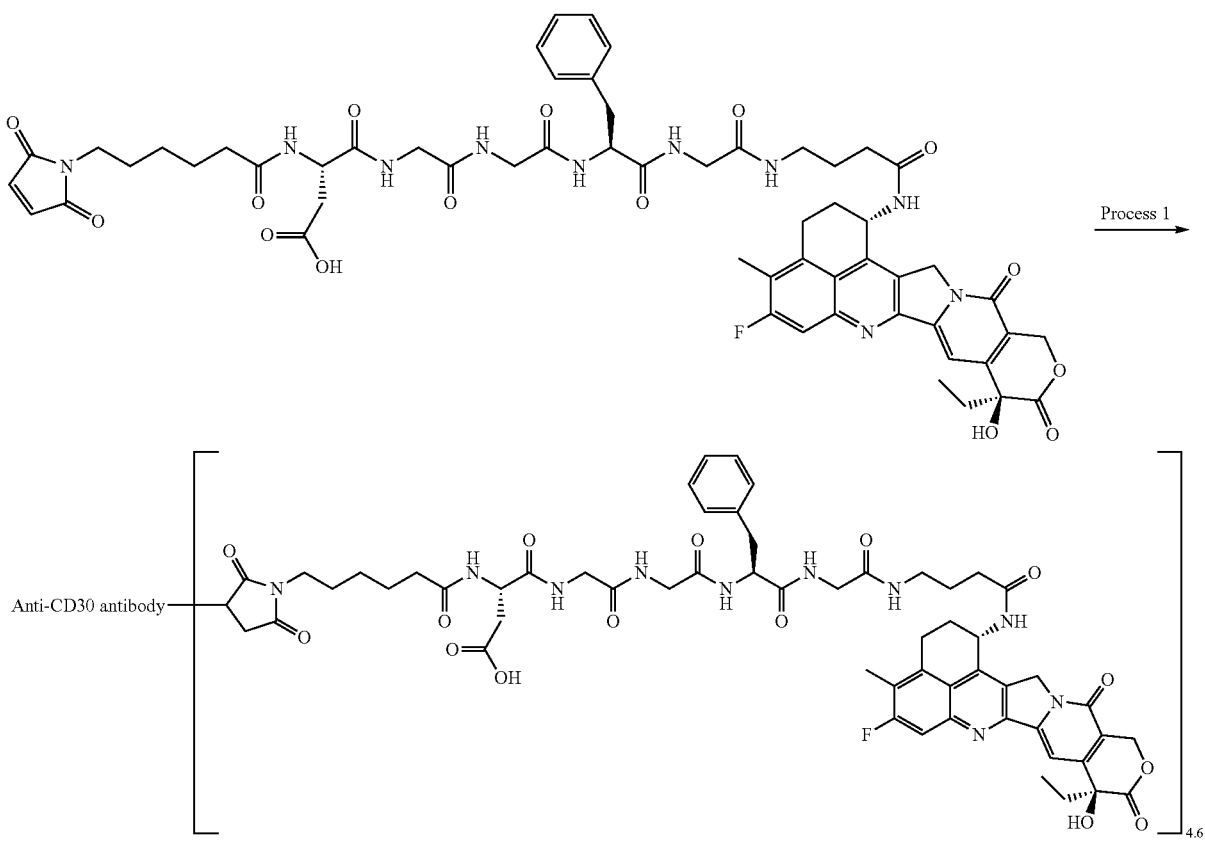

Process 1: Antibody-Drug Conjugate (7)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0148 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=270400 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 1.18 mg/mL, antibody yield: 7.08 mg (71%), and average number of conjugated drug molecules (n) per antibody molecule: 4.6.

Example 9: Antibody-Drug Conjugate (8)

[Formula 61]

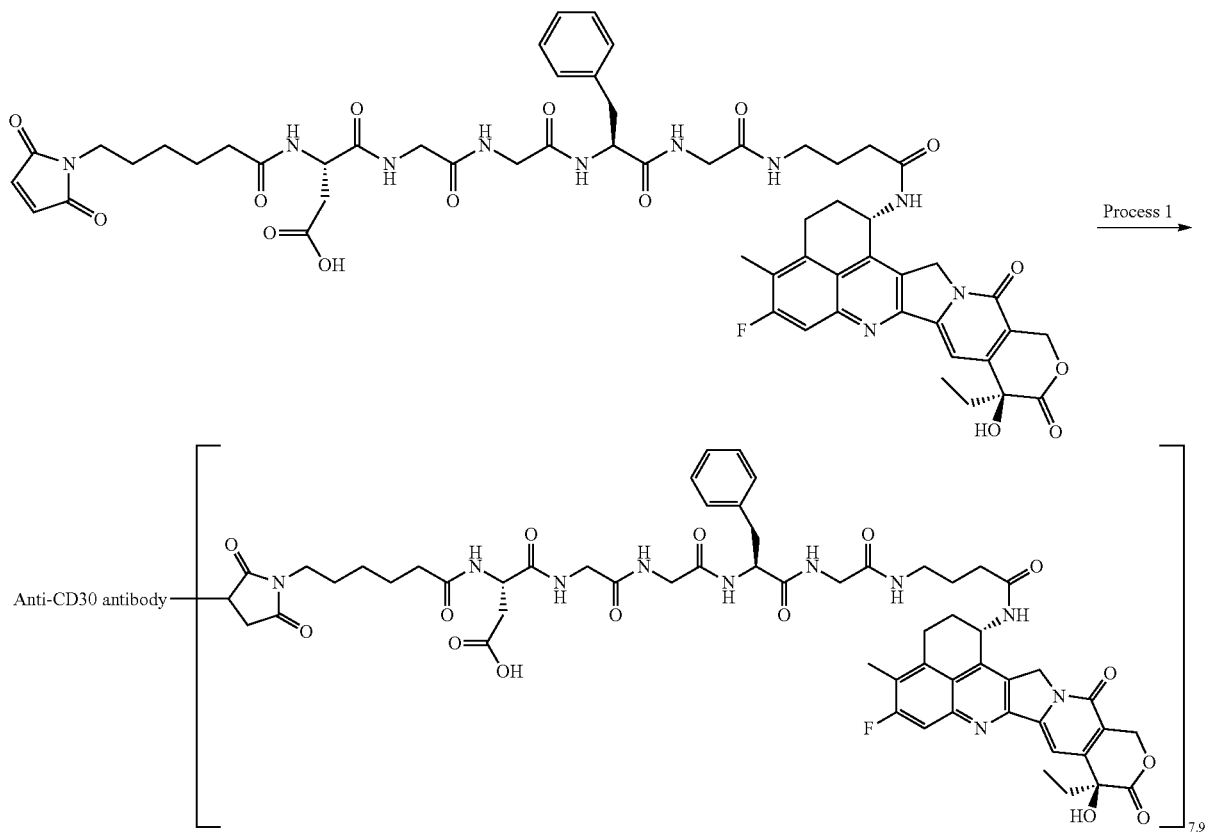

Conjugation between antibody and drug linker: After incubating the above solution at 22° C. for 10 minutes, a dimethyl sulfoxide solution (0.0297 mL; 4.6 equivalents per antibody molecule) containing 10 mM of the compound obtained in Process 5 of Example 2 was added thereto and incubated at 22° C. for 40 minutes for conjugating the drug linker to the antibody. Next, an aqueous solution (0.00593 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as Process 1: Antibody-Drug Conjugate (8)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0593 mL; 9.2 equivalents per antibody molecule) containing 10 mM of the compound obtained in Process 5 of Example 2 was added thereto and incubated at 22° C. for 40 minutes for conjugating the drug linker to the antibody. Next, an aqueous solution (0.0119 mL; 18.4 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=270400 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 1.07 mg/mL, antibody yield: 6.42 mg (64%), and average number of conjugated drug molecules (n) per antibody molecule: 7.9.

Example 10: Antibody-Drug Conjugate (9)

[Formula 62]

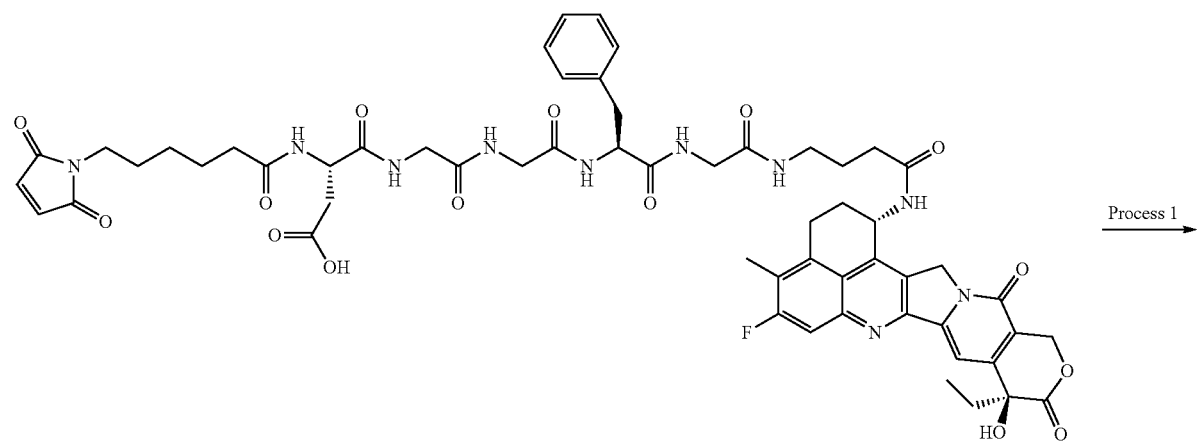

Process 1

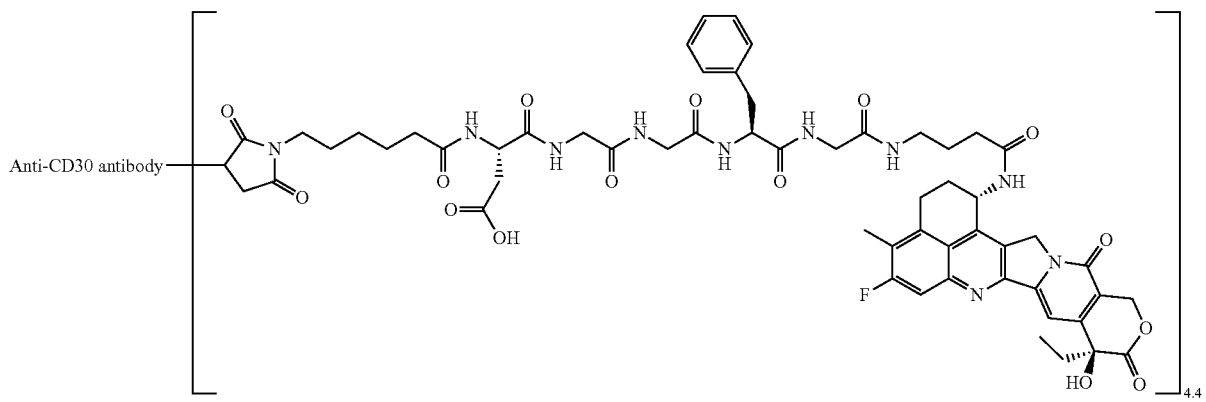

Process 1: Antibody-Drug Conjugate (9)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0148 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0297 mL; 4.6 equivalents per antibody molecule) containing 10 mM of the compound obtained in Process 5 of Example 2 was added thereto and incubated at 22° C. for 40 minutes for conjugating the drug linker to the antibody. Next, an aqueous solution (0.00593 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}=256400$ (estimated calculation value), $\epsilon_{A,370}=0$ (estimated calculation value), $\epsilon_{D,280}=5000$ (measured average value), and $\epsilon_{D,370}=19000$ (measured average value) were used), the following characteristic values were obtained.

Antibody concentration: 1.09 mg/mL, antibody yield: 6.54 mg (65%), and average number of conjugated drug molecules (n) per antibody molecule: 4.4.

Example 11: Antibody-Drug Conjugate (10)

[Formula 63]

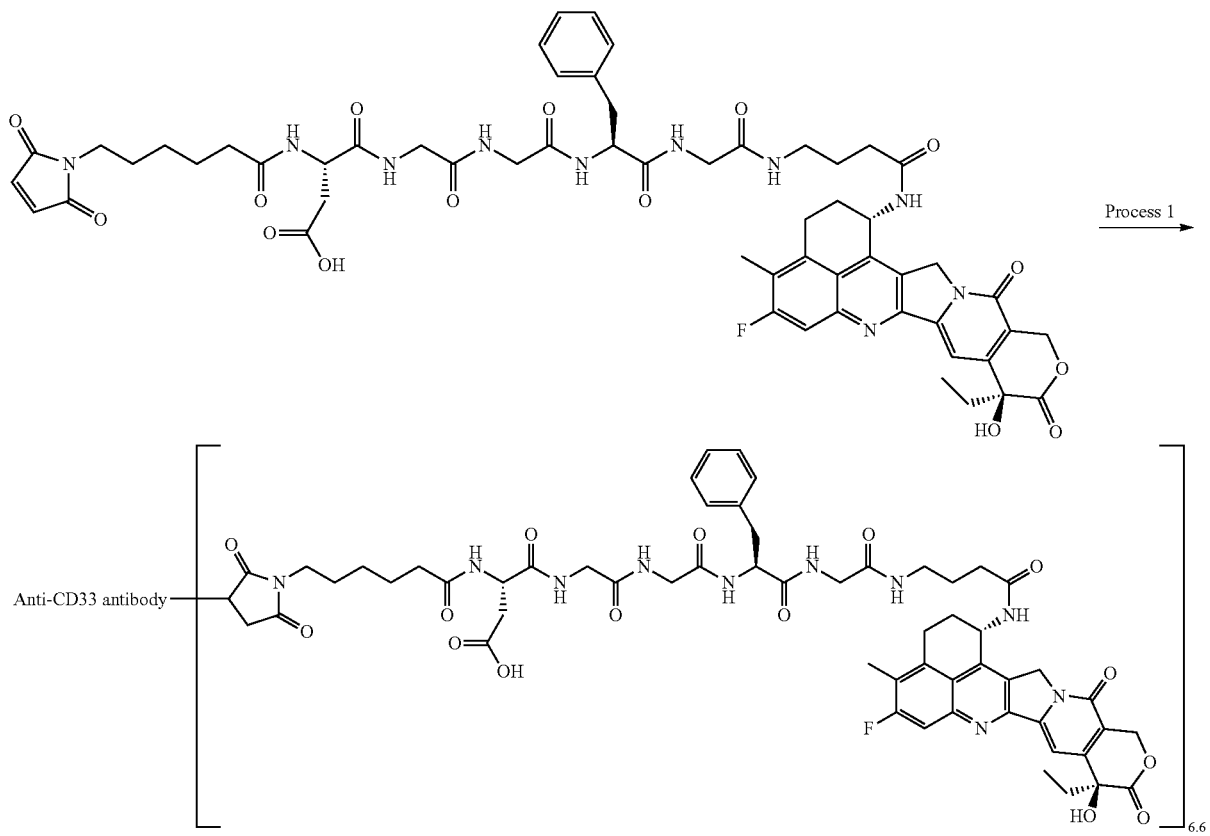

Process 1: Antibody-Drug Conjugate (10)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0593 mL; 9.2 equivalents per antibody molecule) containing 10 mM of the compound obtained in Process 5 of Example 2 was added thereto and incubated at 22° C. for 40 minutes for conjugating the drug linker to the antibody. Next, an aqueous solution (0.0119 mL; 18.4 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=256400 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 1.04 mg/mL, antibody yield: 6.24 mg (62%), and average number of conjugated drug molecules (n) per antibody molecule: 6.6.

Example 12: Antibody-Drug Conjugate (11)

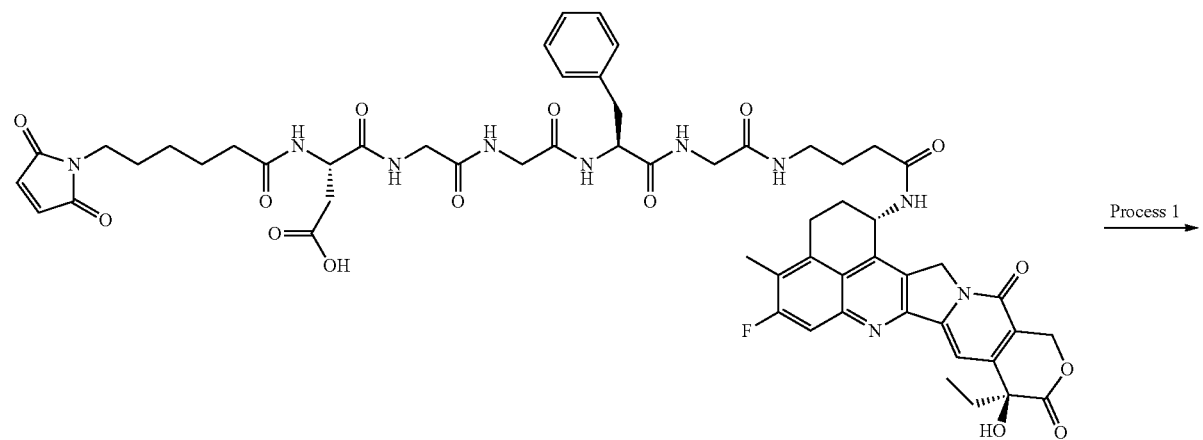

[Formula 64]

Process 1

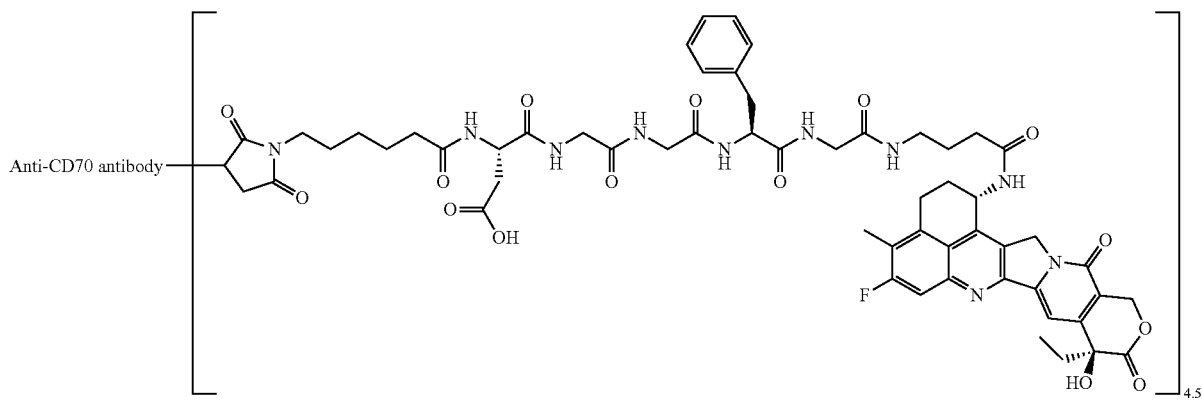

Process 1: Antibody-Drug Conjugate (11)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0148 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=262400 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 1.12 mg/mL, antibody yield: 6.72 mg (67%), and average number of conjugated drug molecules (n) per antibody molecule: 4.5.

Example 13: Antibody-Drug Conjugate (12)

[Formula 65]

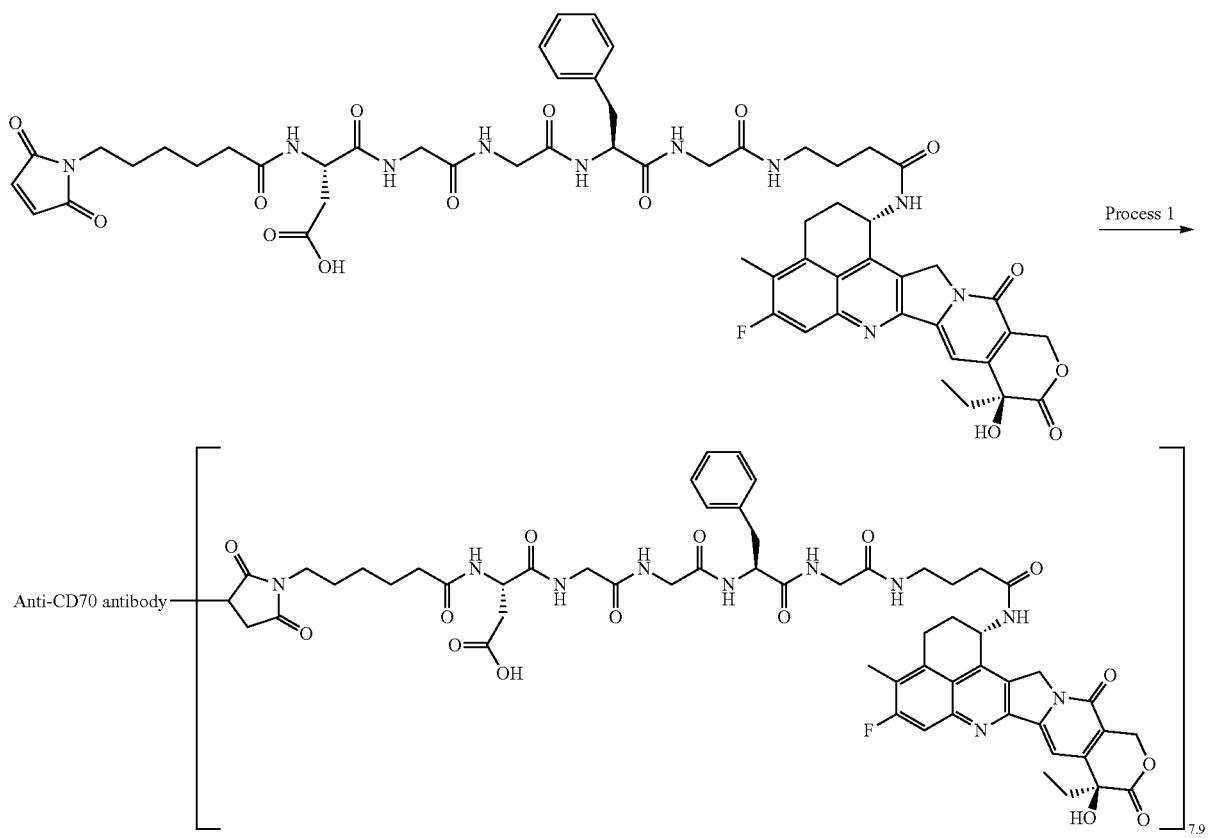

Conjugation between antibody and drug linker: After incubating the above solution at 22° C. for 10 minutes, a dimethyl sulfoxide solution (0.0297 mL; 4.6 equivalents per antibody molecule) containing 10 mM of the compound obtained in Process 5 of Example 2 was added thereto and incubated at 22° C. for 40 minutes for conjugating the drug linker to the antibody. Next, an aqueous solution (0.00593 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as Process 1: Antibody-Drug Conjugate (12)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0593 mL; 9.2 equivalents per antibody molecule) containing 10 mM of the compound obtained in Process 7 of Example 1 was added thereto and incubated at 22° C. for 40 minutes for conjugating the drug linker to the antibody. Next, an aqueous solution (0.0119 mL; 18.4 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=262400 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 1.03 mg/mL, antibody yield: 6.18 mg (62%), and average number of conjugated drug molecules (n) per antibody molecule: 7.9.

Example 14: Antibody-Drug Conjugate (13)

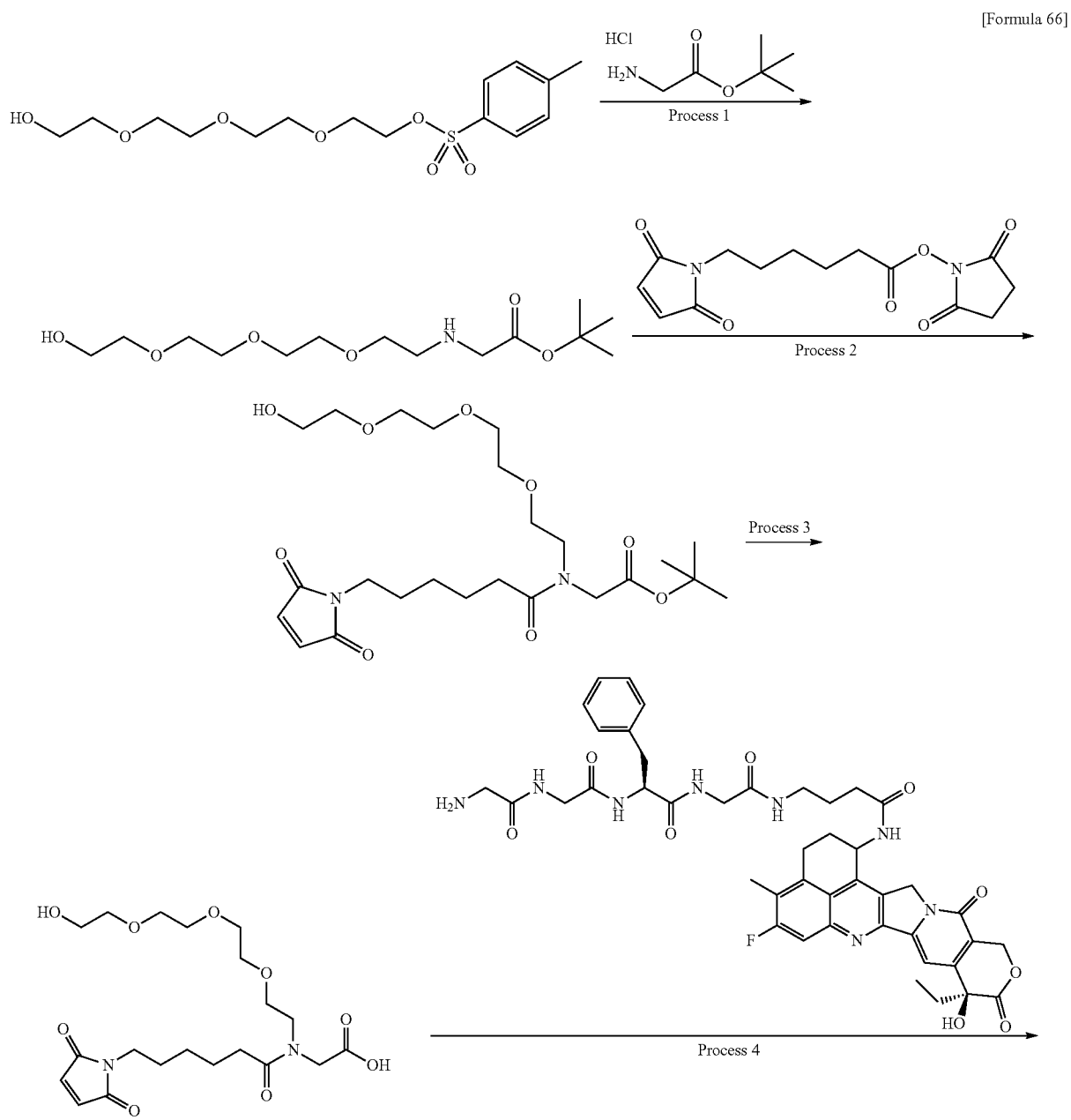

[Formula 66]

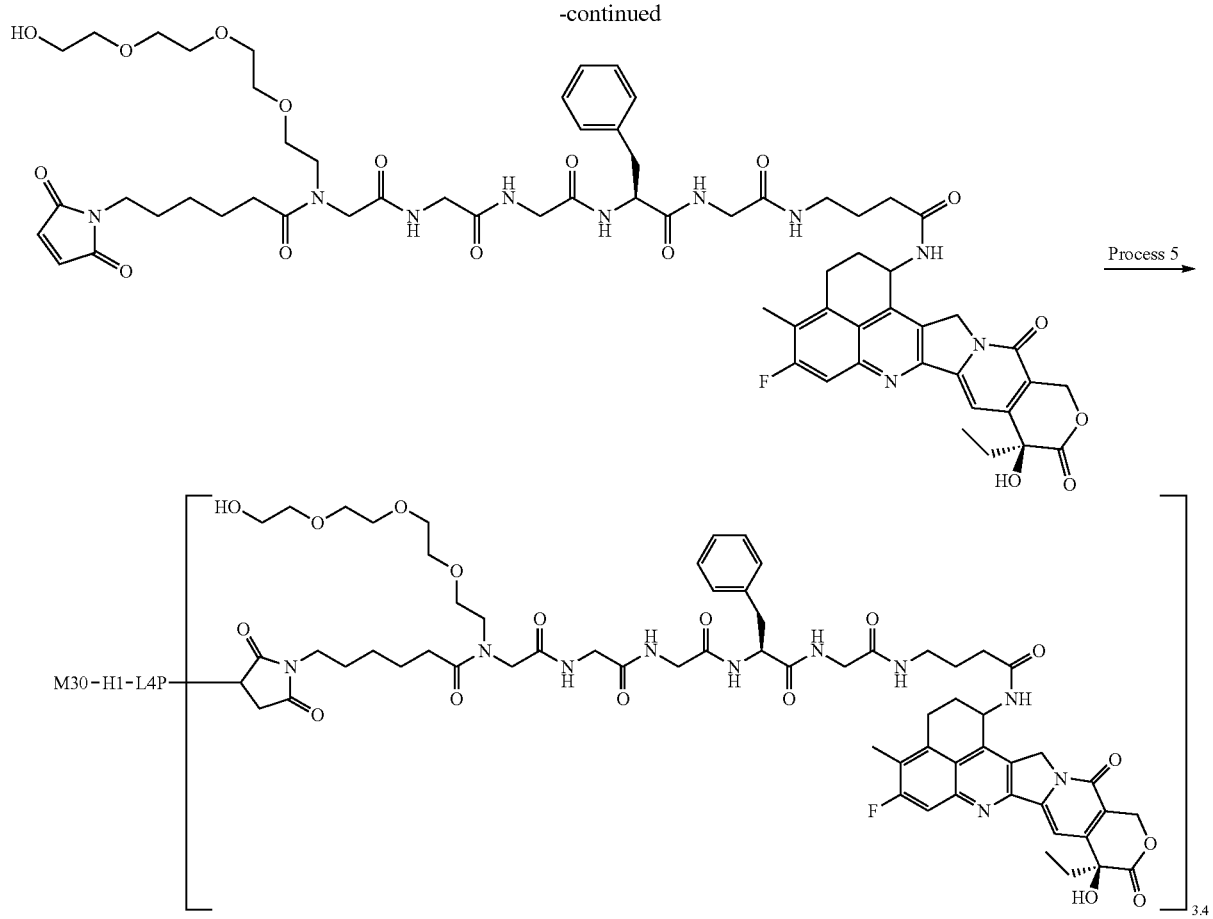

Process 1: tert-Butyl N-(2-{2-[2-(2-hydroxyethoxy)ethoxy]ethoxy}ethyl)glycinate

To an N,N-dimethylformamide (50.0 mL) solution of 2-{2-[2-(2-hydroxyethoxy)ethoxy]ethoxy}ethyl4-methyl-benzene sulfonate (Bioorg. Med. Chem. Lett., 2011, Vol. 21, p. 550; 1.75 g, 5.00 mmol) and glycine tert-butyl hydrochloride (1.26 g, 7.52 mmol), N,N-diisopropylethylamine (1.94 g, 15.0 mmol) was added and stirred at 60° C. for 10 hours. Chloroform was added to the reaction solution, the organic layer was washed with 1 N hydrochloric acid, and the obtained organic layer was dried over sodium sulfate and filtered. The solvent was removed under reduced pressure and the obtained residues were purified by silica gel column chromatography [chloroform to chloroform:methanol=8:1 (v/v)] to yield the titled compound in colorless oily substance (426 mg, 28%).

$^1$H-NMR (400 MHz, CDCl$_3$) δ: 1.47 (9H, s), 2.80 (2H, t, J=5.3 Hz), 3.32 (2H, s), 3.76-3.54 (17H, m).

Process 2: tert-Butyl N-[6-(2,5-dioxo-2,5-dihydro-1H-pyrrol-1-yl)hexanoyl]-N-(2-{2-[2-(2-hydroxyethoxy)ethoxy]ethoxy}ethyl)glycinate The compound (426 mg, 1.39 mmol) obtained in Process 1 above was reacted in the same manner as Process 4 of Example 2 to yield the titled compound in colorless oily substance (489 mg, 70%).

$^1$H-NMR (400 MHz, CDCl$_3$) δ: 1.28-1.36 (2H, m), 1.45 (9H, s), 1.57-1.71 (4H, m), 2.39 (2H, t, J=7.3 Hz), 3.48-3.76 (3H, m), 4.02 (2H, s), 6.68 (2H, s).

Process 3: N-[6-(2,5-dioxo-2,5-dihydro-1H-pyrrol-1-yl)hexanoyl]-N-(2-{2-[2-(2-hydroxyethoxy)ethoxy]ethoxy}ethyl)glycine The compound (489 mg, 0.977 mmol) obtained in Process 2 above was reacted in the same manner as Process 2 of Example 1 to yield the titled compound as a colorless solid (211 mg, 49%).

$^1$H-NMR (400 MHz, CDCl$_3$) δ: 1.38-1.28 (2H, m), 1.73-1.55 (4H, m), 2.28 (2H, t, J=7.0 Hz), 3.50-3.79 (18H, m), 4.12 (2H, s), 6.68 (2H, s).

Process 4: N-[6-(2,5-dioxo-2,5-dihydro-1H-pyrrol-1-yl)hexanoyl]-N-(2-{2-[2-(2-hydroxyethoxy)ethoxy]ethoxy}ethyl)glycylglycylglycyl-L-phenyl-alanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (48.9 mg, 0.110 mmol) obtained in Process 3 above was reacted in the same manner as Process 1 of Example 1 by using the compound (84.0 mg, 0.100 mmol) obtained in Process 2 of Example 2 instead of methanesulfonate of the compound (4) to yield the titled compound as a pale yellow solid (54.0 mg, 43%).

$^1$H-NMR (400 MHz, DMSO-$d_6$) δ: 0.87 (3H, t, J=7.2 Hz), 1.14-1.26 (2H, m), 1.39-1.51 (4H, m), 1.68-1.76 (2H, m), 1.81-1.91 (2H, m), 2.08-2.23 (4H, m), 2.40 (3H, s), 2.73-2.84 (1H, m), 2.98-3.21 (5H, m), 3.25-3.79 (26H, m), 3.93 (2H, s), 4.43-4.49 (1H, m), 4.54-4.61 (1H, m), 5.21 (2H, q, J=18.6 Hz), 5.42 (2H, s), 5.54-5.60 (1H, m), 6.53 (1H, s), 7.00 (2H, s), 7.14-7.27 (5H, m), 7.31 (1H, s), 7.68-7.74 (1H, m), 7.80 (1H, d, J=11.0 Hz), 8.02-8.32 (4H, m), 8.46 (1H, d, J=8.6 Hz).

MS (ESI) m/z: 1265 (M+H)$^+$

Process 5: Antibody-Drug Conjugate (13)

By using the M30-H1-L4P antibody produced in Reference Example 2 and the compound obtained in Process 4 above, the titled antibody-drug conjugate was obtained in the same manner as Process 6 of Example 2.

Antibody concentration: 13.13 mg/mL, antibody yield: 9.2 mg (74%), and average number of conjugated drug molecules (n) per antibody molecule: 3.4.

Example 15: Antibody-Drug Conjugate (14)

[Formula 67]

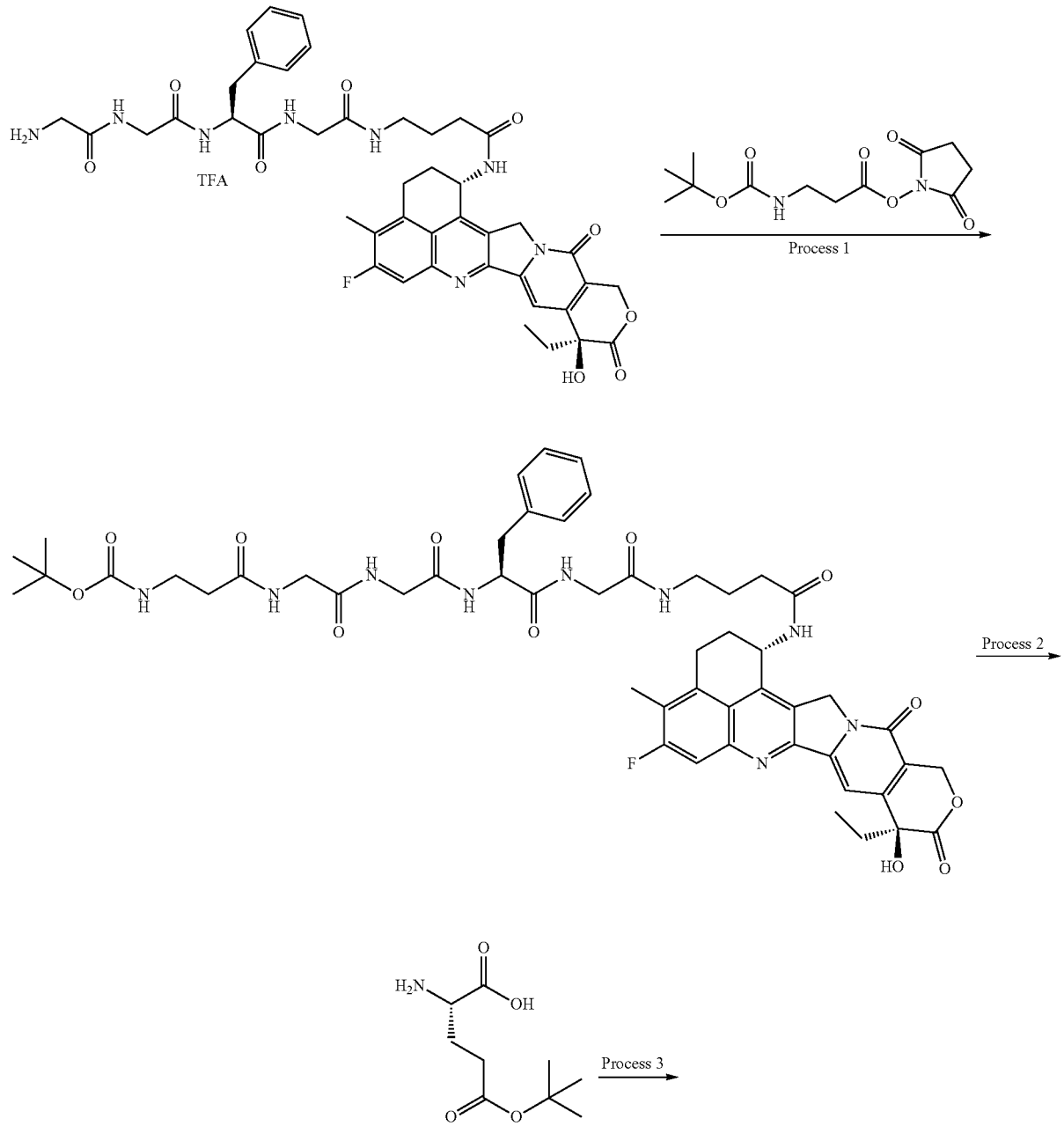

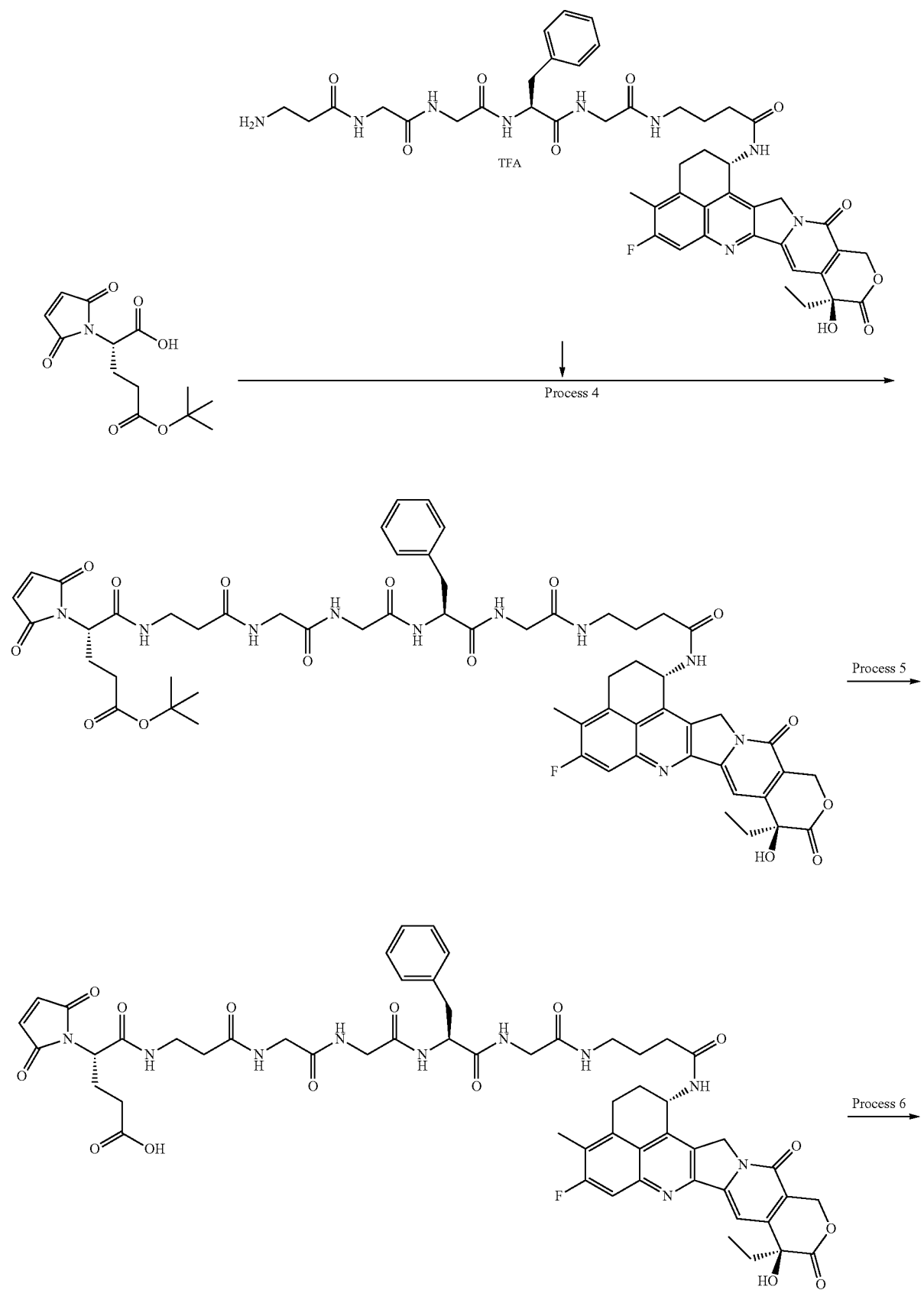

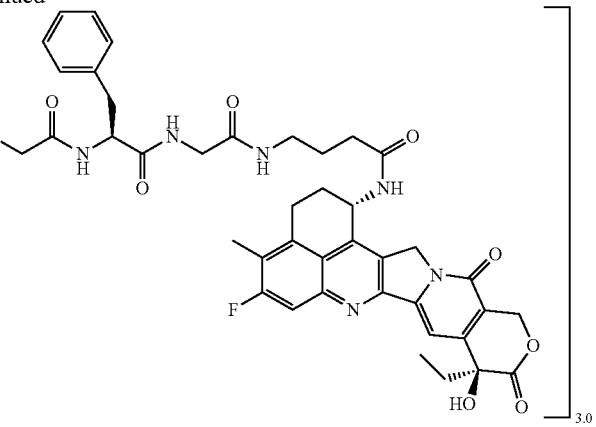

Process 1: N-(tert-butoxycarbonyl)-β-alanylglycyl-glycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (0.839 g, 1.00 mmol) obtained in Process 2 of Example 2 was reacted in the same manner as Process 3 of Example 2 by using N-(tert-butoxycarbonyl)-β-alanine instead of N-succinimidyl 6-maleimide hexanoate. The obtained crude product was used in the next process without purification.

Process 2: β-Alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The crude product obtained in Process 1 was reacted in the same manner as Process 2 of Example 1 to yield the titled compound as a pale yellow solid (0.610 g, 67%).
$^1$H-NMR (400 MHz, DMSO-$d_6$) δ: 0.87 (3H, t, J=7.4 Hz), 1.67-1.77 (2H, m), 1.79-1.92 (2H, m), 2.09-2.22 (4H, m), 2.40 (3H, s), 2.46-2.55 (2H, m), 2.82-2.73 (1H, m), 2.95-3.13 (5H, m), 3.14-3.21 (2H, m), 3.55-3.80 (6H, m), 4.44-4.52 (1H, m), 5.20 (2H, dd, J=35.0, 19.0 Hz), 5.42 (2H, s), 5.53-5.60 (1H, m), 6.54 (1H, s), 7.14-7.28 (5H, m), 7.31 (1H, s), 7.67 (2H, brs), 7.72-7.78 (1H, m), 7.80 (1H, d, J=11.0 Hz), 8.10-8.17 (2H, m), 8.29 (1H, t, J=5.9 Hz), 8.42 (1H, t, J=5.7 Hz), 8.47 (1H, d, J=8.6 Hz).

Process 3: (2S)-5-tert-Butoxy-2-(2,5-dioxo-2,5-dihydro-1H-pyrrol-1-yl)-5-oxopentanoic acid 5-tert-Butyl L-glutamate (1.02 g, 5.00 mmol) was dissolved in a saturated aqueous solution of sodium hydrogen carbonate (20.0 mL), charged with N-methoxycarbonylmaleimide (0.775 g, 5.00 mmol) at 0° C., and stirred at 0° C. for 30 minutes and then stirred at room temperature for 1 hour. The reaction solution was rendered acidic by the addition of 5 N hydrochloric acid at 0° C. and then extracted with ethyl acetate. The obtained organic layer was dried over sodium sulfate and filtered. The solvent was removed under reduced pressure to yield a crude product. The obtained crude product was used in the next process without purification.

Process 4: N-[(2S)-5-tert-butoxy-2-(2,5-dioxo-2,5-dihydro-1H-pyrrol-1-yl)-5-oxopentanoyl]-β-alanyl-glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The crude product (85.0 mg, 0.300 mmol) obtained in Process 3 above was reacted in the same manner as Process 1 of Example 1 by using the compound (182 mg, 0.200 mmol) obtained in Process 2 above instead of methanesulfonate of the compound (4) to yield the titled compound as a pale yellow solid (102 mg, 43%).
$^1$H-NMR (400 MHz, DMSO-$d_6$) δ: 0.87 (3H, t, J=7.2 Hz), 1.35 (9H, s), 1.67-1.76 (2H, m), 1.81-1.90 (2H, m), 2.35-2.05 (10H, m), 2.40 (3H, s), 2.75-2.83 (1H, m), 2.99-3.13 (3H, m), 3.14-3.26 (4H, m), 3.55-3.76 (6H, m), 4.36-4.50 (2H, m), 5.21 (2H, q, J=18.9 Hz), 5.42 (2H, s), 5.54-5.61 (1H, m), 6.53 (1H, s), 7.03 (2H, s), 7.17-7.26 (5H, m), 7.31 (1H, s), 7.68-7.73 (1H, m), 7.80 (1H, d, J=10.6 Hz), 8.00-8.05 (2H, m), 8.12 (1H, d, J=7.8 Hz), 8.16-8.20 (1H, m), 8.23-8.28 (1H, m), 8.46 (1H, d, J=8.6 Hz).

Process 5: N-[(2S)-4-carboxy-2-(2,5-dioxo-2,5-dihydro-1H-pyrrol-1-yl)butanoyl]-β-alanylglycylgly-cyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (102 mg, 86.8 μmol) obtained in Process 4 above was reacted in the same manner as Process 2 of Example 1 to yield the titled compound as a pale yellow solid (76.0 mg, 78%).
$^1$H-NMR (400 MHz, DMSO-$d_6$) δ: 0.87 (3H, t, J=7.4 Hz), 1.68-1.75 (2H, m), 1.84-1.91 (2H, m), 2.35-2.05 (10H, m), 2.40 (3H, s), 2.74-2.83 (1H, m), 2.99-3.12 (3H, m), 3.14-3.26 (4H, m), 3.55-3.77 (6H, m), 4.41-4.49 (2H, m), 5.21 (2H, dd, J=38.7, 18.8 Hz), 5.42 (2H, s), 5.54-5.61 (1H, m), 6.54 (1H, s), 7.03 (2H, s), 7.15-7.27 (5H, m), 7.31 (1H, s), 7.69-7.74 (1H, m), 7.80 (1H, d, J=10.9 Hz), 8.01-8.07 (2H, m), 8.12 (1H, d, J=8.2 Hz), 8.19 (1H, t, J=5.5 Hz), 8.27 (1H, t, J=6.3 Hz), 8.47 (1H, d, J=8.6 Hz), 12.12 (1H, s).
MS (ESI) m/z: 1119 (M+H)$^+$

Process 6: Antibody-Drug Conjugate (14)

By using the M30-H1-L4P antibody produced in Reference Example 2 and the compound obtained in Process 5 above, the titled antibody-drug conjugate was obtained in the same manner as Process 6 of Example 2.

Antibody concentration: 12.77 mg/mL, antibody yield: 8.9 mg (71%), and average number of conjugated drug molecules (n) per antibody molecule: 3.0.

Example 16: Antibody-Drug Conjugate (15)

[Formula 68]

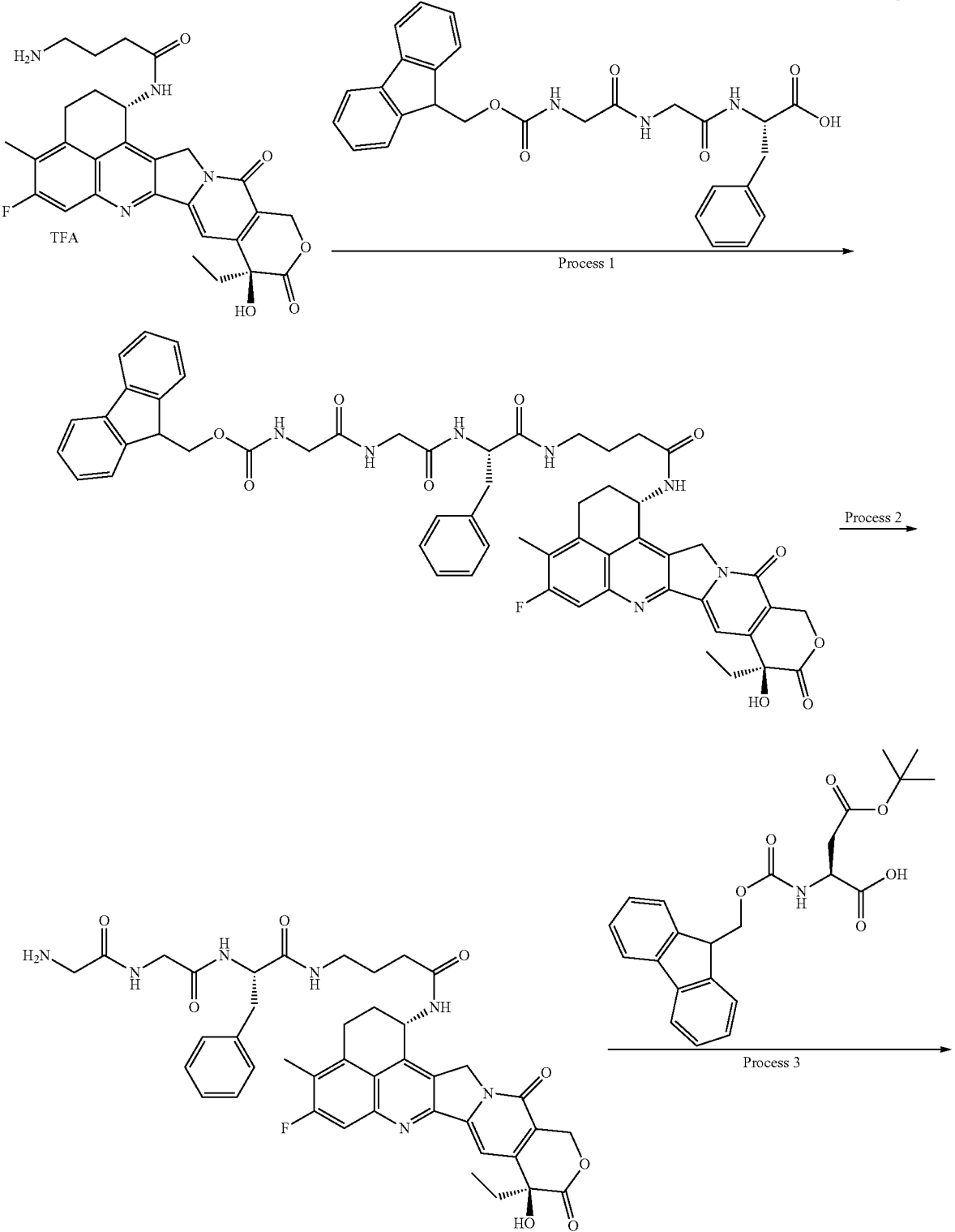

-continued
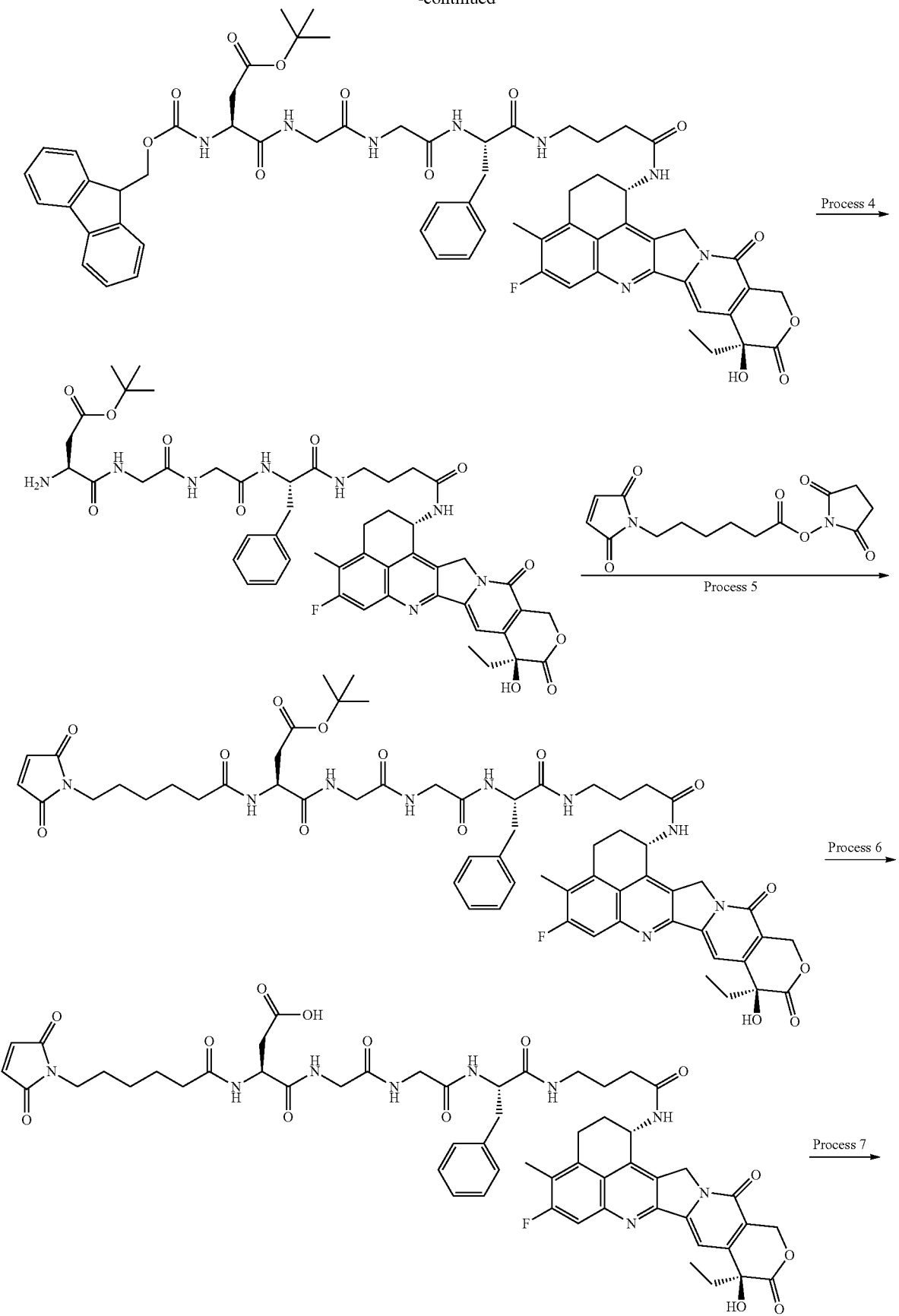

-continued

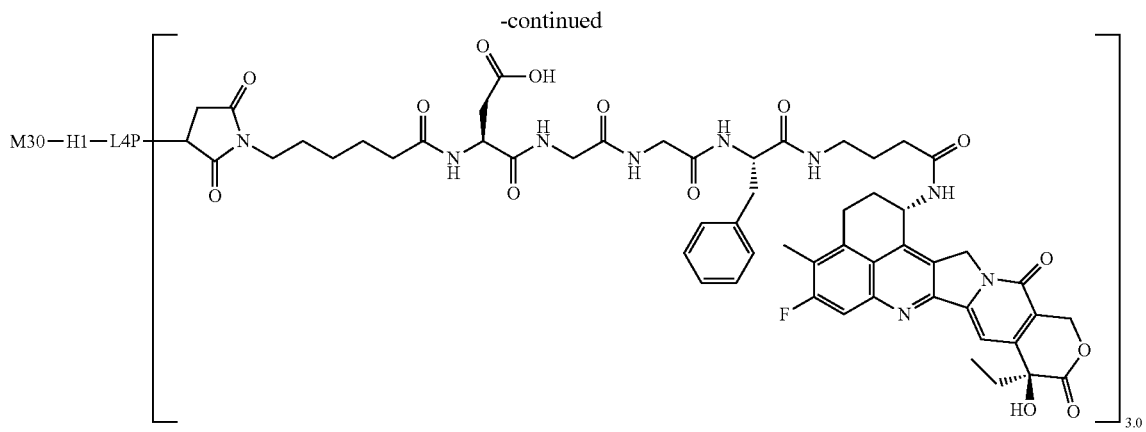

Process 1: N-[(9H-fluoren-9-ylmethoxy)carbonyl]glycylglycyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-phenylalaninamide The compound (300 mg, 0.473 mmol) obtained in Process 2 of Example 1 was reacted in the same manner as Process 1 of Example 1 by using N-[(9H-fluoren-9-ylmethoxy)carbonyl]glycylglycyl-L-phenylalanine (the compound described in Japanese Patent Laid-Open No. 2002-60351; 346 mg, 0.691 mmol) instead of 4-(tert-butoxycarbonylamino)butanoic acid to yield the titled compound as a pale yellow solid (230 mg, 40%).

$^1$H-NMR (400 MHz, DMSO-$d_6$) δ: 0.85 (3H, t, J=7.2 Hz), 1.67-1.68 (2H, m), 1.81-1.84 (2H, m), 2.13 (4H, t, J=6.8 Hz), 2.39 (3H, s), 2.76 (1H, t, J=11.4 Hz), 2.96-3.08 (4H, m), 3.16-3.17 (2H, m), 3.59-3.74 (4H, m), 4.22-4.28 (2H, m), 4.39-4.42 (1H, m), 5.16-5.22 (2H, m), 5.36-5.41 (2H, m), 5.56-5.59 (1H, m), 6.52 (1H, s), 7.14-7.20 (5H, m), 7.29-7.31 (3H, m), 7.38-7.41 (2H, m), 7.61 (1H, t, J=6.0 Hz), 7.69 (2H, d, J=7.4 Hz), 7.79 (1H, d, J=11.0 Hz), 7.87 (2H, d, J=7.8 Hz), 7.95 (1H, s), 8.07 (2H, t, J=4.3 Hz), 8.42 (1H, d, J=8.6 Hz).
MS (APCI) m/z: 1004 (M+H)$^+$

Process 2: Glycylglycyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-phenylalaninamide To an N,N-dimethylformamide (1.00 mL) solution of the compound (226 mg, 0.225 mmol) obtained in Process 1, piperidine (0.223 mL, 2.25 mmol) was added and stirred at room temperature for 5 hours. The solvent was removed under reduced pressure to yield a mixture containing the titled compound. The mixture was used for the next reaction without further purification.

Process 3: tert-Butyl (3S,12S)-12-benzyl-18-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-{[(9H-fluoren-9-ylmethoxy)carbonyl]amino}-4,7,10,13,18-pentaoxo-5,8,11,14-tetraazaoctadecan-1-oate The compound (0.225 mmol) obtained in Process 2 above was reacted in the same manner as Process 1 of Example 1 by using 4-tert-butyl N-[(9H-fluoren-9-ylmethoxy)carbonyl]-L-aspartate (104 mg, 0.337 mmol) instead of 4-(tert-butoxycarbonylamino)butanoic acid to yield the titled compound as a pale yellow solid (114 mg, 43%).

$^1$H-NMR (400 MHz, DMSO-$d_6$) δ: 0.86 (3H, t, J=7.2 Hz), 1.35 (9H, s), 1.66-1.69 (2H, m), 1.84-1.85 (2H, m), 2.11-2.13 (4H, m), 2.39 (3H, s), 2.43-2.45 (1H, m), 2.68-2.79 (2H, m), 2.94-3.16 (5H, m), 3.66 (5H, tt, J=30.5, 10.0 Hz), 4.23-4.30 (3H, m), 4.39-4.41 (1H, m), 5.15 (1H, d, J=19.2 Hz), 5.21 (1H, d, J=18.8 Hz), 5.37 (1H, d, J=17.2 Hz), 5.42 (1H, d, J=16.0 Hz), 5.53-5.57 (1H, m), 6.54 (1H, s), 7.15-7.22 (5H, m), 7.26-7.34 (3H, m), 7.38-7.40 (2H, m), 7.68-7.70 (2H, m), 7.79 (1H, d, J=10.9 Hz), 7.86-7.87 (2H, m), 7.88-7.90 (1H, m), 7.96 (1H, t, J=6.3 Hz), 8.03-8.07 (2H, m), 8.20 (1H, t, J=5.5 Hz), 8.43 (1H, d, J=8.6 Hz).
MS (APCI) m/z: 1175 (M+H)$^+$

Process 4: tert-Butyl (3S,12S)-3-amino-12-benzyl-18-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,18-pentaoxo-5,8,11,14-tetraazaoctadecan-1-oate The compound (110 mg, 0.0936 mmol) obtained in Process 3 above was reacted in the same manner as Process 2 to yield a mixture containing the titled compound. The mixture was used for the next reaction without further purification.

Process 5: tert-Butyl (3S,12S)-12-benzyl-3-{[6-(2,5-dioxo-2,5-dihydro-1H-pyrrol-1-yl)hexanoyl]amino}-18-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,18-pentaoxo-5,8,11,14-tetraazaoctadecan-1-oate The compound (0.0936 mmol) obtained in Process 4 above was reacted in the same manner as Process 4 of Example 2 to yield the titled compound as a pale yellow solid (40.2 mg, 38%).

$^1$H-NMR (400 MHz, DMSO-$d_6$) δ: 0.86 (3H, t, J=7.4 Hz), 1.17-1.19 (2H, m), 1.35 (9H, s), 1.44-1.47 (4H, m), 1.66-1.67 (2H, m), 1.81-1.88 (2H, m), 2.06-2.13 (6H, m), 2.39-2.41 (1H, m), 2.40 (3H, s), 2.67 (1H, dd, J=16.0, 5.5 Hz), 2.76 (1H, dd, J=13.3, 9.0 Hz), 2.96 (1H, dd, J=13.5, 4.9 Hz), 3.04 (2H, td, J=13.4, 6.6 Hz), 3.18 (2H, s), 3.36 (2H, d, J=7.0

Hz), 3.58 (1H, dd, J=16.8, 5.5 Hz), 3.70 (3H, dt, J=21.5, 7.2 Hz), 4.38-4.41 (1H, m), 4.57-4.59 (1H, m), 5.16 (1H, d, J=18.8 Hz), 5.24 (1H, d, J=19.2 Hz), 5.38 (1H, d, J=16.4 Hz), 5.43 (1H, d, J=16.0 Hz), 5.57-5.58 (1H, m), 6.54 (1H, s), 6.99 (2H, s), 7.13-7.25 (5H, m), 7.31 (1H, s), 7.80 (1H, d, J=10.9 Hz), 7.94-8.04 (3H, m), 8.13-8.16 (2H, m), 8.43 (1H, d, J=8.6 Hz). MS (APCI) m/z: 1146 (M+H)$^+$

Process 6: N-[6-(2,5-dioxo-2,5-dihydro-1H-pyrrol-1-yl)hexanoyl]-L-α-aspartylglycylglycyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-phenylalaninamide The compound (40.0 mg, 0.0349 mmol) obtained in Process 5 above was reacted in the same manner as Process 2 of Example 1 to yield the titled compound as a pale yellow solid (33.6 g, 88%).

$^1$H-NMR (400 MHz, DMSO-d$_6$) δ: 0.87 (3H, q, J=7.2 Hz), 1.14-1.20 (2H, m), 1.46 (4H, td, J=14.8, 7.3 Hz), 1.67 (2H, td, J=12.9, 6.3 Hz), 1.84 (2H, dq, J=25.5, 7.2 Hz), 2.11 (6H, dt, J=23.4, 7.3 Hz), 2.39 (3H, s), 2.45-2.47 (1H, m), 2.69 (1H, dd, J=16.5, 5.5 Hz), 2.76 (1H, dd, J=13.7, 9.3 Hz), 2.94-3.01 (1H, m), 3.05 (2H, dq, J=25.1, 6.4 Hz), 3.17-3.19 (1H, m), 3.34-3.46 (4H, m), 3.59 (1H, dd, J=16.6, 5.6 Hz), 3.69 (2H, dt, J=20.1, 6.8 Hz), 4.37-4.41 (1H, m), 4.55 (1H, dd, J=13.5, 7.7 Hz), 5.16 (1H, d, J=19.0 Hz), 5.22 (1H, d, J=18.6 Hz), 5.38 (1H, d, J=16.4 Hz), 5.43 (1H, d, J=16.4 Hz), 5.55-5.59 (1H, m), 6.54 (1H, s), 6.99 (2H, s), 7.19 (5H, dq, J=31.6, 7.9 Hz), 7.31 (1H, s), 7.79 (1H, d, J=11.0 Hz), 7.99 (3H, ddd, J=25.1, 14.2, 6.2 Hz), 8.11 (1H, t, J=5.5 Hz), 8.17 (1H, d, J=7.6 Hz), 8.44 (1H, d, J=8.5 Hz), 12.32 (1H, s).

MS (APCI) m/z: 1090 (M+H)$^+$

Process 7: Antibody-Drug Conjugate (15)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was added to a 1.5 mL polypropylene tube and charged with an aqueous solution of 10 mM TCEP (Tokyo Chemical Industry Co., Ltd.) (0.025 mL; 3.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.102 mL) and a dimethyl sulfoxide solution containing 10 mM of the compound obtained in above Process 6 (0.047 mL; 5.5 equivalents per antibody molecule) to the above solution at room temperature, it was stirred by using a tube rotator (MTR-103, manufactured by AS ONE Corporation) at room temperature for 40 minutes for conjugating the drug linker to the antibody. Next, an aqueous solution (0.009 mL) of 100 mM NAC (Sigma-Aldrich Co. LLC) was added thereto and stirred at room temperature for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 9.16 mg/mL, antibody yield: 6.4 mg (51%), and average number of conjugated drug molecules (n) per antibody molecule: 3.0.

Example 17: Antibody-Drug Conjugate (16)

[Formula 69]

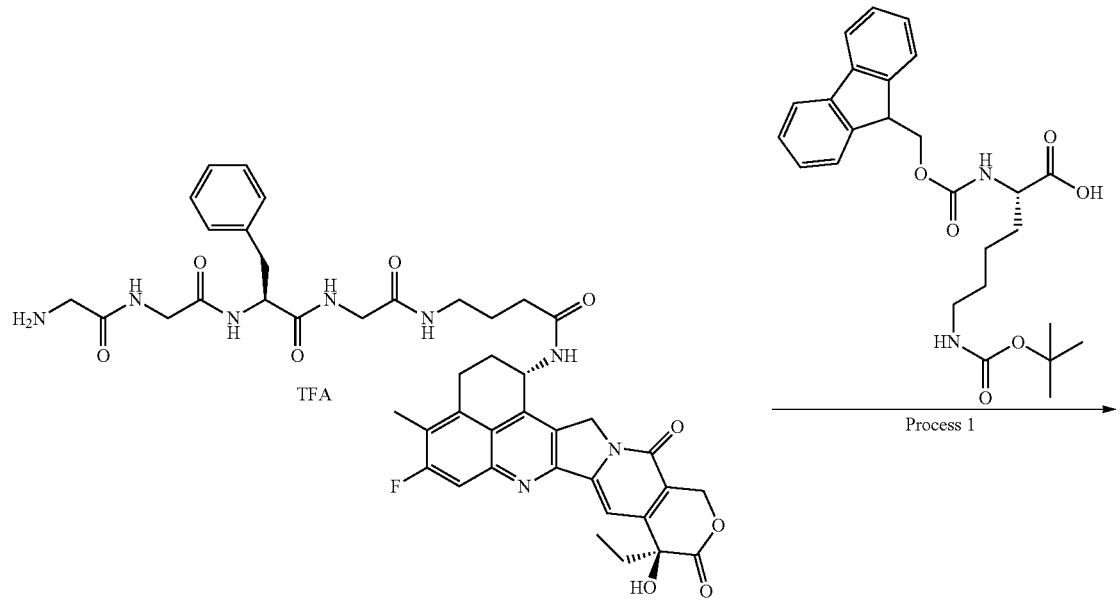

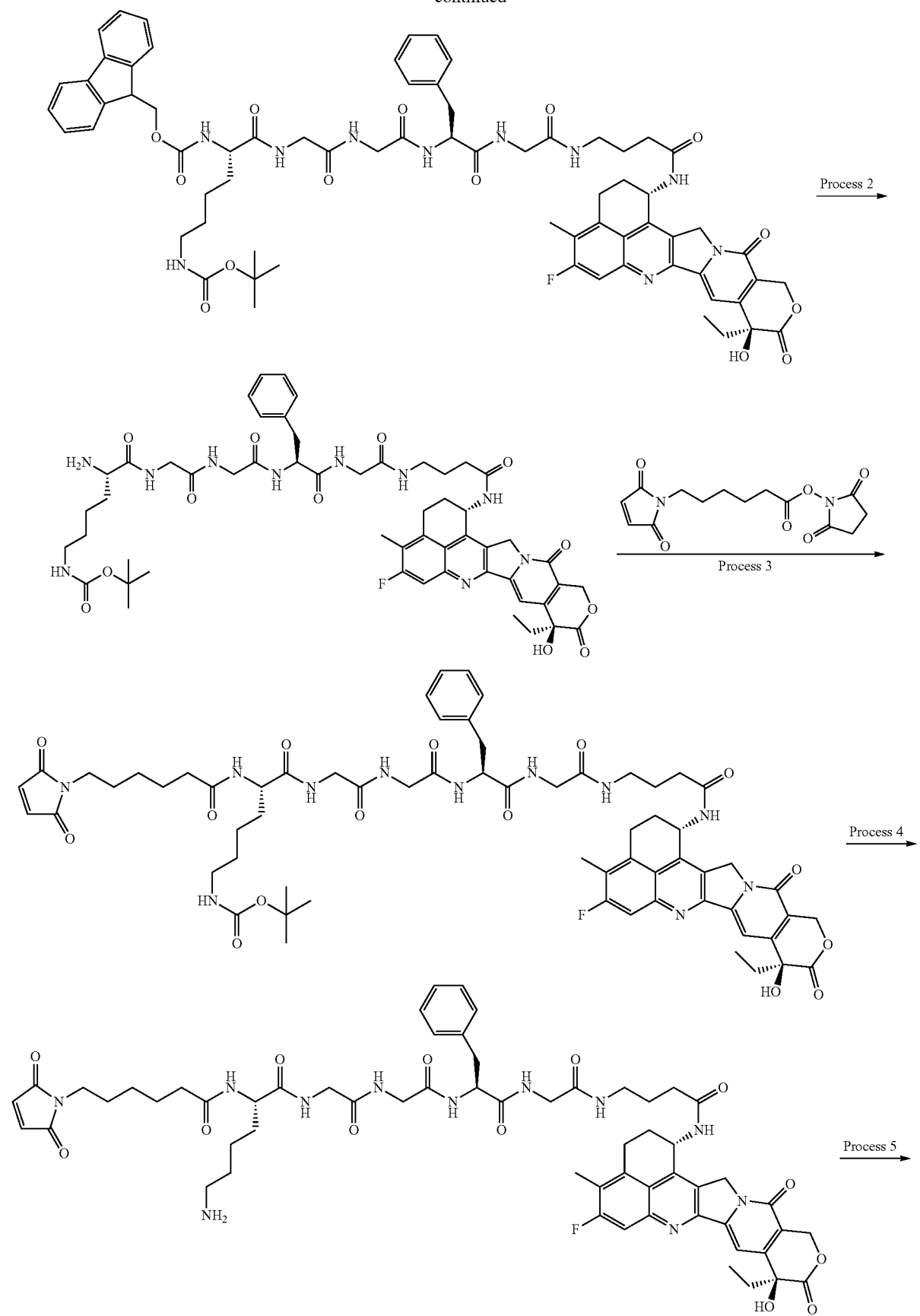

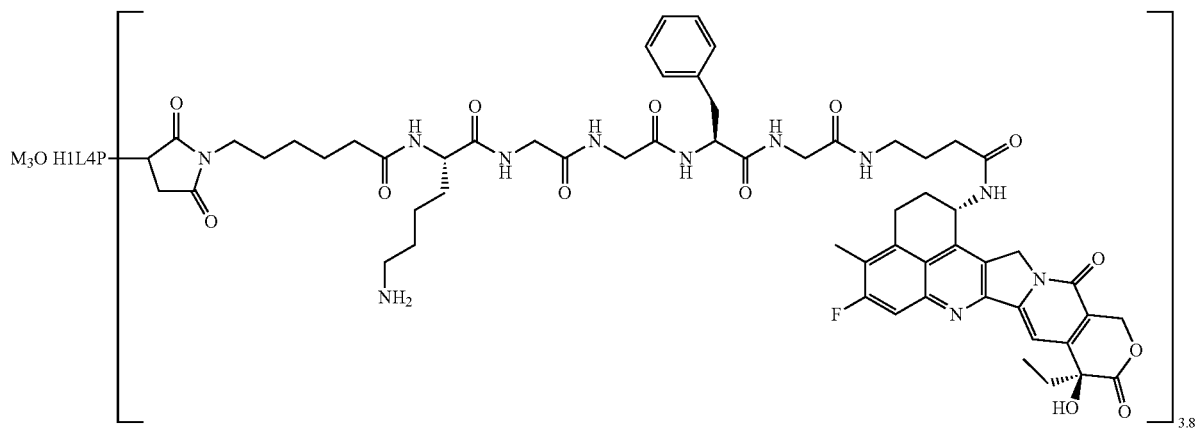

Process 1: N⁶-(tert-butoxycarbonyl)-N²-[(9H-fluoren-9-ylmethoxy)carbonyl]-L-lysylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (167 mg, 0.176 mmol) obtained in Process 2 of Example 2 was reacted in the same manner as Process 1 of Example 1 by using N^ε-(tert-butoxycarbonyl)-N^α-[(9H-fluoren-9-ylmethoxy)carbonyl]-L-lysine (103 mg, 0.22 mmol) instead of 4-(tert-butoxycarbonylamino)butanoic acid. The obtained crude product was used in the next process without purification.

Process 2: N⁶-(tert-butoxycarbonyl)-L-lysylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To an N,N-dimethylformamide (4.00 mL) solution of the crude product obtained in Process 1 above, piperidine (0.400 mL) was added and stirred at room temperature for 2 hours. The solvent was removed under reduced pressure and the obtained residues were purified by silica gel column chromatography [chloroform to partitioned organic layer of chloroform:methanol:water=7:3:1 (v/v/v),] to yield the titled compound as a pale yellow solid (113 mg, 60%).

¹H-NMR (400 MHz, DMSO-d₆) δ: 0.87 (3H, t, J=7.4 Hz), 1.18-1.49 (5H, m), 1.36 (9H, s), 1.51-1.60 (1H, m), 1.67-1.76 (2H, m), 1.80-1.91 (2H, m), 2.09-2.20 (4H, m), 2.39 (3H, s), 2.76-2.89 (3H, m), 2.99-3.22 (6H, m), 3.58-3.77 (6H, m), 4.43-4.49 (1H, m), 5.20 (2H, q, J=18.5 Hz), 5.42 (2H, s), 5.55-5.60 (1H, m), 6.54 (1H, s), 6.76 (1H, t, J=5.5 Hz), 7.15-7.26 (5H, m), 7.31 (1H, s), 7.69-7.74 (1H, m), 7.80 (1H, d, J=10.9 Hz), 8.08 (1H, t, J=5.7 Hz), 8.14 (1H, d, J=7.8 Hz), 8.22-8.30 (2H, m), 8.47 (1H, d, J=8.6 Hz).

Process 3: N⁶-(tert-butoxycarbonyl)-N²-[6-(2,5-dioxo-2,5-dihydro-1H-pyrrol-1-yl)hexanoyl]-L-lysylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (113 mg, 0.106 mmol) obtained in Process 2 above was reacted in the same manner as Process 4 of Example 2 to yield the titled compound as a pale yellow solid (102 mg, 61%).

¹H-NMR (400 MHz, DMSO-d₆) δ: 0.87 (3H, t, J=7.2 Hz), 1.11-1.53 (11H, m), 1.35 (9H, s), 1.56-1.65 (1H, m), 1.68-1.76 (2H, m), 1.81-1.92 (2H, m), 2.06-2.20 (6H, m), 2.40 (3H, s), 2.74-2.90 (3H, m), 2.96-3.39 (7H, m), 3.57-3.74 (6H, m), 4.14-4.21 (1H, m), 4.42-4.49 (1H, m), 5.20 (2H, q, J=18.9 Hz), 5.42 (2H, s), 5.55-5.60 (1H, m), 6.54 (1H, s), 6.72-6.78 (1H, m), 7.00 (2H, s), 7.15-7.26 (5H, m), 7.31 (1H, s), 7.69-7.72 (1H, m), 7.80 (1H, d, J=10.9 Hz), 7.93 (1H, d, J=7.4 Hz), 7.99-8.04 (1H, m), 8.10-8.18 (2H, m), 8.26 (1H, t, J=6.1 Hz), 8.46 (1H, d, J=8.2 Hz).

Process 4: N²-[6-(2,5-dioxo-2,5-dihydro-1H-pyrrol-1-yl)hexanoyl]-L-lysylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To a dichloromethane (4.00 mL) solution of the compound (102 mg, 80.9 μmol) obtained in Process 3 above, trifluoroacetic acid (1.00 mL) was added and stirred at room temperature for 2 hours. The solvent was removed under reduced pressure and the obtained residues were purified by silica gel column chromatography [chloroform to partitioned organic layer of chloroform:methanol:water=7:3:1 (v/v/v)] to yield the titled compound as a pale yellow solid (57.0 mg, 61%).

$^1$H-NMR (400 MHz, DMSO-d$_6$) δ: 0.87 (3H, t, J=7.2 Hz), 1.12-1.35 (4H, m), 1.41-1.55 (7H, m), 1.61-1.77 (3H, m), 1.80-1.91 (2H, m), 2.07-2.22 (6H, m), 2.40 (3H, s), 2.84-2.71 (3H, m), 2.97-3.40 (7H, m), 3.59-3.76 (6H, m), 4.20-4.25 (1H, m), 4.45-4.50 (1H, m), 5.20 (2H, q, J=18.5 Hz), 5.42 (2H, s), 5.54-5.60 (1H, m), 6.55 (1H, s), 7.01 (2H, s), 7.15-7.26 (5H, m), 7.31 (1H, s), 7.74 (1H, t, J=5.7 Hz), 7.81 (1H, d, J=10.9 Hz), 7.97 (1H, d, J=7.8 Hz), 8.05 (1H, t, J=6.1 Hz), 8.13-8.18 (2H, m), 8.28 (1H, t, J=5.7 Hz), 8.47 (1H, d, J=8.6 Hz).

MS (ESI) m/z: 1160 (M+H)$^+$

Process 5: Antibody-Drug Conjugate (16)

By using the M30-H1-L4P antibody produced in Reference Example 2 and the compound obtained in Process 4 above, the titled antibody-drug conjugate was obtained in the same manner as Process 7 of Example 16.

Antibody concentration: 19.26 mg/mL, and average number of conjugated drug molecules (n) per antibody molecule: 3.8.

Example 18 N-[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b] quinolin-1-yl]-β-alaninamide

[Formula 70]

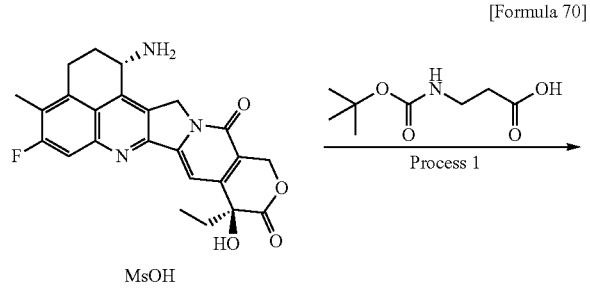

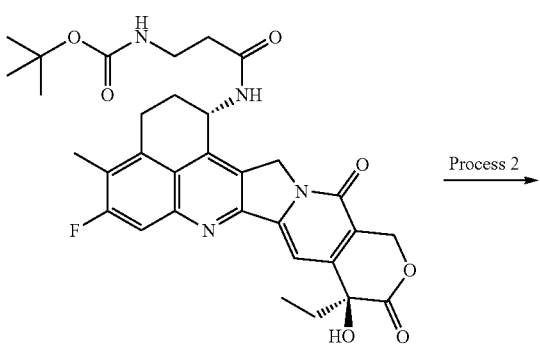

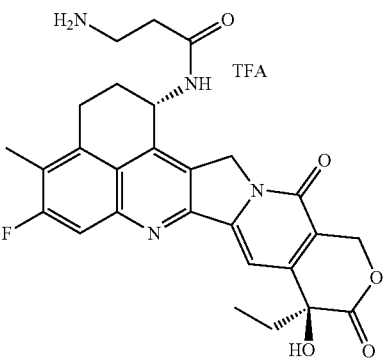

Process 1: tert-Butyl (3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl) carbamate Mesylate of the compound (4) (500 mg, 0.941 mmol) was reacted in the same manner as Process 1 of Example 1 by using N-(tert-butoxycarbonyl)-3-alanine instead of 4-(tert-butoxycarbonylamino)butanoic acid to yield the titled compound as a yellow-brown solid (616 mg, quantitative).

$^1$H-NMR (400 MHz, DMSO-d$_6$) δ: 0.87 (3H, t, J=7.2 Hz), 1.29 (9H, s), 1.86 (2H, dt, J=15.1, 7.3 Hz), 2.04-2.22 (2H, m), 2.31 (2H, t, J=6.8 Hz), 2.40 (3H, s), 3.10-3.26 (4H, m), 5.15 (1H, d, J=18.8 Hz), 5.26 (1H, d, J=19.2 Hz), 5.42 (2H, dd, J=18.8, 16.4 Hz), 5.57 (1H, dt, J=8.5, 4.2 Hz), 6.53 (1H, s), 6.78 (1H, t, J=5.5 Hz), 7.30 (1H, s), 7.80 (1H, d, J=11.0 Hz), 8.46 (1H, d, J=8.6 Hz).

MS (ESI) m/z: 607 (M+H)$^+$

Process 2: N-[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b] quinolin-1-yl]-β-alaninamide The compound obtained in Process 1 above was reacted in the same manner as Process 2 of Example 1 to yield trifluoroacetate of the titled compound as a yellow solid (499 mg, 86%).

$^1$H-NMR (400 MHz, DMSO-d$_6$) δ: 0.87 (3H, t, J=7.2 Hz), 1.86 (2H, dquin, J=14.6, 7.2, 7.2, 7.2, 7.2 Hz), 2.06-2.27 (1H, m), 2.41 (3H, s), 2.46-2.57 (2H, m), 3.08 (2H, t, J=6.8 Hz), 3.14-3.24 (2H, m), 5.22 (1H, d, J=18.8 Hz), 5.29 (1H, d, J=18.8 Hz), 5.43 (2H, s), 5.58 (1H, dt, J=8.5, 4.5 Hz), 6.55 (1H, s), 7.32 (1H, s), 7.74 (3H, brs), 7.82 (1H, d, J=11.0 Hz), 8.67 (1H, d, J=8.6 Hz).

MS (ESI) m/z: 507 (M+H)$^+$

Example 19: Antibody-Drug Conjugate (17)
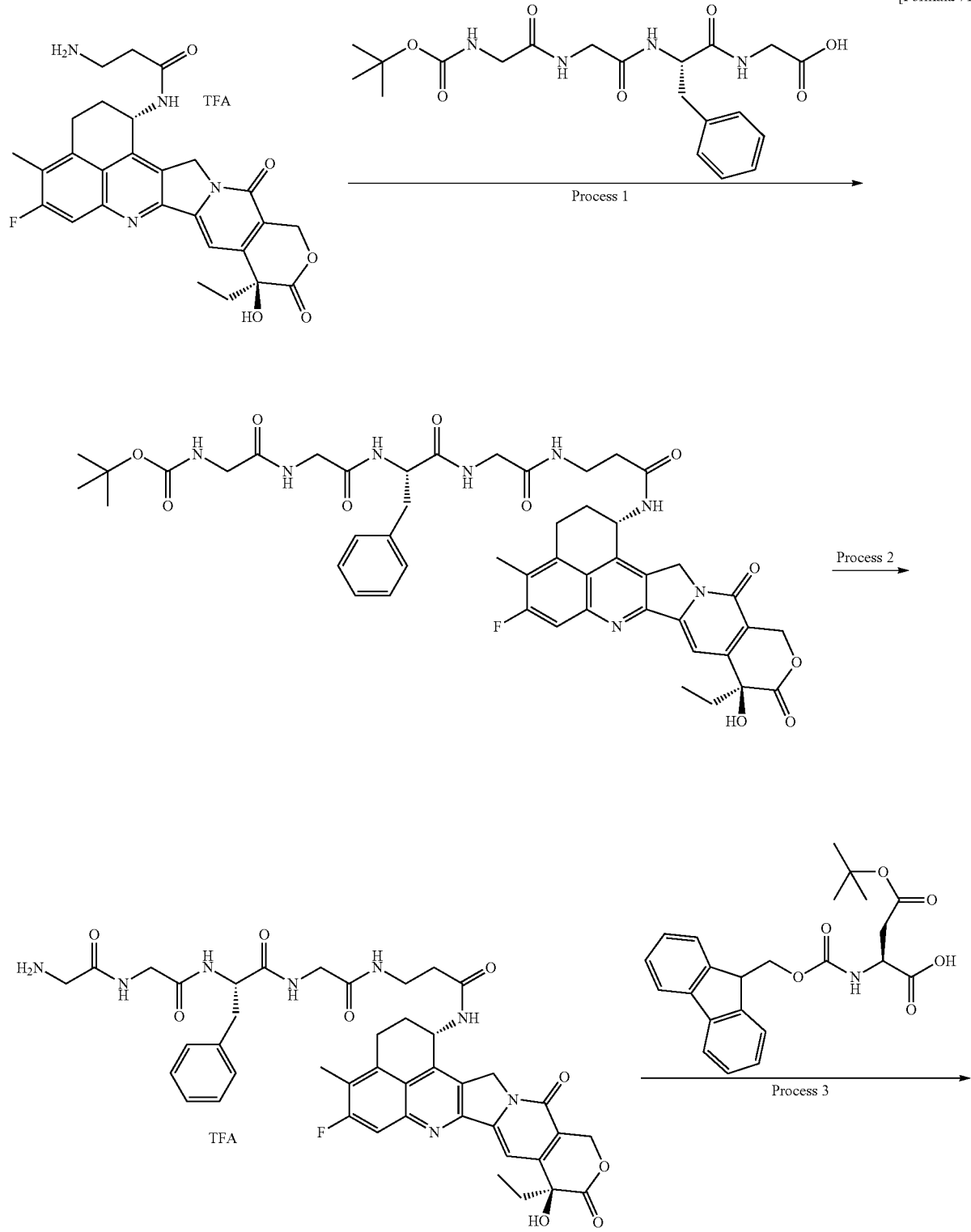

189 190
-continued
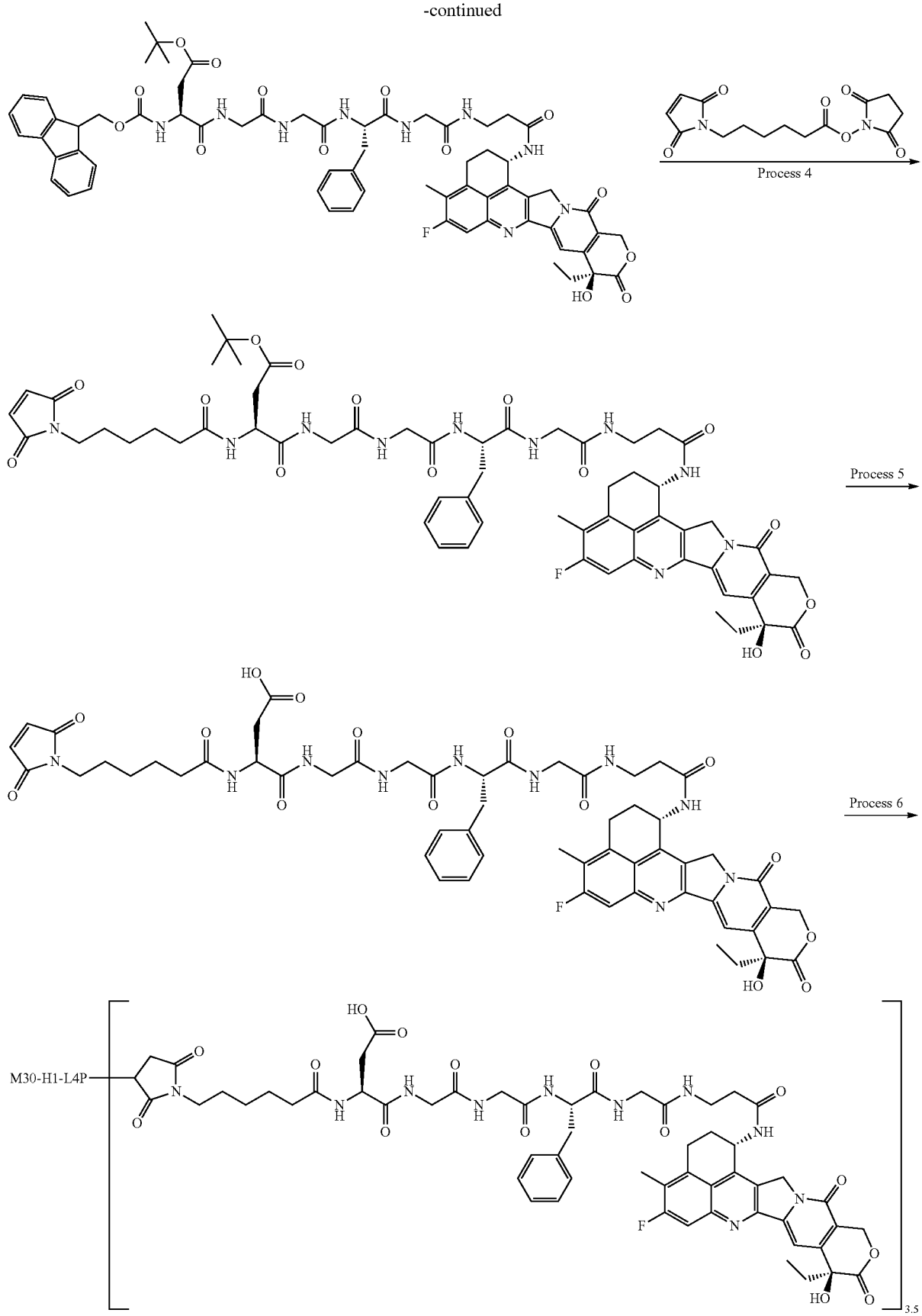

Process 1: N-(tert-butoxycarbonyl)glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (484 mg, 0.780 mmol) of Example 18 was reacted in the same manner as Process 1 of Example 2 to yield the titled compound as a pale yellow solid (626 mg, 87%).

$^1$H-NMR (400 MHz, 400 MHz, DMSO-$d_6$) δ: 0.87 (3H, t, J=7.4 Hz), 1.27-1.42 (9H, m), 1.77-1.93 (2H, m), 2.06-2.22 (2H, m), 2.36 (2H, t, J=7.2 Hz), 2.40 (3H, d, J=1.6 Hz), 2.44-2.54 (2H, m), 2.76 (1H, dd, J=14.5, 10.2 Hz), 3.02 (1H, dd, J=13.9, 4.5 Hz), 3.12-3.22 (2H, m), 3.52 (6H, d, J=6.3 Hz), 4.42-4.54 (1H, m), 5.19 (1H, d, J=19.2 Hz), 5.26 (1H, d, J=18.4 Hz), 5.42 (1H, dd, J=18.4, 16.4 Hz), 5.57 (1H, dt, J=8.7, 4.4 Hz), 6.53 (1H, s), 6.98 (1H, t, J=5.9 Hz), 7.14-7.28 (5H, m), 7.31 (1H, s), 7.77-7.84 (1H, m), 7.91 (1H, t, J=5.5 Hz), 8.16 (1H, d, J=7.8 Hz), 8.27 (1H, t, J=5.1 Hz), 8.52 (1H, d, J=9.0 Hz).

Process 2: Glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolidino[1,2-b]quinolin-1-yl]-β-alanineamide trifluoroacetate The compound (624 mg, 0.675 mmol) obtained in Process 1 above was reacted in the same manner as Process 2 of Example 2 to yield the titled compound as a yellow solid (626 mg, 92%).

$^1$H-NMR (400 MHz, 400 MHz, DMSO-$d_6$) δ: 0.87 (3H, t, J=7.4 Hz), 1.86 (2H, tt, J=14.5, 7.2 Hz), 2.07-2.22 (2H, m), 2.36 (2H, t, J=7.2 Hz), 2.40 (3H, s), 2.44-2.54 (2H, m), 2.75 (1H, dd, J=13.7, 9.8 Hz), 3.04 (1H, dd, J=13.7, 4.3 Hz), 3.12-3.22 (2H, m), 3.58 (2H, d, J=4.7 Hz), 3.69 (3H, td, J=11.2, 5.7 Hz), 3.87 (1H, dd, J=17.0, 5.7 Hz), 4.54 (1H, m, J=17.8, 4.5 Hz), 5.19 (1H, d, J=19.2 Hz), 5.26 (1H, d, J=18.8 Hz), 5.43 (2H, s), 5.51-5.60 (1H, m), 6.55 (1H, s), 7.14-7.29 (5H, m), 7.32 (1H, s), 7.81 (1H, d, J=10.9 Hz), 7.88 (1H, t, J=5.7 Hz), 7.97 (3H, br.s.), 8.29-8.38 (2H, m), 8.50 (1H, t, J=5.7 Hz), 8.55 (1H, d, J=8.6 Hz).

MS (ESI) m/z: 825 (M+H)$^+$

Process 3: tert-Butyl (9S,18S)-9-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-18-{[(9H-fluoren-9-ylmethoxy)carbonyl]amino}-1,5,8,11,14,17-hexaoxo-4,7,10,13,16-pentaazaicosan-20-noate The compound (150 mg, 0.182 mmol) obtained in Process 2 above was reacted in the same manner as Process 1 of Example 2 by using (2S)-4-tert-butoxy-2-{[(9H-fluoren-9-ylmethoxy)carbonyl]amino}-4-oxobutanoic acid (90.0 mg, 0.219 mmol) instead of N-(tert-butoxycarbonyl)glycylglycyl-L-phenylalanylglycine to yield the titled compound as a pale yellow solid (84.0 mg, 38%).

$^1$H-NMR (400 MHz, DMSO-$d_6$) δ: 0.82-0.91 (3H, m), 1.35 (9H, s), 1.85 (2H, tt, J=14.0, 7.3 Hz), 2.06-2.21 (2H, m), 2.39 (3H, s), 2.31-2.53 (5H, m), 2.64-2.73 (1H, m), 2.78 (1H, dd, J=13.7, 9.8 Hz), 3.02 (1H, dd, J=13.9, 4.5 Hz), 3.11-3.20 (2H, m), 3.55-3.80 (6H, m), 4.17-4.35 (3H, m), 4.35-4.43 (1H, m), 4.44-4.51 (1H, m), 5.18 (1H, d, J=19.2 Hz), 5.24 (1H, d, J=19.2 Hz), 5.41 (2H, dd, J=18.8, 16.4 Hz), 5.51-5.60 (1H, m), 6.53 (1H, s), 7.13-7.20 (1H, m), 7.20-7.27 (4H, m), 7.27-7.34 (3H, m), 7.39 (2H, t, J=7.2 Hz), 7.65-7.73 (3H, m), 7.79 (2H, d, J=10.6 Hz), 7.87 (2H, d, J=7.4 Hz), 8.00 (1H, t, J=6.1 Hz), 8.08-8.20 (2H, m), 8.22-8.31 (1H, m), 8.52 (1H, d, J=8.2 Hz).

MS (ESI) m/z: 1218 (M+H)$^+$

Process 4: tert-Butyl (9S,18S)-9-benzyl-18-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,5,8,11,14,17-hexaoxo-4,7,10,13,16-pentaazaicosan-20-noate The compound (81.0 mg, 0.0665 mmol) obtained in Process 3 above was reacted in the same manner as Process 4 of Example 2 to yield the titled compound (56.0 mg, 71%).

MS (ESI) m/z: 1189.5 (M+H)$^+$

Process 5: N-[6-(2,5-dioxo-2,5-dihydro-1H-pyrrol-1-yl)hexanoyl]-L-α-aspartylglycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (52.0 mg, 0.0437 mmol) obtained in Process 4 above was reacted in the same manner as Process 2 of Example 1 to yield the titled compound as a pale yellow solid (35.0 mg, 71%).

$^1$H-NMR (400 MHz, DMSO-$d_6$) δ: 0.87 (3H, t, J=7.4 Hz), 1.12-1.22 (2H, m), 1.39-1.51 (4H, m), 1.78-1.92 (2H, m), 2.04-2.19 (2H, m), 2.08 (2H, t, J=7.2 Hz), 2.40 (3H, s), 2.31-2.46 (6H, m), 2.61-2.72 (1H, m), 2.73-2.85 (1H, m), 3.02 (1H, dd, J=14.1, 4.7 Hz), 3.17 (2H, m, J=5.5 Hz), 3.26-3.43 (2H, m), 3.55-3.77 (6H, m), 4.42-4.50 (1H, m), 4.51-4.58 (1H, m), 5.19 (1H, d, J=18.4 Hz), 5.26 (1H, d, J=18.4 Hz), 5.42 (2H, brs), 5.52-5.60 (1H, m), 6.53 (1H, s), 6.99 (2H, s), 7.12-7.27 (5H, m), 7.31 (1H, s), 7.80 (2H, d, J=10.9 Hz), 7.93-8.02 (1H, m), 8.03-8.17 (3H, m), 8.22-8.31 (1H, m), 8.53 (1H, d, J=8.6 Hz).

MS (ESI) m/z: 1133 (M+H)$^+$

Process 6: Antibody-Drug Conjugate (17)

By using the M30-H1-L4P antibody produced in Reference Example 2 and the compound obtained in Process 5 above, the titled antibody-drug conjugate was obtained in the same manner as Process 1 of Example 4.

Antibody concentration: 9.56 mg/mL, antibody yield: 6.7 mg (54%), and average number of conjugated drug molecules (n) per antibody molecule: 3.5.

Example 20: Antibody-Drug Conjugate (18)
[Formula 72]
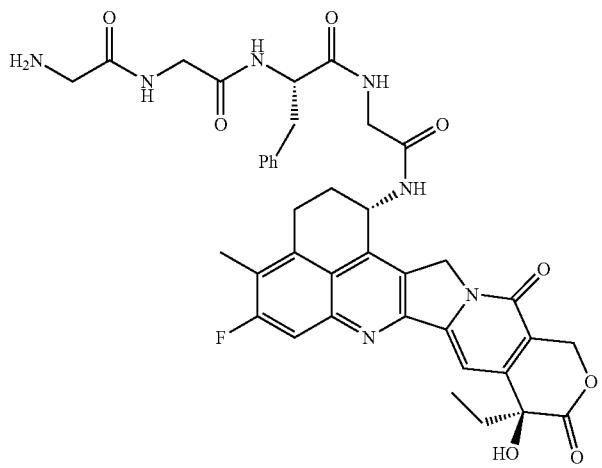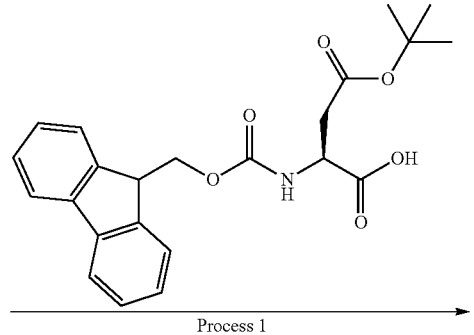
Process 1
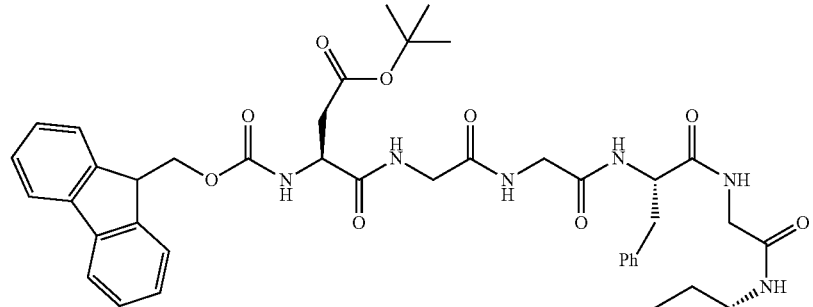
Process 2
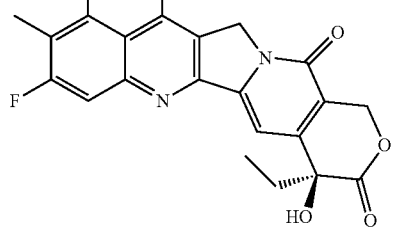
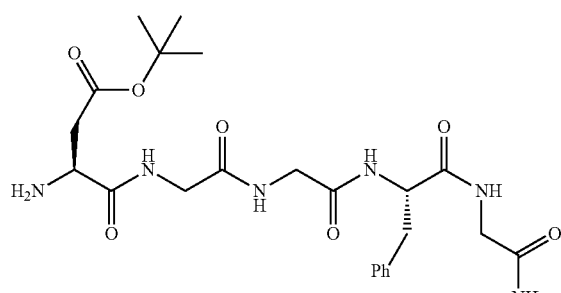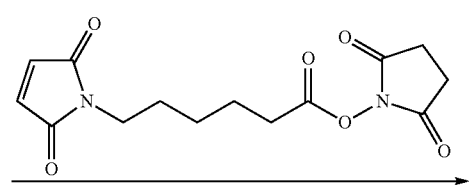
Process 3
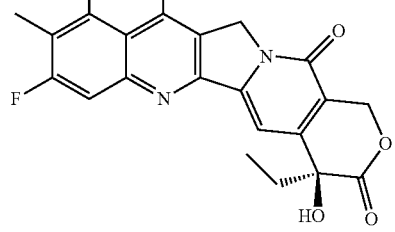

-continued
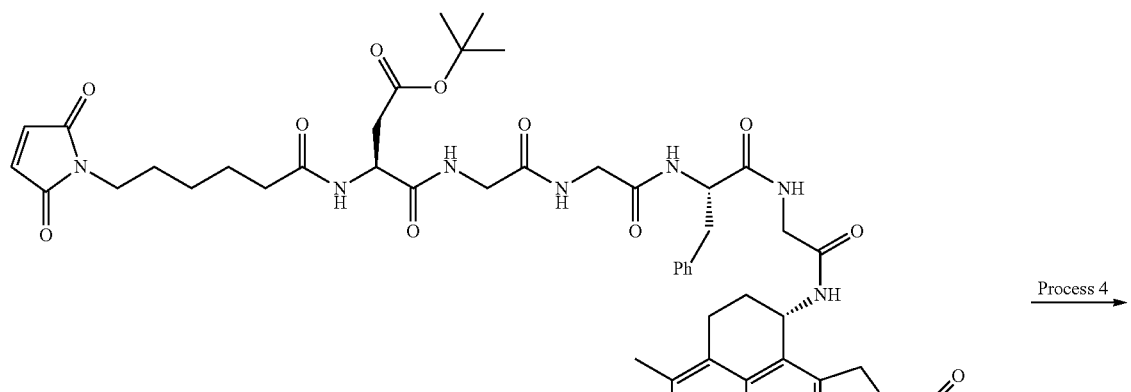
Process 4 →
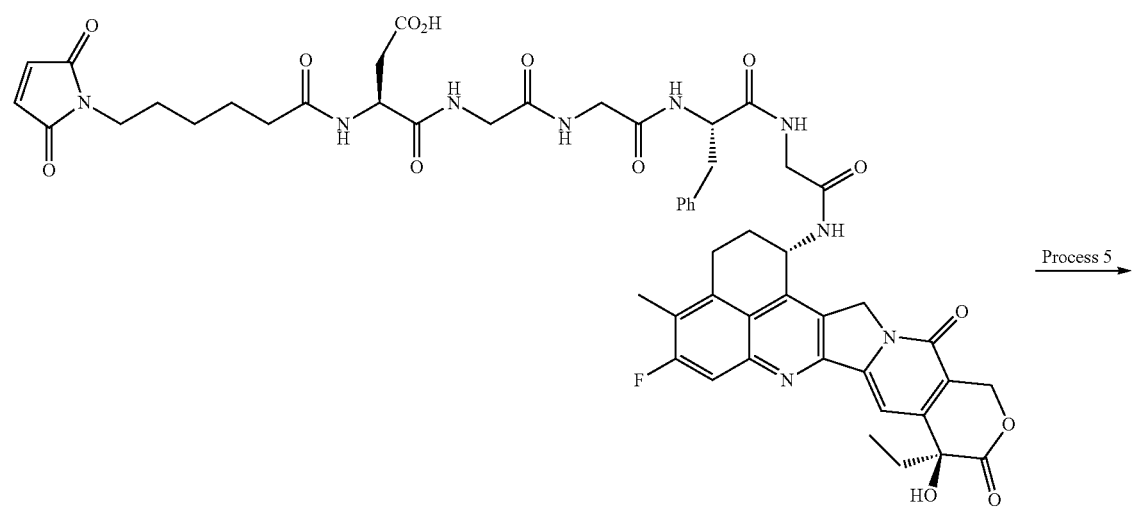
Process 5 →
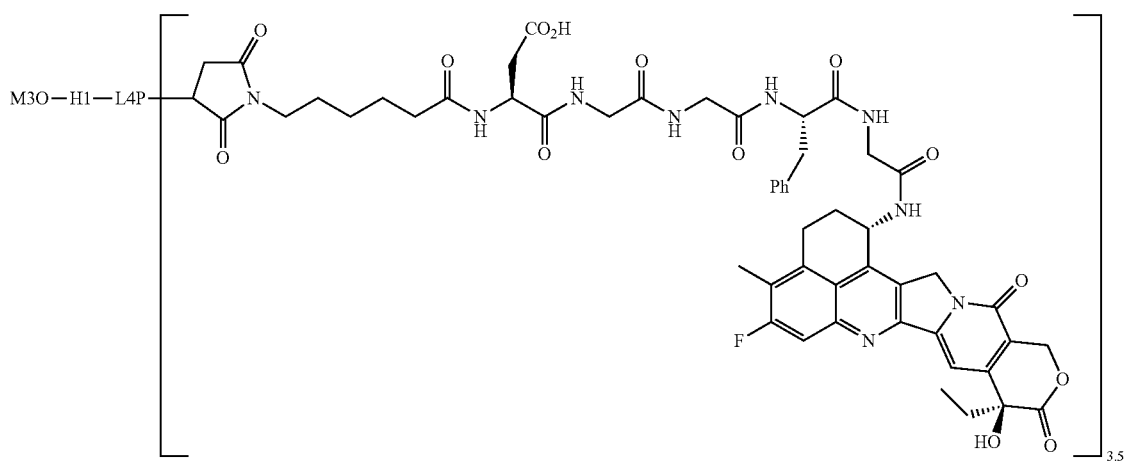

Process 1: tert-Butyl (5S,14S)-5-benzyl-1-{[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-14-{[(9H-fluoren-9-ylmethoxy)carbonyl]amino}-1,4,7,10,13-pentaoxo-3,6,9,12-tetraazahexadecan-16-oate Under ice cooling, to an N,N-dimethylformamide (10.0 mL) solution of glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (a free form of the pharmaceutical compound described in WO97/46260; 0.250 g, 0.332 mmol), N-hydroxysuccinimide (57.2 mg, 0.497 mmol), and 4-tert-butyl N-[(9H-fluoren-9-ylmethoxy)carbonyl]-L-aspartate (0.205 g, 0.497 mmol), N,N'-dicyclohexylcarbodiimide (0.123 g, 0.497 mmol) was added and stirred at room temperature for 2 days. The solvent was removed under reduced pressure and the obtained residues were purified by silica gel column chromatography [chloroform to chloroform:methanol=9:1 (v/v)] to yield the titled compound as a pale yellow solid (0.278 g, 73%).

$^1$H-NMR (400 MHz, DMSO-$d_6$) δ: 0.86 (3H, t, J=7.1 Hz), 1.35 (9H, s), 1.79-1.90 (2H, m), 2.03-2.25 (2H, m), 2.40 (3H, s), 2.40-2.51 (2H, m), 2.64-2.82 (2H, m), 2.98 (1H, dd, J=13.7, 4.6 Hz), 3.16 (2H, brs), 3.55 (1H, dd, J=16.7, 5.7 Hz), 3.63-3.80 (4H, m), 4.16-4.34 (3H, m), 4.36-4.50 (2H, m), 5.23 (2H, s), 5.37 (1H, d, J=16.5 Hz), 5.43 (1H, d, J=16.5 Hz), 5.51-5.62 (1H, m), 6.52 (1H, s), 7.10-7.25 (5H, m), 7.26-7.33 (3H, m), 7.39 (2H, t, J=7.3 Hz), 7.65-7.72 (3H, m), 7.80 (1H, d, J=11.0 Hz), 7.86 (2H, d, J=7.3 Hz), 7.98 (1H, t, J=5.5 Hz), 8.07 (1H, d, J=7.8 Hz), 8.15 (1H, t, J=5.5 Hz), 8.31 (1H, t, J=5.5 Hz), 8.41 (1H, d, J=8.7 Hz).

MS (ESI) m/z: 1147 (M+H)$^+$

Process 2: tert-Butyl (5S,14S)-14-amino-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate To an N,N-dimethylformamide (2.00 mL) solution of the compound (0.279 g, 0.242 mmol) obtained in Process 1 above, piperidine (0.240 mL, 2.42 mmol) was added and stirred at room temperature for 1 hour. The solvent was removed under reduced pressure and the obtained residues were purified by silica gel column chromatography [chloroform to chloroform:methanol=2:1 (v/v)] to yield the titled compound as a pale yellow solid (0.265 g, quantitative).

$^1$H-NMR (400 MHz, DMSO-$d_6$) δ: 0.88 (3H, t, J=7.2 Hz), 1.39 (9H, s), 1.81-1.94 (1H, m), 2.07-2.28 (2H, m), 2.37 (1H, dd, J=15.8, 8.0 Hz), 2.43 (3H, s), 2.60 (1H, dd, J=15.8, 4.9 Hz), 2.75-2.82 (1H, m), 3.00 (1H, dd, J=13.9, 4.5 Hz), 3.16-3.25 (2H, m), 3.50-3.61 (2H, m), 3.65-3.81 (5H, m), 4.40-4.51 (1H, m), 5.27 (2H, dd, J=24.1, 19.0 Hz), 5.43 (2H, dd, J=21.3, 16.2 Hz), 5.56-5.65 (1H, m), 6.55 (1H, s), 7.15-7.28 (5H, m), 7.33 (1H, s), 7.83 (1H, d, J=11.0 Hz), 8.04 (1H, t, J=5.7 Hz), 8.09 (1H, d, J=8.2 Hz), 8.26-8.39 (2H, m), 8.44 (1H, d, J=8.2 Hz).

Process 3: tert-Butyl (5S,14S)-5-benzyl-14-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate To an N,N-dimethylformamide (2.00 mL) solution of the compound (0.100 g, 0.108 mmol) obtained in Process 2 above, N-succinimidyl 6-maleimide hexanoate (40.0 mg, 0.130 mmol) was added and stirred at room temperature for 2 days. The solvent was removed under reduced pressure and the obtained residues were purified by silica gel column chromatography [chloroform to chloroform:methanol=9:1 (v/v)] to yield the titled compound as a pale yellow solid (80.0 mg, 66%).

$^1$H-NMR (400 MHz, DMSO-$d_6$) δ: 0.88 (3H, t, J=7.2 Hz), 1.13-1.23 (2H, m), 1.37 (9H, s), 1.42-1.54 (4H, m), 1.80-1.96 (2H, m), 2.08-2.25 (4H, m), 2.35-3.76 (15H, m), 2.43 (3H, s), 4.39-4.49 (1H, m), 4.55-4.67 (1H, m), 5.21-5.34 (2H, m), 5.43 (2H, dd, J=21.1, 16.4 Hz), 5.56-5.64 (1H, m), 6.55 (1H, s), 7.01 (2H, d, J=0.8 Hz), 7.16-7.26 (5H, m), 7.33 (1H, s), 7.83 (1H, d, J=11.3 Hz), 8.04-8.18 (3H, m), 8.30-8.37 (1H, m), 8.43 (1H, d, J=8.6 Hz).

MS (ESI) m/z: 1118 (M+H)$^+$

Process 4: N-[6-(2,5-dioxo-2,5-dihydro-1H-pyrrol-1-yl)hexanoyl]-L-α-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Under ice cooling, to the compound (70.0 mg, 62.6 mol) obtained in Process 3 above, trifluoroacetic acid (4.00 mL) was added and stirred at room temperature for 1 hour. The solvent was removed under reduced pressure to yield the titled compound as a pale yellow solid (55.0 mg, 83%).

$^1$H-NMR (400 MHz, DMSO-$d_6$) δ: 0.88 (3H, t, J=7.4 Hz), 1.14-1.24 (2H, m), 1.41-1.53 (4H, m), 1.79-1.95 (2H, m), 2.08-2.28 (4H, m), 2.37-2.60 (2H, m), 2.42 (3H, s), 2.63-2.82 (2H, m), 2.99 (1H, dd, J=14.1, 5.1 Hz), 3.12-3.25 (2H, m), 3.29-3.44 (1H, m), 3.52-3.80 (6H, m), 4.38-4.48 (1H, m), 4.56 (1H, dd, J=13.7, 7.4 Hz), 5.27 (2H, dd, J=24.3, 18.8 Hz), 5.43 (2H, dd, J=21.5, 16.4 Hz), 5.57-5.62 (1H, m), 6.55 (1H, s), 7.01 (2H, s), 7.15-7.26 (5H, m), 7.33 (1H, s), 7.82 (1H, d, J=11.0 Hz), 7.98 (1H, brs), 8.08 (1H, d, J=6.7 Hz), 8.15 (1H, d, J=7.8 Hz), 8.34 (1H, brs), 8.44 (1H, d, J=8.6 Hz), 12.26 (1H, brs).

MS (ESI) m/z: 1062 (M+H)$^+$

Process 5: Antibody-Drug Conjugate (18)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (8.0 mL) was collected into a 15 mL tube and charged with an aqueous solution of 10 mM TCEP (Tokyo Chemical Industry Co., Ltd.) (0.124 mL; 2.3 equivalents per antibody molecule) and an aqueous solution of 1 M dipotassium hydrogen phosphate (Nacalai Tesque, Inc.; 0.400 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.249 mL; 4.6 equivalents per antibody molecule) containing 10 mM of the compound obtained in Process 4 above was added thereto and incubated at 22° C. for 40 minutes for conjugating the drug linker to the antibody. Next, an aqueous solution (0.050 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 17.5 mL of a solution containing the titled antibody-drug conjugate.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 3.56 mg/mL, antibody yield: 62 mg (77%), and average number of conjugated drug molecules (n) per antibody molecule: 3.5.

Example 21: Antibody-Drug Conjugate (19)

[Formula 73]

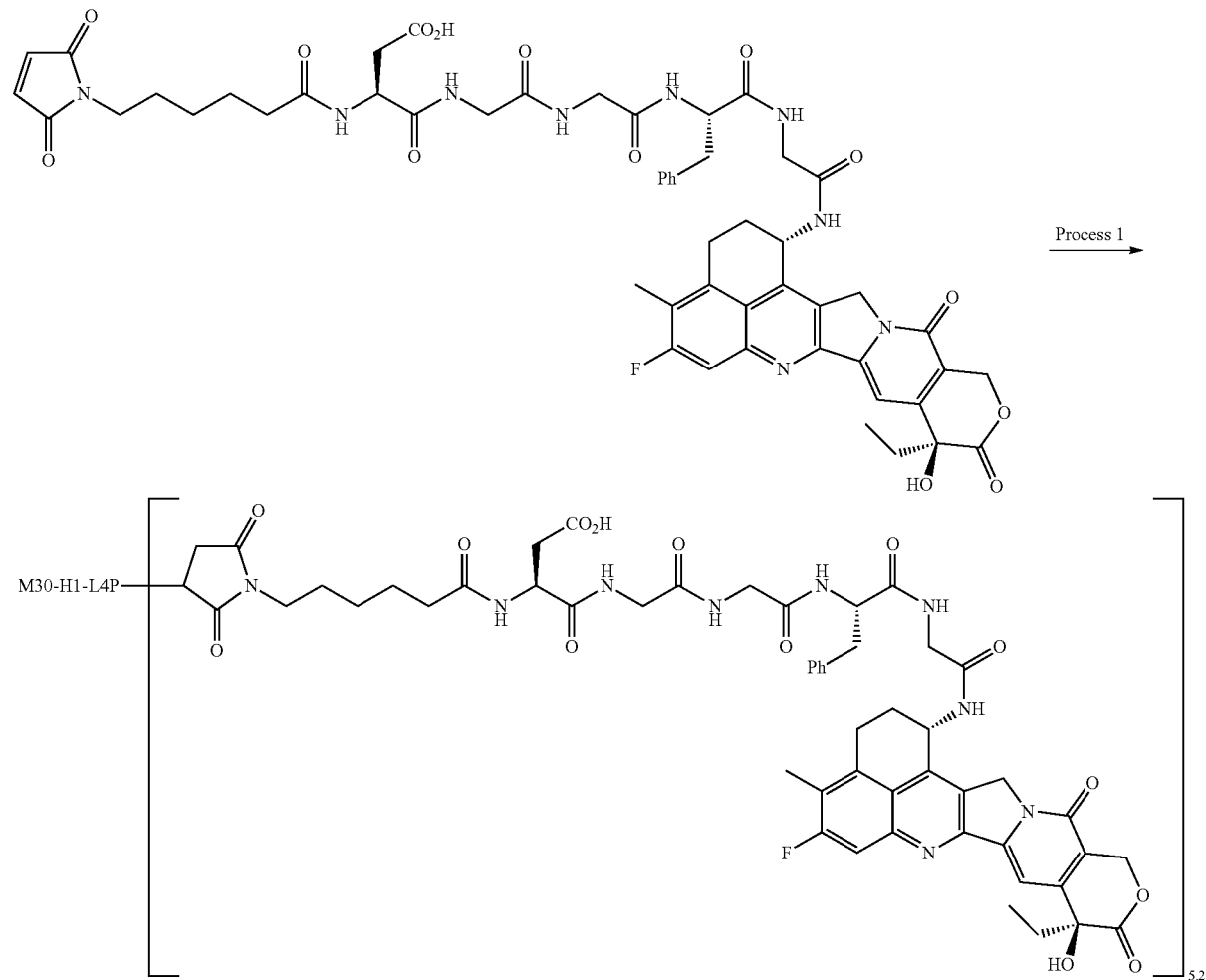

Process 1: Antibody-Drug Conjugate (19)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (8.0 mL) was collected into a 15 mL tube and charged with an aqueous solution of 10 mM TCEP (Tokyo Chemical Industry Co., Ltd.) (0.187 mL; 3.5 equivalents per antibody molecule) and an aqueous solution of 1 M dipotassium hydrogen phosphate (Nacalai Tesque, Inc.; 0.400 mL). After confirming that the solution had pH near 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.373 mL; 6.9 equivalents per antibody molecule) containing 10 mM of the compound obtained in Process 4 of Example 20 was added thereto and incubated at 22° C. for 40 minutes for conjugating the drug linker to the antibody. Next, an aqueous solution (0.075 mL; 13.8 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 16 mL of a solution containing the titled antibody-drug conjugate.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 3.66 mg/mL, antibody yield: 59 mg (74%), and average number of conjugated drug molecules (n) per antibody molecule: 5.2.

Example 22: Antibody-Drug Conjugate (20)

[Formula 74]

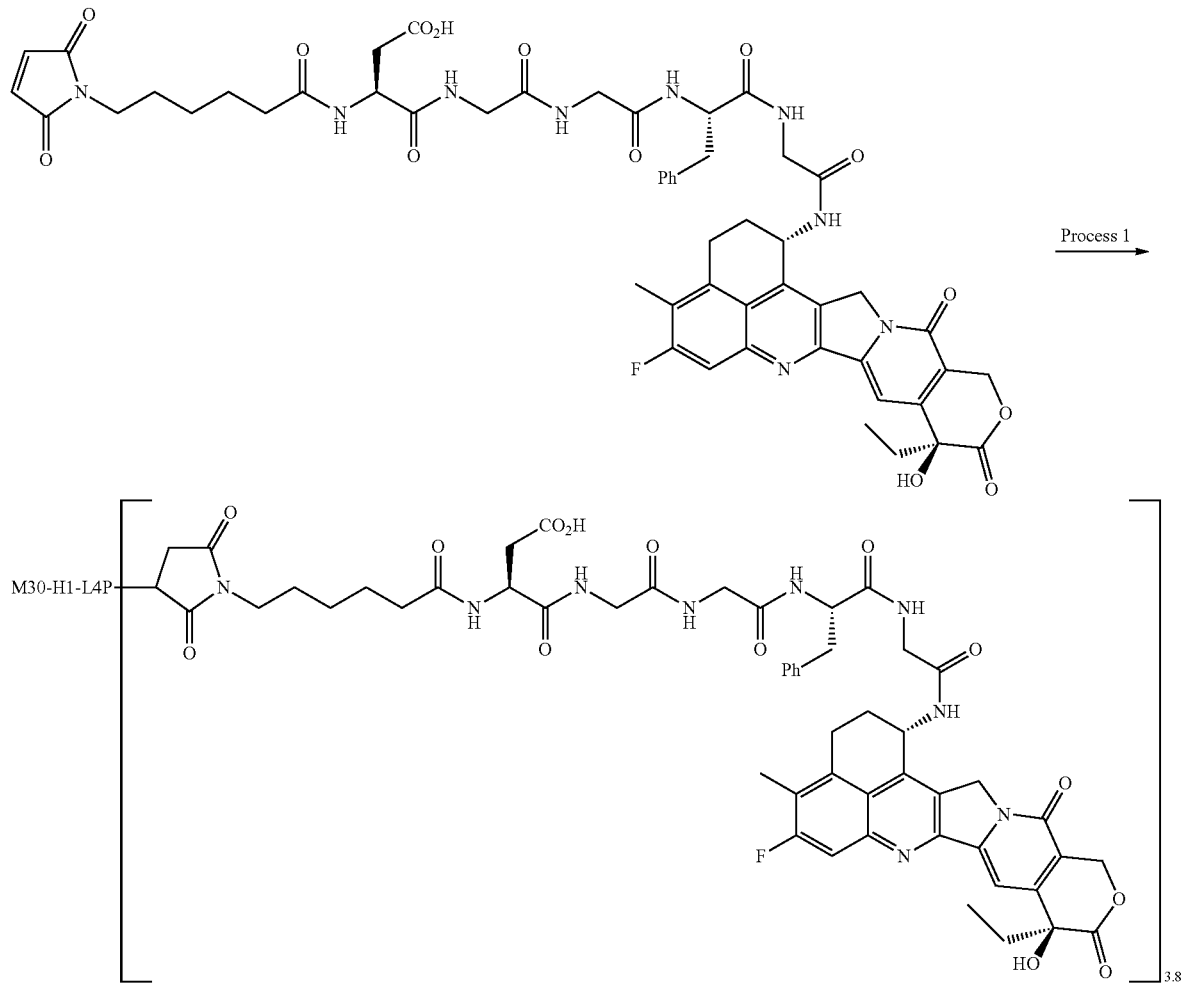

Process 1: Antibody-Drug Conjugate (20)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was added to a 1.5 mL polypropylene tube and charged with an aqueous solution of 10 mM TCEP (Tokyo Chemical Industry Co., Ltd.) (0.025 mL; 3.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.109 mL) and a dimethyl sulfoxide solution containing 10 mM of the compound obtained in Process 4 of Example 20 (0.039 mL; 4.6 equivalents per antibody molecule) to the above solution at room temperature, it was stirred by using a tube rotator (MTR-103, manufactured by AS ONE Corporation) at room temperature for 40 minutes for conjugating the drug linker to the antibody. Next, an aqueous solution of 100 mM NAC (Sigma-Aldrich Co. LLC; 0.008 mL) was added thereto and stirred at room temperature for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A described in Production method 1.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 11.14 mg/mL, antibody yield: 7.8 mg (62%), and average number of conjugated drug molecules (n) per antibody molecule: 3.8.

Example 23: Antibody-Drug Conjugate (21)

[Formula 75]

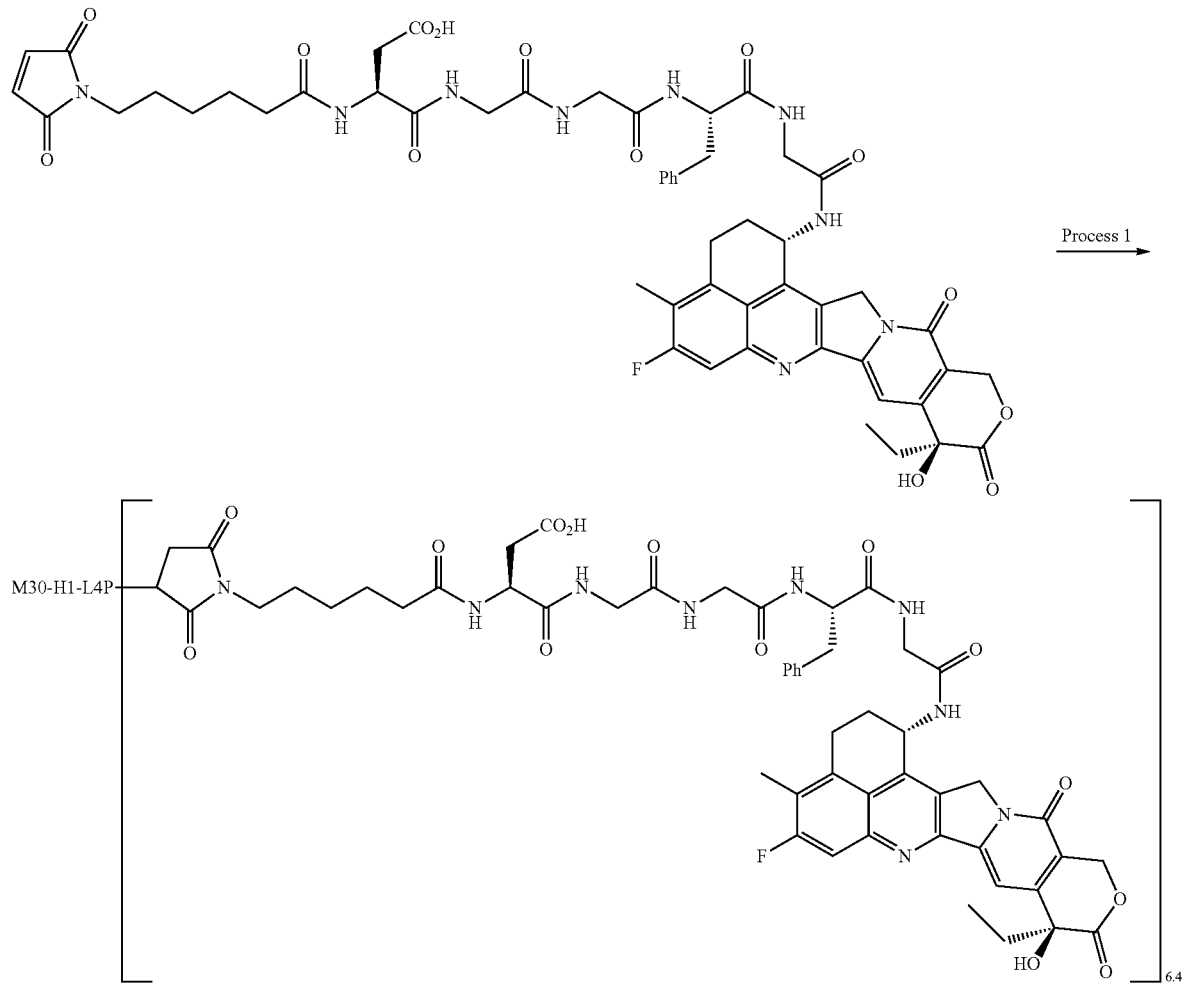

Process 1: Antibody-Drug Conjugate (21)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was added to a 1.5 mL polypropylene tube and charged with an aqueous solution of 10 mM TCEP (Tokyo Chemical Industry Co., Ltd.) (0.051 mL; 6.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.067 mL) and a dimethyl sulfoxide solution containing 10 mM of the compound obtained in Process 4 of Example 20 (0.085 mL; 10.0 equivalents per antibody molecule) to the above solution at room temperature, it was stirred by using a tube rotator (MTR-103, manufactured by AS ONE Corporation) at room temperature for 60 minutes for conjugating the drug linker to the antibody. Next, an aqueous solution (0.013 mL) of 100 mM NAC (Sigma-Aldrich Co. LLC) was added thereto and stirred at room temperature for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 0.88 mg/mL, antibody yield: 5.28 mg (42%), and average number of conjugated drug molecules (n) per antibody molecule: 6.4.

Example 24: Antibody-Drug Conjugate (22)

[Formula 76]

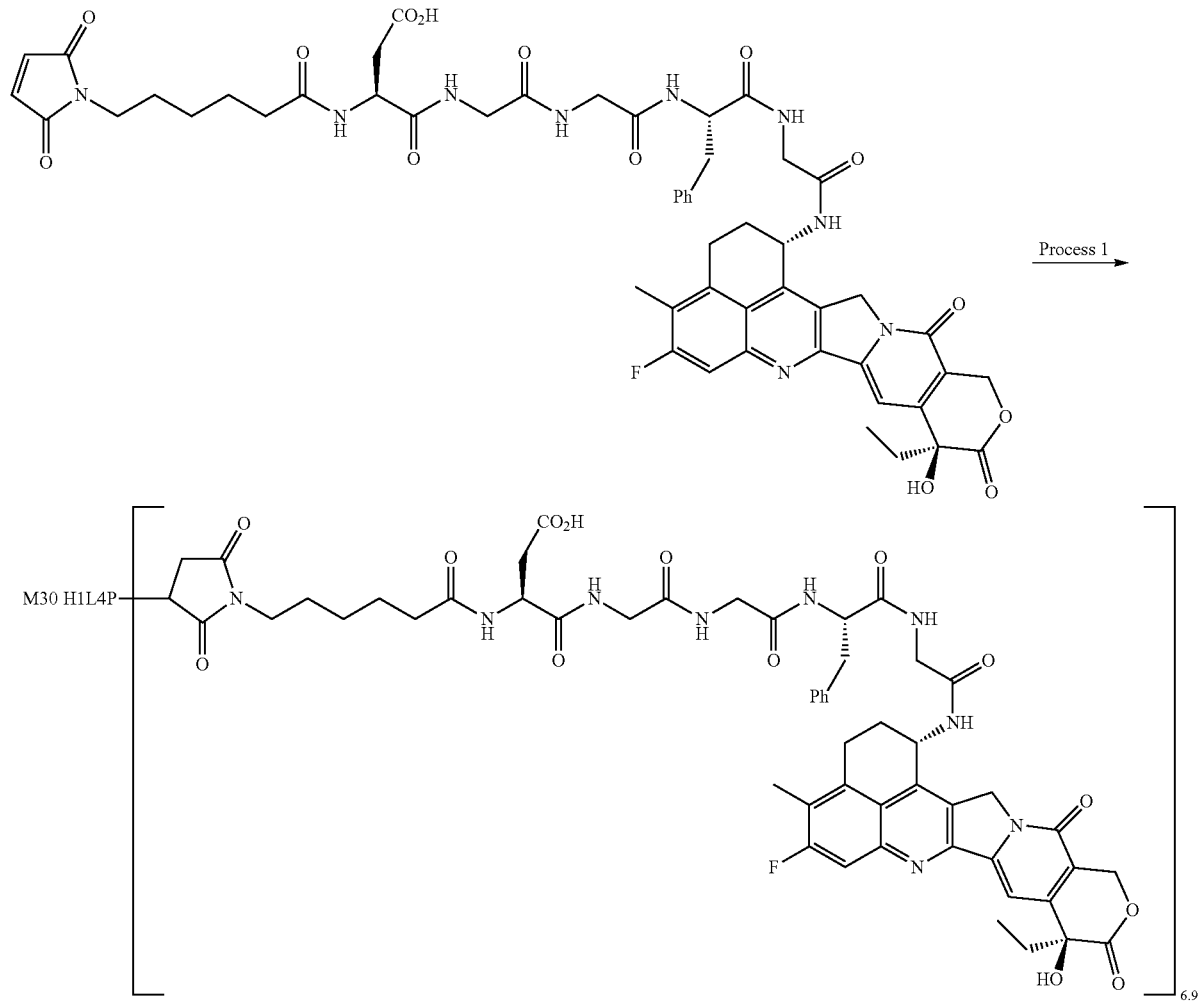

Process 1: Antibody-Drug Conjugate (22)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mL·mg$^{-1}$ cm$^{-1}$ was used) described in Production method 1. The solution (1.25 mL) was added to a 1.5 mL polypropylene tube and charged with an aqueous solution of 10 mM TCEP (Tokyo Chemical Industry Co., Ltd.) (0.051 mL; 6.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.025 mL) and a dimethyl sulfoxide solution (0.127 mL; 15.0 equivalents per antibody molecule) containing 10 mM of the compound obtained in Process 4 of Example 20 to the above solution at room temperature, it was stirred by using a tube rotator (MTR-103, manufactured by AS ONE Corporation) at room temperature for 60 minutes for conjugating the drug linker to the antibody. Next, an aqueous solution (0.019 mL) of 100 mM NAC (Sigma-Aldrich Co. LLC) was added thereto and stirred at room temperature for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A described in Production method 1.

Physicochemical characterization: By using the Common procedure E described in Production method 1 (as molar absorption coefficient, $\epsilon_{A,280}$=235300 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 1.19 mg/mL, antibody yield: 7.14 mg (57%), and average number of conjugated drug molecules (n) per antibody molecule: 6.9.

Example 25: Antibody-Drug Conjugate (23)

[Formula 77]

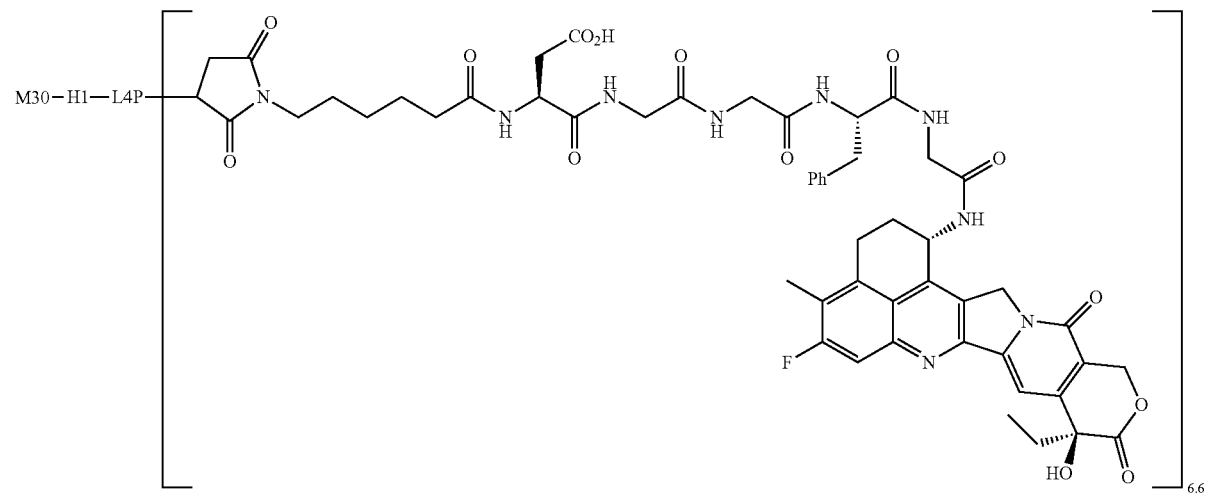

Almost the whole amounts of the antibody-drug conjugates of Examples 23 and 24 were mixed and the solution was concentrated by the Common procedure A described in Production method 1 to yield the titled antibody-drug conjugate.

Antibody concentration: 10.0 mg/mL, antibody yield: 9.07 mg, and average number of conjugated drug molecules (n) per antibody molecule: 6.6.

Example 26: Antibody-Drug Conjugate (24)

[Formula 78]

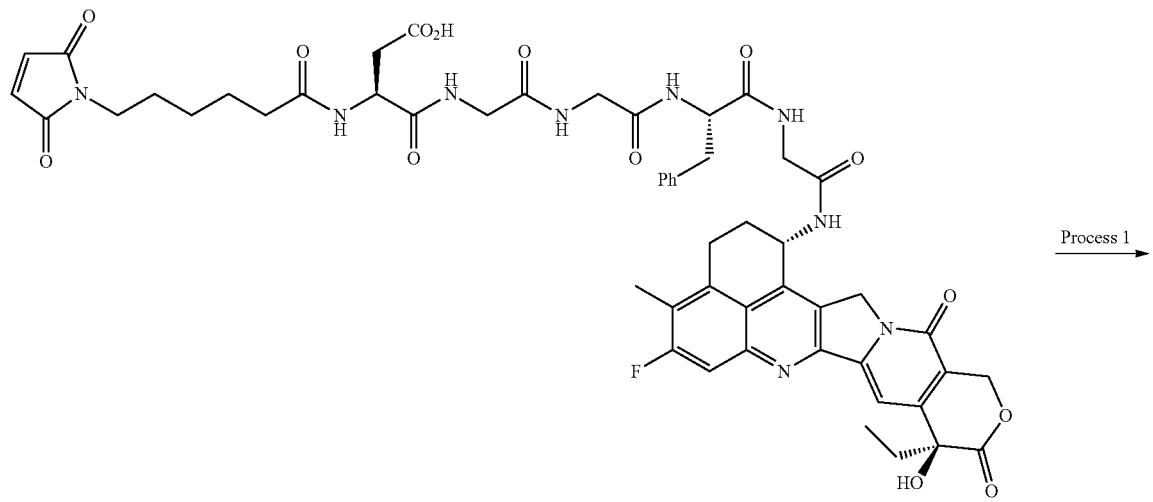

-continued

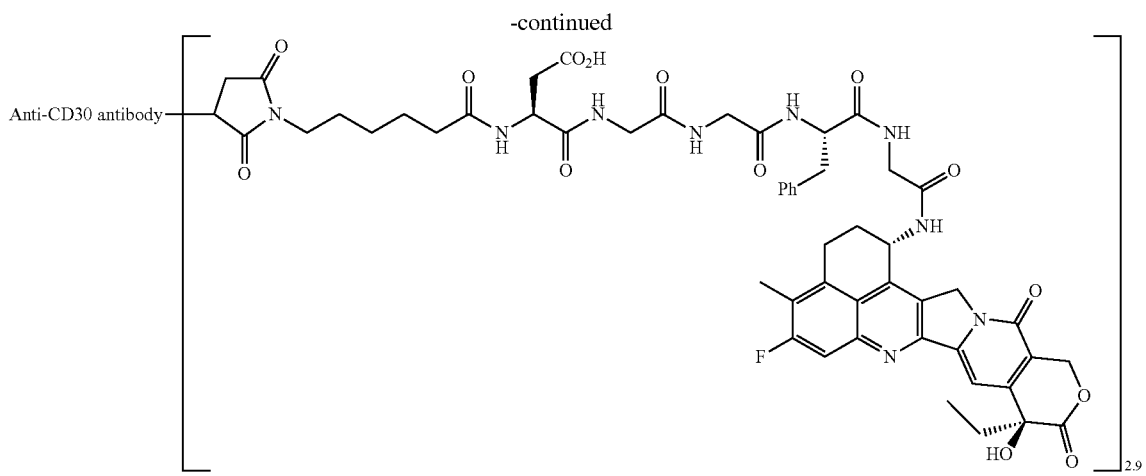

Process 1: Antibody-Drug Conjugate (24)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0148 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0297 mL; 4.6 equivalents per antibody molecule) containing 10 mM of the compound obtained in Process 4 of Example 20 was added thereto and incubated at 22° C. for 40 minutes for conjugating the drug linker to the antibody. Next, an aqueous solution (0.00593 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=270400 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 0.95 mg/mL, antibody yield: 5.70 mg (57%), and average number of conjugated drug molecules (n) per antibody molecule: 2.9.

Example 27: Antibody-Drug Conjugate (25)

[Formula 79]

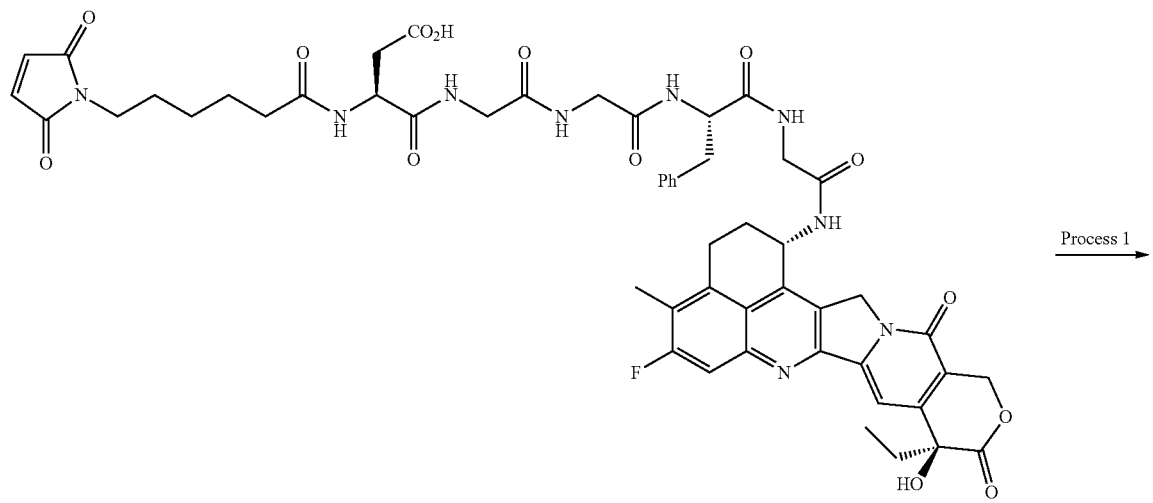

Process 1 →

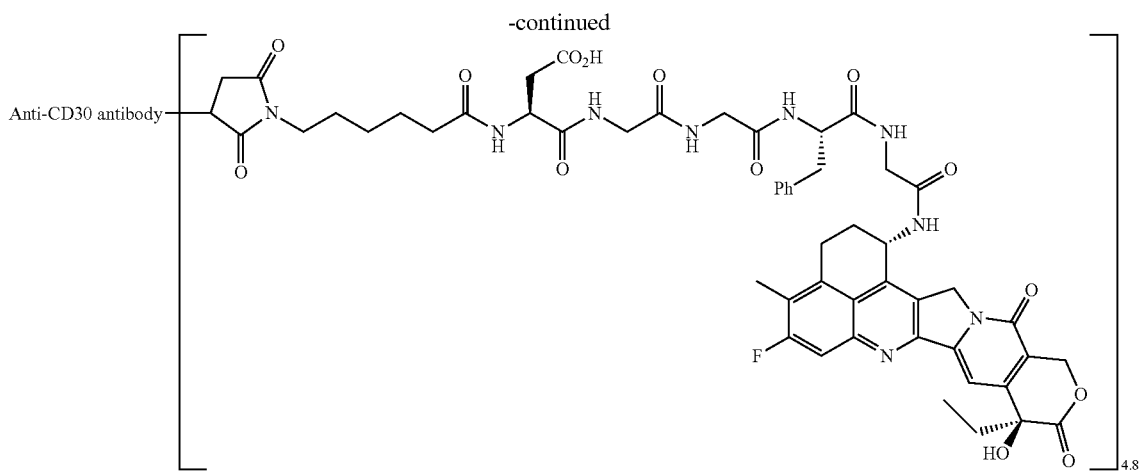

Process 1: Antibody-Drug Conjugate (25)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0593 mL; 9.2 equivalents per antibody molecule) containing 10 mM of the compound obtained in Process 4 of Example 20 was added thereto and incubated at 22° C. for 40 minutes for conjugating the drug linker to the antibody. Next, an aqueous solution (0.0119 mL; 18.4 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}=270400$ (estimated calculation value), $\epsilon_{A,370}=0$ (estimated calculation value), $\epsilon_{D,280}=5000$ (measured average value), and $\epsilon_{D,370}=19000$ (measured average value) were used), the following characteristic values were obtained.

Antibody concentration: 1.04 mg/mL, antibody yield: 6.24 mg (62%), and average number of conjugated drug molecules (n) per antibody molecule: 4.8.

Example 28: Antibody-Drug Conjugate (26)

[Formula 80]

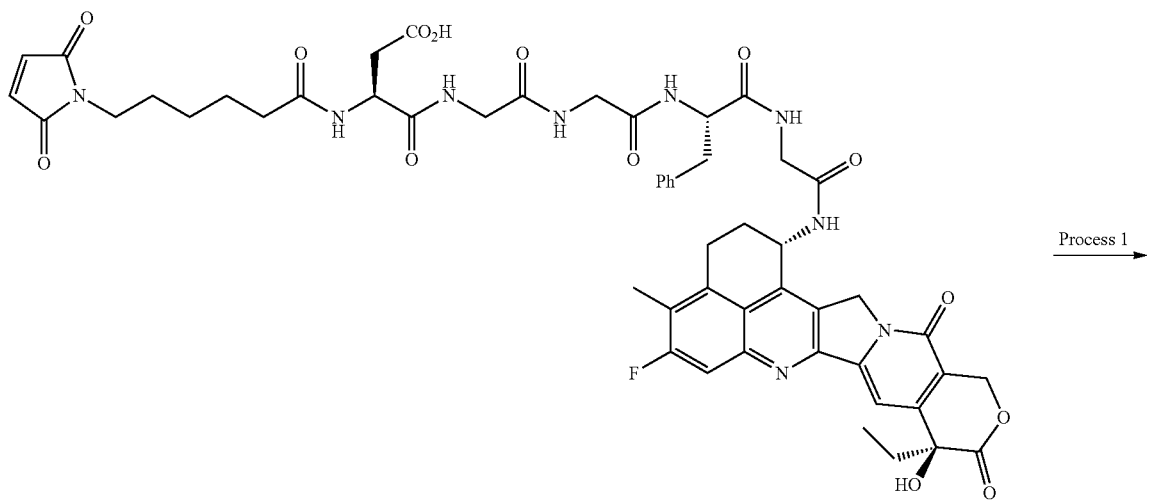

Process 1 →

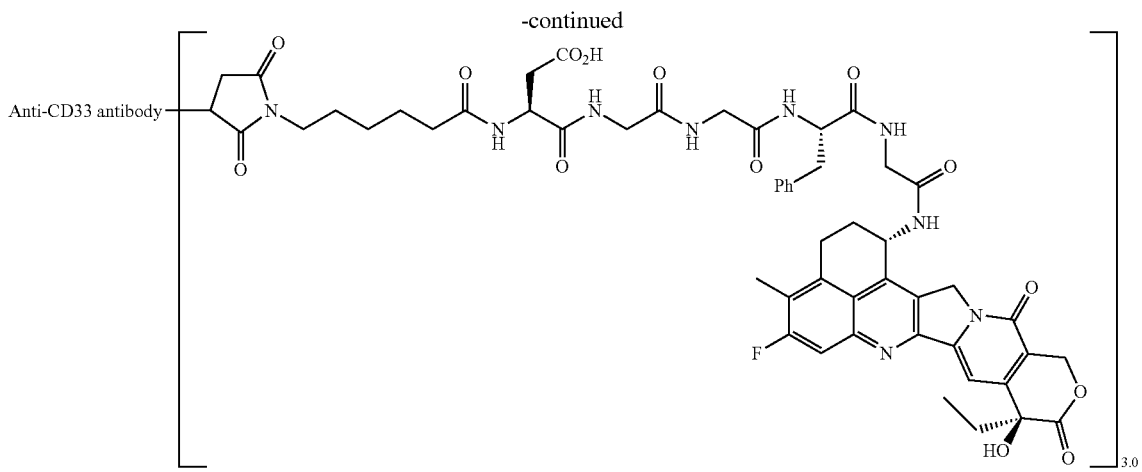

-continued

Process 1: Antibody-Drug Conjugate (26)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0148 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0297 mL; 4.6 equivalents per antibody molecule) containing 10 mM of the compound obtained in Process 4 of Example 20 was added thereto and incubated at 22° C. for 40 minutes for conjugating the drug linker to the antibody. Next, an aqueous solution (0.00593 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}=256400$ (estimated calculation value), $\epsilon_{A,370}=0$ (estimated calculation value), $\epsilon_{D,280}=5000$ (measured average value), and $\epsilon_{D,370}=19000$ (measured average value) were used), the following characteristics values were obtained.

Antibody concentration: 0.96 mg/mL, antibody yield: 5.76 mg (58%), and average number of conjugated drug molecules (n) per antibody molecule: 3.0.

Example 29: Antibody-Drug Conjugate (27)

[Formula 81]

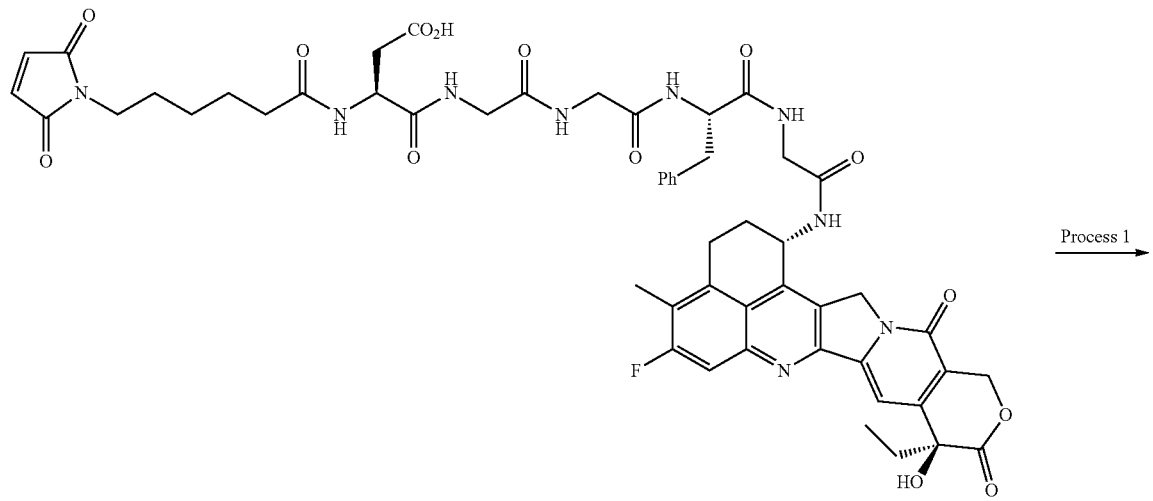

Process 1 →

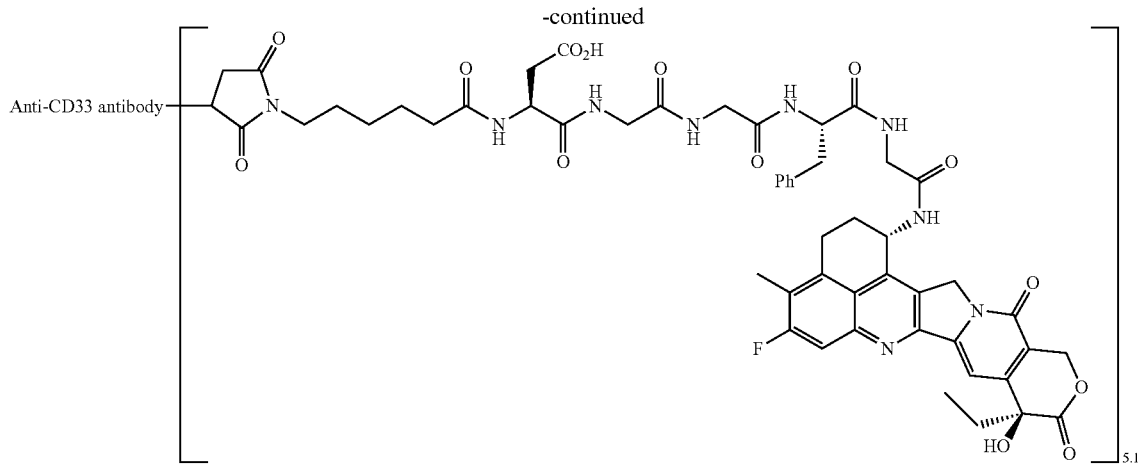

Process 1: Antibody-Drug Conjugate (27)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0593 mL; 9.2 equivalents per antibody molecule) containing 10 mM of the compound obtained in Process 4 of Example 20 was added thereto and incubated at 22° C. for 40 minutes for conjugating the drug linker to the antibody. Next, an aqueous solution (0.0119 mL; 18.4 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=256400 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 0.95 mg/mL, antibody yield: 5.70 mg (57%), and average number of conjugated drug molecules (n) per antibody molecule: 5.1.

Example 30: Antibody-Drug Conjugate (28)

[Formula 82]

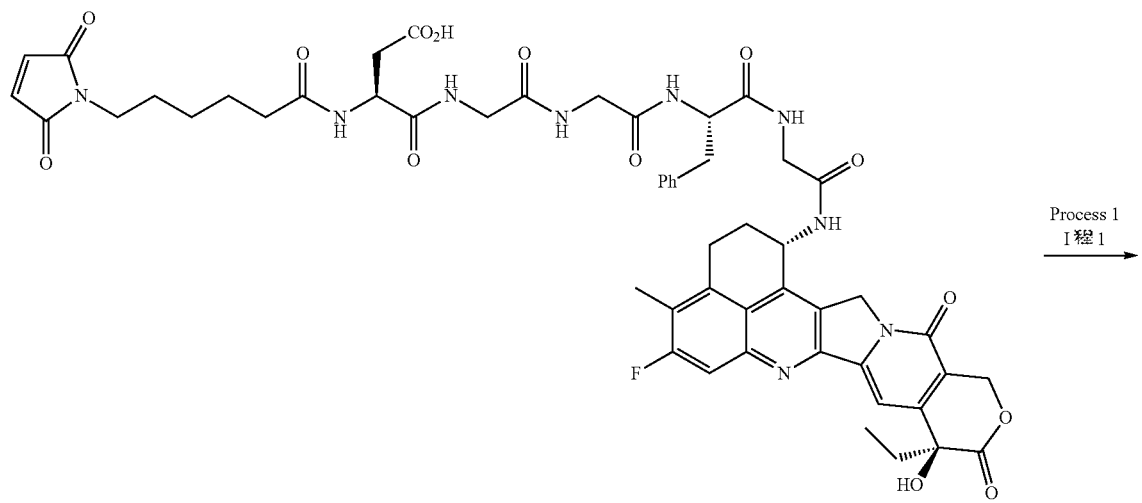

Process 1
I 程 1

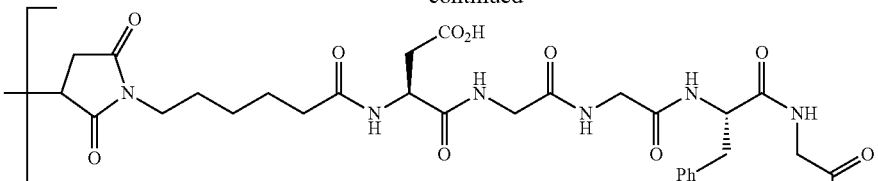
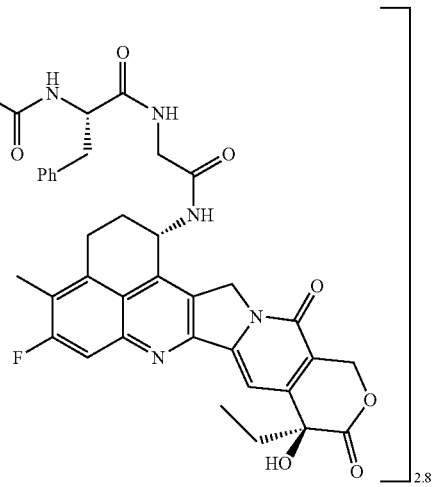

Process 1: Antibody-Drug Conjugate (28)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0148 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0297 mL; 4.6 equivalents per antibody molecule) containing 10 mM of the compound obtained in Process 4 of Example 20 was added thereto and incubated at 22° C. for 40 minutes for conjugating the drug linker to the antibody. Next, an aqueous solution (0.00593 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}=262400$ (estimated calculation value), $\epsilon_{A,370}=0$ (estimated calculation value), $\epsilon_{D,280}=5000$ (measured average value), and $\epsilon_{D,370}=19000$ (measured average value) were used), the following characteristics values were obtained.

Antibody concentration: 1.01 mg/mL, antibody yield: 6.06 mg (61%), and average number of conjugated drug molecules (n) per antibody molecule: 2.8.

Example 31: Antibody-Drug Conjugate (29)

[Formula 83]

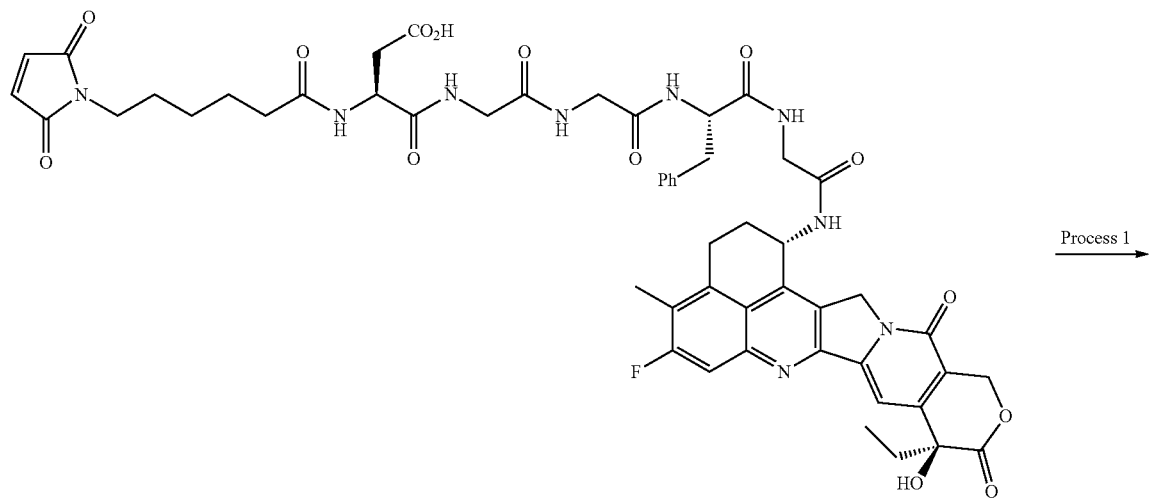

Process 1

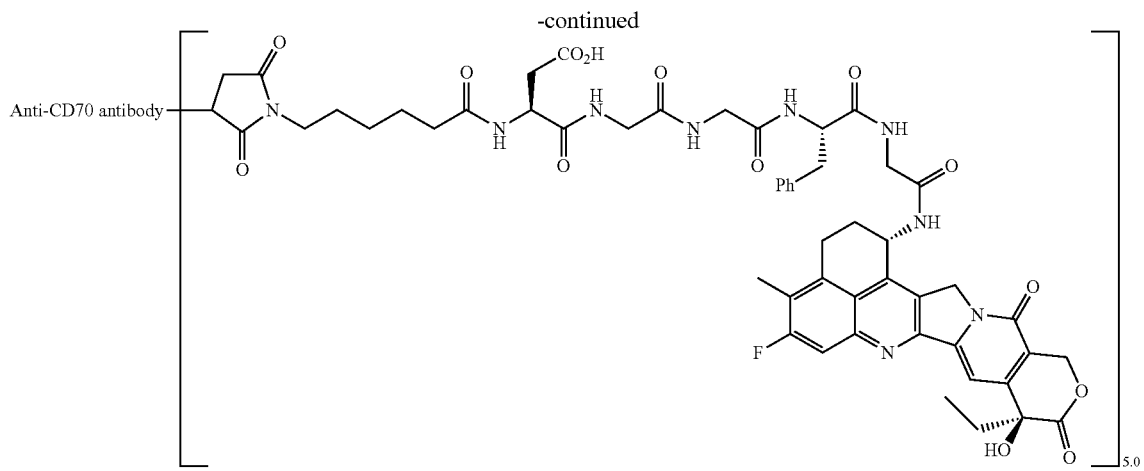

Process 1: Antibody-Drug Conjugate (29)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 mLmg$^{-1}$ cm$^{-1}$ was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0593 mL; 9.2 equivalents per antibody molecule) containing 10 mM of the compound obtained in Process 4 of Example 20 was added thereto and incubated at 22° C. for 40 minutes for conjugating the drug linker to the antibody. Next, an aqueous solution (0.0119 mL; 18.4 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=262400 (estimated calculation value), $\epsilon_{A,370}$=0 (estimated calculation value), $\epsilon_{D,280}$=5000 (measured average value), and $\epsilon_{D,370}$=19000 (measured average value) were used), the following characteristic values were obtained.

Antibody concentration: 1.18 mg/mL, antibody yield: 7.08 mg (71%), and average number of conjugated drug molecules (n) per antibody molecule: 5.0.

Example 32: Antibody-Drug Conjugate (30)

[Formula 84]

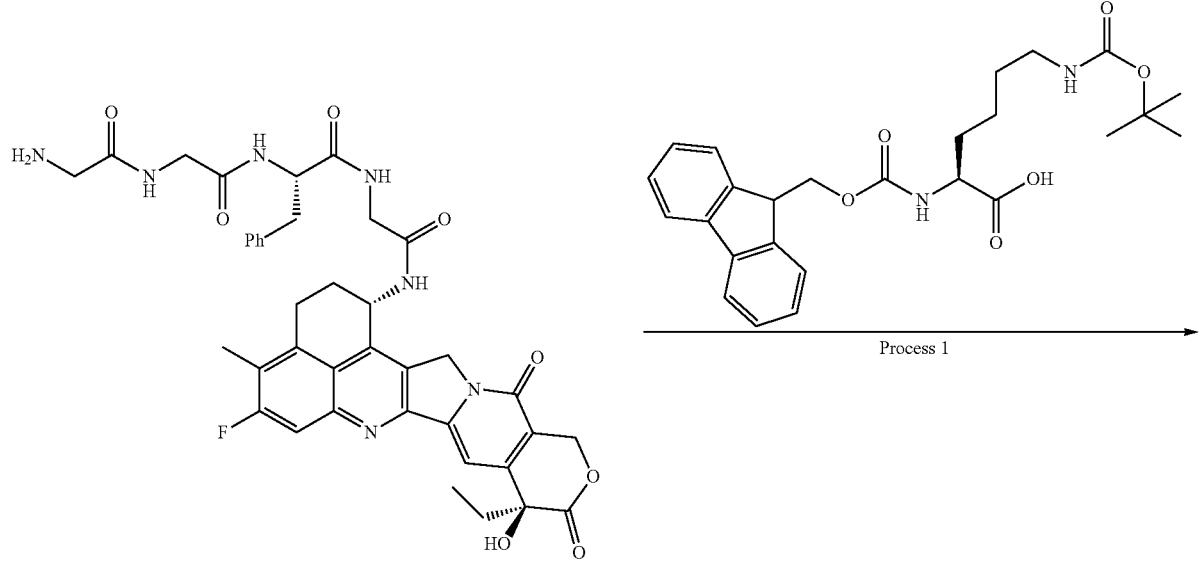

Process 1

221
222
-continued
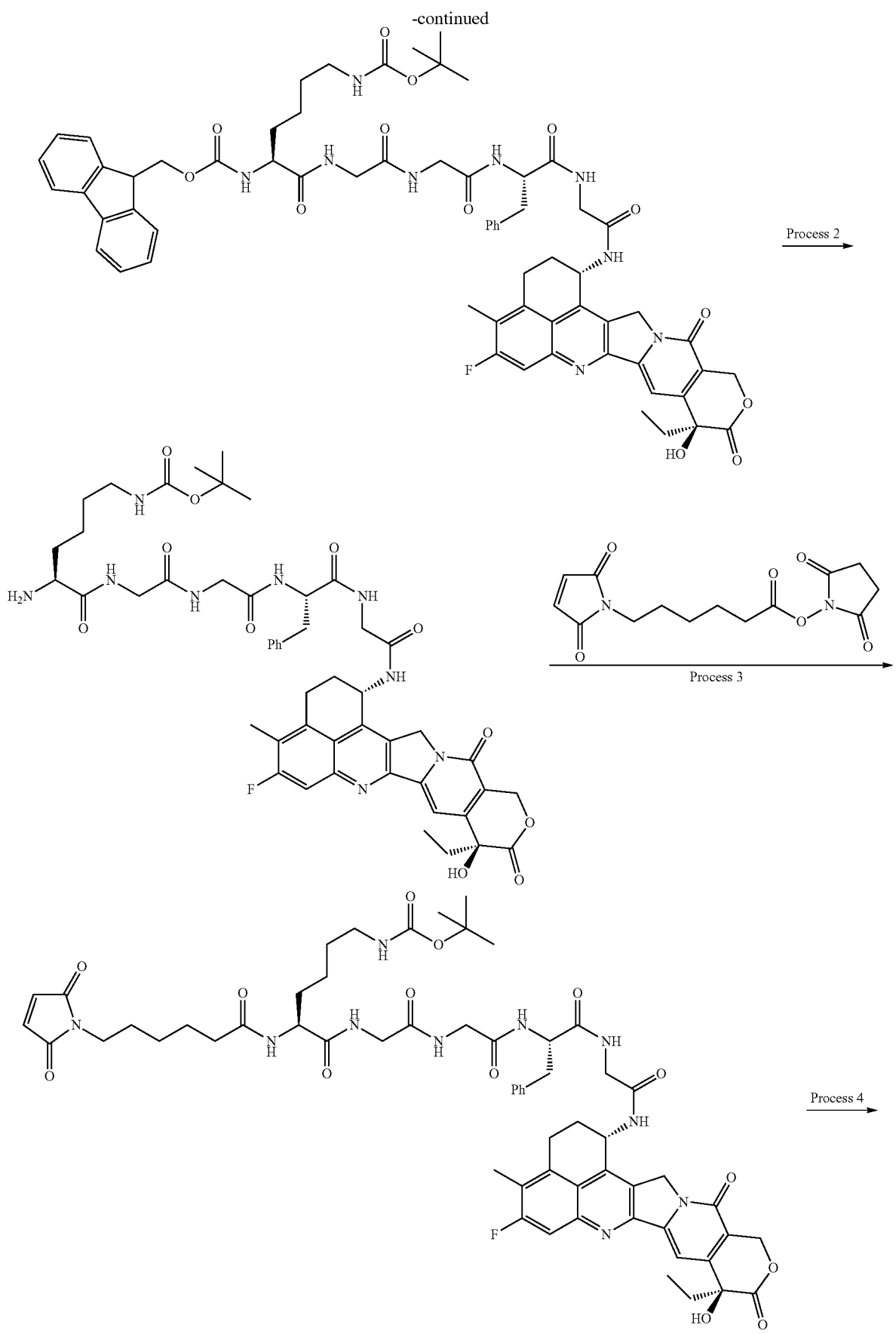

-continued

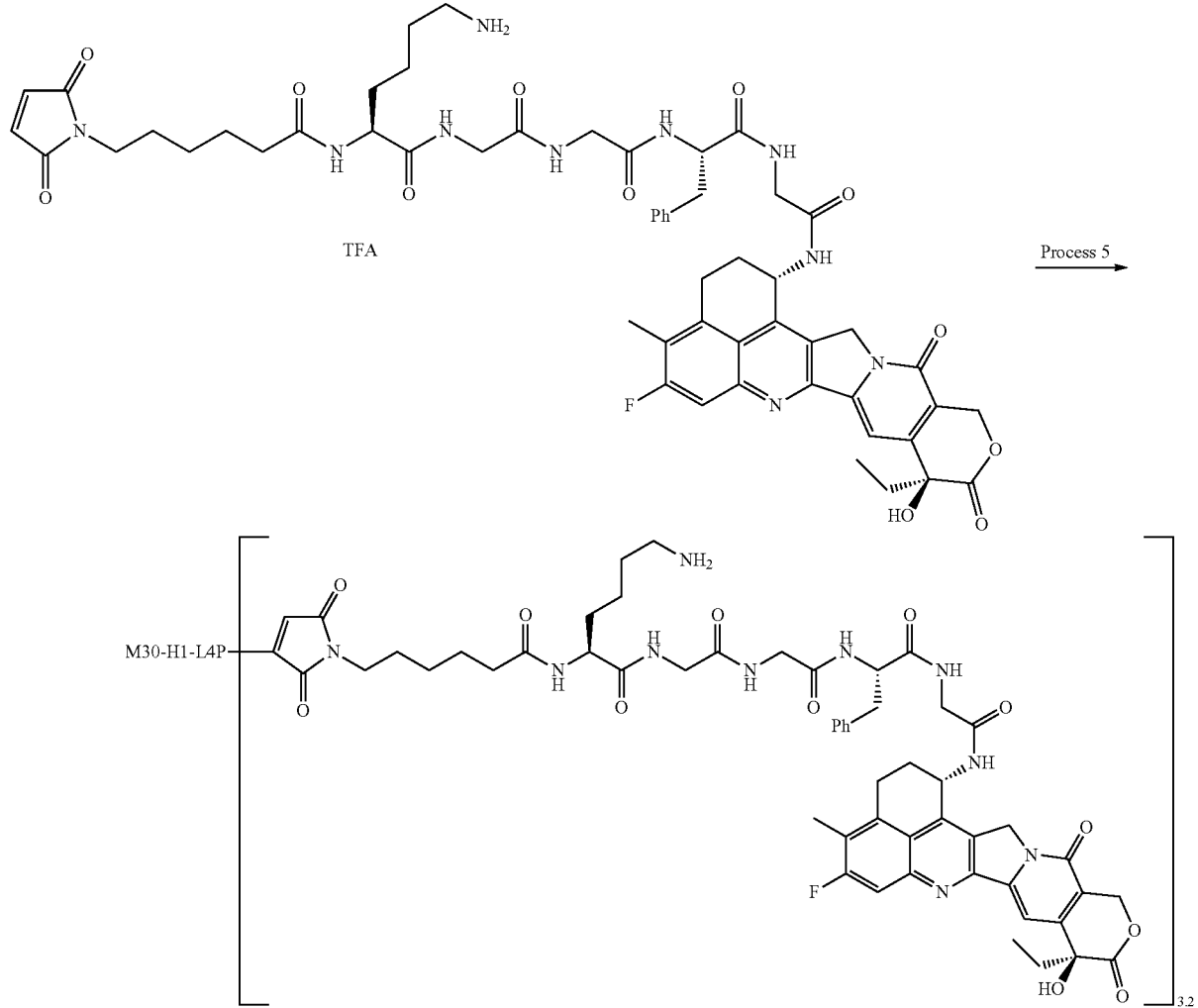

Process 1: $N^6$-(tert-butoxycarbonyl)-$N^2$-[(9H-fluoren-9-ylmethoxy)carbonyl]-L-lysylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (a free form of the pharmaceutical compound described in WO97/46260; 0.300 g, 0.397 mmol) was reacted in the same manner as Process 1 of Example 20 by using $N^\epsilon$-(tert-butoxycarbonyl)-$N^\alpha$-[(9H-fluoren-9-ylmethoxy)carbonyl]-L-lysine instead of 4-tert-butyl N-[(9H-fluoren-9-ylmethoxy)carbonyl]-L-aspartate to yield the titled compound as a yellow solid (0.471 g, 98%).

MS (ESI) m/z: 1204 (M+H)$^+$

Process 2: $N^6$-(tert-butoxycarbonyl)-L-lysylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.417 g, 0.391 mmol) obtained in Process 1 above was reacted in the same manner as Process 2 of Example 20 to yield the titled compound as a pale yellow solid (0.272 g, 71%).

MS (ESI) m/z: 1062 (M+H)$^+$

Process 3: $N^6$-(tert-butoxycarbonyl)-$N^2$-[6-(2,5-dioxo-2,5-dihydro-1H-pyrrol-1-yl)hexanoyl]-L-lysylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.210 g, 0.213 mmol) obtained in Process 2 above was reacted in the same manner as Process 3 of Example 20 to yield the titled compound as a pale yellow solid (63.0 mg, 21%).

MS (ESI) m/z: 1175 (M+H)$^+$

Process 4: N²-[6-(2,5-dioxo-2,5-dihydro-1H-pyrrol-1-yl)hexanoyl]-L-lysylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolidino[1,2-b]quinolin-1-yl]glycineamide trifluoroacetate Under ice cooling, to the compound (63.0 mg, 53.6 mol) obtained in Process 3 above, trifluoroacetic acid (2.00 mL) was added and stirred at room temperature for 1 hour. The solvent was removed under reduced pressure to yield the titled compound as a yellow solid (50.0 mg, 78%).

¹H-NMR (400 MHz, DMSO-d₆) δ: 0.89 (3H, t, J=7.2 Hz), 1.13-1.39 (4H, m), 1.43-1.58 (7H, m), 1.61-1.73 (1H, m), 1.80-1.94 (2H, m), 2.07-2.28 (4H, m), 2.43 (3H, s), 2.72-2.84 (4H, m), 3.00 (1H, dd, J=13.7, 3.9 Hz), 3.20 (2H, brs), 3.55-3.80 (6H, m), 4.20-4.30 (1H, m), 4.42-4.52 (1H, m), 5.27 (2H, dd, J=23.7, 19.8 Hz), 5.43 (2H, dd, J=21.9, 16.4 Hz), 5.55-5.65 (1H, m), 6.56 (1H, s), 7.02 (2H, s), 7.15-7.27 (5H, m), 7.34 (1H, s), 7.64 (3H, brs), 7.83 (1H, d, J=10.6 Hz), 7.98-8.04 (2H, m), 8.09-8.20 (2H, m), 8.37 (1H, t, J=5.5 Hz), 8.47 (1H, d, J=8.6 Hz).

MS (ESI) m/z: 1075 (M+H)⁺

Process 5: Antibody-Drug Conjugate (30)

By using the M30-H1-L4P antibody produced in Reference Example 2 and the compound obtained in Process 4, the titled antibody-drug conjugate was obtained in the same manner as Process 1 of Example 4.

Antibody concentration: 12.04 mg/mL, antibody yield: 8.4 mg (67%), and average number of conjugated drug molecules (n) per antibody molecule: 3.2.

Example 33: Antibody-Drug Conjugate (31)

[Formula 85]

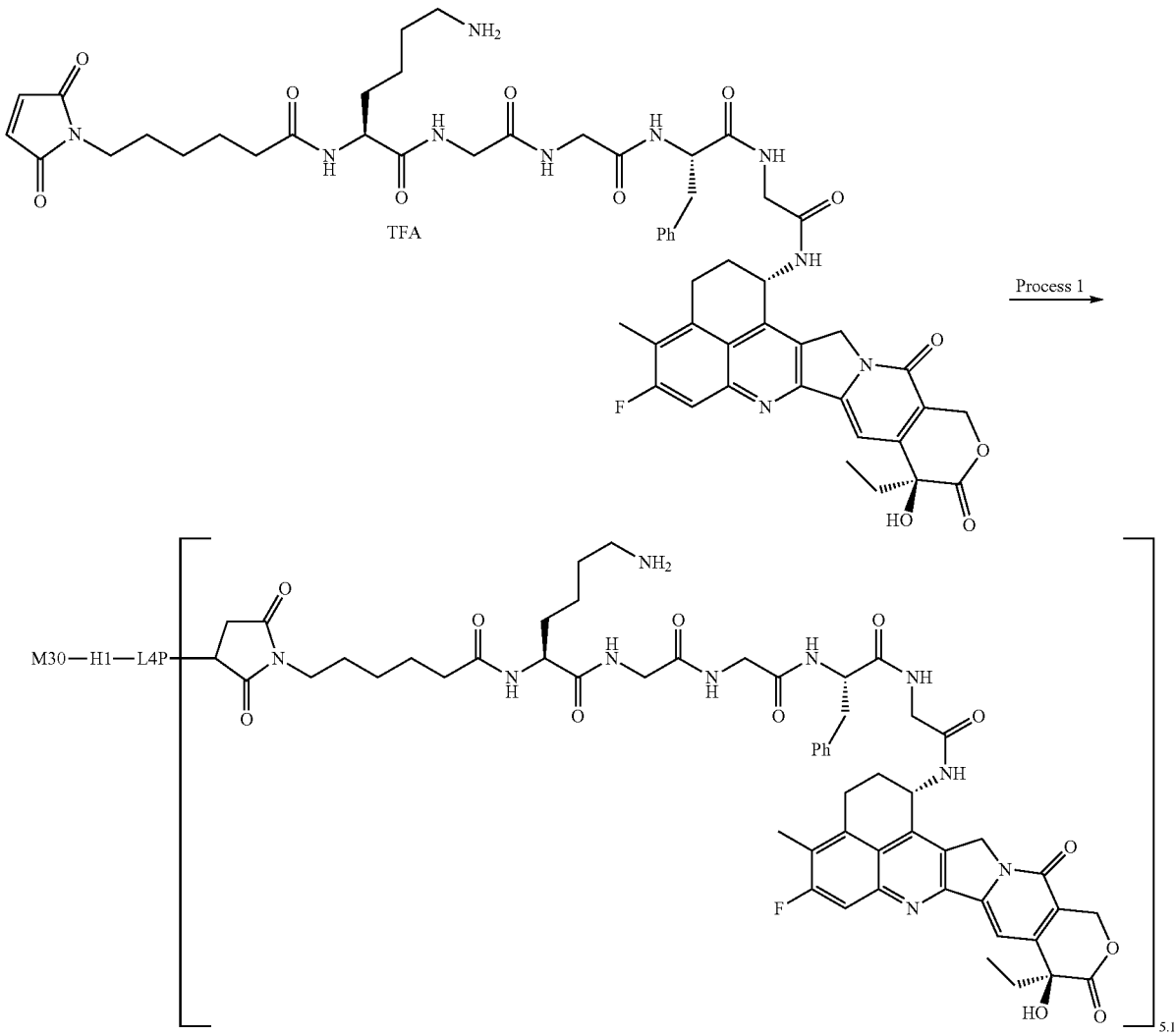

Process 1: Antibody-Drug Conjugate (31)

By using the M30-H1-L4P antibody produced in Reference Example 2 and the compound obtained in Process 4 of Example 32, the titled antibody-drug conjugate was obtained in the same manner as Process 1 of Example 5.

Antibody concentration: 1.79 mg/mL, antibody yield: 10.74 mg (86%), and average number of conjugated drug molecules (n) per antibody molecule: 5.1.

Example 34: Antibody-Drug Conjugate (32)

Process 1: Antibody-Drug Conjugate (32)

By using the M30-H1-L4P antibody produced in Reference Example 2 and the compound obtained in Process 4 of Example 32, the titled antibody-drug conjugate was obtained in the same manner as Process 1 of Example 6.

Antibody concentration: 1.87 mg/mL, antibody yield: 11.22 mg (90%), and average number of conjugated drug molecules (n) per antibody molecule: 7.0.

[Formula 86]

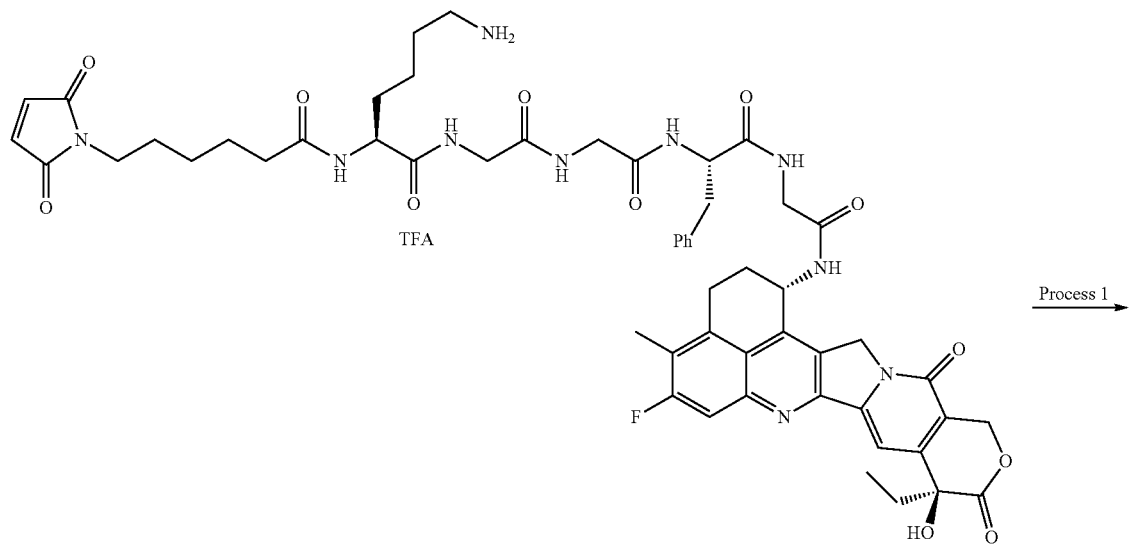

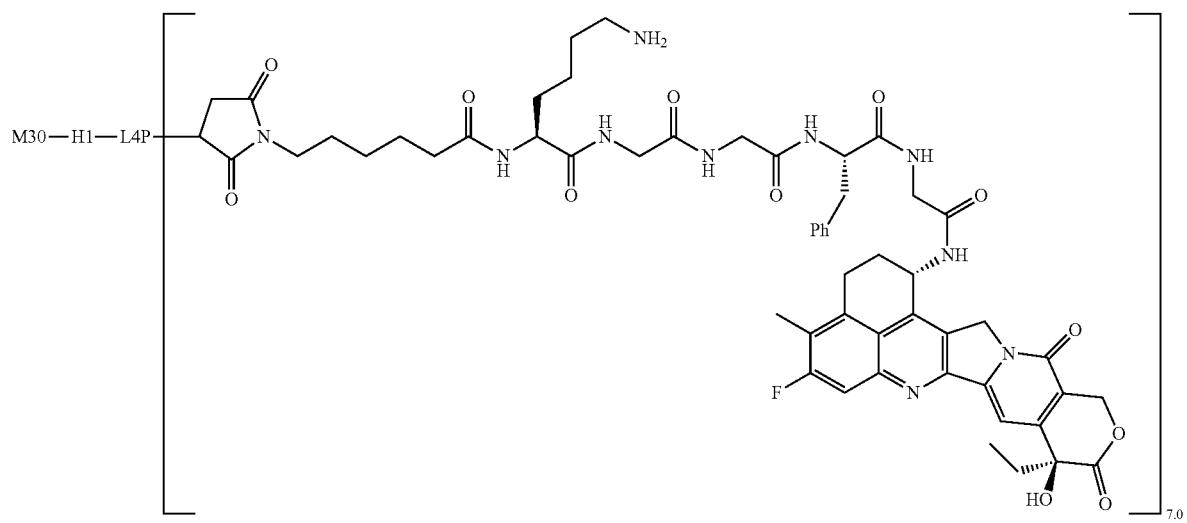

Example 35: Antibody-Drug Conjugate (33)

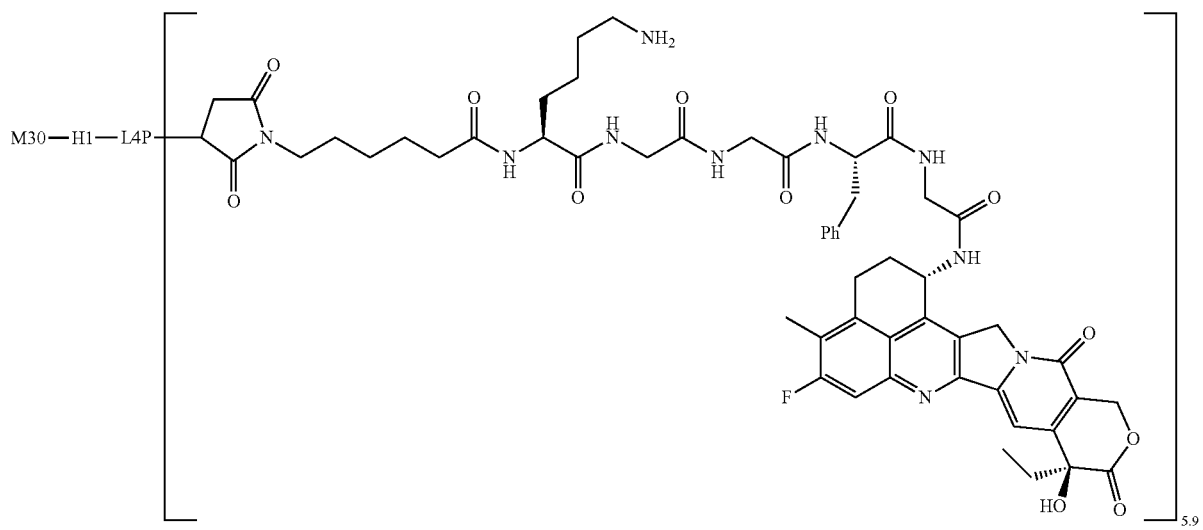

[Formula 87]

Almost the whole amounts of the antibody-drug conjugates of Examples 33 and 34 were mixed and the solution was concentrated by the Common procedure A described in Production method 1 to yield the titled antibody-drug conjugate.

Antibody concentration: 10.0 mg/mL, antibody yield: 22.21 mg, and average number of conjugated drug molecules (n) per antibody molecule: 5.9.

Example 36: N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide

[Formula 88]

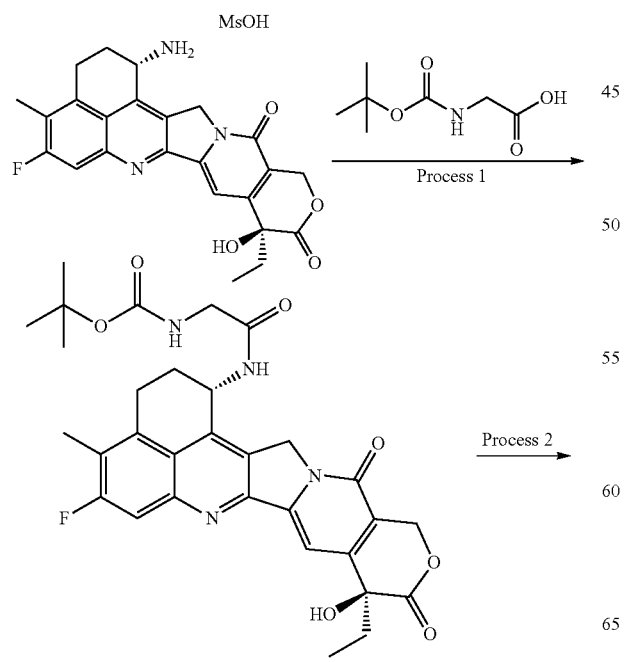

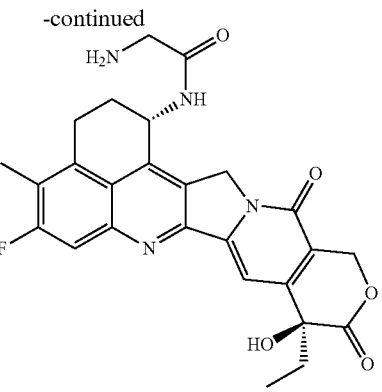

Process 1: tert-Butyl (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)carbamate To a dichloromethane (3.00 mL) solution of N-(tert-butoxycarbonyl)-glycine (0.395 g, 2.26 mmol), N-hydroxysuccinimide (0.260 g, 2.26 mmol) and 1-ethyl-3-(3-dimethylaminopropyl)carbodiimide hydrochloride (0.433 mg, 2.26 mmol) were added and stirred at room temperature for 1 hour. This solution was added to a solution consisting of methanesulfonate of the compound (4) (1.00 g, 1.88 mmol), triethylamine (0.315 mL, 2.26 mmol), and N,N-dimethylformamide (3.00 mL) and stirred at room temperature for 16.5 hours. The reaction solution was diluted with chloroform and washed with 10% citric acid solution, and then the organic layer was dried over anhydrous sodium sulfate. The solvent was removed under reduced pressure and the obtained residues were purified by silica gel column chromatography [chloroform to chloroform:methanol=9:1 (v/v)] to yield the titled compound as a yellow solid (1.16 g, 99%).

¹H-NMR (400 MHz, DMSO-d₆) δ: 0.86 (3H, t, J=7.2 Hz), 1.30 (9H, s), 1.81-1.89 (2H, m), 2.09-2.21 (2H, m), 2.38 (3H, s), 3.15-3.17 (2H, m), 3.55-3.56 (2H, m), 5.15 (1H, d, J=18.8 Hz), 5.23 (1H, d, J=19.2 Hz), 5.41 (2H, s), 5.55-5.56 (1H, m), 6.53 (1H, s), 6.95 (1H, t, J=5.5 Hz), 7.28 (1H, s), 7.77 (1H, d, J=11.0 Hz), 8.39 (1H, d, J=8.6 Hz).

MS (APCI) m/z: 593 (M+H)⁺

Process 2: N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.513 g, 1.01 mmol) obtained in Process 1 above was reacted in the same manner as Process 4 of Example 17 to yield the titled compound as a yellow solid (0.463 g, 93%).

¹H-NMR (400 MHz, CD₃OD) δ: 0.96 (3H, t, J=7.0 Hz), 1.89-1.91 (2H, m), 2.14-2.16 (1H, m), 2.30 (3H, s), 2.40-2.42 (1H, m), 3.15-3.21 (2H, m), 3.79-3.86 (2H, m), 4.63-4.67 (1H, m), 5.00-5.05 (1H, m), 5.23 (1H, d, J=16.0 Hz), 5.48 (1H, d, J=16.0 Hz), 5.62-5.64 (1H, m), 7.40-7.45 (2H, m).

MS (APCI) m/z: 493 (M+H)⁺

Example 37: Antibody-Drug Conjugate (34)

[Formula 89]

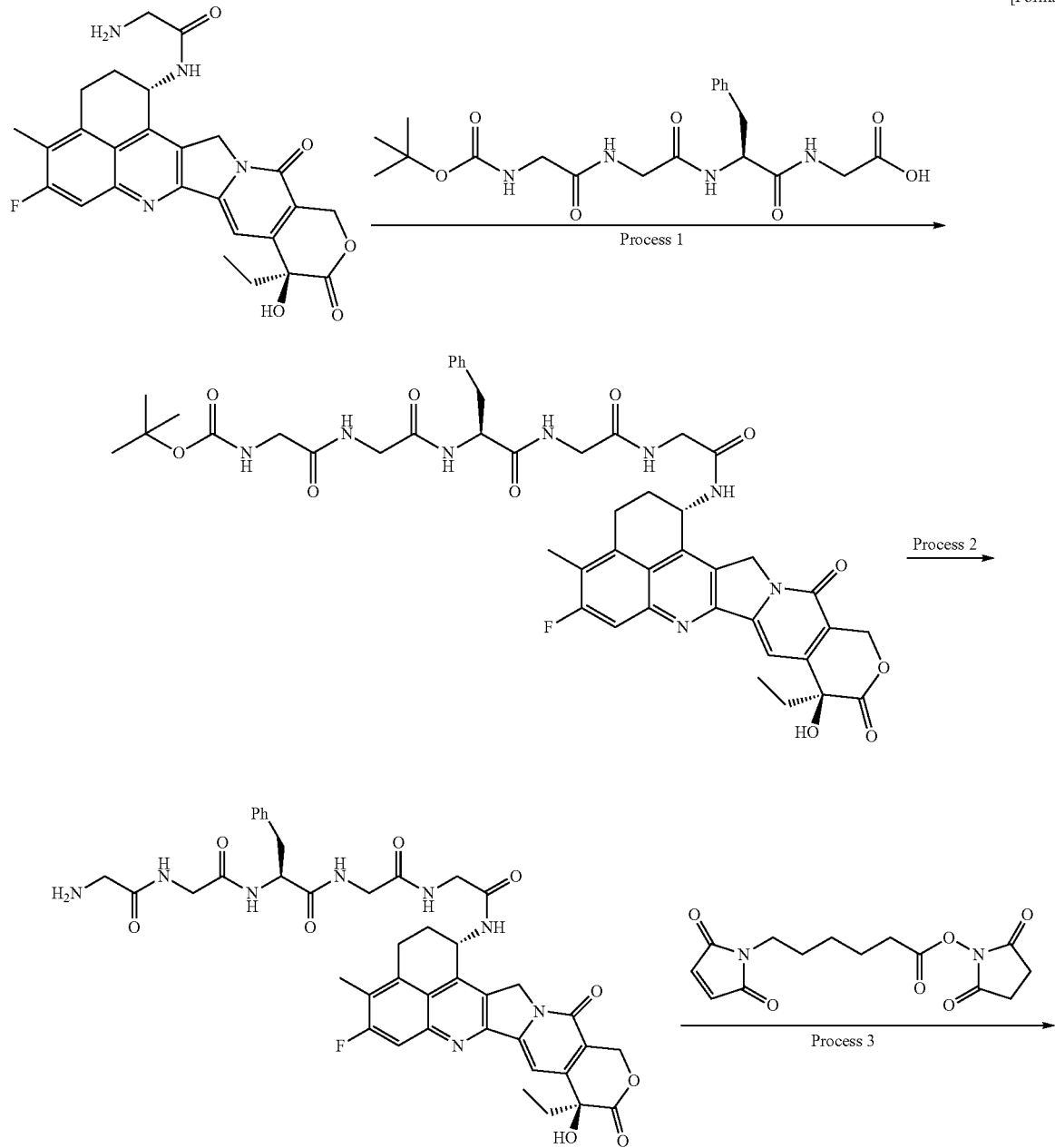

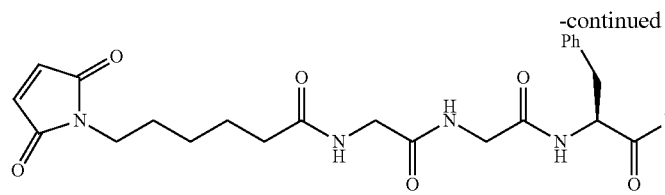
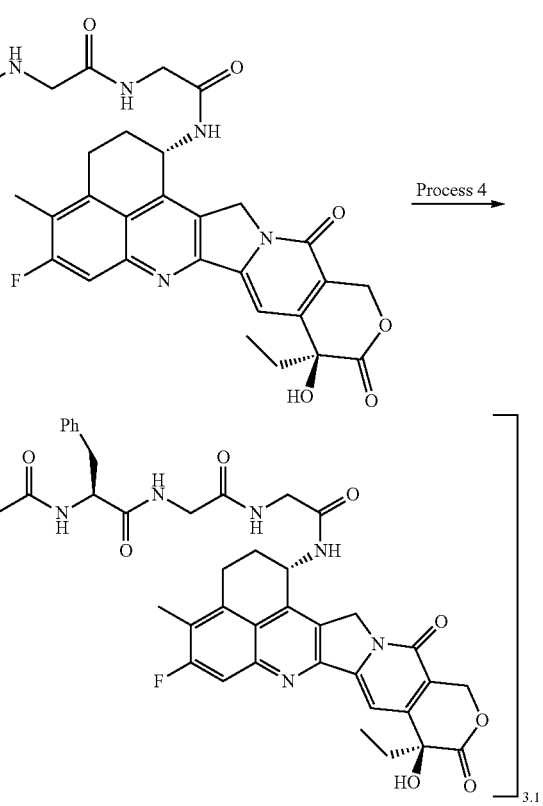
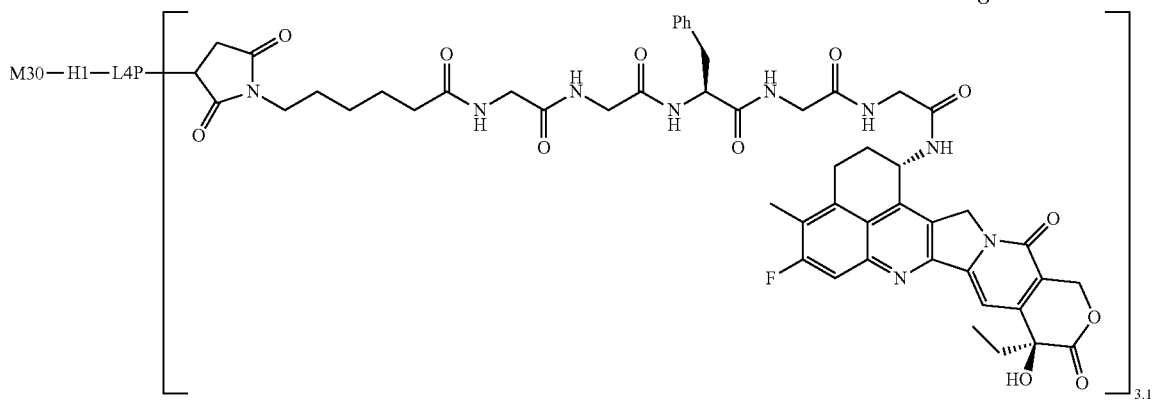

Process 1: N-(tert-butoxycarbonyl)glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide N-(tert-butoxycarbonyl)-glycylglycyl-L-phenylalanyl-glycine (0.292 mg, 0.669 mmol) was dissolved in dichloromethane (5.00 mL), charged with N-hydroxysuccinimide (77.0 mg, 0.0.669 mmol) and N,N'-dicyclohexylcarbodiimide (128 mg, 0.669 mmol), and stirred for 1 hour and 20 minutes. The reaction solution was added dropwise to an N,N-dimethylformamide solution (5.00 mL) of the compound (0.275 g, 0.558 mmol) of Example 36 and stirred at room temperature for 1 day. An aqueous solution of 10% citric acid (20.0 mL) was added thereto and extracted with 20 mL of chloroform three times. The obtained organic layer was evaporated under reduced pressure and the obtained residues were purified by silica gel column chromatography [chloroform to chloroform:methanol=8:2 (v/v)] to yield the titled compound as a pale yellow solid (0.430 g, 85%).

$^1$H-NMR (400 MHz, CD$_3$OD) δ: 0.94 (3H, t, J=7.2 Hz), 1.43 (9H, s), 1.83-1.85 (2H, m), 2.20-2.22 (1H, m), 2.29 (3H, s), 2.36-2.39 (2H, m), 2.50-2.53 (1H, m), 2.67 (1H, s), 3.08-3.11 (1H, m), 3.18-3.21 (1H, m), 3.63-3.67 (4H, m), 3.78-3.82 (1H, m), 3.99 (2H, dd, J=23.5, 16.8 Hz), 4.16 (1H, s), 4.58 (1H, d, J=18.8 Hz), 5.15 (1H, d, J=19.2 Hz), 5.25 (1H, d, J=16.4 Hz), 5.52 (1H, d, J=16.4 Hz), 5.59-5.61 (1H, m), 6.89 (2H, d, J=6.7 Hz), 7.15-7.17 (3H, m), 7.28 (1H, d, J=10.6 Hz), 7.41 (1H, s).
MS (APCI) m/z: 911 (M+H)$^+$

Process 2: Glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.227 g, 0.249 mmol) obtained in Process 1 above was dissolved in dichloromethane (1.00 mL). Trifluoroacetic acid (3.00 mL) was added thereto and stirred for 1 hour. The solvent was removed under reduced pressure and the obtained residues were purified by silica gel column chromatography [chloroform to partitioned organic layer of chloroform:methanol:water=7:3:1 (v/v/v)] to yield the titled compound as a pale yellow solid (0.200 g, 99%).

$^1$H-NMR (400 MHz, CD$_3$OD) δ: 0.93 (3H, t, J=7.4 Hz), 1.85 (2H, q, J=7.3 Hz), 2.24-2.45 (5H, m), 2.32 (3H, s), 2.56 (1H, dd, J=13.7, 5.5 Hz), 3.09-3.25 (2H, m), 3.66-3.76 (6H, m), 4.18-4.24 (1H, m), 4.76 (1H, d, J=19.2 Hz), 5.18 (1H, d, J=18.8 Hz), 5.30 (1H, t, J=18.4 Hz), 5.52 (1H, d, J=16.0 Hz), 5.63 (1H, t, J=5.9 Hz), 6.93 (2H, d, J=6.6 Hz), 7.17 (3H, q, J=7.3 Hz), 7.30 (1H, d, J=10.9 Hz), 7.42 (1H, s).
MS (APCI) m/z: 811 (M+H)$^+$

Process 3: N-[6-(2,5-dioxo-2,5-dihydro-1H-pyrrol-1-yl)hexanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.125 g, 0.154 mmol) obtained in Process 2 above was reacted in the same manner as Process 3 of Example 20 to yield the titled compound as a pale yellow solid (0.0775 g, 50%).

$^1$H-NMR (400 MHz, DMSO-$d_6$) δ: 0.86 (3H, t, J=7.2 Hz), 1.18-1.19 (2H, m), 1.45-1.48 (4H, m), 1.83-1.85 (2H, m), 2.12-2.17 (4H, m), 2.39 (3H, s), 2.68 (1H, dd, J=24.4, 14.7 Hz), 2.83-2.87 (1H, m), 3.17-3.78 (12H, m), 4.42-4.45 (1H, m), 5.23 (2H, s), 5.41 (2H, s), 5.58-5.60 (1H, m), 6.53 (1H, s), 6.99 (2H, s), 7.15-7.29 (6H, m), 7.76 (1H, d, J=10.9 Hz), 7.97-8.00 (1H, m), 8.09-8.12 (3H, m), 8.25-8.28 (1H, m), 8.44 (1H, d, J=8.2 Hz).

MS (APCI) m/z: 1004 (M+H)$^+$

Process 4: Antibody-Drug Conjugate (34)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was added to a 1.5 mL polypropylene tube and charged with an aqueous solution of 10 mM TCEP (Tokyo Chemical Industry Co., Ltd.) (0.025 mL; 3.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.102 mL) and a dimethyl sulfoxide solution (0.047 mL; 5.5 equivalents per antibody molecule) containing 10 mM of the compound obtained in above Process 3 to the above solution at room temperature, it was stirred by using a tube rotator (MTR-103, manufactured by AS ONE Corporation) at room temperature for 40 minutes for conjugating the drug linker to the antibody. Next, an aqueous solution (0.009 mL) of 100 mM NAC (Sigma-Aldrich Co. LLC) was added thereto and stirred at room temperature for another 20 minutes to terminate the reaction of drug linker.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A described in Production method 1.

Physicochemical characterization: By using the Common procedure E described in Production method 1 (as molar absorption coefficient, $\epsilon_{A,280}$=235300 (calculation value), $\epsilon_{A,370}$=0 (calculation value), $\epsilon_{D,280}$=5000 (measured average value), and $\epsilon_{D,370}$=19000 (measured average value) were used), the following characteristic values were obtained.

Antibody concentration: 12.4 mg/mL, antibody yield: 8.7 mg (70%), and average number of conjugated drug molecules (n) per antibody molecule: 3.1.

Example 38: Antibody-Drug Conjugate (35)

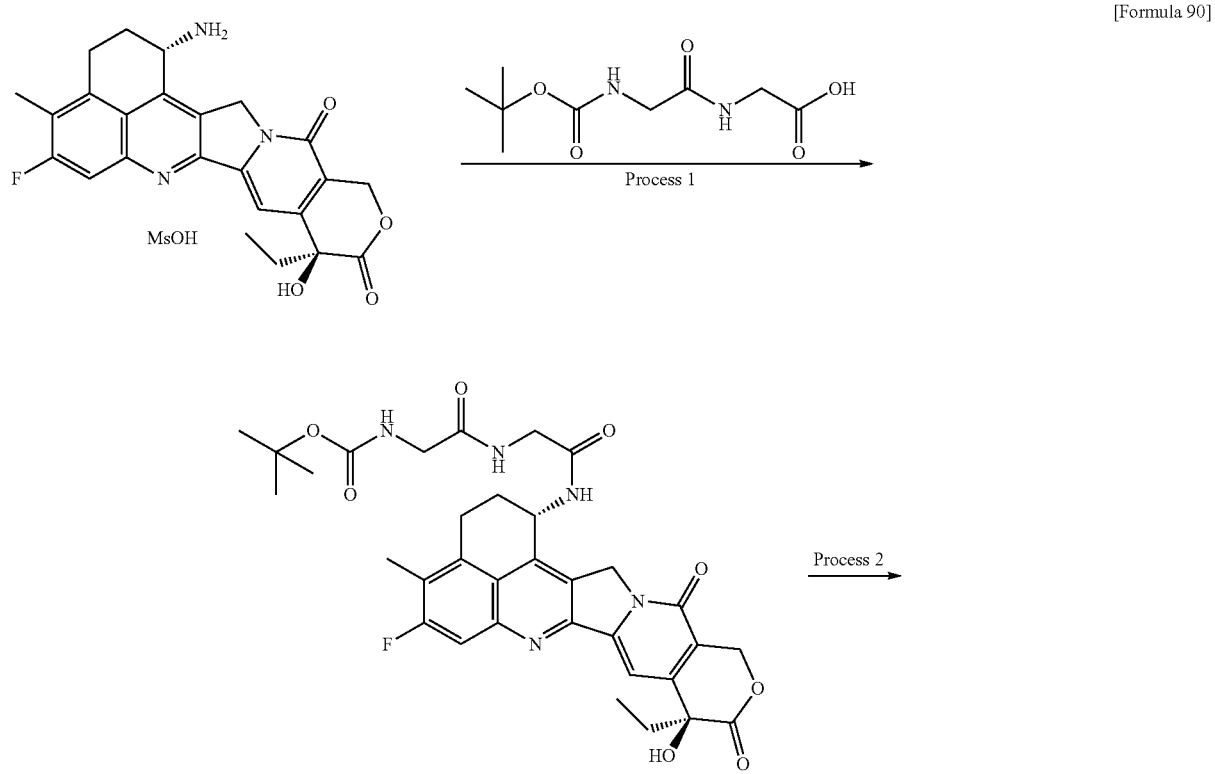

[Formula 90]

-continued
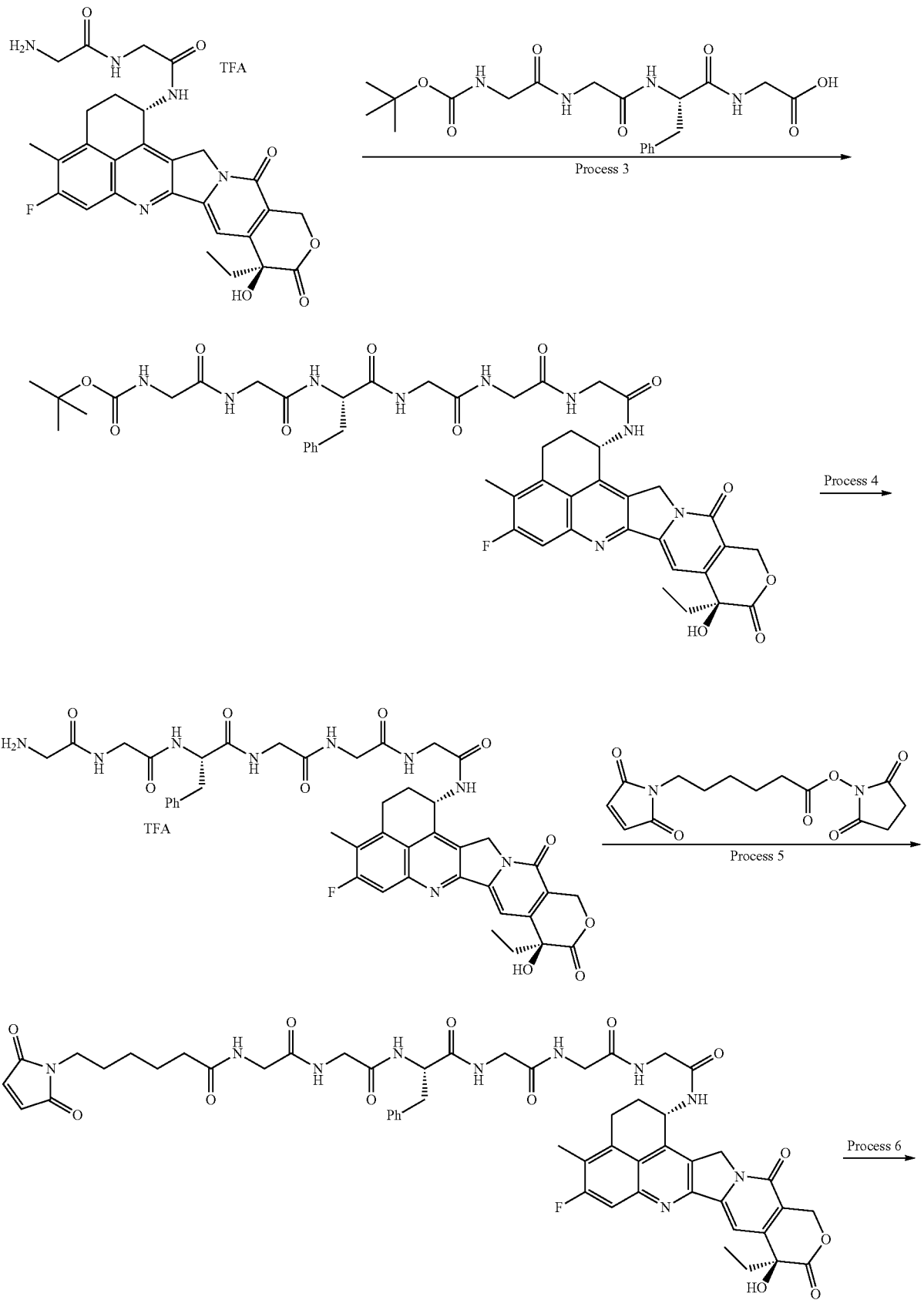

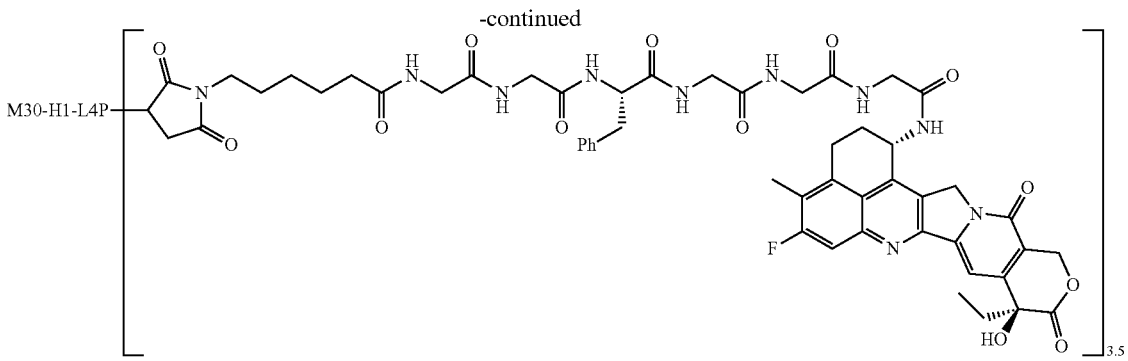

Process 1: N-(tert-butoxycarbonyl)glycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Methanesulfonate of the compound (4) (0.800 g, 1.51 mmol) was reacted in the same manner as Process 1 of Example 1 by using N-(tert-butoxycarbonyl)-glycylglycine (0.419 g, 1.81 mmol) instead of 4-(tert-butoxycarbonylamino)butanoic acid to yield the titled compound as a yellow solid (0.965 g, 99%).

$^1$H-NMR (400 MHz, DMSO-$d_6$) δ: 0.87 (3H, t, J=7.4 Hz), 1.23 (9H, s), 1.82-1.89 (2H, m), 2.11-2.19 (2H, m), 2.40 (3H, s), 3.16-3.17 (2H, m), 3.52 (2H, ddd, J=21.3, 15.5, 4.7 Hz), 3.77 (2H, ddd, J=24.3, 16.8, 5.9 Hz), 5.23 (2H, s), 5.43 (2H, s), 5.56-5.60 (1H, m), 6.53 (1H, s), 7.04 (1H, t, J=5.9 Hz), 7.31 (1H, s), 7.80 (1H, d, J=11.0 Hz), 8.12 (1H, t, J=5.5 Hz), 8.31 (1H, d, J=8.6 Hz).

MS (APCI) m/z: 650 (M+H)$^+$

Process 2: Glycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycineamide trifluoroacetate The compound (0.884 g, 1.36 mmol) obtained in Process 1 above was reacted in the same manner as Process 2 of Example 1 to yield the titled compound as a yellow solid (0.787 g, quantitative).

$^1$H-NMR (400 MHz, DMSO-$d_6$) δ: 0.87 (3H, t, J=7.2 Hz), 1.82-1.89 (2H, m), 2.11-2.18 (2H, m), 2.41 (3H, s), 3.17-3.18 (2H, m), 3.63 (2H, s), 3.88 (2H, d, J=5.5 Hz), 5.19 (1H, d, J=18.8 Hz), 5.25 (1H, d, J=19.2 Hz), 5.42 (2H, s), 5.56-5.61 (1H, m), 6.56 (1H, s), 7.32 (1H, s), 7.81 (1H, d, J=11.0 Hz), 8.01 (3H, brs), 8.65 (1H, d, J=8.6 Hz), 8.72 (1H, t, J=5.5 Hz).

MS (APCI) m/z: 550 (M+H)$^+$

Process 3: N-(tert-butoxycarbonyl)glycylglycylphenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.400 g, 0.728 mmol) obtained in Process 2 above was reacted in the same manner as Process 1 of Example 1 by using N-(tert-butoxycarbonyl)-glycylglycyl-L-phenylalanylglycine (0.381 mg, 0.873 mmol) instead of 4-(tert-butoxycarbonylamino)butanoic acid to yield the titled compound as a pale yellow solid (0.545 g, 77%).

$^1$H-NMR (400 MHz, DMSO-$d_6$) δ: 0.87 (3H, t, J=7.2 Hz), 1.37 (9H, s), 1.80-1.90 (2H, m), 2.09-2.11 (1H, m), 2.18-2.21 (1H, m), 2.40 (3H, s), 2.72-2.77 (1H, m), 3.01 (1H, dd, J=13.7, 4.3 Hz), 3.16-3.17 (2H, m), 3.52-3.83 (10H, m), 4.48-4.51 (1H, m), 5.21 (1H, d, J=19.2 Hz), 5.26 (1H, d, J=18.8 Hz), 5.43 (2H, s), 5.55-5.59 (1H, m), 6.53 (1H, s), 6.99 (1H, t, J=5.9 Hz), 7.18-7.24 (5H, m), 7.31 (1H, s), 7.80 (1H, d, J=11.0 Hz), 7.90 (1H, t, J=5.3 Hz), 8.02 (1H, t, J=5.5 Hz), 8.15-8.19 (2H, m), 8.30 (1H, t, J=5.5 Hz), 8.43 (1H, d, J=8.6 Hz).

MS (APCI) m/z: 968 (M+H)$^+$

Process 4: Glycylglycylphenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolidino[1,2-b]quinolin-1-yl]glycineamide trifluoroacetate The compound (0.429 g, 0.443 mmol) obtained in Process 3 above was reacted in the same manner as Process 2 of Example 1 to yield the titled compound as a yellow solid (0.385 g, quantitative).

$^1$H-NMR (400 MHz, DMSO-$d_6$) δ: 0.87 (3H, t, J=7.4 Hz), 1.82-1.89 (2H, m), 2.11-2.19 (2H, m), 2.40 (3H, s), 2.74 (1H, dd, J=13.7, 9.8 Hz), 3.03 (1H, dd, J=13.7, 4.3 Hz), 3.16-3.18 (2H, m), 3.57-3.58 (2H, m), 3.67-3.76 (7H, m), 3.82-3.90 (1H, m), 4.53-4.56 (1H, m), 5.23 (2H, s), 5.43 (2H, s), 5.55-5.59 (1H, m), 6.55 (1H, s), 7.17-7.19 (1H, m), 7.22-7.29 (4H, m), 7.31 (1H, s), 7.80 (1H, d, J=10.9 Hz), 8.00 (3H, brs), 8.07 (1H, t, J=5.7 Hz), 8.22 (1H, t, J=5.7 Hz), 8.36 (2H, dd, J=10.9, 7.0 Hz), 8.47-8.52 (2H, m).

MS (APCI) m/z: 868 (M+H)$^+$

Process 5: N-[6-(2,5-dioxo-2,5-dihydro-1H-pyrrol-1-yl)hexanoyl]glycylglycylphenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.278 g, 0.320 mmol) obtained in Process 4 above was reacted in the same manner as Process 3 of Example 20 to yield the titled compound as a pale yellow solid (0.166 g, 49%).

$^1$H-NMR (400 MHz, DMSO-$d_6$) δ: 0.87 (3H, t, J=7.2 Hz), 1.14-1.22 (2H, m), 1.44-1.49 (4H, m), 1.80-1.90 (2H, m), 2.06-2.13 (3H, m), 2.20 (1H, d, J=14.1 Hz), 2.40 (3H, s), 2.77 (1H, dd, J=13.3, 8.7 Hz), 3.01 (1H, dd, J=13.3, 4.3 Hz), 3.17 (2H, t, J=6.7 Hz), 3.35-3.38 (2H, m), 3.56-3.84 (10H, m), 4.48 (1H, dd, J=13.1, 9.2 Hz), 5.23 (2H, s), 5.43 (2H, s), 5.55-5.59 (1H, m), 6.53 (1H, s), 6.99 (2H, s), 7.20-7.24 (5H, m), 7.31 (1H, s), 7.80 (1H, d, J=11.0 Hz), 8.00 (2H, q, J=5.5 Hz), 8.06 (1H, t, J=5.9 Hz), 8.13 (1H, d, J=8.2 Hz), 8.18 (1H, t, J=5.7 Hz), 8.28 (1H, t, J=5.7 Hz), 8.43 (1H, d, J=8.6 Hz).

MS (APCI) m/z: 1061 (M+H)$^+$

Process 6: Antibody-Drug Conjugate (35)

By using the M30-H1-L4P antibody produced in Reference Example 2 and the compound obtained in Process 5 above, the titled antibody-drug conjugate was yielded in the same manner as Process 7 of Example 16.

Antibody concentration: 11.7 mg/mL, antibody yield: 8.2 mg (66%), and average number of conjugated drug molecules (n) per antibody molecule: 3.5.

Example 39: Antibody-Drug Conjugate (36)

[Formula 91]

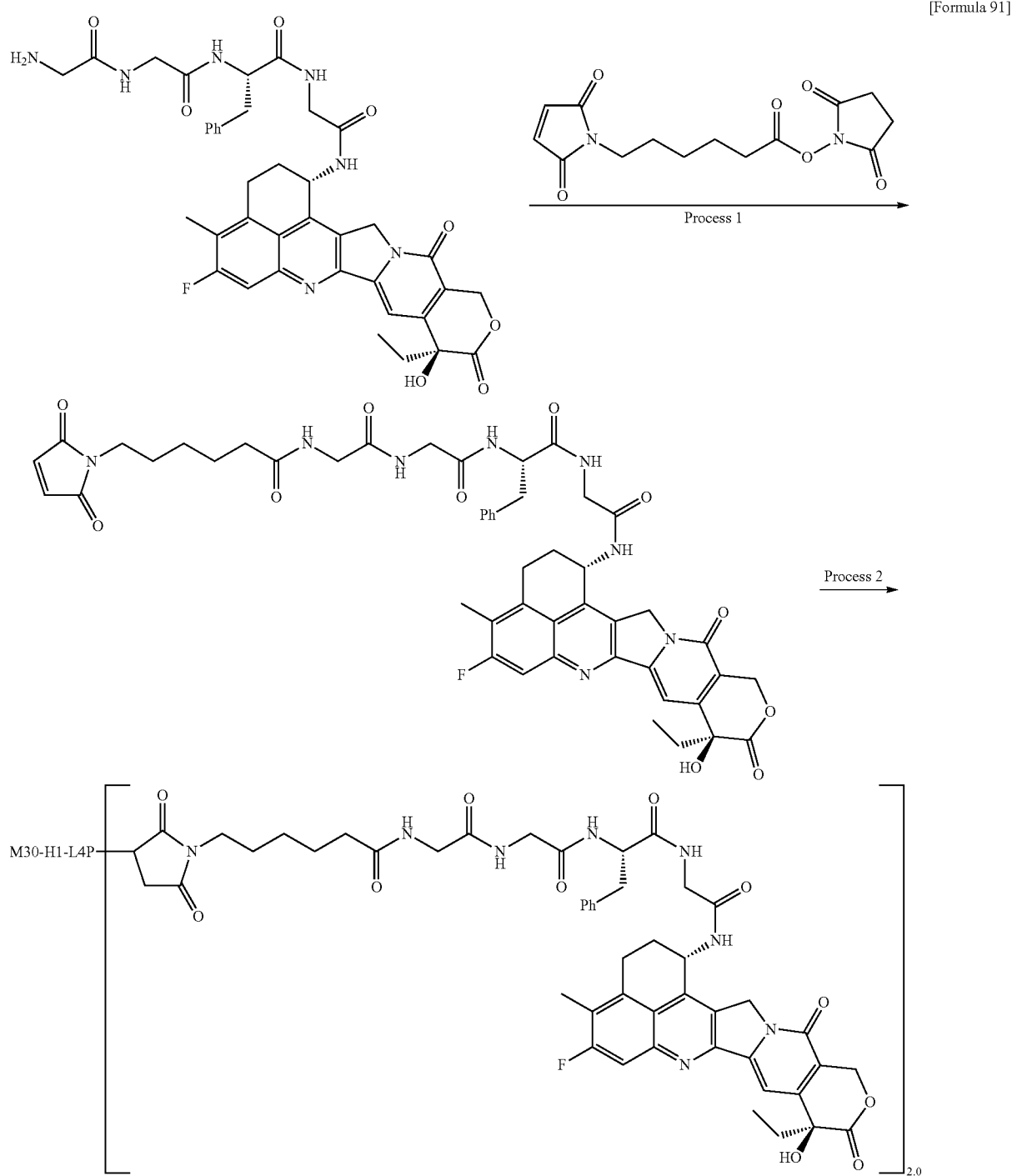

Process 1: N-[6-(2,5-dioxo-2,5-dihydro-1H-pyrrol-1-yl)hexanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (a free form of the pharmaceutical compound described in WO97/46260; 0.150 g, 0.200 mol) was reacted in the same manner as Process 3 of Example 20 to yield the titled compound as a pale yellow solid (70.0 mg, 37%).

$^1$H-NMR (400 MHz, DMSO-$d_6$) δ: 0.87 (3H, t, J=7.4 Hz), 1.15-1.21 (2H, m), 1.41-1.50 (4H, m), 1.80-1.90 (2H, m), 2.07-2.12 (4H, m), 2.17-2.23 (1H, m), 2.35-2.40 (1H, m), 2.41 (3H, s), 2.73-2.81 (1H, m), 2.98 (1H, dd, J=13.7, 4.6 Hz), 3.15-3.20 (2H, m), 3.53 (1H, dd, J=16.6, 5.7 Hz), 3.62-3.77 (5H, m), 4.39-4.45 (1H, m), 5.22 (1H, d, J=18.9 Hz), 5.27 (1H, d, J=18.9 Hz), 5.39 (1H, d, J=16.0 Hz), 5.44 (1H, d, J=16.0 Hz), 5.55-5.60 (1H, m), 6.53 (1H, s), 6.98 (2H, s), 7.13-7.24 (5H, m), 7.32 (1H, s), 7.81 (1H, d, J=10.3 Hz), 7.95-8.00 (1H, m), 8.05-8.09 (2H, m), 8.28-8.31 (1H, m), 8.41 (1H, d, J=8.6 Hz).

MS (APCI) m/z: 947 (M+H)$^+$

Process 2: Antibody-Drug Conjugate (36)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.0 mL) was collected into a 1.5 mL tube and charged with an aqueous solution of 10 mM TCEP (Tokyo Chemical Industry Co., Ltd.) (0.0147 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0295 mL; 4.6 equivalents per antibody molecule) containing 10 mM of the compound obtained in Process 1 was added thereto and incubated at 22° C. for 40 minutes for conjugating the drug linker to the antibody. Next, an aqueous solution (0.00590 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (PBS7.4 was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=235300 (calculation value), $\epsilon_{A,370}$=0 (calculation value), $\epsilon_{D,280}$=5000 (measured average value), and $\epsilon_{D,370}$=19000 (measured average value) were used), the following characteristic values were obtained.

Antibody concentration: 1.23 mg/mL, antibody yield: 7.38 mg (74%), and average number of conjugated drug molecules (n) per antibody molecule: 2.0.

Example 40: Antibody-Drug Conjugate (37)

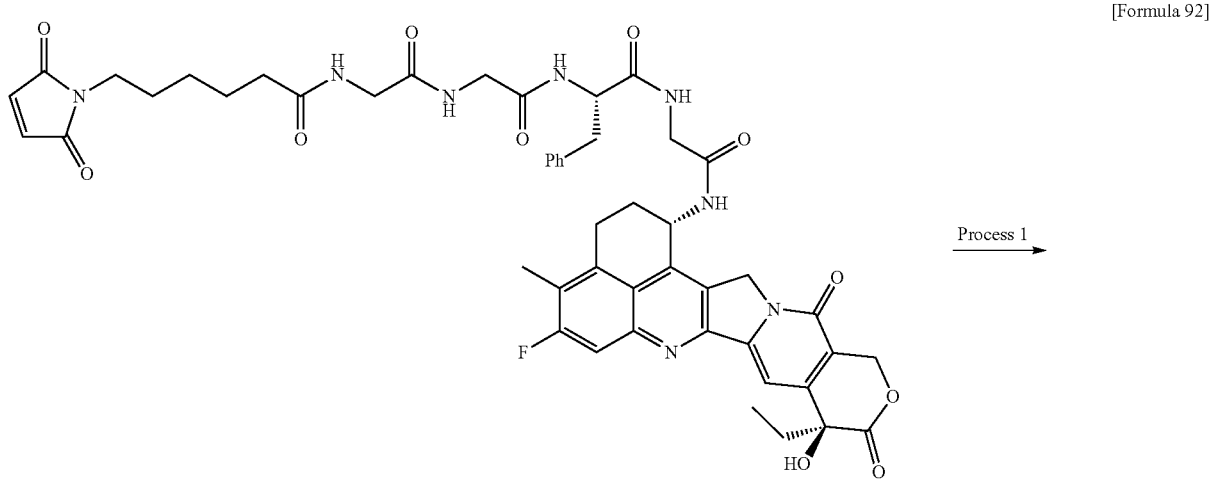

[Formula 92]

Process 1 →

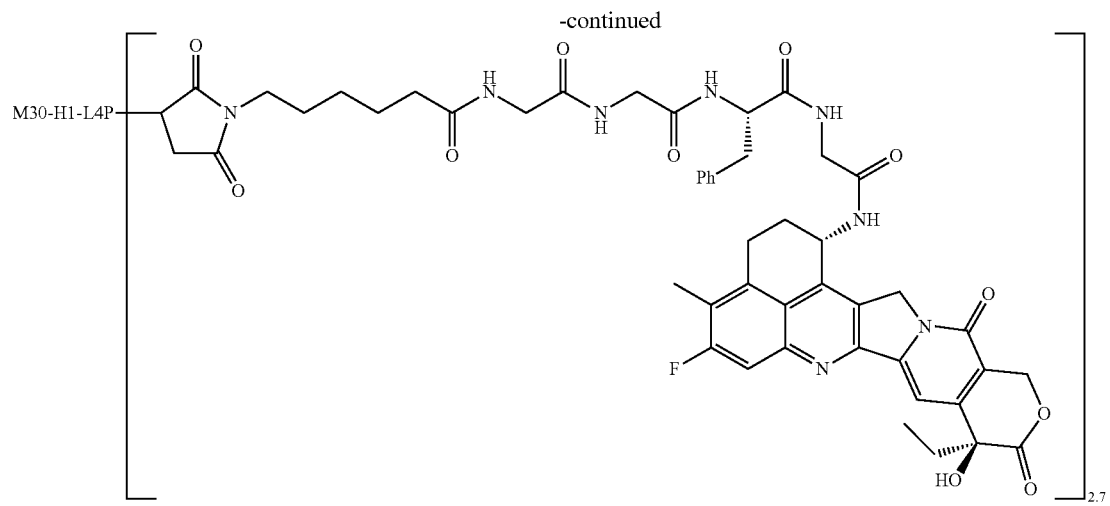

Process 1: Antibody-Drug Conjugate (37)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.0 mL) was collected into a 1.5 mL tube and charged with an aqueous solution of 10 mM TCEP (Tokyo Chemical Industry Co., Ltd.) (0.0295 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0590 mL; 9.2 equivalents per antibody molecule) containing 10 mM of the compound obtained in Process 1 of Example 39 was added thereto and incubated at 22° C. for 40 minutes for conjugating the drug linker to the antibody. Next, an aqueous solution (0.0118 mL; 18.4 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (PBS7.4 was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=235300 (calculation value), $\epsilon_{A,370}$=0 (calculation value), $\epsilon_{D,280}$=5000 (measured average value), and $\epsilon_{D,370}$=19000 (measured average value) were used), the following characteristic values were obtained.

Antibody concentration: 1.22 mg/mL, antibody yield: 7.32 mg (73%), and average number of conjugated drug molecules (n) per antibody molecule: 2.7.

Example 41: Antibody-Drug Conjugate (38)

[Formula 93]

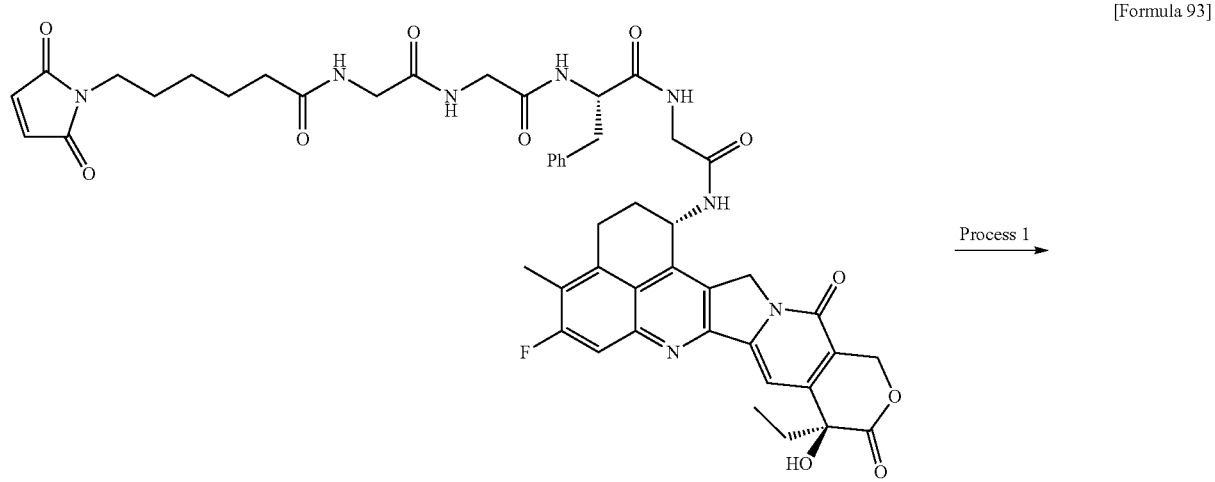

Process 1

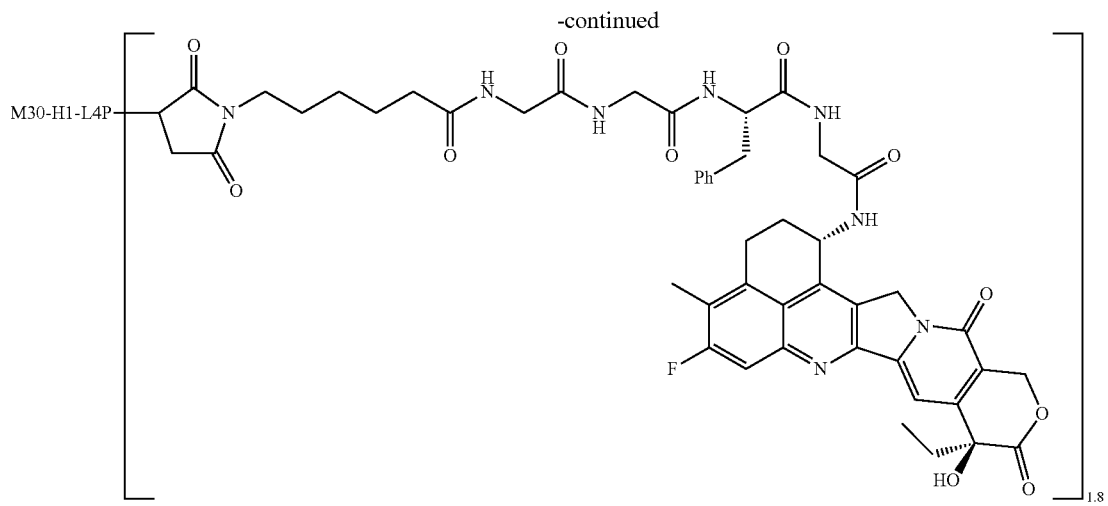

Process 1: Antibody-Drug Conjugate (38)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.0 mL) was collected into a 1.5 mL tube and charged with an aqueous solution of 10 mM TCEP (Tokyo Chemical Industry Co., Ltd.) (0.0147 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0295 mL; 4.6 equivalents per antibody molecule) containing 10 mM of the compound obtained in Process 1 of Example 39 was added thereto and incubated at 22° C. for 40 minutes for conjugating the drug linker to the antibody. Next, an aqueous solution (0.00590 mL; 9.2 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (PBS7.4 was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=235300 (calculation value), $\epsilon_{A,370}$=0 (calculation value), $\epsilon_{D,280}$=5000 (measured average value), and $\epsilon_{D,370}$=19000 (measured average value) were used), the following characteristic values were obtained.

Antibody concentration: 1.11 mg/mL, antibody yield: 6.66 mg (67%), and average number of conjugated drug molecules (n) per antibody molecule: 1.8.

Example 42: Antibody-Drug Conjugate (39)

[Formula 94]

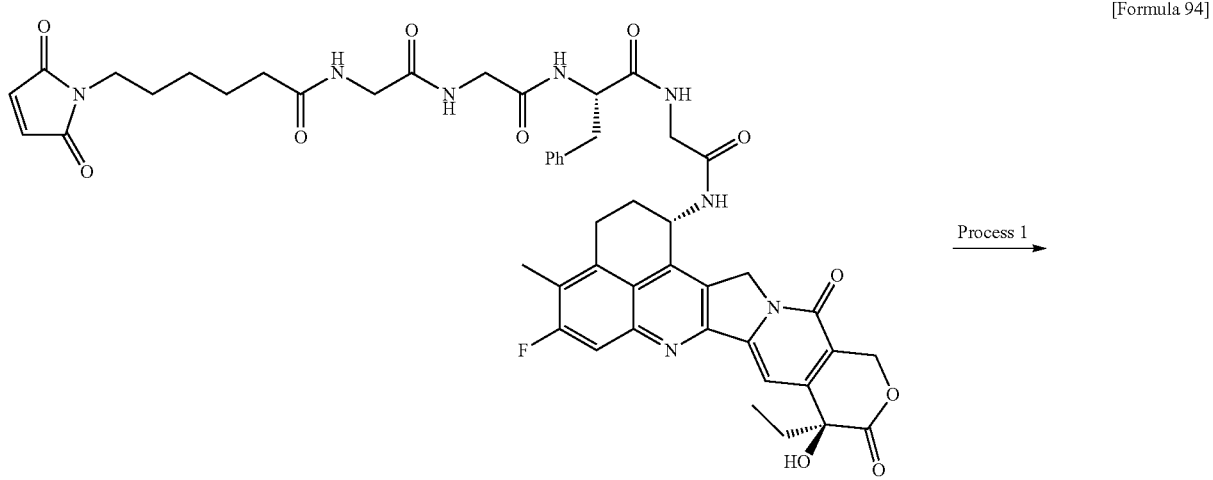

Process 1

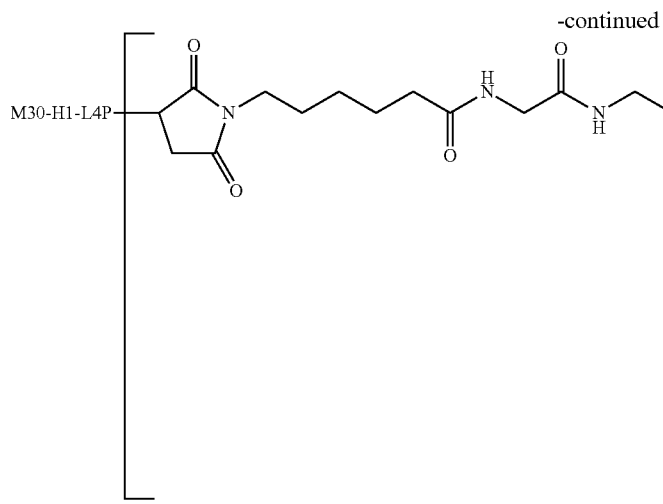
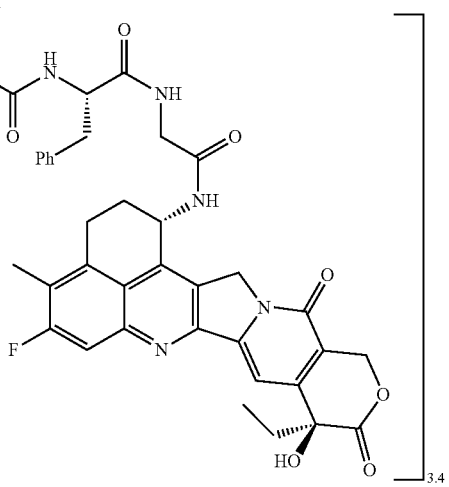

Process 1: Antibody-Drug Conjugate (39)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.0 mL) was collected into a 1.5 mL tube and charged with an aqueous solution of 10 mM TCEP (Tokyo Chemical Industry Co., Ltd.) (0.0295 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0590 mL; 9.2 equivalents per antibody molecule) containing 10 mM of the compound obtained in Process 1 of Example 39 was added thereto and incubated at 22° C. for 40 minutes for conjugating the drug linker to the antibody. Next, an aqueous solution (0.0118 mL; 18.4 equivalents per antibody molecule) of 100 mM NAC (Sigma-Aldrich Co. LLC) was added thereto and incubated at 22° C. for another 20 minutes to terminate the reaction of drug linker.

Purification: The above solution was subjected to purification using the Common procedure D-1 (PBS7.4 was used as buffer solution) described in Production method 1 to yield 6 mL of a solution containing the titled antibody-drug conjugate.

Physicochemical characterization: By using the Common procedure E described in Production method 1 (as molar absorption coefficient, $\epsilon_{A,280}$=235300 (calculation value), $\epsilon_{A,370}$=0 (calculation value), $\epsilon_{D,280}$=5000 (measured average value), and $\epsilon_{D,370}$=19000 (measured average value) were used), the following characteristics values were obtained.

Antibody concentration: 1.00 mg/mL, antibody yield: 6.00 mg (60%), and average number of conjugated drug molecules (n) per antibody molecule: 3.4.

(Test Example 1) Production of Full-Length Human B7-H3 Variant 1 Expression Vector cDNA encoding human B7-H3 variant 1 was amplified by PCR reaction using cDNA synthesized from LNCaP cell (American Type Culture Collection: ATCC) total RNA as a template and the following primer set:

primer 1:
5'-ctataggagacccaagctggctagcatgctgcgtcggcggggcag-3' (SEQ ID NO: 22) and
primer 2:
5'-aacgggccctctagactcgagcggccgctcaggctatttcttgtccat-catcttctt tgctgtcag-3' (SEQ ID NO: 23).

Next, the obtained PCR product was purified by using MagExtractor PCR & Gel cleanup (Toyobo Co., Ltd.). The purified product was further digested with restriction enzymes (NheI/NotI) and thereafter purified by using MagExtractor PCR & Gel cleanup (Toyobo Co., Ltd.). pcDNA3.1 (+) plasmid DNA (Life Technologies) was digested with the same restriction enzymes as above (NheI/NotI) and thereafter purified by using MagExtractor PCR & Gel cleanup (Toyobo Co., Ltd.).

These purified DNA solutions were mixed, further charged with Ligation high (Toyobo Co., Ltd.), and incubated at 16° C. for 8 hours for ligation.

Escherichia coli DH5α competent cells (Life Technologies) were transformed by the addition of the obtained reaction product.

The colonies thus obtained were subjected to colony direct PCR using PCR primers and BGH reverse primer to select candidate clones.

The obtained candidate clones were cultured in a liquid medium (LB/Amp), and plasmid DNA was extracted with MagExtractor-Plasmid- (Toyobo Co., Ltd.).

Each obtained clone was compared with the provided CDS sequence by the sequencing analysis between primer 3 (CMV promoter primer):
5'-cgcaaatgggcggtaggcgtg-3' (SEQ ID NO: 24) and primer 4 (BGH reverse primer):
5'-tagaaggcacagtcgagg-3' (SEQ ID NO: 25) with the obtained plasmid DNA as a template.

After confirming the sequence, the obtained clone was cultured in 200 mL of LB/Amp medium, and plasmid DNA was extracted by using VioGene Plasmid Midi V-100 kit.

The vector was designated as pcDNA3.1-B7-H3. The sequence of an ORF site of the B7-H3 variant 1 gene cloned in the vector is shown in nucleotide positions 1 to 1602 of SEQ ID NO: 26 (FIG. 16) in the Sequence Listing. Also, the amino acid sequence of the B7-H3 variant 1 is shown in SEQ ID NO: 1 in the Sequence Listing.

(Test Example 2) Preparation of CCRF-CEM Cell Stably Expressing B7-H3 Variant 1 Gene pcDNA3.1-B7-H3 produced in Test Example 1 was transfected into CCRF-CEM cells (ATCC) by electroporation using Nucleofector II (manufactured by Lonza Group Ltd.). Then, the cells were further cultured for two nights in RPMI1640 medium (Life Technologies) containing 10% fetal bovine serum (FBS) (hereinafter, referred to as 10% FBS-RPMI1640) under conditions of 37° C. and 5% $CO_2$.

After the 2-day culture, culture was started in 10% FBS-RPMI1640 containing 750 µg/mL G418 (Life Technologies) in order to select CCRF-CEM cells in which pcDNA3.1-B7-H3 was stably integrated.

After the 1-month culture, cloning was carried out by the limiting dilution method in order to yield a single cell clone. Specifically, cells having resistance to G418 were diluted into 10 cells/mL, inoculated to a 96-well plate at a concentration of 100 µL/well, and cultured, and cells allowed to proliferate were recovered from individual wells.

Flow cytometry was used for confirming B7-H3 expression in each recovered clone. Specifically, each recovered clone was washed twice with PBS containing 5% FBS, thereafter suspended by the addition of PBS containing 5% FBS and 10 µg/mL M30, and left standing at 4° C. for 30 minutes. The clone was washed twice with PBS containing 5% FBS, thereafter suspended by the addition of Fluorescein-conjugated goat IgG fraction to mouse IgG (Whole Molecule) (#55493, manufactured by ICN Pharmaceuticals, Inc.) diluted 1000-fold with PBS containing 5% FBS, and left standing at 4° C. for 30 minutes. The clone was washed twice with PBS containing 5% FBS, thereafter resuspended in PBS containing 5% FBS, and detected by using a flow cytometer (FC500: Beckman Coulter, Inc.).

The CCRF-CEM cells stably expressing the B7-H3 variant 1 gene thus obtained by these procedures were designated as CEM_V1_3.1_2 cells. The parent line CCRF-CEM cells were used as a cell line lacking B7-H3 expression.

(Test Example 3) Cell Growth Inhibition Assay (1) of Antibody-Drug Conjugate

The CEM_V1_3.1_2 cells produced in Test Example 2 or CCRF-CEM cells (ATCC) were cultured in RPMI1640 (GIBCO) containing 10% fetal bovine serum (MOREGATE) (hereinafter, referred to as a medium). The CEM_V1_3.1_2 cells or CCRF-CEM cells were prepared to have a concentration of $8\times10^4$ cells/mL by using a medium, added at a concentration of 25 µL/well to a 96-well microplate for cell culture charged with 65 µL/well of a medium, and cultured overnight. On the next day, the M30-H1-L4 antibody, M30-H1-L4P antibody, and antibody-drug conjugate each diluted into 1000 nM, 200 nM, 40 nM, 8 nM, 1.6 nM, 0.32 nM, and 0.064 nM by using a medium were added at a concentration of 10 µL/well to the microplate. A medium was added at a concentration of 10 µL/well to test substance non-supplemented wells. The cells were cultured under 5% $CO_2$ at 37° C. for 3 days. After the culture, the microplate was taken out of the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$$IC_{50}\ (nM)=\text{antilog}((50-d)\times(LOG_{10}b-LOG_{10}a)/(d-c)+LOG_{10}b)$$

a: Concentration a of the test substance
b: Concentration b of the test substance
c: Ratio of live cells supplemented with the test substance having the concentration a
d: Ratio of live cells supplemented with the test substance having the concentration b The concentrations a and b establish the relation a>b crossing 50% ratio of live cells.

The survival rate of cells at each concentration was calculated according to the following equation:

Survival rate of cells (%)=a/b×100 a: Average amount of light emission from the test substance-supplemented wells (n=2)
b: Average amount of light emission from the test substance non-supplemented wells (n=10)

The antibody-drug conjugates (6) and (23) exhibited an anticellular effect of $IC_{50}<0.1$ (nM) against the CEM_V1_3.1_2 cells. The antibody-drug conjugates (3), (33), and (39) exhibited an anticellular effect of $0.1<IC_{50}<1$ (nM) against the cells. The antibody-drug conjugates (13), (14), (15), (16), (17), (20), (30), (35), and (37) exhibited an anticellular effect of $1<IC_{50}<100$ (nM) against the cells. On the other hand, none of the antibody-drug conjugates exhibited an anticellular effect against the CCRF-CEM cells (>100 (nM)). Neither of the M30-H1-L4 antibody nor the M30-H1-L4P antibody exhibited a cytotoxic activity against both of the cells (>100 (nM)).

(Test Example 4) Cell Growth Inhibition Assay (2) of Antibody-Drug Conjugate

Antigen-positive cells SR cells (ATCC) or antigen-negative cells Daudi cells (ATCC) were cultured in RPMI1640 (GIBCO) containing 10% fetal bovine serum (MOREGATE) (hereinafter, referred to as a medium). The SR cells or Daudi cells were prepared to have a concentration of $2.8\times10^4$ cells/mL by using a medium and added at a concentration of 90 µL/well to a 96-well microplate for cell culture. Two hours later, the anti-CD30 antibody and antibody-drug conjugates (7), (8), (24), and (25) each diluted into 40 nM, 8 nM, 1.6 nM, 320 pM, 64 pM, 12.8 pM, and 2.6 pM by using a medium were added at a concentration of 10 µL/well to the microplate. A medium was added at a concentration of 10 µL/well to test substance non-supplemented wells. The cells were cultured under 5% $CO_2$ at 37° C. for 3 days. After the culture, the microplate was taken out of the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$$IC_{50}\ (nM)=\text{antilog}((50-d)\times(LOG_{10}b-LOG_{10}a)/(d-c)+LOG_{10}b)$$

a: Concentration a of the test substance
b: Concentration b of the test substance
c: Ratio of live cells supplemented with the test substance having the concentration a d: Ratio of live cells supplemented with the test substance having the concentration b The concentrations a and b establish the relation a>b crossing 50% ratio of live cells.

The survival rate of cells at each concentration was calculated according to the following equation:

Survival rate of cells (%)=$a/b$×100 a: Average amount of light emission from the test substance-supplemented wells (n=2)
b: Average amount of light emission from the test substance non-supplemented wells (n=12)

The antibody-drug conjugates (7), (8), (24), and (25) exhibited an anticellular effect of $IC_{50}$<0.01 (nM) against the SR cells. On the other hand, none of the antibody-drug conjugates exhibited an anticellular effect against the Daudi cells (>4.0 (nM)). The anti-CD30 antibody exhibited no anticellular effect against both of the cells (>4.0 (nM)).

(Test Example 5) Cell Growth Inhibition Assay (3) of Antibody-Drug Conjugate

Antigen-positive cells HL-60 cells (ATCC) or antigen-negative cells Raji cells (ATCC) were cultured in RPMI1640 (GIBCO) containing 10% fetal bovine serum (MOREGATE) (hereinafter, referred to as a medium). The HL-60 cells or Raji cells were prepared to have a concentration of 8×10$^4$ cells/mL by using a medium and added at a concentration of 25 μL/well to a 96-well microplate for cell culture containing 65 μL/well of medium. The anti-CD33 antibody and antibody-drug conjugates (9), (10), (26), and (27) each diluted into 1000 nM, 200 nM, 40 nM, 8 nM, 1.6 nM, 0.32 nM, and 0.064 nM by using a medium were added at a concentration of 10 μL/well to the microplate. A medium was added at a concentration of 10 μL/well to test substance non-supplemented wells. The cells were cultured under 5% $CO_2$ at 37° C. for 3 days. After the culture, the microplate was taken out of the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$IC_{50}$ (nM)=antilog((50−$d$)×($LOG_{10}b$−$LOG_{10}a$)/($d$−$c$)+$LOG_{10}b$)

a: Concentration a of the test substance
b: Concentration b of the test substance
c: Ratio of live cells supplemented with the test substance having the concentration a
d: Ratio of live cells supplemented with the test substance having the concentration b The concentrations a and b establish the relation a>b crossing 50% ratio of live cells.

The survival rate of cells at each concentration was calculated according to the following equation:

Survival rate of cells (%)=$a/b$×100 a: Average amount of light emission from the test substance-supplemented wells (n=2)
b: Average amount of light emission from the test substance non-supplemented wells (n=5)

The antibody-drug conjugate (10) exhibited a cytotoxic effect of $IC_{50}$<1 (nM) against the HL-60 cells. The antibody-drug conjugates (9), (26), and (27) exhibited an anticellular effect of 1<$IC_{50}$<100 (nM) On the other hand, all of the antibody-drug conjugates exhibited no anticellular effect against the Raji cells (>100 (nM)). The anti-CD33 antibody exhibited no anticellular effect against both of the cells (>100 (nM)).

(Test Example 6) Cytotoxicity Test (4) of Antibody-Drug Conjugate

Antigen-positive cells U251 cells (ATCC) or antigen-negative cells MCF-7 cells (ATCC) were cultured in RPMI1640 (GIBCO) containing 10% fetal bovine serum (MOREGATE) (hereinafter, referred to as a medium). U251 cells and MCF-7 cells were prepared to have a concentration of 2.8×10$^4$ cells/mL by using a medium and added at a concentration of 90 L/well to a 96-well microplate for cell culture, and cultured overnight. On the next day, the anti-CD70 antibody and antibody-drug conjugates (11), (12), (28), and (29) each diluted into 1000 nM, 200 nM, 40 nM, 8 nM, 1.6 nM, 0.32 nM, and 0.064 nM by using a medium were added at a concentration of 10 μL/well to the microplate. A medium was added at a concentration of 10 μL/well to test substance non-supplemented wells. The cells were cultured under 5% $CO_2$ at 37° C. for 6 days. After the culture, the microplate was taken out of the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$IC_{50}$ (nM)=antilog((50−$d$)×($LOG_{10}b$−$LOG_{10}a$)/($d$−$c$)+$LOG_{10}b$)

a: Concentration a of the test substance
b: Concentration b of the test substance
c: Ratio of live cells supplemented with the test substance having the concentration a
d: Ratio of live cells supplemented with the test substance having the concentration b The concentrations a and b establish the relation a>b crossing 50% ratio of live cells.

The survival rate of cells at each concentration was calculated according to the following equation:

Survival rate of cells (%)=$a/b$×100 a: Average amount of light emission from the test substance-supplemented wells (n=2)
b: Average amount of light emission from the test substance non-supplemented wells (n=12)

The antibody-drug conjugate (12) and (29) exhibited a cytotoxic effect of 1<$IC_{50}$<10 (nM) against the U251 cells. The antibody-drug conjugates (11) and (28) exhibited a cytotoxic effect of 10<$IC_{50}$<100 (nM). On the other hand, all of the antibody-drug conjugates exhibited no cytotoxic effect against the MCF-7 cells (≥90 (nM)). The anti-CD70 antibody exhibited no cytotoxic effect against both of the cells (>100 (nM)).

(Test Example 7) Antitumor Test (1)

Mouse: 5- to 6-week-old female BALB/c nude mice (Charles River Laboratories Japan, Inc.) were acclimatized for 4 to 7 days under SPF conditions before use in the experiment. The mice were fed with sterilized solid feed (FR-2, Funabashi Farms Co., Ltd) and given sterilized tap water (prepared by the addition of 5 to 15 ppm sodium hypochlorite solution).

Assay and calculation expression: In all studies, the major axis and minor axis of tumor were measured twice a week by using an electronic digital caliper (CD-15C, Mitutoyo Corp.), and the tumor volume (mm$^3$) was calculated. The calculation expression is as shown below.

Tumor volume (mm$^3$)=½×Major axis (mm)×[Minor axis (mm)]$^2$

All of the antibody-drug conjugates were diluted with physiological saline (Otsuka Pharmaceutical Factory, Inc.) and used at a volume of 10 mL/kg for intravenous administration to the tail of each mouse. Human melanoma line A375 cells were purchased from ATCC (American Type Culture Collection). 8×10$^6$ cells suspended in physiological saline were subcutaneously transplanted to the right abdomen of each female nude mouse (Day 0), and the mice were randomly grouped at Day 11. The M30-H1-L4P antibody and antibody-drug conjugate (1), (2), (18), and (19) were each intravenously administered at a dose of 10 mg/kg to the tail of each mouse at Days 11, 18, and 25 in a schedule of qw×3.

The results are shown in FIG. 17. In the drawing, the line with open rhombuses depicts the results about untreated tumor, the line with filled rhombuses depicts the effect of the M30-H1-L4P antibody, the line with filled squares depicts the effect of the administered antibody-drug conjugate (1), the line with open squares depicts the effect of the administered antibody-drug conjugate (2), the line with filled triangles depicts the effect of the administered antibody-drug conjugate (18), and the line with open triangles depicts the effect of the administered antibody-drug conjugate (19).

The administration of the antibody-drug conjugate (1), (2), (18), or (19) remarkably decreased the tumor volume. Particularly, as a result of the administration of the antibody-drug conjugate (2) or (19), the tumor completely regressed by Day 18 and was not confirmed to recur even after Day 39.

In addition, the mice that received the antibody-drug conjugate (1), (2), (18), or (19) were free from notable signs such as weight loss, suggesting that these antibody-drug conjugates are low toxic and highly safe.

(Test Example 8) Antitumor Test (2)

Human melanoma line A375 cells were purchased from ATCC (American Type Culture Collection). 6×10$^6$ cells suspended in physiological saline were subcutaneously transplanted to the right abdomen of each female nude mouse (Day 0), and the mice were randomly grouped at Day 18. The antibody-drug conjugate (2) and (19) were each intravenously administered at a dose of 1.3 mg/kg to the tail of each mouse at Days 18, 25, and 32 in a schedule of qw×3.

Figure 18:
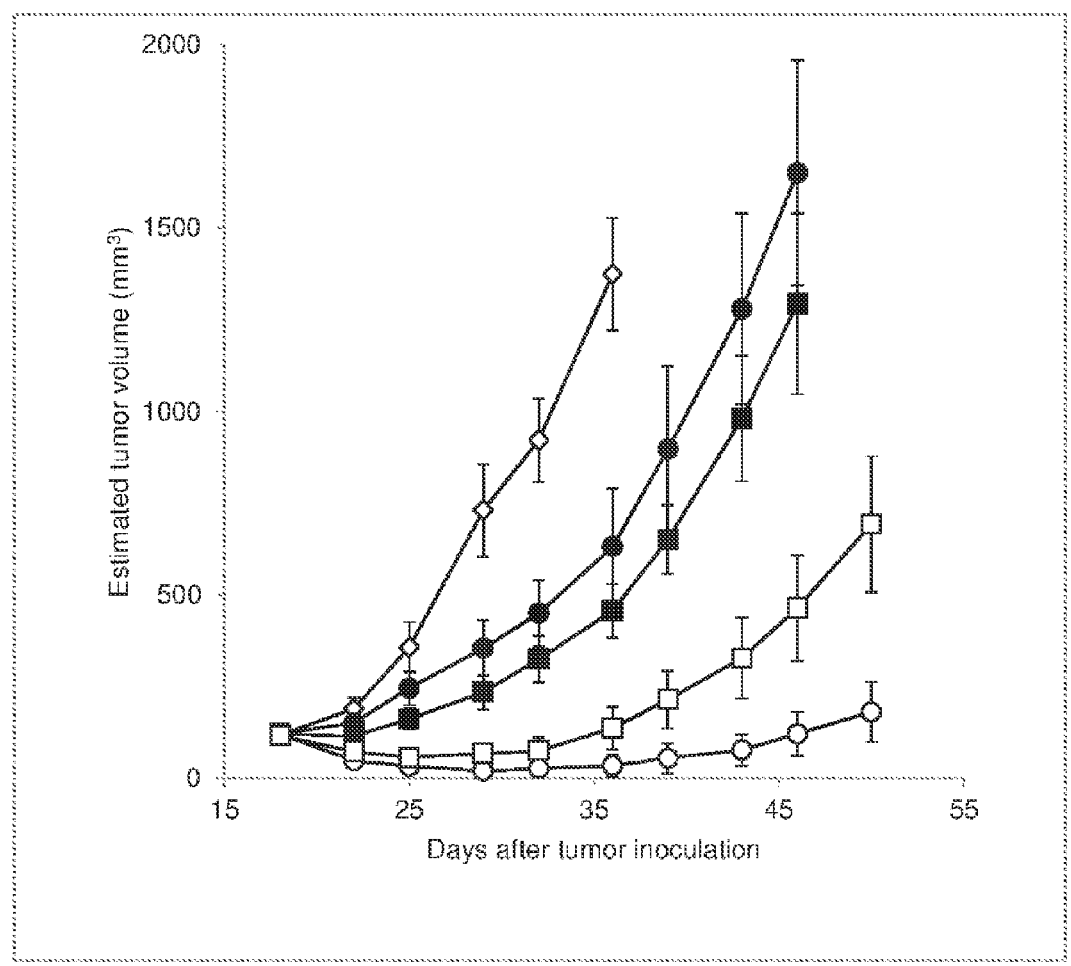
FIG. 18 shows the effects of the antibody-drug conjugates (2) and (19) administered at 1 mg/kg and 3 mg/kg on human melanoma line A375 cells transplanted in mice. The line with open rhombuses depicts results about untreated tumor, the line with filled squares depicts the effect of the antibody-drug conjugate (2) administered at 1 mg/kg, the line with open squares depicts the effect of the antibody-drug conjugate (2) administered at 3 mg/kg, the line with filled circles depicts the effect of the antibody-drug conjugate (19) administered at 1 mg/kg, and the line with open circles depicts the effect of the antibody-drug conjugate (19) administered at 3 mg/kg.

The results are shown in FIG. 18. In the drawing, the line with open rhombuses depicts the results about untreated tumor, the line with filled squares depicts the effect of the antibody-drug conjugate (2) administered at 1 mg/kg, the line with open squares depicts the effect of the antibody-drug conjugate (2) administered at 3 mg/kg, the line with filled circles depicts the effect of the antibody-drug conjugate (19) administered at 1 mg/kg, and the line with open circles depicts the effect of the antibody-drug conjugate (19) administered at 3 mg/kg. The antibody-drug conjugates (2) and (19) exhibited a tumor growth inhibitory effect in a dose-dependent manner.

(Test Example 9) Antitumor Test (3)

Human non-small cell lung cancer line Calu-6 cells were purchased from ATCC (American Type Culture Collection).

5×10$^6$ cells suspended in physiological saline were subcutaneously transplanted to the right abdomen of each female nude mouse (Day 0), and the mice were randomly grouped at Day 11. The M30-H1-L4P antibody and antibody-drug conjugate (1), (2), (18), or (19) were each intravenously administered at a dose of 10 mg/kg to the tail of each mouse at Days 11, 18, and 25 in a schedule of qw×3.

Figure 19:
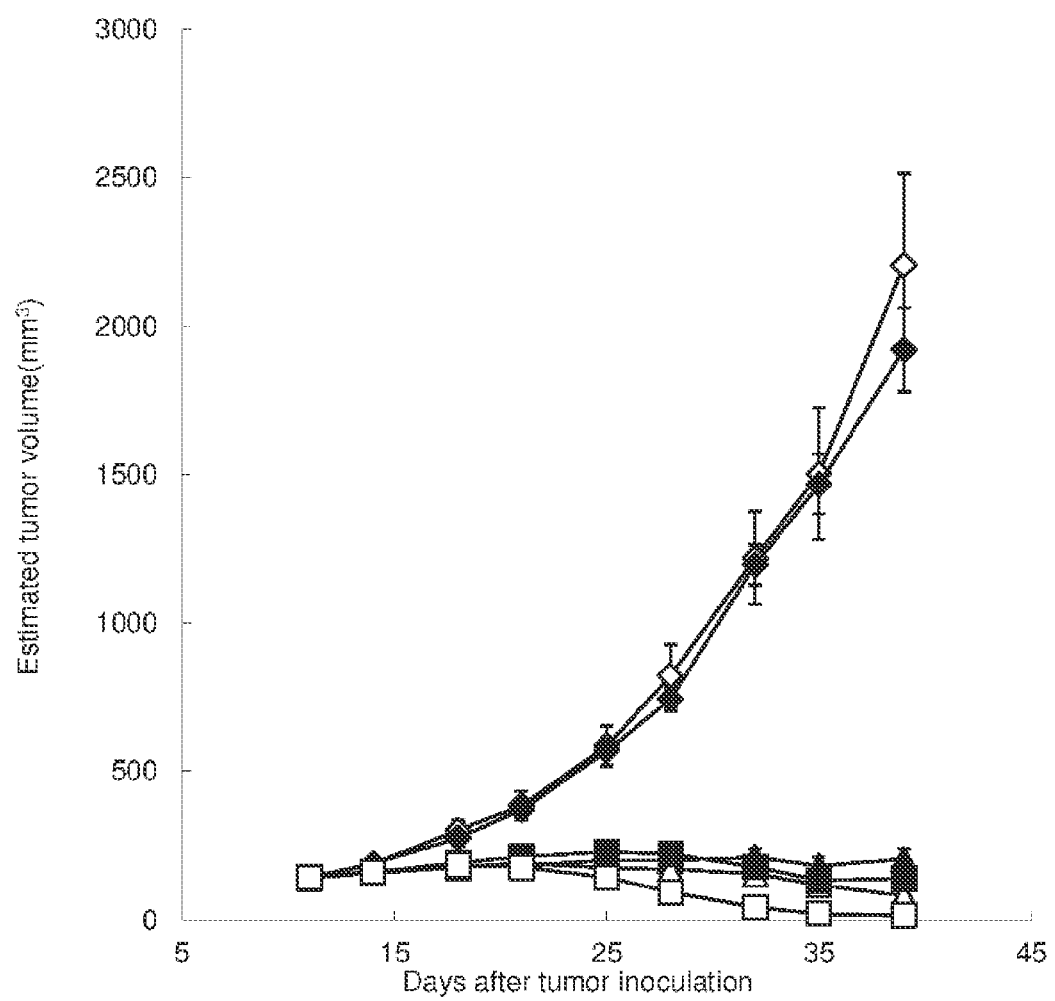
FIG. 19 shows the effects of an M30-H1-L4P antibody and the antibody-drug conjugates (1), (2), (18), and (19) administered at 10 mg/kg on human non-small cell lung cancer line Calu-6 cells transplanted in mice. The line with open rhombuses depicts results about untreated tumor, the line with filled rhombuses depicts the effect of the M30-H1-L4P antibody, the line with filled squares depicts the effect of the antibody-drug conjugate (1), the line with open squares depicts the effect of the antibody-drug conjugate (2), the line with filled triangles depicts the effect of the antibody-drug conjugate (18), and the line with open triangles depicts the effect of the antibody-drug conjugate (19).

The results are shown in FIG. 19. In the drawing, the line with open rhombuses depicts the results about untreated tumor, the line with filled rhombuses depicts the effect of the M30-H1-L4P antibody, the line with filled squares depicts the effect of the administered antibody-drug conjugate (1), the line with open squares depicts the effect of the administered antibody-drug conjugate (2), the line with filled triangles depicts the effect of the administered antibody-drug conjugate (18), and the line with open triangles depicts the effect of the administered antibody-drug conjugate (19).

The administration of the antibody-drug conjugate (1), (2), (18), or (19) remarkably decreased the tumor volume, and no further tumor growth was observed after the final administration.

In addition, the mice that received the antibody-drug conjugate (1), (2), (18), or (19) were free from notable signs such as weight loss, suggesting that these antibody-drug conjugates are low toxic and highly safe.

(Test Example 10) Antitumor Test (4)

Human melanoma line A375 cells were purchased from ATCC (American Type Culture Collection). 8×10$^6$ cells suspended in physiological saline were subcutaneously transplanted to the right abdomen of each female nude mouse (Day 0), and the mice were randomly grouped at Day 14. The antibody-drug conjugates (3), (20), and (30) were each intravenously administered at each dose (3 and 10 mg/kg) to the tail of each mouse at Day 14 in a schedule of qd×1.

Figure 20:
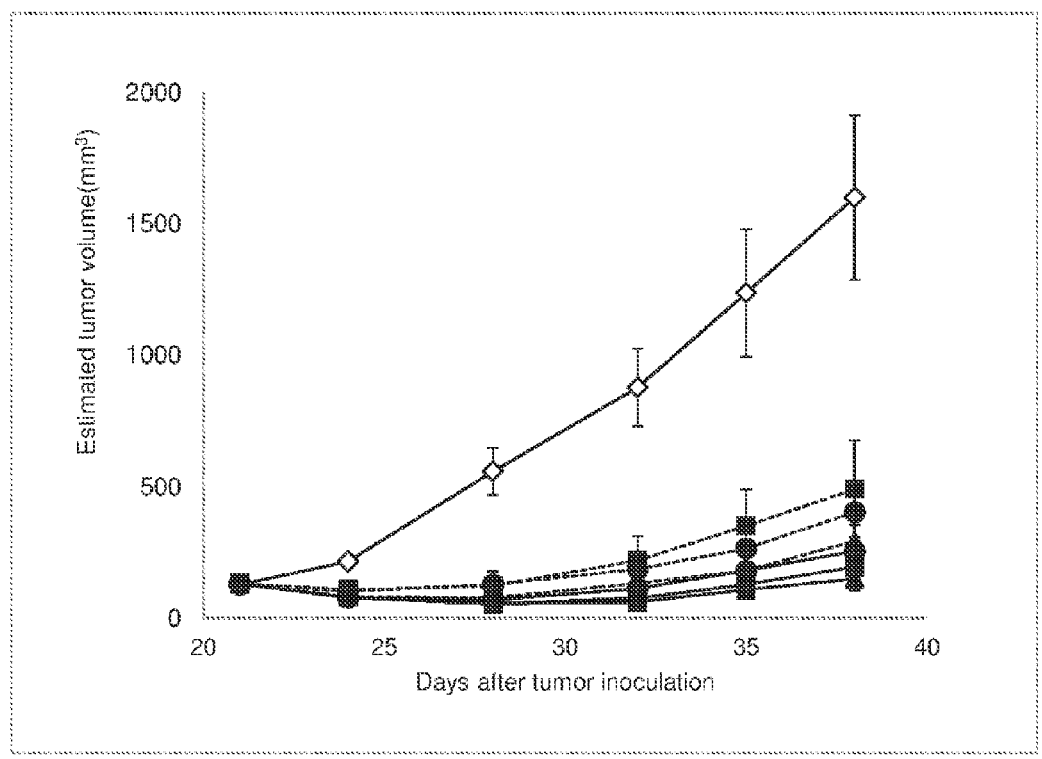
FIG. 20 shows the effects of antibody-drug conjugates (3), (20), and (30) administered at 3 mg/kg and 10 mg/kg on human melanoma line A375 cells transplanted in mice. The line with open rhombuses depicts results about untreated tumor, the dotted line with filled squares depicts the effect of the antibody-drug conjugate (3) administered at 3 mg/kg, the solid line with filled squares depicts the effect of the antibody-drug conjugate (3) administered at 10 mg/kg, the dotted line with filled triangles depicts the effect of the antibody-drug conjugate (20) administered at 3 mg/kg, the solid line with filled triangles depicts the effect of the antibody-drug conjugate (20) administered at 10 mg/kg, the dotted line with filled circles depicts the effect of the antibody-drug conjugate (30) administered at 3 mg/kg, and the solid line with filled circles depicts the effect of the antibody-drug conjugate (30) administered at 10 mg/kg.

The results are shown in FIG. 20. In the drawing, the line with open rhombuses depicts the results about untreated tumor, the dotted line with filled squares depicts the effect of the antibody-drug conjugate (3) administered at 3 mg/kg, the solid line with filled squares depicts the effect of the antibody-drug conjugate (3) administered at 10 mg/kg, the dotted line with filled triangles depicts the effect of the antibody-drug conjugate (20) administered at 3 mg/kg, the solid line with filled triangles depicts the effect of the antibody-drug conjugate (20) administered at 10 mg/kg, the dotted line with filled circles depicts the effect of the antibody-drug conjugate (30) administered at 3 mg/kg, and the solid line with filled circles depicts the effect of the antibody-drug conjugate (30) administered at 10 mg/kg.

The administration of the antibody-drug conjugate (3), (20), or (30) remarkably decreased the tumor volume, and all of these antibody-drug conjugates exerted a tumor growth inhibitory effect in a dose-dependent manner.

In addition, the mice that received the antibody-drug conjugate (3), (20), or (30) were free from notable signs such as weight loss, suggesting that these antibody-drug conjugates are low toxic and highly safe.

FREE TEXT OF SEQUENCE LISTING

SEQ ID NO: 1—Amino acid sequence of the B7-H3 variant 1
SEQ ID NO: 2—Amino acid sequence of the B7-H3 variant 2

SEQ ID NO: 3—Amino acid sequence of CDRH1 of the M30 antibody
SEQ ID NO: 4—Amino acid sequence of CDRH2 of the M30 antibody
SEQ ID NO: 5—Amino acid sequence of CDRH3 of the M30 antibody
SEQ ID NO: 6—Amino acid sequence of CDRL1 of the M30 antibody
SEQ ID NO: 7—Amino acid sequence of CDRL2 of the M30 antibody
SEQ ID NO: 8—Amino acid sequence of CDRL3 of the M30 antibody
SEQ ID NO: 9—Amino acid sequence of the M30-H1-type heavy chain
SEQ ID NO: 10—Amino acid sequence of the M30-H2-type heavy chain
SEQ ID NO: 11—Amino acid sequence of the M30-H3-type heavy chain
SEQ ID NO: 12—Amino acid sequence of the M30-H4-type heavy chain
SEQ ID NO: 13—Amino acid sequence of the M30-L1-type light chain
SEQ ID NO: 14—Amino acid sequence of the M30-L2-type light chain
SEQ ID NO: 15—Amino acid sequence of the M30-L3-type light chain
SEQ ID NO: 16—Amino acid sequence of the M30-L4-type light chain
SEQ ID NO: 17—Amino acid sequence of the M30-L5-type light chain
SEQ ID NO: 18—Amino acid sequence of the M30-L6-type light chain
SEQ ID NO: 19—Amino acid sequence of the M30-L7-type light chain
SEQ ID NO: 20—Amino acid sequence of a heavy chain of the M30 antibody
SEQ ID NO: 21—Amino acid sequence of a light chain of the M30 antibody
SEQ ID NO: 22—PCR primer 1
SEQ ID NO: 23—PCR primer 2
SEQ ID NO: 24—CMV promoter primer: primer 3
SEQ ID NO: 25—BGH reverse primer: primer 4
SEQ ID NO: 26—Nucleotide sequence of the B7-H3 variant 1
SEQ ID NO: 27—Amino acid sequence of a heavy chain of the anti-CD30 antibody
SEQ ID NO: 28—Amino acid sequence of a light chain of the anti-CD30 antibody
SEQ ID NO: 29—Amino acid sequence of a heavy chain of the anti-CD33 antibody
SEQ ID NO: 30—Amino acid sequence of a light chain of the anti-CD33 antibody
SEQ ID NO: 31—Amino acid sequence of a heavy chain of the anti-CD70 antibody
SEQ ID NO: 32—Amino acid sequence of a light chain of the anti-CD70 antibody

The invention claimed is:
1. An antibody-drug conjugate comprising an antitumor compound represented by the following formula:

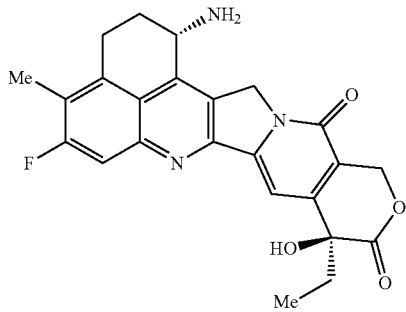 [SMILES: CC[C@@]1(O)C(=O)OCc2c1cc1n(c2=O)Cc2c-1nc1cc(F)c(C)c3c1c2[C@@H](N)CC3]

wherein the antitumor compound is conjugated to an antibody via a linker having a structure represented by the following formula:
-$L^1$-$L^2$-$L^P$-NH—($CH_2$)$n^1$-$L^a$-$L^b$-$L^c$- or -$L^1$-$L^2$-$L^P$-
wherein the antibody is connected to the terminal of $L^1$, the antitumor compound is connected to the terminal of $L^c$ or $L^P$,
wherein
$n^1$ represents an integer of 0 to 6,
$L^1$ represents -(Succinimid-3-yl-N)—($CH_2$)$n^2$-C(=O)—, -(Succinimid-3-yl-N)—CH[—($CH_2$)$n^3$-COOH]—C(=O)—, —$CH_2$—C(=O)—NH—($CH_2$)$n^4$-C(=O)—,
—C(=O)-cyc.Hex(1,4)-$CH_2$—(N-ly-3-Succinimid)-, or —C(=O)—($CH_2$)$n^5$-C(=O)—,
wherein $n^2$ represents an integer of 2 to 8, $n^3$ represents an integer of 1 to 8, $n^4$ represents an integer of 1 to 8, $n^5$ represents an integer of 1 to 8,
$L^2$ represents —NH—($CH_2$—$CH_2$—O)$n^6$-$CH_2$—$CH_2$—C(=O)—, —N[—($CH_2CH_2$—O)$n^7$-$CH_2CH_2$—OH]—$CH_2$—C(=O)—, —S—($CH_2$)$n^8$-C(=O)—, or a single bond,
wherein $n^6$ represents an integer of 0 to 6, $n^7$ represents an integer of 1 to 4, $n^8$ represents an integer of 1 to 6,
$L^P$ represents: (i) a peptide residue consisting of 3 to 8 amino acids wherein the peptide residue has a hydrophilic amino acid other than glycine at the N terminal, or (ii) a peptide residue comprising GGFGG (SEQ ID NO: 40) or GGFGGG (SEQ ID NO: 41),
$L^a$ represents —C(=O)—NH—, —$NR^1$—($CH_2$)$n^9$-, —O—, or a single bond,
wherein $n^9$ represents an integer of 1 to 6, $R^1$ represents a hydrogen atom, an alkyl group having 1 to 6 carbon atoms, —($CH_2$)$n^a$-COOH, or —($CH_2$)$n^b$-OH, $n^a$ represents an integer of 1 to 4, $n^b$ represents an integer of 1 to 6,
$L^b$ represents —$CR^2$(—$R^3$)—, —O—, —$NR^4$—, or a single bond,
wherein $R^2$ and $R^3$ each independently represent a hydrogen atom, an alkyl group having 1 to 6 carbon atoms, —($CH_2$)$n^c$-$NH_2$, —($CH_2$)$n^d$-COOH, or —($CH_2$)$n^e$-OH, $R^4$ represents a hydrogen atom or an alkyl group having 1 to 6 carbon atoms, $n^c$ represents an integer of 0 to 6, $n^d$ represents an integer of 1 to 4, $n^e$ represents an integer of 1 to 4, provided that when $n^c$ is 0, $R^2$ and $R^3$ are not the same as each other,
$L^c$ represents —$CH_2$— or —C(=O)—,
-(Succinimid-3-yl-N)— has a structure represented by the following formula:

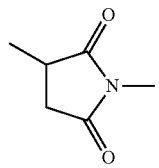

which is connected to the antibody at position 3 thereof and is connected to a methylene group in the linker structure containing this structure on the nitrogen atom at position 1,
—(N-ly-3-Succinimid)- has a structure represented by the following formula:

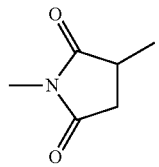

which is connected to $L^2$ at position 3 thereof and is connected to a methylene group in the linker structure containing this structure on the nitrogen atom at position 1,
cyc.Hex(1,4) represents a 1,4-cyclohexylene group,
when $L^2$ is —S—($CH_2$)$n^8$-C(=O)—, $L^1$ is —C(=O)-cyc.Hex(1,4)-$CH_2$—(N-ly-3-Succinimid)-.
2. The antibody-drug conjugate according to claim 1, wherein
$L^1$ is -(Succinimid-3-yl-N)—($CH_2$)$n^2$-C(=O)—, -(Succinimid-3-yl-N)—CH[—($CH_2$)$n^3$-COOH]—C(=O)—, or —$CH_2$—C(=O)—NH—($CH_2$)$n^4$-C(=O)—,
wherein $n^2$ represents an integer of 2 to 8, $n^3$ represents an integer of 1 to 8, $n^4$ represents an integer of 1 to 8,
$L^2$ is —NH—($CH_2$—$CH_2$—O)$n^6$-$CH_2$—$CH_2$—C(=O)—, —N[—($CH_2CH_2$—O)$n^7$-$CH_2CH_2$—OH]—$CH_2$—C(=O)—, or a single bond,
wherein $n^6$ represents an integer of 0 to 6, $n^7$ represents an integer of 1 to 4,
$L^P$ is (i) a peptide residue consisting of 3 to 8 amino acids wherein the peptide residue has a hydrophilic amino acid other than glycine at the N terminal, or (ii) a peptide residue comprising GGFGG (SEQ ID NO: 40) or GGFGGG (SEQ ID NO: 41), each of $L^a$ and $L^b$ is a single bond, and
$L^c$ is —C(=O)—.

3. The antibody-drug conjugate according to claim 1, wherein $L^P$ is a peptide residue having a hydrophilic amino acid other than glycine at the N terminal.

4. The antibody-drug conjugate according to claim 3, wherein the hydrophilic amino acid other than glycine is aspartic acid, glutamic acid, lysine, serine, threonine, glutamine, asparagine, histidine, tyrosine, or arginine.

5. The antibody-drug conjugate according to claim 3, wherein the N-terminal hydrophilic amino acid other than glycine in $L^P$ is glutamic acid, aspartic acid, or lysine.

6. The antibody-drug conjugate according to claim 4, wherein the peptide residue following the N-terminal hydrophilic amino acid in $L^P$ is an amino acid residue comprising an amino acid selected from phenylalanine, glycine, valine, lysine, citrulline, serine, glutamic acid, and aspartic acid.

7. The antibody-drug conjugate according to claim 6, wherein a peptide residue following the N-terminal hydrophilic amino acid in $L^P$ is a peptide residue consisting of 3 or 4 amino acids.

8. The antibody-drug conjugate according to claim 7, wherein the peptide residue following the N-terminal hydrophilic amino acid in $L^P$ is GGF or GGFG (SEQ ID NO. 33).

9. The antibody-drug conjugate according to claim 8, wherein $L^P$ is DGGF (SEQ ID NO. 34), KGGF (SEQ ID NO. 35), EGGF (SEQ ID NO. 36), DGGFG (SEQ ID NO. 37), KGGFG (SEQ ID NO. 38), or EGGFG (SEQ ID NO. 39).

10. The antibody-drug conjugate according to claim 8, wherein $L^P$ is DGGFG (SEQ ID NO. 37), KGGFG (SEQ ID NO. 38), or EGGFG (SEQ ID NO. 39).

11. The antibody-drug conjugate according to any one of claims 1 to 10, wherein the linker is a linker having a structure represented by -$L^1$-$L^2$-$L^P$-NH—(CH$_2$)n$^1$-$L^a$-$L^b$-$L^c$-.

12. The antibody-drug conjugate according to claim 11, wherein $L^c$ is —C(=O)—.

13. The antibody-drug conjugate according to claim 12, wherein $L^1$ is -(Succinimid-3-yl-N)—(CH$_2$)n$^2$-C(=O)—, n$^2$ is an integer of 2 to 5, and $L^2$ is a single bond.

14. The antibody-drug conjugate according to claim 13, wherein n$^2$ is 5.

15. The antibody-drug conjugate according to claim 14, wherein n$^1$ is 1 to 3.

16. The antibody-drug conjugate according to claim 15, wherein the structure of the —NH—(CH$_2$)n$^1$-$L^a$-$L^b$-$L^c$- moiety in the linker is
—NH—CH$_2$—C(=O)—,
—NH—(CH$_2$)$_2$—C(=O)—,
—NH—(CH$_2$)$_3$—C(=O)—,
—NH—CH$_2$—O—CH$_2$—C(=O)—, or
—NH—(CH$_2$)$_2$—O—CH$_2$—C(=O)—.

17. The antibody-drug conjugate according to claim 15, wherein
the structure of the —NH—(CH$_2$)n$^1$-$L^a$-$L^b$-$L^c$- moiety in the linker is
—NH—CH$_2$—C(=O)—,
—NH—(CH$_2$)$_2$—C(=O)—, or
—NH—(CH$_2$)$_3$—C(=O)—.

18. The antibody-drug conjugate according to any one of claims 1 to 10, wherein the linker is a linker having a structure represented by -$L^1$-$L^2$-$L^c$-.

19. The antibody-drug conjugate according to claim 18, wherein $L^1$ is -(Succinimid-3-yl-N)—(CH$_2$)n$^2$-C(=O)—, n$^2$ is an integer of 2 to 5, and $L^2$ is a single bond.

20. The antibody-drug conjugate according to claim 19, wherein n$^2$ is 5.

21. The antibody-drug conjugate according to claim 1, wherein the peptide residue consists of 4 to 8 amino acids in the linker.

22. The antibody-drug conjugate according to claim 1, wherein $L^P$ is GGFGG (SEQ ID NO: 40) or GGFGGG (SEQ ID NO: 40).

23. The antibody-drug conjugate according to claim 22, wherein $L^1$ is -(Succinimid-3-yl-N)—(CH$_2$)n$^2$-C(=O)— and n$^2$ is an integer of 2 to 5.

24. The antibody-drug conjugate according to claim 23, wherein n$^2$ is 5.

25. The antibody-drug conjugate according to claim 22, wherein $L^1$ is -(Succinimid-3-yl-N)—CH[—(CH$_2$)n$^3$-COOH]—C(=O)—.

26. The antibody-drug conjugate according to claim 25, wherein n$^3$ is 2 or 3.

27. The antibody-drug conjugate according to claim 22, wherein $L^2$ is —N[—(CH$_2$CH$_2$—O)n$^7$-CH$_2$CH$_2$—OH]—CH$_2$—C(=O)—.

28. The antibody-drug conjugate according to claim 27, wherein n$^7$ is 2 to 4.

29. The antibody-drug conjugate according to any one of claims 25 to 28, wherein the linker is a linker having a structure represented by -$L^1$-$L^2$-$L^P$-NH—(CH$_2$)n$^1$-$L^a$-$L^b$-$L^c$-.

30. The antibody-drug conjugate according to claim 29, wherein $L^c$ is —C(=O)—.

31. The antibody-drug conjugate according to claim 30, wherein n$^1$ is 1 to 3.

32. The antibody-drug conjugate according to claim 1 or 2, wherein the drug-linker structure moiety in the antibody-drug conjugate has one structure selected from the following drug-linker structure group:

-(Succinimid-3-yl-N)—CH$_2$CH$_2$CH$_2$CH$_2$CH$_2$—C(=O)-DGGF (SEQ ID NO. 34)-NH—CH$_2$CH$_2$CH$_2$—C(=O)—(NH-DX), -(Succinimid-3-yl-N)—CH$_2$CH$_2$CH$_2$CH$_2$CH$_2$—C(=O)-DGGF (SEQ ID NO. 34)-NH—CH$_2$-O—CH$_2$—C(=O)—(NH-DX), -(Succinimid-3-yl-N)—CH$_2$CH$_2$CH$_2$CH$_2$CH$_2$—C(=O)-DGGF (SEQ ID NO. 34)-NH—CH$_2$CH$_2$—O—CH$_2$—C(=O)—(NH-DX), -(Succinimid-3-yl-N)—CH$_2$CH$_2$CH$_2$CH$_2$CH$_2$—C(=O)-DGGFG (SEQ ID NO. 37)-NH—CH$_2$CH$_2$CH$_2$—C(=O)—(NH-DX), -(Succinimid-3-yl-N)—CH$_2$CH$_2$CH$_2$CH$_2$CH$_2$—C(=O)-DGGFG (SEQ ID NO. 37)-NH—CH$_2$-O—CH$_2$—C(=O)—(NH-DX), -(Succinimid-3-yl-N)—CH$_2$CH$_2$CH$_2$CH$_2$CH$_2$—C(=O)-DGGFG (SEQ ID NO. 37)-NH—CH$_2$CH$_2$—O—CH$_2$—C(=O)—(NH-DX), -(Succinimid-3-yl-N)—CH$_2$CH$_2$CH$_2$CH$_2$CH$_2$—C(=O)-KGGF (SEQ ID NO. 35)-NH—CH$_2$CH$_2$CH$_2$—C(=O)—(NH-DX), -(Succinimid-3-yl-N)—CH$_2$CH$_2$CH$_2$CH$_2$CH$_2$—C(=O)-KGGF (SEQ ID NO. 35)-NH—CH$_2$—O—CH$_2$—C(=O)—(NH-DX), -(Succinimid-3-yl-N)—CH$_2$CH$_2$CH$_2$CH$_2$CH$_2$—C(=O)-KGGF (SEQ ID NO. 35)-NH—CH$_2$CH$_2$—O—CH$_2$—C(=O)—(NH-DX), -(Succinimid-3-yl-N)—CH$_2$CH$_2$CH$_2$CH$_2$CH$_2$—C(=O)-KGGFG (SEQ ID NO. 38)-NH—CH$_2$CH$_2$CH$_2$—C(=O)—(NH-DX), -(Succinimid-3-yl-N)—CH₂CH₂CH₂CH₂CH₂—C(=O)-KGGFG (SEQ ID NO. 38)-NH—CH₂—O—CH₂—C(=O)—(NH-DX), -(Succinimid-3-yl-N)—CH₂CH₂CH₂CH₂CH₂—C(=O)-KGGFG (SEQ ID NO. 38)-NH—CH₂CH₂—O—CH₂—C(=O)—(NH-DX),

—CH₂—C(=O)—NH—CH₂CH₂—C(=O)-DGGF (SEQ ID NO. 34)-NH—CH₂CH₂CH₂—C(=O)—(NH-DX),

—CH₂—C(=O)—NH—CH₂CH₂—C(=O)-DGGF (SEQ ID NO. 34)-NH—CH₂—O—CH₂—C(=O)—(NH-DX),

—CH₂—C(=O)—NH—CH₂CH₂—C(=O)-DGGF (SEQ ID NO. 34)-NH—CH₂CH₂—O—CH₂—C(=O)—(NH-DX),

—CH₂—C(=O)—NH—CH₂CH₂—C(=O)-DGGFG (SEQ ID NO. 37)-NH—CH₂CH₂CH₂—C(=O)—(NH-DX),

—CH₂—C(=O)—NH—CH₂CH₂—C(=O)-DGGFG (SEQ ID NO. 37)-NH—CH₂—O—CH₂—C(=O)—(NH-DX),

—CH₂—C(=O)—NH—CH₂CH₂—C(=O)-DGGFG (SEQ ID NO. 37)-NH—CH₂CH₂—O—CH₂—C(=O)—(NH-DX),

—CH₂—C(=O)—NH—CH₂CH₂—C(=O)-KGGF (SEQ ID NO. 35)-NH—CH₂CH₂CH₂—C(=O)—(NH-DX),

—CH₂—C(=O)—NH—CH₂CH₂—C(=O)-KGGF (SEQ ID NO. 35)-NH—CH₂—O—CH₂—C(=O)—(NH-DX),

—CH₂—C(=O)—NH—CH₂CH₂—C(=O)-KGGF (SEQ ID NO. 35)-NH—CH₂CH₂—O—CH₂—C(=O)—(NH-DX),

—CH₂—C(=O)—NH—CH₂CH₂—C(=O)-KGGFG (SEQ ID NO. 38)-NH—CH₂CH₂CH₂—C(=O)—(NH-DX),

—CH₂—C(=O)—NH—CH₂CH₂—C(=O)-KGGFG (SEQ ID NO. 38)-NH—CH₂—O—CH₂—C(=O)—(NH-DX),

—CH₂—C(=O)—NH—CH₂CH₂—C(=O)-KGGFG (SEQ ID NO. 38)-NH—CH₂CH₂—O—CH₂—C(=O)—(NH-DX),

—C(=O)-cyc.Hex(1,4)-CH₂—(N-ly-3-Succinimid)-S—CH₂CH₂—C(=O)-DGGF (SEQ ID NO. 34)-NH—CH₂CH₂CH₂—C(=O)—(NH-DX), —C(=O)-cyc.Hex(1,4)-CH₂—(N-ly-3-Succinimid)-S—CH₂CH₂—C(=O)-DGGF (SEQ ID NO. 34)-NH—CH₂—O—CH₂—C(=O)—(NH-DX), —C(=O)-cyc.Hex(1,4)-CH₂—(N-ly-3-Succinimid)-S—CH₂CH₂—C(=O)-DGGF (SEQ ID NO. 34)-NH—CH₂CH₂—O—CH₂—C(=O)—(NH-DX), —C(=O)-cyc.Hex(1,4)-CH₂—(N-ly-3-Succinimid)-S—CH₂CH₂—C(=O)-DGGFG (SEQ ID NO. 37)-NH—CH₂CH₂CH₂—C(=O)—(NH-DX), —C(=O)-cyc.Hex(1,4)-CH₂—(N-ly-3-Succinimid)-S—CH₂CH₂—C(=O)-DGGFG (SEQ ID NO. 37)-NH—CH₂—O—CH₂—C(=O)—(NH-DX), —C(=O)-cyc.Hex(1,4)-CH₂—(N-ly-3-Succinimid)-S—CH₂CH₂—C(=O)-DGGFG (SEQ ID NO. 37)-NH—CH₂CH₂—O—CH₂—C(=O)—(NH-DX), —C(=O)-cyc.Hex(1,4)-CH₂—(N-ly-3-Succinimid)-S—CH₂CH₂—C(=O)-KGGF (SEQ ID NO. 35)-NH—CH₂CH₂CH₂—C(=O)—(NH-DX), —C(=O)-cyc.Hex(1,4)-CH₂—(N-ly-3-Succinimid)-S—CH₂CH₂—C(=O)-KGGF (SEQ ID NO. 35)-NH—CH₂—O—CH₂—C(=O)—(NH-DX), —C(=O)-cyc.Hex(1,4)-CH₂—(N-ly-3-Succinimid)-S—CH₂CH₂—C(=O)-KGGF (SEQ ID NO. 35)-NH—CH₂CH₂—O—CH₂—C(=O)—(NH-DX), —C(=O)-cyc.Hex(1,4)-CH₂—(N-ly-3-Succinimid)-S—CH₂CH₂—C(=O)-KGGFG (SEQ ID NO. 38)-NH—CH₂CH₂CH₂—C(=O)—(NH-DX), —C(=O)-cyc.Hex(1,4)-CH₂—(N-ly-3-Succinimid)-S—CH₂CH₂—C(=O)-KGGFG (SEQ ID NO. 38)-NH—CH₂—O—CH₂—C(=O)—(NH-DX), —C(=O)-cyc.Hex(1,4)-CH₂—(N-ly-3-Succinimid)-S—CH₂CH₂—C(=O)-KGGFG (SEQ ID NO. 38)-NH—CH₂CH—O—CH—C(=O)—(NH-DX),

—C(=O)—CH₂CH₂CH₂CH₂CH₂—C(=O)-DGGF (SEQ ID NO. 34)-NH—CH₂CH₂CH₂—C(=O)—(NH-DX),

—C(=O)—CH₂CH₂CH₂CH₂CH₂—C(=O)-DGGF (SEQ ID NO. 34)-NH—CH₂—O—CH₂—C(=O)—(NH-DX),

—C(=O)—CH₂CH₂CH₂CH₂CH₂—C(=O)-DGGF (SEQ ID NO. 34)-NH—CH₂CH₂—O—CH₂—C(=O)—(NH-DX),

—C(=O)—CH₂CHCHH₂CH₂CH₂CH₂—C(=O)-KGGF (SEQ ID NO. 35)-NH—CH₂CH₂CH₂—C(=O)—(NH-DX),

—C(=O)—CH₂CHCHH₂CH₂CH₂CH₂—C(=O)-KGGF (SEQ ID NO. 35)-NH—CH₂—O—CH₂—C(=O)—(NH-DX),

—C(=O)—CH₂CHCHH₂CH₂CH₂CH₂—C(=O)-KGGF (SEQ ID NO. 35)-NH—CH₂CH₂—O—CH₂—C(=O)—(NH-DX),

—C(=O)—CH₂CHCHH₂CH₂CH₂CH₂—C(=O)-DGGFG (SEQ ID NO. 37)-NH—CH₂CH₂CH₂—C(=O)—(NH-DX),

—C(=O)—CH₂CHCHH₂CH₂CH₂CH₂—C(=O)-DGGFG (SEQ ID NO. 37)-NH—CH₂—O—CH₂—C(=O)—(NH-DX),

—C(=O)—CH₂CH₂CH₂CH₂CH₂CH₂—C(=O)-DGGFG (SEQ ID NO. 37)-NH—CH₂CH₂—O—CH₂—C(=O)—(NH-DX),

—C(=O)—CH₂CH₂CH₂CH₂CH₂CH₂—C(=O)-KGGFG (SEQ ID NO. 38)-NH—CH₂CH₂CH₂—C(=O)—(NH-DX),

—C(=O)—CH₂CH₂CH₂CH₂CH₂CH₂—C(=O)-KGGFG (SEQ ID NO. 38)-NH—CH₂—O—CH₂—C(=O)—(NH-DX),

—C(=O)—CH₂CH₂CH₂CH₂CH₂CH₂—C(=O)-KGGFG (SEQ ID NO. 38)-NH—CH₂CH₂—O—CH₂—C(=O)—(NH-DX),

-(Succinimid-3-yl-N)—CH₂CH₂CH₂CH₂CH₂—C(=O)-DGGF (SEQ ID NO. 34)-(NH-DX),

-(Succinimid-3-yl-N)—CH₂CH₂CH₂CH₂CH₂—C(=O)-KGGF (SEQ ID NO. 35)-(NH-DX),

-(Succinimid-3-yl-N)—CH₂CH₂CH₂CH₂CH₂—C(=O)-DGGFG (SEQ ID NO. 37)-(NH-DX),

-(Succinimid-3-yl-N)—CH₂CH₂CH₂CH₂CH₂—C(=O)-KGGFG (SEQ ID NO. 38)-(NH-DX),

—CH₂—C(=O)—NH—CH₂CH₂—C(=O)-DGGF (SEQ ID NO. 34)-(NH-DX),

—CH₂—C(=O)—NH—CH₂CH₂—C(=O)-KGGF (SEQ ID NO. 35)-(NH-DX),

—CH₂—C(=O)—NH—CH₂CH₂—C(=O)-DGGFG (SEQ ID NO. 37)-(NH-DX),

—CH₂—C(=O)—NH—CH₂CH₂—C(=O)-KGGFG (SEQ ID NO. 38)-(NH-DX),

—C(=O)-cyc.Hex(1,4)-CH₂—(N-ly-3-Succinimid)-S—CH₂CH₂—C(=O)-DGGF (SEQ ID NO. 34)-(NH-DX), —C(=O)-cyc.Hex(1,4)-CH₂—(N-ly-3-Succinimid)-S—CH₂CH₂—C(=O)-KGGF (SEQ ID NO. 35)-(NH-DX),
—C(=O)-cyc.Hex(1,4)-CH₂—(N-ly-3-Succinimid)-S—CH₂CH₂—C(=O)-DGGFG (SEQ ID NO. 37)-(NH-DX),
—C(=O)-cyc.Hex(1,4)-CH₂—(N-ly-3-Succinimid)-S—CH₂CH₂—C(=O)-KGGFG (SEQ ID NO. 38)-(NH-DX),
—C(=O)—CH₂CH₂CH₂CH₂CH₂CH₂—C(=O)-DGGF (SEQ ID NO. 34)-(NH-DX),
—C(=O)—CH₂CH₂CH₂CH₂CH₂CH₂—C(=O)-KGGF (SEQ ID NO. 35)-(NH-DX),
—C(=O)—CH₂CH₂CH₂CH₂CH₂CH₂—C(=O)-DGGFG (SEQ ID NO. 37)-(NH-DX),
—C(=O)—CH₂CH₂CH₂CH₂CH₂CH₂—C(=O)-KGGFG (SEQ ID NO. 38)-(NH-DX),
-(Succinimid-3-yl-N)—CH₂CH₂CH₂CH₂CH₂—C(=O)-GGFGG (SEQ ID NO. 40)-(NH-DX),
-(Succinimid-3-yl-N)—CH₂CH₂CH₂CH₂CH₂—C(=O)-GGFGGG (SEQ ID NO. 41)-(NH-DX),
—CH₂—C(=O)—NH—CH₂CHz-C(=O)-GGFGG (SEQ ID NO. 40)-(NH-DX),
—CH₂—C(=O)—NH—CH₂CH₂—C(=O)-GGFGGG (SEQ ID NO. 41)-(NH-DX),
—C(=O)-cyc.Hex(1,4)-CH₂—(N-ly-3-Succinimid)-S—CH₂CH₂—C(=O)-GGFGG (SEQ ID NO. 40)-(NH-DX),
—C(=O)-cyc.Hex(1,4)-CH₂—(N-ly-3-Succinimid)-S—CH₂CH₂—C(=O)-GGFGGG (SEQ ID NO. 41)-(NH-DX),
—C(=O)—CH₂CH₂CH₂CH₂CH₂CH₂—C(=O)-GGFGG (SEQ ID NO. 40)-(NH-DX),
—C(=O)—CH₂CH₂CH₂CH₂CH₂CH₂—C(=O)-GGFGGG (SEQ ID NO. 41)-(NH-DX)

wherein -(Succinimid-3-yl-N)— has a structure represented by the following formula:

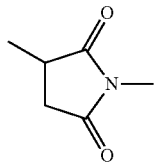

which is connected to the antibody at position 3 thereof and is connected to a methylene group in the linker structure containing this structure on the nitrogen atom at position 1,
cyc.Hex(1,4) represents a 1,4-cyclohexylene group,
—(N-ly-3-Succinimid)- has a structure represented by the following formula:

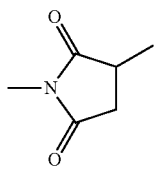

which is connected to L² at position 3 thereof and is connected to a methylene group in the linker structure containing this structure on the nitrogen atom at position 1, and —(NH-DX) is a group represented by the following formula:

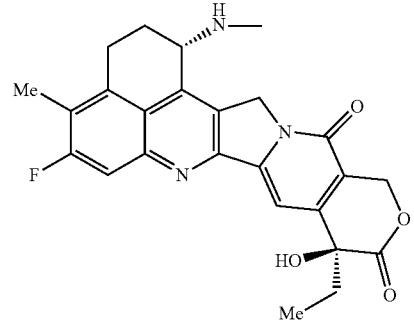 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is the connecting position.

33. The antibody-drug conjugate according to claim 1, wherein an average number of conjugated antitumor compounds per antibody is in a range of from 1 to 10.

34. The antibody-drug conjugate according to claim 1, wherein an average number of conjugated antitumor compounds per antibody is in a range of from 1 to 8.

35. The antibody-drug conjugate according to claim 1, wherein an average number of conjugated antitumor compounds per antibody is in a range of from 3 to 8.

36. The antibody-drug conjugate according to claim 1, wherein the antibody is an antibody having one or more of a property of recognizing a target cell, a property of binding to a target cell, a property of internalizing in a target cell, and a property of damaging a target cell.

37. The antibody-drug conjugate according to claim 36, wherein the target cell is a tumor cell.

38. The antibody-drug conjugate according to claim 36, wherein the antibody is an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-Cripto antibody, an anti-EphA2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, or an anti-mesothelin antibody.

39. The antibody-drug conjugate according to claim 36, wherein the antibody is an anti-B7-H3 antibody, an anti-CD30 antibody, an anti-CD33 antibody, or an anti-CD70 antibody.

40. The antibody-drug conjugate according to claim 36, wherein the antibody is an anti-B7-H3 antibody.

41. A drug containing the antibody-drug conjugate according to claim 1 or a salt thereof.

42. An antitumor drug and/or anticancer drug containing the antibody-drug conjugate according to claim 1 or a salt thereof.

43. The antitumor drug and/or anticancer drug according to claim 42, which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.

44. A pharmaceutical composition containing the antibody-drug conjugate according to claim 1, a salt thereof or a hydrate thereof as an active component, and a pharmaceutically acceptable formulation component.

45. The pharmaceutical composition according to claim 44, which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.

46. A method for treating tumor and/or cancer comprising administering the antibody-drug conjugate according to claim 1, a salt thereof or a hydrate thereof.

47. The treatment method according to claim 46, which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.

* * * * *

UNITED STATES PATENT AND TRADEMARK OFFICE
CERTIFICATE OF CORRECTION

PATENT NO. : 9,872,924 B2
APPLICATION NO. : 14/436458
DATED : January 23, 2018
INVENTOR(S) : Hiroyuki Naito et al.

Page 1 of 1

It is certified that error appears in the above-identified patent and that said Letters Patent is hereby corrected as shown below:

In the Claims

Claim 18, Column 309, Line 64:
Delete "$L^1$-$L^2$-$L^c$" after --represented by--, and before --.--.
Insert --$L^1$-$L^2$-$L^p$-- after --represented by--, and before --.--.

Claim 32, Column 310, Lines 33-34:
Delete "claim" after --The antibody-drug conjugate according to--, and before --1 or 2--.
Insert --claims-- after --The antibody-drug conjugate according to--, and before --1 or 2--.

Signed and Sealed this
Twelfth Day of February, 2019

Andrei Iancu
*Director of the United States Patent and Trademark Office*

SEQUENCE LISTING

```
<160> NUMBER OF SEQ ID NOS: 43

<210> SEQ ID NO 1
<211> LENGTH: 534
<212> TYPE: PRT
<213> ORGANISM: Homo sapiens

<400> SEQUENCE: 1

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175
```

```
Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Ile Leu
            195                 200                 205

Arg Val Val Leu Gly Ala Asn Gly Thr Tyr Ser Cys Leu Val Arg Asn
        210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530

<210> SEQ ID NO 2
<211> LENGTH: 316
<212> TYPE: PRT
<213> ORGANISM: Homo sapiens

<400> SEQUENCE: 2

Met Leu Arg Arg Arg Gly Ser Pro Gly Met Gly Val His Val Gly Ala
1               5                   10                  15
```

-continued

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
 50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
            195                 200                 205

Arg Val Val Leu Gly Ala Asn Gly Thr Tyr Ser Cys Leu Val Arg Asn
            210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Asn Ala Gly Ala Glu Asp Gln
            275                 280                 285

Asp Gly Glu Gly Glu Gly Ser Lys Thr Ala Leu Gln Pro Leu Lys His
            290                 295                 300

Ser Asp Ser Lys Glu Asp Asp Gly Gln Glu Ile Ala
305                 310                 315

<210> SEQ ID NO 3
<211> LENGTH: 5
<212> TYPE: PRT
<213> ORGANISM: Mus musculus

<400> SEQUENCE: 3

Asn Tyr Val Met His
1               5

<210> SEQ ID NO 4
<211> LENGTH: 17
<212> TYPE: PRT
<213> ORGANISM: Mus musculus

<400> SEQUENCE: 4

Tyr Ile Asn Pro Tyr Asn Asp Asp Val Lys Tyr Asn Glu Lys Phe Lys
1               5                   10                  15

Gly

<210> SEQ ID NO 5
<211> LENGTH: 13
<212> TYPE: PRT
<213> ORGANISM: Mus musculus

<400> SEQUENCE: 5

Trp Gly Tyr Tyr Gly Ser Pro Leu Tyr Tyr Phe Asp Tyr
1               5                   10

<210> SEQ ID NO 6
<211> LENGTH: 10
<212> TYPE: PRT
<213> ORGANISM: Mus musculus

<400> SEQUENCE: 6

Arg Ala Ser Ser Arg Leu Ile Tyr Met His
1               5                   10

<210> SEQ ID NO 7
<211> LENGTH: 7
<212> TYPE: PRT
<213> ORGANISM: Mus musculus

<400> SEQUENCE: 7

Ala Thr Ser Asn Leu Ala Ser
1               5

<210> SEQ ID NO 8
<211> LENGTH: 9
<212> TYPE: PRT
<213> ORGANISM: Mus musculus

<400> SEQUENCE: 8

Gln Gln Trp Asn Ser Asn Pro Pro Thr
1               5

<210> SEQ ID NO 9
<211> LENGTH: 471
<212> TYPE: PRT
<213> ORGANISM: Artificial Sequence
<220> FEATURE:
<223> OTHER INFORMATION: Description of Artificial Sequence: Synthetic
      humanized heavy chain sequence of M30

<400> SEQUENCE: 9

Met Lys His Leu Trp Phe Phe Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Arg Gln Ala Pro Gly Gln Gly Leu
    50                  55                  60

Glu Trp Met Gly Tyr Ile Asn Pro Tyr Asn Asp Val Lys Tyr Asn
65                  70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

```
Tyr Tyr Cys Ala Arg Trp Gly Tyr Gly Ser Pro Leu Tyr Tyr Phe
            115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 10
<211> LENGTH: 471
<212> TYPE: PRT
<213> ORGANISM: Artificial Sequence
<220> FEATURE:
<223> OTHER INFORMATION: Description of Artificial Sequence: Synthetic
      humanized heavy chain sequence of M30

<400> SEQUENCE: 10
```

-continued

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
            35                  40                  45

Thr Asn Tyr Val Met His Trp Val Arg Gln Ala Pro Gly Gln Gly Leu
        50                  55                  60

Glu Trp Ile Gly Tyr Ile Asn Pro Tyr Asn Asp Asp Val Lys Tyr Asn
65                  70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

```
Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 11
<211> LENGTH: 471
<212> TYPE: PRT
<213> ORGANISM: Artificial Sequence
<220> FEATURE:
<223> OTHER INFORMATION: Description of Artificial Sequence: Synthetic
      humanized heavy chain sequence of M30

<400> SEQUENCE: 11

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Lys Gln Ala Pro Gly Gln Gly Leu
    50                  55                  60

Glu Trp Ile Gly Tyr Ile Asn Pro Tyr Asn Asp Val Lys Tyr Asn
65              70                  75                  80

Glu Lys Phe Lys Gly Lys Ala Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300
```

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 12
<211> LENGTH: 471
<212> TYPE: PRT
<213> ORGANISM: Artificial Sequence
<220> FEATURE:
<223> OTHER INFORMATION: Description of Artificial Sequence: Synthetic
      humanized heavy chain sequence of M30

<400> SEQUENCE: 12

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Lys Gln Ala Pro Gly Gln Gly Leu
    50                  55                  60

Glu Trp Ile Gly Tyr Ile Asn Pro Tyr Asn Asp Val Lys Tyr Asn
65                  70                  75                  80

Glu Lys Phe Lys Gly Lys Ala Thr Gln Thr Ser Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His

```
                180             185             190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
        210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 13
<211> LENGTH: 233
<212> TYPE: PRT
<213> ORGANISM: Artificial Sequence
<220> FEATURE:
<223> OTHER INFORMATION: Description of Artificial Sequence: Synthetic
      humanized light chain sequence of M30

<400> SEQUENCE: 13

Met Val Leu Gln Thr Gln Val Phe Ile Ser Leu Leu Leu Trp Ile Ser
1               5                   10                  15
Gly Ala Tyr Gly Glu Ile Val Leu Thr Gln Ser Pro Ala Thr Leu Ser
            20                  25                  30
Leu Ser Pro Gly Glu Arg Ala Thr Leu Ser Cys Arg Ala Ser Ser Arg
        35                  40                  45
Leu Ile Tyr Met His Trp Tyr Gln Gln Lys Pro Gly Gln Ala Pro Arg
    50                  55                  60
```

```
Leu Leu Ile Tyr Ala Thr Ser Asn Leu Ala Ser Gly Ile Pro Ala Arg
 65                  70                  75                  80

Phe Ser Gly Ser Gly Ser Gly Thr Asp Phe Thr Leu Thr Ile Ser Arg
                 85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 14
<211> LENGTH: 233
<212> TYPE: PRT
<213> ORGANISM: Artificial Sequence
<220> FEATURE:
<223> OTHER INFORMATION: Description of Artificial Sequence: Synthetic
      humanized light chain sequence of M30

<400> SEQUENCE: 14

Met Val Leu Gln Thr Gln Val Phe Ile Ser Leu Leu Leu Trp Ile Ser
1                5                  10                  15

Gly Ala Tyr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Ser Arg
            35                  40                  45

Leu Ile Tyr Met His Trp Tyr Gln Gln Lys Pro Gly Gln Ala Pro Arg
        50                  55                  60

Leu Trp Ile Tyr Ala Thr Ser Asn Leu Ala Ser Gly Ile Pro Ala Arg
 65                  70                  75                  80

Phe Ser Gly Ser Gly Ser Gly Thr Asp Tyr Thr Leu Thr Ile Ser Arg
                 85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190
```

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 15
<211> LENGTH: 233
<212> TYPE: PRT
<213> ORGANISM: Artificial Sequence
<220> FEATURE:
<223> OTHER INFORMATION: Description of Artificial Sequence: Synthetic
      humanized light chain sequence of M30

<400> SEQUENCE: 15

Met Val Leu Gln Thr Gln Val Phe Ile Ser Leu Leu Leu Trp Ile Ser
1               5                   10                  15

Gly Ala Tyr Gly Gln Ile Val Leu Ser Gln Ser Pro Ala Thr Leu Ser
            20                  25                  30

Leu Ser Pro Gly Glu Arg Ala Thr Leu Thr Cys Arg Ala Ser Ser Arg
        35                  40                  45

Leu Ile Tyr Met His Trp Tyr Gln Gln Lys Pro Gly Ser Ala Pro Lys
    50                  55                  60

Leu Trp Ile Tyr Ala Thr Ser Asn Leu Ala Ser Gly Ile Pro Ala Arg
65                  70                  75                  80

Phe Ser Gly Ser Gly Ser Gly Thr Ser Tyr Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 16
<211> LENGTH: 233
<212> TYPE: PRT
<213> ORGANISM: Artificial Sequence
<220> FEATURE:
<223> OTHER INFORMATION: Description of Artificial Sequence: Synthetic
      humanized light chain sequence of M30

<400> SEQUENCE: 16

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
 50                  55                  60

Pro Leu Ile Tyr Ala Thr Ser Asn Leu Ala Ser Gly Ile Pro Ala Arg
 65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 17
<211> LENGTH: 233
<212> TYPE: PRT
<213> ORGANISM: Artificial Sequence
<220> FEATURE:
<223> OTHER INFORMATION: Description of Artificial Sequence: Synthetic
      humanized light chain sequence of M30

<400> SEQUENCE: 17

Met Val Leu Gln Thr Gln Val Phe Ile Ser Leu Leu Leu Trp Ile Ser
1               5                   10                  15

Gly Ala Tyr Gly Gln Ile Val Leu Ser Gln Ser Pro Ala Thr Leu Ser
            20                  25                  30

Leu Ser Pro Gly Glu Arg Ala Thr Leu Thr Cys Arg Ala Ser Ser Arg
        35                  40                  45

Leu Ile Tyr Met His Trp Tyr Gln Gln Lys Pro Gly Ser Ala Pro Lys
 50                  55                  60

Pro Trp Ile Tyr Ala Thr Ser Asn Leu Ala Ser Gly Ile Pro Ala Arg
 65                  70                  75                  80

Phe Ser Gly Ser Gly Ser Gly Thr Ser Tyr Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu

```
                130             135             140
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 18
<211> LENGTH: 233
<212> TYPE: PRT
<213> ORGANISM: Artificial Sequence
<220> FEATURE:
<223> OTHER INFORMATION: Description of Artificial Sequence: Synthetic
      humanized light chain sequence of M30

<400> SEQUENCE: 18

Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Ser Arg
            35                  40                  45

Leu Ile Tyr Met His Trp Tyr Gln Gln Lys Pro Gly Gln Ala Pro Arg
        50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 19
<211> LENGTH: 233
```

```
<212> TYPE: PRT
<213> ORGANISM: Artificial Sequence
<220> FEATURE:
<223> OTHER INFORMATION: Description of Artificial Sequence: Synthetic
      humanized light chain sequence of M30

<400> SEQUENCE: 19

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Tyr Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 20
<211> LENGTH: 471
<212> TYPE: PRT
<213> ORGANISM: Mus musculus

<400> SEQUENCE: 20

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asn Tyr Val Met His Trp Val Lys Gln Lys Pro Gly Gln Gly Leu
    50                  55                  60

Glu Trp Ile Gly Tyr Ile Asn Pro Tyr Asn Asp Val Lys Tyr Asn
65                  70                  75                  80

Glu Lys Phe Lys Gly Lys Ala Thr Gln Thr Ser Asp Lys Ser Ser Ser
                85                  90                  95
```

Thr Ala Tyr Met Glu Leu Ser Ser Leu Thr Ser Glu Asp Ser Ala Val
            100                 105                 110

Tyr Tyr Cys Ala Arg Trp Gly Tyr Gly Ser Pro Leu Tyr Tyr Phe
        115                 120                 125

Asp Tyr Trp Gly Gln Gly Thr Thr Leu Thr Val Ser Ser Ala Lys Thr
130                 135                 140

Thr Ala Pro Ser Val Tyr Pro Leu Ala Pro Val Cys Gly Asp Thr Thr
145                 150                 155                 160

Gly Ser Ser Val Thr Leu Gly Cys Leu Val Lys Gly Tyr Phe Pro Glu
                165                 170                 175

Pro Val Thr Leu Thr Trp Asn Ser Gly Ser Leu Ser Ser Gly Val His
                180                 185                 190

Thr Phe Pro Ala Val Leu Gln Ser Asp Leu Tyr Thr Leu Ser Ser Ser
            195                 200                 205

Val Thr Val Thr Ser Ser Thr Trp Pro Ser Gln Ser Ile Thr Cys Asn
        210                 215                 220

Val Ala His Pro Ala Ser Ser Thr Lys Val Asp Lys Lys Ile Glu Pro
225                 230                 235                 240

Arg Gly Pro Thr Ile Lys Pro Cys Pro Pro Cys Lys Cys Pro Ala Pro
                245                 250                 255

Asn Leu Leu Gly Gly Pro Ser Val Phe Ile Phe Pro Pro Lys Ile Lys
                260                 265                 270

Asp Val Leu Met Ile Ser Leu Ser Pro Ile Val Thr Cys Val Val Val
            275                 280                 285

Asp Val Ser Glu Asp Asp Pro Asp Val Gln Ile Ser Trp Phe Val Asn
            290                 295                 300

Asn Val Glu Val His Thr Ala Gln Thr Gln Thr His Arg Glu Asp Tyr
305                 310                 315                 320

Asn Ser Thr Leu Arg Val Val Ser Ala Leu Pro Ile Gln His Gln Asp
                325                 330                 335

Trp Met Ser Gly Lys Glu Phe Lys Cys Lys Val Asn Asn Lys Asp Leu
                340                 345                 350

Pro Ala Pro Ile Glu Arg Thr Ile Ser Lys Pro Lys Gly Ser Val Arg
            355                 360                 365

Ala Pro Gln Val Tyr Val Leu Pro Pro Pro Glu Glu Glu Met Thr Lys
            370                 375                 380

Lys Gln Val Thr Leu Thr Cys Met Val Thr Asp Phe Met Pro Glu Asp
385                 390                 395                 400

Ile Tyr Val Glu Trp Thr Asn Asn Gly Lys Thr Glu Leu Asn Tyr Lys
                405                 410                 415

Asn Thr Glu Pro Val Leu Asp Ser Asp Gly Ser Tyr Phe Met Tyr Ser
            420                 425                 430

Lys Leu Arg Val Glu Lys Lys Asn Trp Val Glu Arg Asn Ser Tyr Ser
        435                 440                 445

Cys Ser Val Val His Glu Gly Leu His Asn His Thr Thr Lys Ser
450                 455                 460

Phe Ser Arg Thr Pro Gly Lys
465                 470

<210> SEQ ID NO 21
<211> LENGTH: 235
<212> TYPE: PRT
<213> ORGANISM: Mus musculus

<400> SEQUENCE: 21

```
Met Asp Phe Leu Val Gln Ile Phe Ser Phe Leu Leu Ile Ser Ala Ser
1               5                   10                  15

Val Ile Met Ser Arg Gly Gln Ile Val Leu Ser Gln Ser Pro Thr Ile
            20                  25                  30

Leu Ser Ala Ser Pro Gly Glu Lys Val Thr Met Thr Cys Arg Ala Ser
        35                  40                  45

Ser Arg Leu Ile Tyr Met His Trp Tyr Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Asn Ser Asn Pro Pro Thr Phe Gly Thr Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      PCR primer sequence

<400> SEQUENCE: 22 ctataggag acccaagctg gctagcatgc tgcgtcggcg gggcag                    46

<210> SEQ ID NO 23
<211> LENGTH: 66
<212> TYPE: DNA
<213> ORGANISM: Artificial Sequence
<220> FEATURE:
<223> OTHER INFORMATION: Description of Artificial Sequence: Synthetic
      PCR primer sequence

<400> SEQUENCE: 23
aacgggccct ctagactcga gcggccgctc aggctatttc ttgtccatca tcttctttgc   60
tgtcag                                                               66

<210> SEQ ID NO 24
<211> LENGTH: 21
<212> TYPE: DNA
<213> ORGANISM: Artificial Sequence
```

<220> FEATURE:
<223> OTHER INFORMATION: Description of Artificial Sequence: Synthetic
      PCR primer sequence

<400> SEQUENCE: 24
cgcaaatggg cggtaggcgt g                                          21

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR primer sequence

<400> SEQUENCE: 25
tagaaggcac agtcgagg                                              18

<210> SEQ ID NO 26
<211> LENGTH: 1815
<212> TYPE: DNA
<213> ORGANISM: Homo sapiens

<400> SEQUENCE: 26
atgctgcgtc ggcggggcag ccctggcatg ggtgtgcatg tgggtgcagc cctgggagca    60
ctgtggttct gcctcacagg agccctggag gtccaggtcc ctgaagaccc agtggtggca   120
ctggtgggca ccgatgccac cctgtgctgc tccttctccc ctgagcctgg cttcagcctg   180
gcacagctca acctcatctg gcagctgaca gataccaaac agctggtgca cagctttgct   240
gagggccagg accagggcag cgcctatgcc aaccgcacgg ccctcttccc ggacctgctg   300
gcacagggca acgcatccct gaggctgcag cgcgtgcgtg tggcggacga gggcagcttc   360
acctgcttcg tgagcatccg ggatttcggc agcgctgccg tcagcctgca ggtggccgct   420
ccctactcga agcccagcat gaccctggag cccaacaagg acctgcggcc aggggacacg   480
gtgaccatca cgtgctccag ctaccagggc taccctgagg ctgaggtgtt ctggcaggat   540
gggcagggtg tgcccctgac tggcaacgtg accacgtcgc agatggccaa cgagcagggc   600
ttgtttgatg tgcacagcat cctgcggggtg gtgctgggtg caaatggcac ctacagctgc   660
ctggtgcgca ccccgtgct gcagcaggat gcgcacagct ctgtcaccat cacccccag   720 agaagcccca caggagccgt ggaggtccag gtccctgagg accgtggt ggccctagtg   780 ggcaccgatg ccacccctgcg ctgctccttc tcccccgagc ctggcttcag cctggcacag   840
ctcaacctca tctggcagct gacagacacc aaacagctgg tgcacagttt cacccgaaggc   900 cgggaccagg gcagcgccta tgccaaccgc acggccctct tcccggacct gctggcacaa   960
ggcaatgcat ccctgaggct gcagcgcgtg cgtgtggcgg acgagggcag cttcacctgc  1020
ttcgtgagca tccgggattt cggcagcgct gccgtcagcc tgcaggtggc cgctccctac  1080
tcgaagccca gcatgaccct ggagcccaac aaggacctgc ggccagggga cacggtgacc  1140
atcacgtgct ccagctaccg ggctaccct gaggctgagg tgttctggca ggatgggcag  1200
ggtgtgcccc tgactggcaa cgtgaccacg tcgcagatgg ccaacgagca gggcttgttt  1260
gatgtgcaca gcgtcctgcg ggtggtgctg gtgcgaatg cacctacag ctgcctggtg  1320 cgcaaccccg tgctgcagca ggatgcgcac ggctctgtca ccatcacagg cagcctatg  1380 acattccccc cagaggccct gtgggtgacc gtggggctgt ctgtctgtct cattgcactg  1440
ctggtggccc tggcttcgt gtgctggaga aagatcaaac agagctgtga ggaggagaat  1500

-continued

```
gcaggagctg aggaccagga tggggaggga aaggctcca agacagccct gcagcctctg    1560
aaacactctg acagcaaaga agatgatgga caagaaatag cctgagcggc cgccactgtg    1620
ctggatatct gcagaattcc accacactgg actagtggat ccgagctcgg taccaagctt    1680
aagtttaaac cgctgatcag cctcgactgt gccttctagt tgccagccat ctgttgtttg    1740
cccctccccc gtgccttcct tgaccctgga aggtgccact cccactgtcc tttcctaata    1800
aaatgaggaa attgc                                                   1815
```

<210> SEQ ID NO 27
<211> LENGTH: 466
<212> TYPE: PRT
<213> ORGANISM: Artificial Sequence
<220> FEATURE:
<223> OTHER INFORMATION: Description of Artificial Sequence: Synthetic
      heavy chain sequence of chimeric CD30 antibody

<400> SEQUENCE: 27

```
Met Lys His Leu Trp Phe Phe Leu Leu Leu Val Ala Ala Pro Arg Trp
1               5                   10                  15

Val Leu Ser Gln Ile Gln Leu Gln Gln Ser Gly Pro Glu Val Val Lys
            20                  25                  30

Pro Gly Ala Ser Val Lys Ile Ser Cys Lys Ala Ser Gly Tyr Thr Phe
        35                  40                  45

Thr Asp Tyr Tyr Ile Thr Trp Val Lys Gln Lys Pro Gly Gln Gly Leu
    50                  55                  60

Glu Trp Ile Gly Trp Ile Tyr Pro Gly Ser Gly Asn Thr Lys Tyr Asn
65                  70                  75                  80

Glu Lys Phe Lys Gly Lys Ala Thr Leu Thr Val Asp Thr Ser Ser Ser
                85                  90                  95

Thr Ala Phe Met Gln Leu Ser Ser Leu Thr Ser Glu Asp Thr Ala Val
            100                 105                 110

Tyr Phe Cys Ala Asn Tyr Gly Asn Tyr Trp Phe Ala Tyr Trp Gly Gln
        115                 120                 125

Gly Thr Gln Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300
```

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 28
<211> LENGTH: 238
<212> TYPE: PRT
<213> ORGANISM: Artificial Sequence
<220> FEATURE:
<223> OTHER INFORMATION: Description of Artificial Sequence: Synthetic
      light chain sequences of chimeric CD30 antibody

<400> SEQUENCE: 28

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Phe Asp Gly Asp Ser Tyr Met Asn Trp Tyr Gln Gln Lys Pro
    50                  55                  60

Gly Gln Pro Pro Lys Val Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
            85                  90                  95

Leu Asn Ile His Pro Val Glu Glu Glu Asp Ala Ala Thr Tyr Tyr Cys
            100                 105                 110

Gln Gln Ser Asn Gln Asp Pro Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
            165                 170                 175

Ala Leu Gln Ser Gly Asn Ser Gln Glu Ser Val Thr Glu Gln Asp Ser

```
                180                 185                 190
Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 29
<211> LENGTH: 465
<212> TYPE: PRT
<213> ORGANISM: Artificial Sequence
<220> FEATURE:
<223> OTHER INFORMATION: Description of Artificial Sequence: Synthetic
      heavy chain sequence of humanized CD33 antibody

<400> SEQUENCE: 29

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Ile
        35                  40                  45

Thr Asp Ser Asn Ile His Trp Val Arg Gln Ala Pro Gly Gln Ser Leu
    50                  55                  60

Glu Trp Ile Gly Tyr Ile Tyr Pro Tyr Asn Gly Gly Thr Asp Tyr Asn
65                  70                  75                  80

Gln Lys Phe Lys Asn Arg Ala Thr Leu Thr Val Asp Asn Pro Thr Asn
                85                  90                  95

Thr Ala Tyr Met Glu Leu Ser Ser Leu Arg Ser Glu Asp Thr Ala Phe
            100                 105                 110

Tyr Tyr Cys Val Asn Gly Asn Pro Trp Leu Ala Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300
```

```
Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
    450                 455                 460

Lys
465

<210> SEQ ID NO 30
<211> LENGTH: 238
<212> TYPE: PRT
<213> ORGANISM: Artificial Sequence
<220> FEATURE:
<223> OTHER INFORMATION: Description of Artificial Sequence: Synthetic
      light chain sequence of humanized CD33 antibody

<400> SEQUENCE: 30

Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Thr Leu Ser
            20                  25                  30

Ala Ser Val Gly Asp Arg Val Thr Ile Thr Cys Arg Ala Ser Gln Ser
        35                  40                  45

Leu Asp Asn Tyr Gly Ile Arg Phe Leu Thr Trp Phe Gln Gln Lys Pro
    50                  55                  60

Gly Lys Ala Pro Lys Leu Leu Met Tyr Ala Ala Ser Asn Gln Gly Ser
65                  70                  75                  80

Gly Val Pro Ser Arg Phe Ser Gly Ser Gly Ser Gly Thr Glu Phe Thr
            85                  90                  95

Leu Thr Ile Ser Ser Leu Gln Pro Asp Asp Phe Ala Thr Tyr Tyr Cys
            100                 105                 110

Gln Gln Thr Lys Glu Val Pro Trp Ser Phe Gly Gln Gly Thr Lys Val
            115                 120                 125

Glu Val Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
            165                 170                 175

Ala Leu Gln Ser Gly Asn Ser Gln Glu Ser Val Thr Glu Gln Asp Ser
            180                 185                 190
```

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 31
<211> LENGTH: 467
<212> TYPE: PRT
<213> ORGANISM: Artificial Sequence
<220> FEATURE:
<223> OTHER INFORMATION: Description of Artificial Sequence: Synthetic
      heavy chain sequence of humanized CD70 antibody

<400> SEQUENCE: 31

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr

```
                305                 310                 315                 320
Arg Val Val Ser Val Leu Thr Val Leu His Gln Asp Trp Leu Asn Gly
                    325                 330                 335

Lys Glu Tyr Lys Cys Lys Val Ser Asn Lys Ala Leu Pro Ala Pro Ile
                    340                 345                 350

Glu Lys Thr Ile Ser Lys Ala Lys Gly Gln Pro Arg Glu Pro Gln Val
                    355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                    405                 410                 415

Val Leu Asp Ser Asp Gly Ser Phe Phe Leu Tyr Ser Lys Leu Thr Val
                    420                 425                 430

Asp Lys Ser Arg Trp Gln Gln Gly Asn Val Phe Ser Cys Ser Val Met
                    435                 440                 445

His Glu Ala Leu His Asn His Tyr Thr Gln Lys Ser Leu Ser Leu Ser
            450                 455                 460

Pro Gly Lys
465

<210> SEQ ID NO 32
<211> LENGTH: 238
<212> TYPE: PRT
<213> ORGANISM: Artificial Sequence
<220> FEATURE:
<223> OTHER INFORMATION: Description of Artificial Sequence: Synthetic
      light chain sequence of humanized CD70 antibody

<400> SEQUENCE: 32

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Arg Ala Ser Lys Ser
            35                  40                  45

Val Ser Thr Ser Gly Tyr Ser Phe Met His Trp Tyr Gln Gln Lys Pro
        50                  55                  60

Gly Gln Pro Pro Lys Leu Leu Ile Tyr Leu Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln His Ser Arg Glu Val Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190
```

```
Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Phe Gly
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Gly Gly Phe
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Gly Gly Phe
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Gly Gly Phe
1

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Gly Gly Phe Gly
1               5
```

```
<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Gly Gly Phe Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Gly Gly Phe Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Phe Gly Gly
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Phe Gly Gly Gly
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 42

His His His His His His
1               5

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 43

Gly Phe Leu Gly
1
```